US011104950B2

(12) United States Patent
Wyrobek et al.

(10) Patent No.: US 11,104,950 B2
(45) Date of Patent: Aug. 31, 2021

(54) HUMAN BLOOD MOLECULAR BIODOSIMETER PANEL FOR DISTINGUISHING RADIATION EXPOSURE FROM INFLAMMATION STRESS

(71) Applicants: Andrew J. Wyrobek, Walnut Creek, CA (US); Antoine M. Snijders, Antioch, CA (US)

(72) Inventors: Andrew J. Wyrobek, Walnut Creek, CA (US); Antoine M. Snijders, Antioch, CA (US)

(73) Assignee: The Regents of the University of California, Oakland, CA (US)

( * ) Notice: Subject to any disclaimer, the term of this patent is extended or adjusted under 35 U.S.C. 154(b) by 304 days.

(21) Appl. No.: 14/536,543

(22) Filed: Nov. 7, 2014

(65) Prior Publication Data

US 2016/0348173 A1    Dec. 1, 2016

Related U.S. Application Data

(60) Provisional application No. 61/901,372, filed on Nov. 7, 2013.

(51) Int. Cl.
*C12Q 1/68*   (2018.01)
*C12P 19/34*  (2006.01)
*C12Q 1/6883* (2018.01)

(52) U.S. Cl.
CPC ..... *C12Q 1/6883* (2013.01); *C12Q 2600/158* (2013.01)

(58) Field of Classification Search
CPC ........... G01N 33/6893; G01N 2800/40; G01N 2800/60; G01N 2440/14; G01N 2800/56; G01T 1/04; G01T 1/02; C12Q 2600/158; C12Q 1/6883; C12Q 2600/16; C12Q 2600/112
See application file for complete search history.

(56) References Cited

U.S. PATENT DOCUMENTS

2005/0118634 A1  6/2005  Pinkel et al.
2006/0292591 A1  12/2006 Gray et al.
2008/0176755 A1* 7/2008  Amundson ........... B01L 3/5027
                                                        506/7
2008/0312096 A1  12/2008 Gray et al.

OTHER PUBLICATIONS

GEO Browser—GEO—NCBI, plaform sdearhc homepage, printed on Sep. 4, 2017, 3 pages, from https://www.ncbi.nlm.nih.gov/geo/browse.*
Kim K.H. et al. Experimental and Molecular Medicine, vol. 43, No. 7, 419-426, Jul. 2011.*
Budworth H, Snijders AM, Marchetti F, Mannion B, Bhatnagar S, et al. (2012) DNA Repair and Cell Cycle Biomarkers of Radiation Exposure and Inflammation Stress in Human Blood. PLoS ONE 7(11): e48619. doi:10.1371/journal.pone.004861.*
Abdelmohsen, K. et al. Mol Cell. Feb. 23, 2007; 25(4): 543-557 (Year: 2007).*
Niziolek-Kierecka, M. et al. Chem. Res. Toxicol. 2012, 25, 862-872 (Year: 2012).*
Hudelist, G. et al. "Use of high-throughput protein array for profiling of differentially expressed proteins in normal and malignant breast tissue" Breast Cancer Research and Treatment 86: 281-291,2004. (Year: 2004).*
Eckel-Passow, J. E., et al. "Experimental Design and Analysis of Antibody Microarrays: Applying Methods from cDNA Arrays", Cancer Res 2005; 65: (8). Apr. 15, 2005 (Year: 2005).*
Fenech et al., "Current status, new frontiers and challenges in radiation biodosimetry using cytogenetic, transcriptomic and proteomic technologies." Radiation Measurements 46: 737-741 (2011).
Lemos Pinto et al.,"Current status of biodosimetry based on standard cytogenetic methods." Radiat Environ Biophys 49: 567-581 (2010).
Falt et al., "Long-term global gene expression patterns in irradiated human lymphocytes." Carcinogenesis 24: 1837-1845 (2003).
Amundson et al., "Identification of potential mRNA biomarkers in peripheral blood lymphocytes for human exposure to ionizing radiation." Radiat Res 154: 342-346 (2000).
Turtoi et al., "Proteomic and genomic modulations induced by gamma-irradiation of human blood lymphocytes." Int J Radiat Biol 86: 888-904 (2010).
Kabacik et al., "Gene expression following ionising radiation: identification of biomarkers for dose estimation and prediction of individual response." Int J Radiat Biol 87: 115-129 (2011).
Amundson et al., "Human in vivo radiation-induced biomarkers: gene expression changes in radiotherapy patients." Cancer Res 64: 6368-6371 (2004).
Kang et al., "Possible biomarkers for ionizing radiation exposure in human peripheral blood lymphocytes." Radiat Res 159: 312-319 (2003).
Dressman et al., Gene expression signatures that predict radiation exposure in mice and humans. PLoS Med 4: e106 (2007).
Paul et al., "Development of gene expression signatures for practical radiation biodosimetry." Int J Radiat Oncol Biol Phys 71: 1236-1244 (2008).
Daino et al., "Early induction of CDKN1A (p21) and GADD45 mRNA by a low dose of ionizing radiation is due to their dose-dependent post-transcriptional regulation." Radiat Res 157: 478-482 (2002).
Paul et al., "Prediction of in vivo radiation dose status in radiotherapy patients using ex vivo and in vivo gene expression signatures." Radiat res 175: 257-265 (2011).

(Continued)

*Primary Examiner* — Stephen T Kapushoc
(74) *Attorney, Agent, or Firm* — Robin C. Chiang; Michelle Chew Wong; Lawrence Berkeley National Laboratory

(57) ABSTRACT

Panels of 8-, 9- and 12-biomarker for diagnostic and prognostic methods to determine a subject's radiation exposure and discriminates between persons who have been exposed to radiation only, inflammation stress only, or a combination of the two.

5 Claims, 16 Drawing Sheets

Specification includes a Sequence Listing.

(56) References Cited

OTHER PUBLICATIONS

Marchetti et al., "Candidate protein biodosimeters of human exposure to ionizing radiation." Int J Radiat Biol 82: 305-639 (2006).
Breen et al., "Reactions of oxyl radicals with DNA." Free Radic Biol Med 18: 1033-1077 (1995).
Inoue et al., Expression of the oxidative base excision repair enzymes is not induced in TK6 human lymphoblastoid cells after low doses of ionizing radiation. Radiat Res 161: 409-417 (2004).
Batty et al., Damage recognition in nucleotide excision repair of DNA Gene 241: 193-204 (2000).
Bessho et al., "Nucleotide excision repair 3' endonuclease XPG stimulates the activity of base excision repairenzyme thymine glycol DNA glycosylase." Nucleic Acids Res 27: 979-983 (1999).
Klungland et al., "Base excision repair of oxidative DNA damage activated by XPG protein." Mol Cell 3: 33-42 (1999).
Shimizu et al., "Stimulation of DNA Glycosylase Activities by XPC Protein Complex: Roles of Protein—Protein Interactions." J Nucleic Acids, vol. 2010, Article ID 805698 (2010), 12 pages.
Shimizu et al., "Xeroderma pigmentosum group C protein interacts physically and functionally with thymine DNA glycosylase." EMBO J 22: 164-173 (2003).
D'Errico et al., "New functions of XPC in the protection of human skin cells from oxidative damage." EMBO J 25: 4305-4315 (2006).
Zschenker et al., "Lymphoblastoid cell lines differing in p53 status show clear differences in basal gene expression with minor changes after irradiation." Radiother Oncol 80: 236-249 (2006).
Mayer et al., "A radiation-induced gene expression signature as a tool to predict acute radiotherapy-induced adverse side effects." Cancer Lett 302: 20-28 (2011).
Amundson et al., "Induction of stress genes by low doses of gamma rays." Radiat Res 152: 225-231 (1999).
Brengues et al., "Biodosimetry on small blood volume using gene expression assay." Health Phys 98: 179-185 (2010).
Tichy et al., Gammaradiation-induced ATM-dependent signalling in human T-lymphocyte leukemic cells, MOLT-4. Acta biochimica Polonica 54: 281-287 (2007).
Wang et al., "The catalytic subunit of DNA-dependent protein kinase selectively regulates p53-dependent apoptosis but not cell-cycle arrest." Proceedings of the National Academy of Sciences of the United States of America 97: 1584-1588 (2000).
Zhang et al., "The effects of NBS1 knockdown by small interfering RNA on the ionizing radiation-induced apoptosis in human lymphoblastoid cells with different p53 status." Toxicology letters 171: 50-59 (2007).
Paul et al., "Gene expression signatures of radiation exposure in peripheral white blood cells of smokers and non-smokers." Int J Radiat Biol 87: 791-801 (2011).
Tucker et al., "Gene expression-based detection of radiation exposure in mice after treatment with granulocyte colony-stimulating factor and lipopolysaccharide." Radiat res 177: 209-219 (2012).
Guha et al., "LPS induction of gene expression in human monocytes." Cell Signal 13: 85-94 (2001).
Lavnikova et al., "Unique patterns of regulation of nitric oxide production in fibroblasts." J Leukoc Biol 58: 451-458. (1995).
Schroeder et al., "The RIN: an RNA integrity number for assigning integrity values to RNA measurements." BMC Mol Biol 7: 3 (2006), 14 pages.
Quinlan, "Induction of decision trees." Machine Learning 1:81-106 (1986).
Meadows et al., "Gene expression signatures of radiation response are specific, durable and accurate in mice and humans." PloS one 3: e1912 (2008), 9 pages.
Ahn et al., "Threonine 68 phosphorylation by ataxia telangiectasia mutated is required for efficient activation of Chk2 in response to ionizing radiation." Cancer Res 60: 5934-5936(2000).
Amundson et al., "A nucleotide excision repair master-switch: p53 regulated coordinate induction of global genomic repair genes." Cancer biology & therapy 1: 145-149 (2002).
Zhang et al., "Two-phase dynamics of p53 in the DNA damage response." Proceedings of the National Academy of Sciences of the United States of America 108: 8990-8995 (2011).
Antoni et al., "CHK2 kinase: cancer susceptibility and cancer therapy—two sides of the same coin?" Nature reviews Cancer 7: 925-936 (2007).
Zhivotovsky et al., "Apoptosis and genomic instability." Nature reviews Molecular cell biology 5: 752-762 (2004).
Hirao et al., "DNA damage-induced activation of p53 by the checkpoint kinase Chk2." Science 287: 1824-1827 (2000).
Li et al., "Radiation dose effect of DNA repair-related gene expression in mouse white blood cells." Medical science monitor : international medical journal of experimental and clinical research 17: BR290-297 (2011).
Russell et al., "Gleevec-mediated inhibition of Rad51 expression and enhancement of tumor cell radiosensitivity." Cancer Res 63: 7377-7383 (2003).
Ring et al., "The Cdknia gene (p21Waf1/Cip1) is an inflammatory response gene in the mouse central nervous system." Neurosci Lett 350: 73-76 (2003).
Eslick et al., "IL-4 and IL-10 inhibition of spontaneous monocyte apoptosis is associated with Flip upregulation." Inflammation 28: 139-145 (2004).
Han et al., "Expression of bbc3, a pro-apoptotic BH3-only gene, is regulated by diverse cell death and survival signals." Proceedings of the National Academy of Sciences of the United States of America 98: 11318-11323 (2001).
Riecke et al., "Gene expression comparisons performed for biodosimetry purposes on in vitro peripheral blood cellular subsets and irradiated individuals." Radiat res 178: 234-243(2012).
Kallioniemi et al., "ERBB2 amplification in breast cancer analyzed by fluorescence in situ hybridization" Proc. Natl Acad Sci USA, 89: 5321-5325 (1992).
Budworth et al., "DNA Repair and Cell Cycle Biomarkers of Radiation Exposure and Inflammation Stress in Human Blood", PLOS, 7:e48619 (2012).

* cited by examiner p21 (CDKN1A)

BBC3 (PUMA)

FDXR

Figure 13A
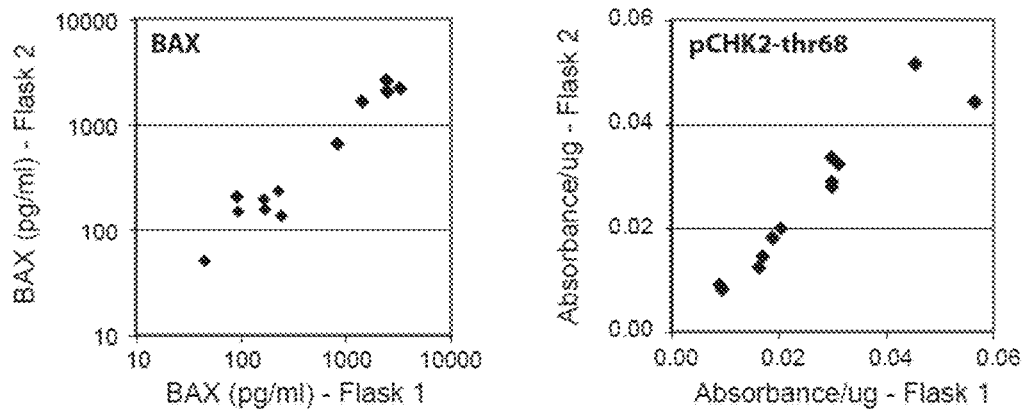
Figure 13B
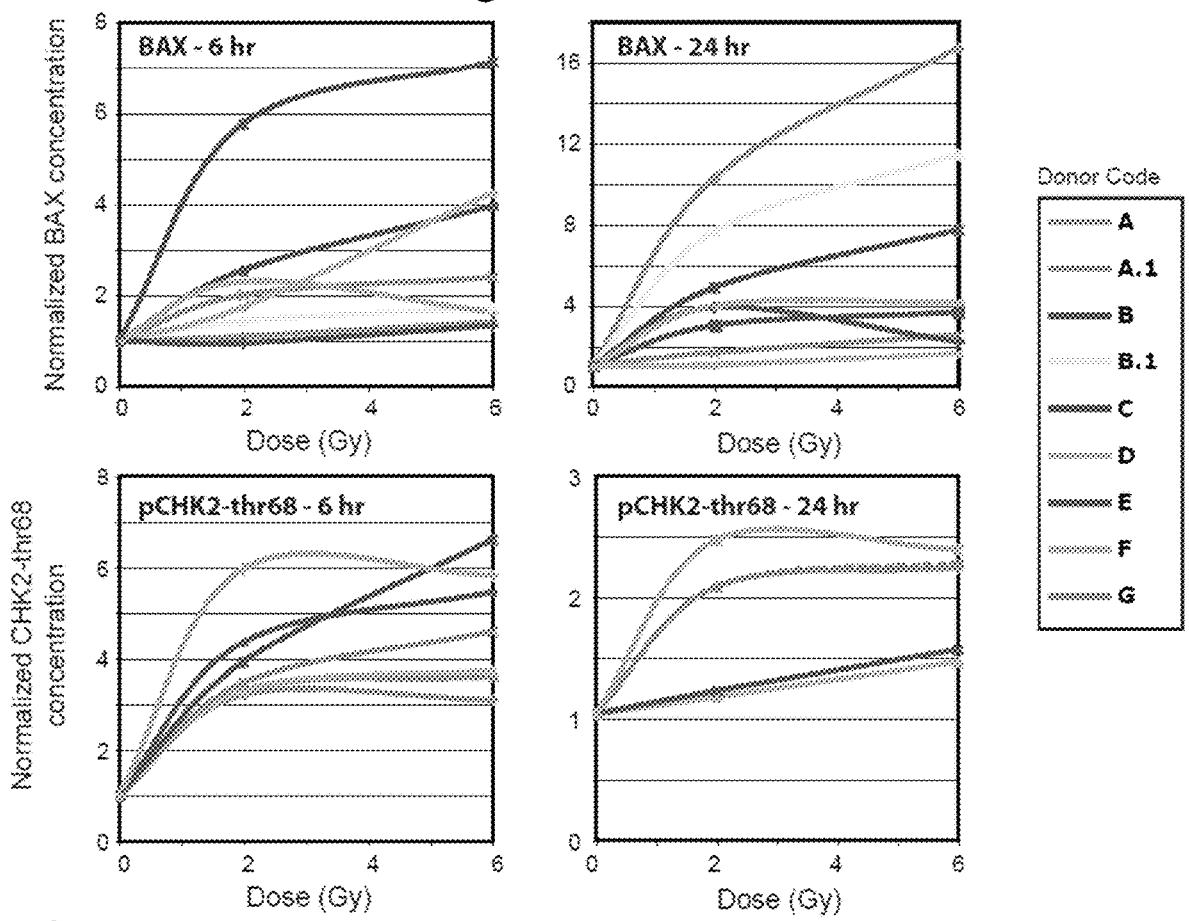
Figure 13C
| t-statistic (p-value) | BAX 6 hr | 24hr | pCHK2-thr68 6 hr | 24 hr |
|---|---|---|---|---|
| 2 Gy vs sham | -2.09 (0.046) | -4.95 (<0.0001) | -9.23 (<0.0001) | -2.54 (0.02) |
| 6 Gy vs sham | -3.14 (0.004) | -5.41 (<0.0001) | -10.47 (<0.0001) | -3.33 (0.004) |

SEQUENCE LISTING

<160> NUMBER OF SEQ ID NOS: 54

<210> SEQ ID NO 1
<211> LENGTH: 164
<212> TYPE: PRT

<213> ORGANISM: Homo sapiens

<400> SEQUENCE: 1

```
Met Ser Glu Pro Ala Gly Asp Val Arg Gln Asn Pro Cys Gly Ser Lys
1               5                   10                  15
Ala Cys Arg Arg Leu Phe Gly Pro Val Asp Ser Glu Gln Leu Ser Arg
            20                  25                  30
Asp Cys Asp Ala Leu Met Ala Gly Cys Ile Gln Glu Ala Arg Glu Arg
        35                  40                  45
Trp Asn Phe Asp Phe Val Thr Glu Thr Pro Leu Glu Gly Asp Phe Ala
    50                  55                  60
Trp Glu Arg Val Arg Gly Leu Gly Leu Pro Lys Leu Tyr Leu Pro Thr
65                  70                  75                  80
Gly Pro Arg Arg Gly Arg Asp Glu Leu Gly Gly Gly Arg Arg Pro Gly
                85                  90                  95
Thr Ser Pro Ala Leu Leu Gln Gly Thr Ala Glu Glu Asp His Val Asp
            100                 105                 110
Leu Ser Leu Ser Cys Thr Leu Val Pro Arg Ser Gly Glu Gln Ala Glu
        115                 120                 125
Gly Ser Pro Gly Gly Pro Gly Asp Ser Gln Gly Arg Lys Arg Arg Gln
    130                 135                 140
Thr Ser Met Thr Asp Phe Tyr His Ser Lys Arg Arg Leu Ile Phe Ser
145                 150                 155                 160
Lys Arg Lys Pro
```

<210> SEQ ID NO 2
<211> LENGTH: 2119
<212> TYPE: DNA
<213> ORGANISM: Homo sapiens

<400> SEQUENCE: 2

```
aacatgttga gctctggcat agaagaggct ggtggctatt ttgtccttgg gctgcctgtt      60
ttcaggcgcc atgtcagaac cggctgggga tgtccgtcag aacccatgcg gcagcaaggc     120
ctgccgccgc tcttcggcc cagtggacag cgagcagctg agccgcgact gtgatgcgct      180
aatggcgggc tgcatccagg aggcccgtga gcgatggaac ttcgactttg tcaccgagac     240
accactggag ggtgacttcg cctgggagcg tgtgcgggc cttggcctgc caagctcta      300
ccttcccacg gggccccggc gaggccggga tgagttggga ggaggcaggc ggcctggcac     360
ctcacctgct ctgctgcagg ggacagcaga ggaagaccat gtggaccgt cactgtcttg      420
taccccttgtg cctcgctcag gggagcaggc tgaagggtcc ccaggtggac ctggagactc     480
tcagggtcga aaacggcggc agaccagcat gacagatttc taccactcca acgccggct      540
gatcttctcc aagaggaagc cctaatccgc ccacaggaag cctgcagtcc tggaagcgcg     600
agggcctcaa aggcccgctc tacatcttct gccttagtct cagtttgtgt gtcttaatta     660
ttatttgtgt tttaatttaa acacctcctc atgtacatac cctggccgcc cctgccccc      720
cagcctctgg cattagaatt atttaaacaa aaactaggcg gttgaatgag aggttcctaa     780
gagtgctggg cattttttatt ttatgaaata ctatttaaag cctcctcatc ccgtgttctc     840
cttttcctct ctcccggagg ttgggtgggc cggcttcatg ccagctactt cctcctcccc     900
acttgtccgc tgggtggtac cctctggagg ggtgtggctc cttcccatcg ctgtcacagg     960
cggttatgaa attcacccc tttcctggac actcagacct gaattctttt tcatttgaga    1020
agtaaacaga tggcactttg aaggggcctc accgagtggg ggcatcatca aaaactttgg    1080
```

```
agtcccctca cctcctctaa ggttgggcag ggtgaccctg aagtgagcac agcctagggc    1140
tgagctgggg acctggtacc ctcctggctc ttgataccc cctctgtctt gtgaaggcag     1200
ggggaaggtg gggtcctgga gcagaccacc ccgcctgccc tcatggcccc tctgacctgc    1260 actgggagc ccgtctcagt gttgagcctt ttccctcttt ggctcccctg taccttttga    1320
ggagccccag ctaccttct ctccagctg ggctctgcaa ttcccctctg ctgctgtccc      1380
tcccccttgt cctttcccttt cagtaccctc tcagctccag gtggctctga ggtgcctgtc   1440 ccaccccac cccagctca atggactgga aggggaaggg acacacaaga agaagggcac      1500
cctagttcta cctcaggcag ctcaagcagc gaccgccccc tcctctagct gtgggggtga   1560
gggtcccatg tggtggcaca ggccccccttg agtggggtta tctctgtgtt aggggtatat  1620 gatggggag tagatctttc taggagggag acactggccc ctcaaatcgt ccagcgacct    1680
tcctcatcca ccccatccct ccccagttca ttgcactttg attagcagcg aacaaggag    1740 tcagacattt taagatggtg gcagtagagg ctatggacag gcatgccac gtgggctcat    1800 atggggctgg gagtagttgt cttcctggc actaacgttg agccctgga ggcactgaag     1860 tgcttagtgt acttggagta ttggggtctg accccaaaca ccttccagct cctgtaacat   1920
actggcctgg actgttttct ctcggctccc catgtgtcct ggttcccgtt tctccaccta   1980
gactgtaaac ctctcgaggg cagggaccac accctgtact gttctgtgtc tttcacagct   2040
cctcccacaa tgctgaatat acagcaggtg ctcaataaat gattcttagt gactttactt   2100
gtaaaaaaaa aaaaaaaaa                                                2119
```

<210> SEQ ID NO 3
<211> LENGTH: 1936
<212> TYPE: DNA
<213> ORGANISM: Homo sapiens

<400> SEQUENCE: 3

```
gcttgtgggc gggcccgggc aggagcgggc ttgccctgcg gagcagtagc taggaacaga     60
tccacttgca ggttgctgtt cccagccatg gcttcgcgct gctggcgctg gtggggctgg    120
tcggcgtggc ctcggacccg gctgcctccc gccgggagca ccccgagctt ctgccaccat    180
ttctccacac aggagaagac ccccagatc tgtgtggtgg gcagtggccc agctggcttc    240
tacacggccc aacacctgct aaagcacccc caggcccacg tggacatcta cgagaaacag    300
cctgtgccct ttggcctggt gcgctttggt gtggcgcctg atcaccccga ggtgaagaat    360
gtcatcaaca catttaccca gacgcccat tctggccgct gtgccttctg gggcaacgtg    420
gaggtgggca gggacgtgac ggtgccggag ctgcgggagg cctaccacgc tgtggtgctg    480
agctacgggg cagaggacca tcgggccctg gaaattcctg gtgaggagct gccaggtgtg    540
tgctccgccc gggccttcgt gggctggtac aacgggcttc ctgagaacca ggagctggag    600
ccagacctga gctgtgacac agccgtgatt ctggggcagg gaacgtggc tctggacgtg    660 gcccgcatcc tactgacccc acctgagcac ctggaggccc tccttttgtg ccagagaacg    720
gacatcacga aggcagccct gggtgtactg aggcagagtc gagtgaagac agtgtggcta    780
gtgggccggc gtgacccct gcaagtggcc ttcaccatta aggagcttcg ggagatgatt    840
cagttaccgg gagcccggcc catttttggat cctgtggatt tcttgggtct ccaggacaag   900
atcaaggagg tccccgcccc gaggaagcgg ctgacggaac tgctgcttcg aacgccaca    960 gagaagccag ggccggcgga agctgccgc caggcatcgg cctcccgtgc ctggggcctc  1020
```

-continued

```
cgctttttcc gaagccccca gcaggtgctg ccctcaccag atgggcggcg ggcagcaggt    1080
gtccgcctag cagtcactag actggagggt gtcgatgagg ccacccgtgc agtgcccacg    1140
ggagacatgg aagacctccc ttgtgggctg gtgctcagca gcattgggta taagagccgc    1200
cctgtcgacc caagcgtgcc ctttgactcc aagcttgggg tcatcccaa tgtggagggc     1260 cgggttatgg atgtgccagg cctctactgc agcggctggg tgaagagagg acctacaggt    1320
gtcatagcca caaccatgac tgacagcttc ctcaccggcc agatgctgct gcaggacctg    1380
aaggctgggt tgctcccctc tggccccagg cctggctacg cagccatcca ggccctgctc    1440
agcagccgag gggtccggcc agtctctttc tcagactggg agaagctgga tgccgaggag    1500
gtggcccggg gccagggcac ggggaagccc agggagaagc tggtggatcc tcaggagatg    1560
ctgcgcctcc tgggccactg agcccagccc cagccccggc cccagcagg gaagggatga     1620 gtgttgggag gggaagggct gggtccgtct gagtgggact ttgcacctct gctgatcccg    1680
gccggccctg gcttggaggc ttggctgctc ttccagcgtc tctcctccct cctggggaag    1740
gtcgcccttg cgcgcaaggt tttagctttc agcaactgag gtaaccttag ggacaggtgg    1800
aggtgtgggc cgatctaacc ccttacccat ctctctactg ctggactgtg gagggtcacc    1860
aggttgggaa catgctggaa ataaaacagc tgcaaccaag aaaaaaaaaa aaaaaaaaa    1920 aaaaaaaaaa aaaaaa                                                   1936
```

<210> SEQ ID NO 4
<211> LENGTH: 497
<212> TYPE: PRT
<213> ORGANISM: Homo sapiens

<400> SEQUENCE: 4

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Arg Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Ala Leu Leu Leu Cys
        195                 200                 205
```

Gln Arg Thr Asp Ile Thr Lys Ala Ala Leu Gly Val Leu Arg Gln Ser
210                 215                 220

Arg Val Lys Thr Val Trp Leu Val Gly Arg Arg Gly Pro Leu Gln Val
225                 230                 235                 240

Ala Phe Thr Ile Lys Glu Leu Arg Glu Met Ile Gln Leu Pro Gly Ala
                245                 250                 255

Arg Pro Ile Leu Asp Pro Val Asp Phe Leu Gly Leu Gln Asp Lys Ile
            260                 265                 270

Lys Glu Val Pro Arg Pro Arg Lys Arg Leu Thr Glu Leu Leu Leu Arg
        275                 280                 285

Thr Ala Thr Glu Lys Pro Gly Pro Ala Glu Ala Ala Arg Gln Ala Ser
290                 295                 300

Ala Ser Arg Ala Trp Gly Leu Arg Phe Phe Arg Ser Pro Gln Gln Val
305                 310                 315                 320

Leu Pro Ser Pro Asp Gly Arg Arg Ala Gly Val Arg Leu Ala Val
                325                 330                 335

Thr Arg Leu Glu Gly Val Asp Glu Ala Thr Arg Ala Val Pro Thr Gly
            340                 345                 350

Asp Met Glu Asp Leu Pro Cys Gly Leu Val Leu Ser Ser Ile Gly Tyr
        355                 360                 365

Lys Ser Arg Pro Val Asp Pro Ser Val Pro Phe Asp Ser Lys Leu Gly
370                 375                 380

Val Ile Pro Asn Val Glu Gly Arg Val Met Asp Val Pro Gly Leu Tyr
385                 390                 395                 400

Cys Ser Gly Trp Val Lys Arg Gly Pro Thr Gly Val Ile Ala Thr Thr
                405                 410                 415

Met Thr Asp Ser Phe Leu Thr Gly Gln Met Leu Leu Gln Asp Leu Lys
            420                 425                 430

Ala Gly Leu Leu Pro Ser Gly Pro Arg Pro Gly Tyr Ala Ala Ile Gln
        435                 440                 445

Ala Leu Leu Ser Ser Arg Gly Val Arg Pro Val Ser Phe Ser Asp Trp
450                 455                 460

Glu Lys Leu Asp Ala Glu Glu Val Ala Arg Gly Gln Gly Thr Gly Lys
465                 470                 475                 480

Pro Arg Glu Lys Leu Val Asp Pro Gln Glu Met Leu Arg Leu Leu Gly
                485                 490                 495

His

<210> SEQ ID NO 5
<211> LENGTH: 2029
<212> TYPE: DNA
<213> ORGANISM: Homo sapiens

<400> SEQUENCE: 5
gcttgtgggc gggcccgggc aggagcgggc ttgccctgcg gagcagtagc taggaacaga      60
tccacttgca ggttgctgtt cccagccatg gcttcgcgct gctggcgctg gtggggctgg     120
tcggcgtggc ctcggacccg gctgcctccc gccgggagca ccccgagctt ctgccaccat     180
ttctccacac aggagaagac cccccagatc tgtgtggtgg cagtggccc agctggcttc      240 tacacggccc aacacctgct aaagagggtg gaagccttgt gttctcagcc cagggtcctg     300
aactctcctg ctctgtctgg ggaagggag gacctggggg cgtcccagcc tctctctctc      360
gacccccacc gctgccaccc tgttcccag cagcaccccc aggcccacgt ggacatctac      420
gagaaacagc ctgtgccctt tggcctggtg cgctttggtg tggcgcctga tcaccccgag     480

```
gtgaagaatg tcatcaacac atttacccag acggcccatt ctggccgctg tgccttctgg        540
ggcaacgtgg aggtgggcag ggacgtgacg gtgccggagc tgcgggaggc ctaccacgct        600
gtggtgctga gctacggggc agaggaccat cgggccctgg aaattcctgg tgaggagctg        660
ccaggtgtgt gctccgcccg ggccttcgtg ggctggtaca acgggcttcc tgagaaccag        720
gagctggagc cagacctgag ctgtgacaca gccgtgattc tggggcaggg aacgtggct         780 ctggacgtgg cccgcatcct actgaccccc cctgagcacc tggagagaac ggacatcacg        840
aaggcagccc tgggtgtact gaggcagagt cgagtgaaga cagtgtggct agtgggccgg        900
cgtggacccc tgcaagtggc cttcaccatt aaggagcttc gggagatgat tcagttaccg        960
ggagcccggc ccattttgga tcctgtggat ttcttgggtc tccaggacaa gatcaaggag       1020
gtcccccgcc cgaggaagcg gctgacggaa ctgctgcttc gaacggccac agagaagcca       1080
gggccggcgg aagctgcccg ccaggcatcg gcctcccgtg cctggggcct ccgctttttc       1140
cgaagccccc agcaggtgct gccctcacca gatgggcggc gggcagcagg tgtccgccta       1200
gcagtcacta gactggaggg tgtcgatgag gccacccgtg cagtgcccac gggagacatg       1260
gaagacctcc cttgtgggct ggtgctcagc agcattgggt ataagagccg ccctgtcgac       1320
ccaagcgtgc cctttgactc caagcttggg gtcatcccca atgtggaggg ccgggttatg       1380
gatgtgccag gcctctactg cagcggctgg gtgaagagag gacctacagg tgtcatagcc       1440
acaaccatga ctgacagctt cctcaccggc cagatgctgc tgcaggacct gaaggctggg       1500
ttgctcccct ctggccccag gcctggctac gcagccatcc aggccctgct cagcagccga       1560
ggggtccggc cagtctcttt ctcagactgg agaagctgg atgccgagga ggtggcccgg       1620
ggccagggca cggggaagcc cagggagaag ctggtggatc ctcaggagat gctgcgcctc       1680
ctgggccact gagcccagcc ccagccccgg ccccagcag ggaagggatg agtgttggga       1740
ggggaagggc tgggtccgtc tgagtgggac tttgcacctc tgctgatccc ggccggccct       1800
ggcttggagg cttggctgct cttccagcgt ctctcctccc tcctggggaa ggtcgccctt       1860
gcgcgcaagg ttttagcttt cagcaactga ggtaacctta gggacaggtg gaggtgtggg       1920
ccgatctaac cccttaccca tctctctact gctggactgt ggagggtcac caggttggga       1980
acatgctgga aataaaacag ctgcaaccaa gaaaaaaaa aaaaaaaaa                   2029
```

<210> SEQ ID NO 6
<211> LENGTH: 534
<212> TYPE: PRT
<213> ORGANISM: Homo sapiens

<400> SEQUENCE: 6

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys Arg Val Glu Ala Leu
    50                  55                  60

Cys Ser Gln Pro Arg Val Leu Asn Ser Pro Ala Leu Ser Gly Glu Gly
65                  70                  75                  80

Glu Asp Leu Gly Ala Ser Gln Pro Leu Ser Leu Asp Pro Thr Ser Cys
                85                  90                  95
```

His Pro Val Pro Gln Gln His Pro Gln Ala His Val Asp Ile Tyr Glu
            100                 105                 110

Lys Gln Pro Val Pro Phe Gly Leu Val Arg Phe Gly Val Ala Pro Asp
        115                 120                 125

His Pro Glu Val Lys Asn Val Ile Asn Thr Phe Thr Gln Thr Ala His
    130                 135                 140

Ser Gly Arg Cys Ala Phe Trp Gly Asn Val Glu Val Gly Arg Asp Val
145                 150                 155                 160

Thr Val Pro Glu Leu Arg Glu Ala Tyr His Ala Val Val Leu Ser Tyr
                165                 170                 175

Gly Ala Glu Asp His Arg Ala Leu Glu Ile Pro Gly Glu Glu Leu Pro
            180                 185                 190

Gly Val Cys Ser Ala Arg Ala Phe Val Gly Trp Tyr Asn Gly Leu Pro
        195                 200                 205

Glu Asn Gln Glu Leu Glu Pro Asp Leu Ser Cys Asp Thr Ala Val Ile
    210                 215                 220

Leu Gly Gln Gly Asn Val Ala Leu Asp Val Ala Arg Ile Leu Leu Thr
225                 230                 235                 240

Pro Pro Glu His Leu Glu Arg Thr Asp Ile Thr Lys Ala Ala Leu Gly
                245                 250                 255

Val Leu Arg Gln Ser Arg Val Lys Thr Val Trp Leu Val Gly Arg Arg
            260                 265                 270

Gly Pro Leu Gln Val Ala Phe Thr Ile Lys Glu Leu Arg Glu Met Ile
        275                 280                 285

Gln Leu Pro Gly Ala Arg Pro Ile Leu Asp Pro Val Asp Phe Leu Gly
    290                 295                 300

Leu Gln Asp Lys Ile Lys Glu Val Pro Arg Pro Arg Lys Arg Leu Thr
305                 310                 315                 320

Glu Leu Leu Leu Arg Thr Ala Thr Glu Lys Pro Gly Pro Ala Glu Ala
                325                 330                 335

Ala Arg Gln Ala Ser Ala Ser Arg Ala Trp Gly Leu Arg Phe Phe Arg
            340                 345                 350

Ser Pro Gln Gln Val Leu Pro Ser Pro Asp Gly Arg Arg Ala Ala Gly
        355                 360                 365

Val Arg Leu Ala Val Thr Arg Leu Glu Gly Val Asp Glu Ala Thr Arg
    370                 375                 380

Ala Val Pro Thr Gly Asp Met Glu Asp Leu Pro Cys Gly Leu Val Leu
385                 390                 395                 400

Ser Ser Ile Gly Tyr Lys Ser Arg Pro Val Asp Pro Ser Val Pro Phe
                405                 410                 415

Asp Ser Lys Leu Gly Val Ile Pro Asn Val Glu Gly Arg Val Met Asp
            420                 425                 430

Val Pro Gly Leu Tyr Cys Ser Gly Trp Val Lys Arg Gly Pro Thr Gly
        435                 440                 445

Val Ile Ala Thr Thr Met Thr Asp Ser Phe Leu Thr Gly Gln Met Leu
    450                 455                 460

Leu Gln Asp Leu Lys Ala Gly Leu Leu Pro Ser Gly Pro Arg Pro Gly
465                 470                 475                 480

Tyr Ala Ala Ile Gln Ala Leu Leu Ser Ser Arg Gly Val Arg Pro Val
                485                 490                 495

Ser Phe Ser Asp Trp Glu Lys Leu Asp Ala Glu Glu Val Ala Arg Gly
            500                 505                 510

Gln Gly Thr Gly Lys Pro Arg Glu Lys Leu Val Asp Pro Gln Glu Met 515                 520                 525
Leu Arg Leu Leu Gly His
    530

<210> SEQ ID NO 7
<211> LENGTH: 1839
<212> TYPE: DNA
<213> ORGANISM: Homo sapiens

<400> SEQUENCE: 7

```
gaggcgattg cgattgggtg agacccagta aggatggaaa gtgtagagga gacaggaatc      60
cacggctttg gaaaaggaa ggacaaaact caccaaacca gagcagggca ggaagtaaca     120
atgagaaact gaaaagaaa cggaatggaa agctatgaga caggatgaaa tttggcatgg     180
ggtctgccca gcatgtcca tgccaggtgc ccagggctgc ttccacgacg tgggtcccct     240
gccagatttg tggccccagg gagcgccatg gcccgcgcac gccaggaggg cagctccccg     300
gagcccgtag agggcctggc ccgcgacgg ccgcgccct tcccgctcgg ccgcctggtg     360
ccctcggcag tgtcctgcgg cctctgcgag cccggcctgg ctgccgcccc cgccgccccc     420
accctgctgc ccgctgccta cctctgcgcc ccaccgccc cacccgccgt caccgccgcc     480
ctgggggtt cccgctggcc tgggggtccc cgcagccggc cccgaggccc cgcccggac     540
ggtcctcagc cctcgctctc gctggcggag cagcacctgg agtcgcccgt gcccagcgcc     600
ccgggggctc tggcgggcgg tcccacccag gcggccccgg gagtccgcgg ggaggaggaa     660
cagtgggccc gggagatcgg ggcccagctg cggcggatgg cggacgacct caacgcacag     720
tacgagcggc ggagacaaga ggagcagcag cggcaccgcc cctcaccctg gagggtcctg     780
tacaatctca tcatgggact cctgccctta cccagggggcc acagagcccc cgagatggag     840
cccaattagg tgcctgcacc cgcccggtgg acgtcaggga ctcgggggc aggcccctcc     900
cacctcctga caccctggcc agcgcggggg actttctctg caccatgtag catactggac     960
tcccagccct gcctgtcccg ggggcgggcc ggggcagcca ctccagcccc agcccagcct    1020
ggggtgcact gacggagatg cggactcctg ggtccctggc caagaagcca ggagagggac    1080
ggctgatgga ctcagcatcg gaaggtggcg gtgaccgagg gggtggggac tgagccgccc    1140
gcctctgccg cccaccacca tctcaggaaa ggctgttgtg ctggtgcccg ttccagctgc    1200
aggggtgaca ctggggggg ggggctctcc tctcggtgct ccttcactct gggcctggcc    1260
tcaggcccct ggtgcttccc ccctcctcc tgggagggg cccgtgaaga gcaaatgagc    1320
caaacgtgac cactagcctc ctggagccag agagtgggc tcgtttgccg gttgctccag    1380
cccggcgccc agccatcttc cctgagccag ccggcgggtg gtgggcatgc ctgcctcacc    1440
ttcatcaggg ggtggccagg aggggcccag actgtgaatc ctgtgctctg cccgtgaccg    1500
cccccgccc catcaatccc attgcatagg tttagagaga gcacgtgtga ccactggcat    1560
tcatttgggg ggtgggagat tttggctgaa gccgccccag ccttagtccc cagggccaag    1620
cgctgggggg aagacgggga gtcagggagg ggggaaatc tcggaagagg gaggagtctg    1680
ggagtgggga gggatggccc agcctgtaag atactgtata tgcgctgctg tagataccgg    1740
aatgaatttt ctgtacatgt ttggttaatt ttttttgtac atgattttg tatgtttcct    1800
tttcaataaa atcagattgg aacagtggaa aaaaaaaaa                           1839
```

<210> SEQ ID NO 8
<211> LENGTH: 261
<212> TYPE: PRT

<213> ORGANISM: Homo sapiens

<400> SEQUENCE: 8

Met Lys Phe Gly Met Gly Ser Ala Gln Ala Cys Pro Cys Gln Val Pro
1               5                   10                  15

Arg Ala Ala Ser Thr Thr Trp Val Pro Cys Gln Ile Cys Gly Pro Arg
            20                  25                  30

Glu Arg His Gly Pro Arg Thr Pro Gly Gly Gln Leu Pro Gly Ala Arg
        35                  40                  45

Arg Gly Pro Gly Pro Arg Arg Pro Ala Pro Leu Pro Ala Arg Pro Pro
    50                  55                  60

Gly Ala Leu Gly Ser Val Leu Arg Pro Leu Arg Ala Arg Pro Gly Cys
65                  70                  75                  80

Arg Pro Arg Arg Pro His Pro Ala Ala Arg Cys Leu Pro Leu Arg Pro
                85                  90                  95

His Arg Pro Thr Arg Arg His Arg Arg Pro Gly Gly Phe Pro Leu Ala
            100                 105                 110

Trp Gly Ser Pro Gln Pro Ala Pro Arg Pro Ala Pro Gly Arg Ser Ser
        115                 120                 125

Ala Leu Ala Leu Ala Gly Gly Ala Ala Pro Gly Val Ala Arg Ala Gln
    130                 135                 140

Arg Pro Gly Gly Ser Gly Gly Arg Ser His Pro Gly Gly Pro Gly Ser
145                 150                 155                 160

Pro Arg Gly Gly Gly Thr Val Gly Pro Gly Asp Arg Gly Pro Ala Ala
                165                 170                 175

Ala Asp Gly Gly Arg Pro Gln Arg Thr Val Arg Ala Ala Glu Thr Arg
            180                 185                 190

Gly Ala Ala Ala Ala Pro Pro Leu Thr Leu Glu Gly Pro Val Gln Ser
        195                 200                 205

His His Gly Thr Pro Ala Leu Thr Gln Gly Pro Gln Ser Pro Arg Asp
    210                 215                 220

Gly Ala Gln Leu Gly Ala Cys Thr Arg Pro Val Asp Val Arg Asp Ser
225                 230                 235                 240

Gly Gly Arg Pro Leu Pro Pro Pro Asp Thr Leu Ala Ser Ala Gly Asp
                245                 250                 255

Phe Leu Cys Thr Met
            260

<210> SEQ ID NO 9
<211> LENGTH: 1853
<212> TYPE: DNA
<213> ORGANISM: Homo sapiens

<400> SEQUENCE: 9
gcggcgcgag ccacatgcga gcgggcgcct ggcggcggcg gcggcggcac cagcgatccc      60
agcagcggcc acgacgcgga cgcgcctgcg gcccggggag cagcagcagc cacagccaca     120
gcagccgcca ctgcagttag agcggcagca gcagcgacag ccacagcagc agccgccgcg     180
gagagcggcg ctcggcgggc gcgccctcct gaaggaagcc gcccgccccc caccgccgcc     240
ccctccggcg tgttcatgcc ccggggccc caggagcgc catggcccgc gcacgccagg       300
agggcagctc cccggagccc gtagagggcc tggcccgcga cggcccgcgc ccttcccgc      360 tcggccgcct ggtgccctcg gcagtgtcct gcggcctctg cgagcccggc ctggctgccg     420 ccccgccgc ccccaccctg ctgccgctg cctacctctg cgcccccacc gccccacccg       480

| | |
|---|---|
| ccgtcaccgc cgccctgggg ggttcccgct ggcctggggg tccccgcagc cggccccgag | 540 |
| gcccgcgccc ggacggtcct cagccctcgc tctcgctggc ggagcagcac ctggagtcgc | 600 |
| ccgtgcccag cgccccgggg gctctggcgg gcggtcccac ccaggcggcc ccgggagtcc | 660 |
| gcggggagga ggaacagtgg gcccgggaga tcggggccca gctgcggcgg atggcggacg | 720 |
| acctcaacgc acagtacgag cggcggagac aagaggagca gcagcggcac cgcccctcac | 780 |
| cctggagggt cctgtacaat ctcatcatgg gactcctgcc cttacccagg gccacagag | 840 |
| cccccgagat ggagcccaat taggtgcctg cacccgcccg gtggacgtca gggactcggg | 900 |
| gggcaggccc ctcccacctc ctgacaccct ggccagcgcg ggggactttc tctgcaccat | 960 |
| gtagcatact ggactcccag ccctgcctgt cccggggcg ggccggggca gccactccag | 1020 |
| ccccagccca gctggggtg cactgacgga gatgcggact cctgggtccc tggccaagaa | 1080 |
| gccaggagag ggacggctga tggactcagc atcggaaggt ggcggtgacc gagggggtgg | 1140 |
| ggactgagcc gcccgcctct gccgcccacc accatctcag gaaaggctgt tgtgctggtg | 1200 |
| cccgttccag ctgcaggggt gacactgggg ggggggggct ctcctctcgg tgctccttca | 1260 |
| ctctgggcct ggcctcaggc ccctggtgct tcccccctc ctcctgggag ggggcccgtg | 1320 |
| aagagcaaat gagccaaacg tgaccactag cctcctggag ccagagagtg gggctcgttt | 1380 |
| gccggttgct ccagcccggc gcccagccat cttccctgag ccagccggcg ggtggtgggc | 1440 |
| atgcctgcct caccttcatc aggggtggc caggaggggc ccagactgtg aatcctgtgc | 1500 |
| tctgcccgtg accgccccc gccccatcaa tcccattgca taggtttaga gagagcacgt | 1560 |
| gtgaccactg gcattcattt gggggtggg agattttggc tgaagccgcc ccagccttag | 1620 |
| tccccagggc caagcgctgg ggggaagacg gggagtcagg gagggggga aatctcggaa | 1680 |
| gagggaggag tctgggagtg gggagggatg gcccagcctg taagatactg tatatgcgct | 1740 |
| gctgtagata ccggaatgaa ttttctgtac atgtttggtt aattttttt gtacatgatt | 1800 |
| tttgtatgtt tccttttcaa taaaatcaga ttggaacagt ggaaaaaaaa aaa | 1853 |

<210> SEQ ID NO 10
<211> LENGTH: 193
<212> TYPE: PRT
<213> ORGANISM: Homo sapiens

<400> SEQUENCE: 10

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
                20                  25                  30

Ser Ala Val Ser Cys Gly Leu Cys Glu Pro Gly Leu Ala Ala Ala Pro
            35                  40                  45

Ala Ala Pro Thr Leu Leu Pro Ala Ala Tyr Leu Cys Ala Pro Thr Ala
        50                  55                  60

Pro Pro Ala Val Thr Ala Ala Leu Gly Gly Ser Arg Trp Pro Gly Gly
65                  70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110

Gly Ala Leu Ala Gly Gly Pro Thr Gln Ala Ala Pro Gly Val Arg Gly
        115                 120                 125

Glu Glu Glu Gln Trp Ala Arg Glu Ile Gly Ala Gln Leu Arg Arg Met

```
            130                 135                 140
Ala Asp Asp Leu Asn Ala Gln Tyr Glu Arg Arg Gln Glu Glu Gln
145                 150                 155                 160

Gln Arg His Arg Pro Ser Pro Trp Arg Val Leu Tyr Asn Leu Ile Met
                165                 170                 175

Gly Leu Leu Pro Leu Pro Arg Gly His Arg Ala Pro Glu Met Glu Pro
            180                 185                 190

Asn

<210> SEQ ID NO 11
<211> LENGTH: 1550
<212> TYPE: DNA
<213> ORGANISM: Homo sapiens

<400> SEQUENCE: 11
gaggcgattg cgattgggtg agacccagta aggatggaaa gtgtagagga gacaggaatc       60
cacggctttg gaaaaggaa ggacaaaact caccaaacca gagcagggca ggaagtaaca      120
atgagaaact gaaaagaaa cggaatggaa agctatgaga caggatgaaa tttggcatgg      180
ggtctgccca ggcatgtcca tgccaggtgc ccagggctgc ttccacgacg tgggtcccct      240
gccagatttg tggtcctcag ccctcgctct cgctggcgga gcagcacctg gagtcgcccg      300
tgcccagcgc cccgggggct ctggcggcg gtcccaccca gcggccccg ggagtccgcg      360 gggaggagga acagtgggcc cgggagatcg gggcccagct gcggcggatg gcggacgacc      420
tcaacgcaca gtacgagcgg cggagacaag aggagcagca gcggcaccgc ccctcaccct      480
ggagggtcct gtacaatctc atcatgggac tcctgccctt acccaggggc cacagagccc      540
ccgagatgga gcccaattag gtgcctgcac ccgcccggtg gacgtcaggg actcggggg      600 caggcccctc ccacctcctg acaccctggc cagcgcgggg gactttctct gcaccatgta      660
gcatactgga ctcccagccc tgcctgtccc ggggcgggc cggggcagcc actccagccc      720
cagcccagcc tggggtgcac tgacggagat gcggactcct gggtccctgg ccaagaagcc      780
aggagaggga cggctgatgg actcagcatc ggaaggtggc ggtgaccgag ggggtgggga      840
ctgagccgcc cgcctctgcc gcccaccacc atctcaggaa aggctgttgt gctggtgccc      900
gttccagctg caggggtgac actggggggg ggggctctc ctctcggtgc tccttcactc      960
tgggcctggc ctcaggcccc tggtgcttcc cccctcctc ctgggagggg gcccgtgaag     1020
agcaaatgag ccaaacgtga ccactagcct cctggagcca gagagtgggg ctcgtttgcc     1080
ggttgctcca gccggcgcc cagccatctt ccctgagcca gccggcgggt ggtgggcatg     1140
cctgcctcac cttcatcagg gggtggccag gaggggccca gactgtgaat cctgtgctct     1200
gcccgtgacc gccccgcc ccatcaatcc cattgcatag gtttagagag agcacgtgtg     1260
accactggca ttcatttggg gggtgggaga ttttggctga agccgcccca gccttagtcc     1320
ccagggccaa gcgctggggg gaagacgggg agtcagggag ggggggaaat ctcggaagag     1380
ggaggagtct gggagtgggg agggatggcc cagcctgtaa gatactgtat atgcgctgct     1440
gtagataccg gaatgaattt tctgtacatg tttggttaat ttttttttgta catgattttt     1500 gtatgtttcc ttttcaataa aatcagattg gaacagtgga aaaaaaaaaa              1550

<210> SEQ ID NO 12
<211> LENGTH: 131
<212> TYPE: PRT
<213> ORGANISM: Homo sapiens
```

<400> SEQUENCE: 12

```
Met Lys Phe Gly Met Gly Ser Ala Gln Ala Cys Pro Cys Gln Val Pro
1               5                   10                  15
Arg Ala Ala Ser Thr Thr Trp Val Pro Cys Gln Ile Cys Gly Pro Gln
            20                  25                  30
Pro Ser Leu Ser Leu Ala Glu Gln His Leu Glu Ser Pro Val Pro Ser
        35                  40                  45
Ala Pro Gly Ala Leu Ala Gly Gly Pro Thr Gln Ala Ala Pro Gly Val
    50                  55                  60
Arg Gly Glu Glu Glu Gln Trp Ala Arg Glu Ile Gly Ala Gln Leu Arg
65                  70                  75                  80
Arg Met Ala Asp Asp Leu Asn Ala Gln Tyr Glu Arg Arg Gln Glu
                85                  90                  95
Glu Gln Gln Arg His Arg Pro Ser Pro Trp Arg Val Leu Tyr Asn Leu
                100                 105                 110
Ile Met Gly Leu Leu Pro Leu Pro Arg Gly His Arg Ala Pro Glu Met
            115                 120                 125
Glu Pro Asn
    130
```

<210> SEQ ID NO 13
<211> LENGTH: 1359
<212> TYPE: DNA
<213> ORGANISM: Homo sapiens

<400> SEQUENCE: 13

| | | |
|---|---|---|
| gaggcgattg cgattgggtg agacccagta aggatggaaa gtgtagagga gacaggaatc | 60 |
| cacggctttg gaaaaggaa ggacaaaact caccaaacca gagcagggca ggaagtaaca | 120 |
| atgagaaact gaaaagaaa cggaatggaa agctatgaga caggatgaaa tttggcatgg | 180 |
| ggtctgccca ggcatgtcca tgccaggtgc ccagggctgc ttccacgacg tgggtcccct | 240 |
| gccagatttg tgagacaaga ggagcagcag cggcaccgcc cctcaccctg gagggtcctg | 300 |
| tacaatctca tcatgggact cctgccctta cccaggggcc acagagcccc cgagatggag | 360 |
| cccaattagg tgcctgcacc cgcccggtgg acgtcaggga ctcgggggc aggcccctcc | 420 |
| cacctcctga cacccctggcc agcgcggggg actttctctg caccatgtag catactggac | 480 |
| tcccagccct gcctgtcccg ggggcgggcc ggggcagcca ctccagcccc agcccagcct | 540 |
| ggggtgcact gacggagatg cggactcctg gtccctggc caagaagcca ggagagggac | 600 |
| ggctgatgga ctcagcatcg gaaggtggcg gtgaccgagg gggtggggac tgagccgccc | 660 |
| gcctctgccg cccaccacca tctcaggaaa ggctgttgtg ctggtgcccg ttccagctgc | 720 |
| aggggtgaca ctgggggggg ggggctctcc tctcggtgct ccttcactct gggcctggcc | 780 |
| tcaggcccct ggtgcttccc ccctcctcc tgggagggg cccgtgaaga gcaaatgagc | 840 |
| caaacgtgac cactagcctc ctggagccag agagtgggc tcgtttgccg gttgctccag | 900 |
| cccggcgccc agccatcttc cctgagccag ccggcgggtg gtgggcatgc ctgcctcacc | 960 |
| ttcatcaggg ggtggccagg aggggccag actgtgaatc ctgtgctctg cccgtgaccg | 1020 |
| cccccgccc catcaatccc attgcatagg tttagagaga gcacgtgtga ccactggcat | 1080 |
| tcatttgggg ggtgggagat tttggctgaa gccgccccag ccttagtccc caggcccaag | 1140 |
| cgctgggggg aagacgggga gtcagggagg ggggaaatc tcggaagagg gaggagtctg | 1200 |
| ggagtgggga gggatggccc agcctgtaag atactgtata tgcgctgctg tagataccgg | 1260 |

| aatgaatttt ctgtacatgt ttggttaatt ttttttgtac atgatttttg tatgtttcct | 1320 |
| tttcaataaa atcagattgg aacagtggaa aaaaaaaaa | 1359 |

<210> SEQ ID NO 14
<211> LENGTH: 101
<212> TYPE: PRT
<213> ORGANISM: Homo sapiens

<400> SEQUENCE: 14

Met Lys Phe Gly Met Gly Ser Ala Gln Ala Cys Pro Cys Gln Val Pro
1               5                   10                  15

Arg Ala Ala Ser Thr Thr Trp Val Pro Cys Gln Ile Cys Glu Thr Arg
            20                  25                  30

Gly Ala Ala Ala Pro Pro Leu Thr Leu Glu Gly Pro Val Gln Ser
        35                  40                  45

His His Gly Thr Pro Ala Leu Thr Gln Gly Pro Gln Ser Pro Arg Asp
    50                  55                  60

Gly Ala Gln Leu Gly Ala Cys Thr Arg Pro Val Asp Val Arg Asp Ser
65                  70                  75                  80

Gly Gly Arg Pro Leu Pro Pro Asp Thr Leu Ala Ser Ala Gly Asp
                85                  90                  95

Phe Leu Cys Thr Met
            100

<210> SEQ ID NO 15
<211> LENGTH: 1355
<212> TYPE: DNA
<213> ORGANISM: Homo sapiens

<400> SEQUENCE: 15

| ggatggccgg agctggcgcc ctggttctgg aggtaaccgg ttactgaggg cgagaagcgc | 60 |
| cacccggagg ctctagcctg acaaatgctt gctgacctgg gccagagctc ttcccttacg | 120 |
| caagtctcag ccggtcgtcg cgacgttcgc ccgctcgctc tgaggctcct gaagccgaaa | 180 |
| ccagctagac tttcctcctt cccgcctgcc tgtagcggcg ttgttgccac tccgccacca | 240 |
| tgttcgaggc gcgcctggtc cagggctcca tcctcaagaa ggtgttggag gcactcaagg | 300 |
| acctcatcaa cgaggcctgc tgggatatta gctccagcgg tgtaaacctg cagagcatgg | 360 |
| actcgtccca cgtctctttg gtgcagctca ccctgcggtc tgagggcttc gacacctacc | 420 |
| gctgcgaccg caacctggcc atgggcgtga acctcaccag tatgtccaaa atactaaaat | 480 |
| gcgccggcaa tgaagatatc attacactaa gggccgaaga taacgcggat accttggcgc | 540 |
| tagtatttga agcaccaaac caggagaaag tttcagacta tgaaatgaag ttgatggatt | 600 |
| tagatgttga acaacttgga attccagaac aggagtacag ctgtgtagta aagatgcctt | 660 |
| ctggtgaatt tgcacgtata tgccgagatc tcagccatat ggagatgct gttgtaattt | 720 |
| cctgtgcaaa agacggagtg aaattttctg caagtggaga acttggaaat ggaaacatta | 780 |
| aattgtcaca gacaagtaat gtcgataaag aggaggaagc tgttaccata gagatgaatg | 840 |
| aaccagttca actaactttt gcactgaggt acctgaactt ctttacaaaa gccactccac | 900 |
| tctcttcaac ggtgacactc agtatgtctg cagatgtacc ccttgttgta gagtataaaa | 960 |
| ttgcggatat gggacactta aaatactact ggctcccaa gatcgaggat gaagaaggat | 1020 |
| cttaggcatt cttaaaattc aagaaaataa aactaagctc tttgagaact gcttctaaga | 1080 |
| tgccagcata tactgaagtc ttttctgtca ccaaatttgt acctctaagt acatatgtag | 1140 |

```
atattgtttt ctgtaaataa cctattttt tctctattct ctgcaatttg tttaaagaat    1200
aaagtccaaa gtcagatctg gtctagttaa cctagaagta ttttttgtctc ttagaaatac   1260 ttgtgatttt tataatacaa aagggtcttg actctaaatg cagttttaag aattgttttt    1320
gaatttaaat aaagttactt gaatttcaaa catca                               1355
```

<210> SEQ ID NO 16
<211> LENGTH: 261
<212> TYPE: PRT
<213> ORGANISM: Homo sapiens

<400> SEQUENCE: 16

```
Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260
```

<210> SEQ ID NO 17
<211> LENGTH: 786
<212> TYPE: DNA
<213> ORGANISM: Homo sapiens

<400> SEQUENCE: 17

```
atgttcgagg cgcgcctggt ccagggctcc atcctcaaga aggtgttgga ggcactcaag     60
gacctcatca acgaggcctg ctgggatatt agctccagcg gtgtaaacct gcagagcatg    120
```

```
gactcgtccc acgtctcttt ggtgcagctc accctgcggt ctgagggctt cgacacctac    180
cgctgcgacc gcaacctggc catgggcgtg aacctcacca gtatgtccaa aatactaaaa    240
tgcgccggca atgaagatat cattacacta agggccgaag ataacgcgga taccttggcg    300
ctagtatttg aagcaccaaa ccaggagaaa gtttcagact atgaaatgaa gttgatggat    360
ttagatgttg aacaacttgg aattccagaa caggagtaca gctgtgtagt aaagatgcct    420
tctggtgaat tgcatgtat atgccgagat ctcagccata ttggagatgc tgttgtaatt    480
tcctgtgcaa aagacggagt gaaattttct gcaagtggag aacttggaaa tggaaacatt    540
aaattgtcac agacaagtaa tgtcgataaa gaggaggaag ctgttaccat agagatgaat    600
gaaccagttc aactaacttt tgcactgagg tacctgaact tctttacaaa agccactcca    660
ctctcttcaa cggtgacact cagtatgtct gcagatgtac cccttgttgt agagtataaa    720
attgcggata tgggacactt aaaatactac ttggctccca agatcgagga tgaagaagga    780
tcttag                                                              786
```

<210> SEQ ID NO 18
<211> LENGTH: 261
<212> TYPE: PRT
<213> ORGANISM: Homo sapiens

<400> SEQUENCE: 18

```
Met Phe Glu Ala Arg Leu Val Gln Gly Ser Ile Leu Lys Lys Val Leu
  1               5                  10                  15

Glu Ala Leu Lys Asp Leu Ile Asn Glu Ala Cys Trp Asp Ile Ser Ser
             20                  25                  30

Ser Gly Val Asn Leu Gln Ser Met Asp Ser Ser His Val Ser Leu Val
         35                  40                  45

Gln Leu Thr Leu Arg Ser Glu Gly Phe Asp Thr Tyr Arg Cys Asp Arg
     50                  55                  60

Asn Leu Ala Met Gly Val Asn Leu Thr Ser Met Ser Lys Ile Leu Lys
 65                  70                  75                  80

Cys Ala Gly Asn Glu Asp Ile Ile Thr Leu Arg Ala Glu Asp Asn Ala
                 85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Cys Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255
```

Asp Glu Glu Gly Ser
        260

<210> SEQ ID NO 19
<211> LENGTH: 1398
<212> TYPE: DNA
<213> ORGANISM: Homo sapiens

<400> SEQUENCE: 19

```
ggagagcggg gcccttttgtc ctccagtggc tggtaggcag tggctgggag gcagcggccc      60
aattagtgtc gtgcggcccg tggcgaggcg aggtccgggg agcgagcgag caagcaaggc     120
gggaggggtg gccggagctg cggcggctgg cacaggagga ggagcccggg cgggcgaggg     180
gcggccggag agcgccaggg cctgagctgc cggagcggcg cctgtgagtg agtgcagaaa     240
gcaggcgccc gcgcgctagc cgtggcagga gcagcccgca cgccgcgctc tctccctggg     300
cgacctgcag tttgcaatat gactttggag gaattctcgg ctggagagca gaagaccgaa     360
aggatggata aggtggggga tgccctggag gaagtgctca gcaaagccct gagtcagcgc     420
acgatcactg tcggggtgta cgaagcggcc aagctgctca acgtcgaccc cgataacgtg     480
gtgttgtgcc tgctggcggc ggacgaggac gacgacagag atgtggctct gcagatccac     540
ttcaccctga tccaggcgtt ttgctgcgag aacgacatca acatcctgcg cgtcagcaac     600
ccgggccggc tggcggagct cctgctcttg gagaccgacg ctggccccgc ggcgagcgag     660
ggcgccgagc agcccccgga cctgcactgc gtgctggtga cgaatccaca ttcatctcaa     720
tggaaggatc ctgccttaag tcaacttatt tgttttttgcc gggaaagtcg ctacatggat     780
caatgggttc cagtgattaa tctccctgaa cggtgatggc atctgaatga aaataactga     840
accaaattgc actgaagttt ttgaaatacc tttgtagtta ctcaagcagt tactccctac     900
actgatgcaa ggattacaga aactgatgcc aaggggctga gtgagttcaa ctacatgttc     960
tgggggcccg gagatagatg actttgcaga tggaaagagg tgaaaatgaa gaaggaagct    1020
gtgttgaaac agaaaaataa gtcaaaagga acaaaaatta caagaaccca tgcaggaagg    1080
aaaactatgt attaatttag aatggttgag ttacattaaa ataaaccaaa tatgttaaag    1140
tttaagtgtg cagccatagt ttgggtattt ttggttttata tgccctcaag taaaagaaaa    1200
gccgaaaggg ttaatcatat ttgaaaacca tattttattg tattttgatg agatattaaa    1260
ttctcaaagt tttattataa attctactaa gttattttat gacatgaaaa gttatttatg    1320
ctataaattt tttgaaacac aatacctaca ataaactggt atgaataatt gcatcatttc    1380
aaaaaaaaaa aaaaaaaa                                                  1398
```

<210> SEQ ID NO 20
<211> LENGTH: 165
<212> TYPE: PRT
<213> ORGANISM: Homo sapiens

<400> SEQUENCE: 20

Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
            20                  25                  30

Gln Arg Thr Ile Thr Val Gly Val Tyr Glu Ala Ala Lys Leu Leu Asn
        35                  40                  45

Val Asp Pro Asp Asn Val Val Leu Cys Leu Leu Ala Ala Asp Glu Asp
    50                  55                  60

Asp Asp Arg Asp Val Ala Leu Gln Ile His Phe Thr Leu Ile Gln Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Glu Thr Asp Ala Gly Pro Ala Ala
            100                 105                 110

Ser Glu Gly Ala Glu Gln Pro Pro Asp Leu His Cys Val Leu Val Thr
        115                 120                 125

Asn Pro His Ser Ser Gln Trp Lys Asp Pro Ala Leu Ser Gln Leu Ile
            130                 135                 140

Cys Phe Cys Arg Glu Ser Arg Tyr Met Asp Gln Trp Val Pro Val Ile
145                 150                 155                 160

Asn Leu Pro Glu Arg
            165

<210> SEQ ID NO 21
<211> LENGTH: 1296
<212> TYPE: DNA
<213> ORGANISM: Homo sapiens

<400> SEQUENCE: 21
ggagagcggg gcccttttgtc ctccagtggc tggtaggcag tggctgggag gcagcggccc      60
aattagtgtc gtgcggcccg tggcgaggcg aggtccgggg agcgagcgag caagcaaggc     120
gggaggggtg gccggagctg cggcggctgg cacaggagga ggagcccggg cgggcgaggg     180
gcggccggag agcgccaggg cctgagctgc cggagcggcg cctgtgagtg agtgcagaaa     240
gcaggcgccc gcgcgctagc cgtggcagga gcagcccgca cgccgcgctc tctccctggg     300
cgacctgcag tttgcaatat gactttggag gaattctcgg ctggagagca gaagaccgaa     360
agcgaccccg ataacgtggt gttgtgcctg ctggcggcgg acgaggacga cgacagagat     420
gtggctctgc agatccactt caccctgatc caggcgtttt gctgcgagaa cgacatcaac     480
atcctgcgcg tcagcaaccc gggccggctg gcggagctcc tgctcttgga gaccgacgct     540
ggccccgcgg cgagcgaggg cgccgagcag ccccccggacc tgcactgcgt gctggtgacg     600
aatccacatt catctcaatg gaaggatcct gccttaagtc aacttatttg ttttttgccgg     660 gaaagtcgct acatggatca atgggttcca gtgattaatc tccctgaacg gtgatggcat     720
ctgaatgaaa ataactgaac caaattgcac tgaagttttt gaaataccct tgtagttact     780
caagcagtta ctccctacac tgatgcaagg attacagaaa ctgatgccaa ggggctgagt     840
gagttcaact acatgttctg ggggcccgga gatagatgac tttgcagatg gaaagaggtg     900
aaaatgaaga aggaagctgt gttgaaacag aaaaataagt caaaaggaac aaaaaattaca     960 aagaaccatg caggaaggaa aactatgtat taatttagaa tggttgagtt acattaaaat    1020
aaaccaaata tgttaaagtt taagtgtgca gccatagttt gggtattttt ggtttatatg    1080
ccctcaagta aagaaaagc cgaaagggtt aatcatattt gaaaaccata ttttattgta    1140
ttttgatgag atattaaatt ctcaaagttt tattataaat tctactaagt tattttatga    1200
catgaaaagt tatttatgct ataaatttt tgaaacacaa tacctacaat aaactggtat    1260
gaataattgc atcatttcaa aaaaaaaaaa aaaaaa                              1296

<210> SEQ ID NO 22
<211> LENGTH: 131
<212> TYPE: PRT
<213> ORGANISM: Homo sapiens

<400> SEQUENCE: 22

Met Thr Leu Glu Glu Phe Ser Ala Gly Glu Gln Lys Thr Glu Ser Asp
1               5                   10                  15

Pro Asp Asn Val Val Leu Cys Leu Leu Ala Ala Asp Glu Asp Asp Asp
            20                  25                  30

Arg Asp Val Ala Leu Gln Ile His Phe Thr Leu Ile Gln Ala Phe Cys
        35                  40                  45

Cys Glu Asn Asp Ile Asn Ile Leu Arg Val Ser Asn Pro Gly Arg Leu
50                  55                  60

Ala Glu Leu Leu Leu Leu Glu Thr Asp Ala Gly Pro Ala Ala Ser Glu
65                  70                  75                  80

Gly Ala Glu Gln Pro Pro Asp Leu His Cys Val Leu Val Thr Asn Pro
                85                  90                  95

His Ser Ser Gln Trp Lys Asp Pro Ala Leu Ser Gln Leu Ile Cys Phe
            100                 105                 110

Cys Arg Glu Ser Arg Tyr Met Asp Gln Trp Val Pro Val Ile Asn Leu
        115                 120                 125

Pro Glu Arg
    130

<210> SEQ ID NO 23
<211> LENGTH: 1160
<212> TYPE: DNA
<213> ORGANISM: Homo sapiens

<400> SEQUENCE: 23
ggagagcggg gcccttttgtc ctccagtggc tggtaggcag tggctgggag gcagcggccc        60
aattagtgtc gtgcggcccg tggcgaggcg aggtccgggg agcgagcgag caagcaaggc       120
gggaggggtg gccggagctg cggcggctgg cacaggagga ggagcccggg cgggcgaggg       180
gcggccggag agcgccaggg cctgagctgc cggagcggcg cctgtgagtg agtgcagaaa       240
gcaggcgccc gcgcgctagc cgtggcagga gcagcccgca cgccgcgctc tctccctggg       300
cgacctgcag tttgcaatat gactttggag gaattctcgg ctggagagca aagaccgaa        360 aggatggata aggtggggga tgccctggag gaagtgctca gcaaagccct gagtcagcgc       420
acgatcactg tcggggtgta cgaagcggcc aagctgctca acgtaatcca cattcatctc       480
aatggaagga tcctgcctta agtcaactta tttgttttg ccgggaaagt cgctacatgg        540
atcaatgggt tccagtgatt aatctccctg aacggtgatg gcatctgaat gaaaataact       600
gaaccaaatt gcactgaagt tttgaaata cctttgtagt tactcaagca gttactccct        660
acactgatgc aaggattaca gaaactgatg ccaaggggct gagtgagttc aactacatgt       720
tctgggggcc cggagataga tgactttgca gatggaaaga ggtgaaaatg aagaaggaag       780
ctgtgttgaa acagaaaaat aagtcaaaag gaacaaaaat tacaaagaac catgcaggaa       840
ggaaaactat gtattaattt agaatggttg agttacatta aaataaacca aatatgttaa       900
agtttaagtg tgcagccata gtttgggtat ttttggttta tatgccctca agtaaaagaa       960
aagccgaaag ggttaatcat atttgaaaac catattttat tgtatttga tgagatatta      1020 aattctcaaa gttttattat aaattctact aagttatttt atgacatgaa aagttattta      1080
tgctataaat tttttgaaac acaataccta caataaactg gtatgaataa ttgcatcatt      1140
tcaaaaaaaa aaaaaaaaaa                                                  1160

```
<210> SEQ ID NO 24
<211> LENGTH: 60
<212> TYPE: PRT
<213> ORGANISM: Homo sapiens

<400> SEQUENCE: 24

Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
            20                  25                  30

Gln Arg Thr Ile Thr Val Gly Val Tyr Glu Ala Ala Lys Leu Leu Asn
        35                  40                  45

Val Ile His Ile His Leu Asn Gly Arg Ile Leu Pro
    50                  55                  60

<210> SEQ ID NO 25
<211> LENGTH: 3729
<212> TYPE: DNA
<213> ORGANISM: Homo sapiens

<400> SEQUENCE: 25
```

| | | | | | |
|---|---|---|---|---|---|
| cgaaggggcg | tggccaagcg | caccgcctcg | gggcggggcc | ggcgttctag | cgcatcgcgg | 60 |
| ccgggtgcgt | cactcgcgaa | gtggaatttg | cccagacaag | caacatggct | cggaaacgcg | 120 |
| cggccggcgg | ggagccgcgg | ggacgcgaac | tgcgcagcca | gaaatccaag | gccaagagca | 180 |
| aggcccggcg | tgaggaggag | gaggaggatg | cctttgaaga | tgagaaaccc | caaagaaga | 240 |
| gccttctctc | caaagtttca | caaggaaaga | ggaaaagagg | ctgcagtcat | cctgggggtt | 300 |
| cagcagatgg | tccagcaaaa | agaaagtgg | ccaaggtgac | tgttaaatct | gaaaacctca | 360 |
| aggttataaa | ggatgaagcc | ctcagcgatg | gggatgacct | cagggacttt | ccaagtgacc | 420 |
| tcaagaaggc | acaccatctg | aagagagggg | ctaccatgaa | tgaagacagc | aatgaagaag | 480 |
| aggaagaaag | tgaaaatgat | tgggaagagg | ttgaagaact | tagtgagcct | gtgctgggtg | 540 |
| acgtgagaga | aagtacagcc | ttctctcgat | ctcttctgcc | tgtgaagcca | gtggagatag | 600 |
| agattgaaac | gccagagcag | gcgaagacaa | gagaaagaag | tgaaaagata | aaactggagt | 660 |
| ttgagacata | tcttcggagg | gcgatgaaac | gtttcaataa | aggggtccat | gaggacacac | 720 |
| acaaggttca | ccttctctgc | ctgctagcaa | atggcttcta | tcgaaataac | atctgcagcc | 780 |
| agccagatct | gcatgctatt | ggcctgtcca | tcatcccagc | ccgctttacc | agagtgctgc | 840 |
| ctcgagatgt | ggacacctac | tacctctcaa | acctggtgaa | gtggttcatt | ggaacattta | 900 |
| cagttaatgc | agaactttca | gccagtgaac | aagataacct | gcagactaca | ttggaaagga | 960 |
| gatttgctat | ttactctgct | cgagatgatg | aggaattggt | ccatatattc | ttactgattc | 1020 |
| tccgggctct | gcagctcttg | acccggctgg | tattgtctct | acagccaatt | cctctgaagt | 1080 |
| cagcaacagc | aaagggaaag | aaaccttcca | aggaaagatt | gactgcggat | ccaggaggct | 1140 |
| cctcagaaac | ttccagccaa | gttctagaaa | accacaccaa | accaaagacc | agcaaaggaa | 1200 |
| ccaaacaaga | ggaaaccttt | gctaagggca | cctgcaggcc | aagtgccaaa | gggaagagga | 1260 |
| acaagggagg | cagaaagaaa | cggagcaagc | cctcctccag | cgaggaagat | gagggcccag | 1320 |
| gagacaagca | ggagaaggca | acccagcgac | gtccgcatgg | ccgggagcgg | cggtggcct | 1380 |
| ccagggtgtc | ttataaagag | gagagtggga | gtgatgaggc | tggcagcggc | tctgattttg | 1440 |
| agctctccag | tggagaagcc | tctgatccct | ctgatgagga | ttccgaacct | ggccctccaa | 1500 |
| agcagaggaa | agccccgct | cctcagagga | caaaggctgg | gtccaagagt | gcctccagga | 1560 |

| | | | | |
|---|---|---|---|---|
| cccatcgtgg | gagccatcgt | aaggacccaa | gcttgccagc | ggcatcctca agctcttcaa | 1620 |
| gcagtaaaag | aggcaagaaa | atgtgcagcg | atggtgagaa | ggcagaaaaa agaagcatag | 1680 |
| ctggtataga | ccagtggcta | gaggtgttct | gtgagcagga | ggaaaagtgg gtatgtgtag | 1740 |
| actgtgtgca | cggtgtggtg | ggccagcctc | tgacctgtta | caagtacgcc accaagccca | 1800 |
| tgacctatgt | ggtgggcatt | gacagtgacg | gctgggtccg | agatgtcaca cagaggtacg | 1860 |
| acccagtctg | gatgacagtg | acccgcaagt | gccgggttga | tgctgagtgg tgggccgaga | 1920 |
| ccttgagacc | ataccagagc | ccatttatgg | acagggagaa | gaaagaagac ttggagtttc | 1980 |
| aggcaaaaca | catggaccag | cctttgccca | ctgccattgg | cttatataag aaccaccctc | 2040 |
| tgtatgccct | gaagcggcat | ctcctgaaat | atgaggccat | ctatcccgag acagctgcca | 2100 |
| tccttgggta | ttgtcgtgga | gaagcggtct | actccaggga | ttgtgtgcac actctgcatt | 2160 |
| ccagggacac | gtggctgaag | aaagcaagag | tggtgaggct | tggagaagta ccctacaaga | 2220 |
| tggtgaaagg | cttttctaac | cgtgctcgga | aagcccgact | tgctgagccc cagctgcggg | 2280 |
| aagaaaatga | cctgggcctg | tttggctact | ggcagacaga | ggagtatcag cccccagtgg | 2340 |
| ccgtggacgg | gaaggtgccc | cggaacgagt | ttgggaatgt | gtacctcttc ctgcccagca | 2400 |
| tgatgcctat | tggctgtgtc | cagctgaacc | tgcccaatct | acaccgcgtg gcccgcaagc | 2460 |
| tggacatcga | ctgtgtccag | gccatcactg | gctttgattt | ccatggcggc tactcccatc | 2520 |
| ccgtgactga | tggatacatc | gtctgcgagg | aattcaaaga | cgtgctcctg actgcctggg | 2580 |
| aaaatgagca | ggcagtcatt | gaaggaagg | agaaggagaa | aaaggagaag cgggctctag | 2640 |
| ggaactggaa | gttgctggcc | aaaggtctgc | tcatcaggga | gaggctgaag cgtcgctacg | 2700 |
| ggcccaagag | tgaggcagca | gctccccaca | cagatgcagg | aggtggactc tcttctgatg | 2760 |
| aagaggaggg | gaccagctct | caagcagaag | cggccaggat | actggctgcc tcctggcctc | 2820 |
| aaaccgaga | agatgaagaa | aagcagaagc | tgaagggtgg | gcccaagaag accaaaaggg | 2880 |
| aaaagaaagc | agcagcttcc | cacctgttcc | catttgagca | gctgtgagct gagcgcccac | 2940 |
| tagagggca | cccaccagtt | gctgctgccc | cactacaggc | cccacacctg ccctgggcat | 3000 |
| gcccagcccc | tggtggtggg | ggcttctctg | ctgagaaggc | aaactgaggc agcatgcacg | 3060 |
| gaggcggggt | caggggagac | gaggccaagc | tgaggaggtg | ctgcaggtcc cgtctggctc | 3120 |
| cagcccttgt | cagattcacc | cagggtgaag | ccttcaaagc | ttttttgctac caaagcccac | 3180 |
| tcaccctttg | agctacagaa | cactttgcta | ggagatactc | ttctgcctcc tagacctgtt | 3240 |
| ctttccatct | ttagaaacat | cagtttttgt | atggaagcca | ccgggagatt tctggatggt | 3300 |
| ggtgcatccg | tgaatgcgct | gatcgtttct | tccagttaga | gtcttcatct gtccgacaag | 3360 |
| ttcactcgcc | tcggttgcgg | acctaggacc | atttctctgc | aggccactta ccttcccctg | 3420 |
| agtcaggctt | actaatgctg | ccctcactgc | ctctttgcag | taggggagag agcagagaag | 3480 |
| tacaggtcat | ctgctgggat | ctagtttttcc | aagtaacatt | ttgtggtgac agaagcctaa | 3540 |
| aaaaagctaa | aatcaggaaa | gaaaggaaa | aatacgaatt | gaaaattaag gaaatgttag | 3600 |
| taaaatagat | gagtgttaaa | ctagattgta | ttcattacta | gataaaatgt ataaagctct | 3660 |
| ctgtactaag | gagaaatgac | ttttataaca | ttttgagaaa | ataataaagc atttatctaa | 3720 |
| aaaaaaaaa | | | | | 3729 |

<210> SEQ ID NO 26
<211> LENGTH: 940
<212> TYPE: PRT
<213> ORGANISM: Homo sapiens

<400> SEQUENCE: 26

```
Met Ala Arg Lys Arg Ala Ala Gly Gly Glu Pro Arg Gly Arg Glu Leu
1               5                   10                  15

Arg Ser Gln Lys Ser Lys Ala Lys Ser Lys Ala Arg Arg Glu Glu Glu
            20                  25                  30

Glu Glu Asp Ala Phe Glu Asp Glu Lys Pro Pro Lys Lys Ser Leu Leu
        35                  40                  45

Ser Lys Val Ser Gln Gly Lys Arg Lys Arg Gly Cys Ser His Pro Gly
50                  55                  60

Gly Ser Ala Asp Gly Pro Ala Lys Lys Val Ala Lys Val Thr Val
65                  70                  75                  80

Lys Ser Glu Asn Leu Lys Val Ile Lys Asp Glu Ala Leu Ser Asp Gly
                85                  90                  95

Asp Asp Leu Arg Asp Phe Pro Ser Asp Leu Lys Lys Ala His His Leu
            100                 105                 110

Lys Arg Gly Ala Thr Met Asn Glu Asp Ser Asn Glu Glu Glu Glu
        115                 120                 125

Ser Glu Asn Asp Trp Glu Glu Val Glu Leu Ser Glu Pro Val Leu
130                 135                 140

Gly Asp Val Arg Glu Ser Thr Ala Phe Ser Arg Ser Leu Leu Pro Val
145                 150                 155                 160

Lys Pro Val Glu Ile Glu Ile Glu Thr Pro Glu Gln Ala Lys Thr Arg
                165                 170                 175

Glu Arg Ser Glu Lys Ile Lys Leu Glu Phe Glu Thr Tyr Leu Arg Arg
            180                 185                 190

Ala Met Lys Arg Phe Asn Lys Gly Val His Glu Asp Thr His Lys Val
        195                 200                 205

His Leu Leu Cys Leu Leu Ala Asn Gly Phe Tyr Arg Asn Asn Ile Cys
210                 215                 220

Ser Gln Pro Asp Leu His Ala Ile Gly Leu Ser Ile Ile Pro Ala Arg
225                 230                 235                 240

Phe Thr Arg Val Leu Pro Arg Asp Val Asp Thr Tyr Tyr Leu Ser Asn
                245                 250                 255

Leu Val Lys Trp Phe Ile Gly Thr Phe Thr Val Asn Ala Glu Leu Ser
            260                 265                 270

Ala Ser Glu Gln Asp Asn Leu Gln Thr Thr Leu Glu Arg Arg Phe Ala
        275                 280                 285

Ile Tyr Ser Ala Arg Asp Asp Glu Glu Leu Val His Ile Phe Leu Leu
290                 295                 300

Ile Leu Arg Ala Leu Gln Leu Leu Thr Arg Leu Val Leu Ser Leu Gln
305                 310                 315                 320

Pro Ile Pro Leu Lys Ser Ala Thr Ala Lys Gly Lys Lys Pro Ser Lys
                325                 330                 335

Glu Arg Leu Thr Ala Asp Pro Gly Gly Ser Ser Glu Thr Ser Ser Gln
            340                 345                 350

Val Leu Glu Asn His Thr Lys Pro Lys Thr Ser Lys Gly Thr Lys Gln
        355                 360                 365

Glu Glu Thr Phe Ala Lys Gly Thr Cys Arg Pro Ser Ala Lys Gly Lys
370                 375                 380

Arg Asn Lys Gly Gly Arg Lys Lys Arg Ser Lys Pro Ser Ser Ser Glu
385                 390                 395                 400

Glu Asp Glu Gly Pro Gly Asp Lys Gln Glu Lys Ala Thr Gln Arg Arg
```

```
            405                 410                 415
Pro His Gly Arg Glu Arg Arg Val Ala Ser Arg Val Ser Tyr Lys Glu
            420                 425                 430

Glu Ser Gly Ser Asp Glu Ala Gly Ser Gly Ser Asp Phe Glu Leu Ser
            435                 440                 445

Ser Gly Glu Ala Ser Asp Pro Ser Asp Glu Asp Ser Glu Pro Gly Pro
        450                 455                 460

Pro Lys Gln Arg Lys Ala Pro Ala Pro Gln Arg Thr Lys Ala Gly Ser
465                 470                 475                 480

Lys Ser Ala Ser Arg Thr His Arg Gly Ser His Arg Lys Asp Pro Ser
                485                 490                 495

Leu Pro Ala Ala Ser Ser Ser Ser Ser Ser Lys Arg Gly Lys Lys
            500                 505                 510

Met Cys Ser Asp Gly Glu Lys Ala Glu Lys Arg Ser Ile Ala Gly Ile
            515                 520                 525

Asp Gln Trp Leu Glu Val Phe Cys Glu Gln Glu Lys Trp Val Cys
530                 535                 540

Val Asp Cys Val His Gly Val Val Gly Gln Pro Leu Thr Cys Tyr Lys
545                 550                 555                 560

Tyr Ala Thr Lys Pro Met Thr Tyr Val Val Gly Ile Asp Ser Asp Gly
                565                 570                 575

Trp Val Arg Asp Val Thr Gln Arg Tyr Asp Pro Val Trp Met Thr Val
            580                 585                 590

Thr Arg Lys Cys Arg Val Asp Ala Glu Trp Trp Ala Glu Thr Leu Arg
            595                 600                 605

Pro Tyr Gln Ser Pro Phe Met Asp Arg Glu Lys Lys Glu Asp Leu Glu
        610                 615                 620

Phe Gln Ala Lys His Met Asp Gln Pro Leu Pro Thr Ala Ile Gly Leu
625                 630                 635                 640

Tyr Lys Asn His Pro Leu Tyr Ala Leu Lys Arg His Leu Leu Lys Tyr
                645                 650                 655

Glu Ala Ile Tyr Pro Glu Thr Ala Ala Ile Leu Gly Tyr Cys Arg Gly
            660                 665                 670

Glu Ala Val Tyr Ser Arg Asp Cys Val His Thr Leu His Ser Arg Asp
            675                 680                 685

Thr Trp Leu Lys Lys Ala Arg Val Val Arg Leu Gly Glu Val Pro Tyr
        690                 695                 700

Lys Met Val Lys Gly Phe Ser Asn Arg Ala Arg Lys Ala Arg Leu Ala
705                 710                 715                 720

Glu Pro Gln Leu Arg Glu Glu Asn Asp Leu Gly Leu Phe Gly Tyr Trp
                725                 730                 735

Gln Thr Glu Glu Tyr Gln Pro Pro Val Ala Val Asp Gly Lys Val Pro
            740                 745                 750

Arg Asn Glu Phe Gly Asn Val Tyr Leu Phe Leu Pro Ser Met Met Pro
            755                 760                 765

Ile Gly Cys Val Gln Leu Asn Leu Pro Asn Leu His Arg Val Ala Arg
        770                 775                 780

Lys Leu Asp Ile Asp Cys Val Gln Ala Ile Thr Gly Phe Asp Phe His
785                 790                 795                 800

Gly Gly Tyr Ser His Pro Val Thr Asp Gly Tyr Ile Val Cys Glu Glu
                805                 810                 815

Phe Lys Asp Val Leu Leu Thr Ala Trp Glu Asn Glu Gln Ala Val Ile
            820                 825                 830
```

```
Glu Arg Lys Glu Lys Glu Lys Glu Lys Arg Ala Leu Gly Asn Trp
        835                 840                 845
Lys Leu Leu Ala Lys Gly Leu Leu Ile Arg Glu Arg Leu Lys Arg Arg
    850                 855                 860
Tyr Gly Pro Lys Ser Glu Ala Ala Pro His Thr Asp Ala Gly Gly
865                 870                 875                 880
Gly Leu Ser Ser Asp Glu Glu Gly Thr Ser Ser Gln Ala Glu Ala
                885                 890                 895
Ala Arg Ile Leu Ala Ala Ser Trp Pro Gln Asn Arg Glu Asp Glu Glu
            900                 905                 910
Lys Gln Lys Leu Lys Gly Gly Pro Lys Lys Thr Lys Arg Glu Lys Lys
        915                 920                 925
Ala Ala Ala Ser His Leu Phe Pro Phe Glu Gln Leu
    930                 935                 940

<210> SEQ ID NO 27
<211> LENGTH: 3618
<212> TYPE: DNA
<213> ORGANISM: Homo sapiens

<400> SEQUENCE: 27
cgaaggggcg tggccaagcg caccgcctcg gggcggggcc ggcgttctag cgcatcgcgg      60
ccgggtgcgt cactcgcgaa gtggaatttg cccagacaag caacatggct cggaaacgcg     120
cggccggcgg ggagccgcgg ggacgcgaac tgcgcagcca gaaatccaag gccaagagca     180
aggcccggcg tgaggaggag gaggaggatg cctttgaaga tgagaaaccc ccaaagaaga     240
gccttctctc caaagtttca caaggaaaga ggaaaagagg ctgcagtcat cctgggggtt     300
cagcagatgt ccagcaaaaa agaaagtgg ccaaggtgac tgttaaatct gaaaacctca     360
aggttataaa ggatgaagcc ctcagcgatg gggatgacct cagggacttt ccaagtgacc     420
tcaagaaggc acaccatctg aagagagggg ctaccatgaa tgaagacagc aatgaagaag     480
aggaagaaag tgaaaatgat tgggaagagg cgaagacaag agaagaagt gaaaagataa     540 aactggagtt tgagacatat cttcggaggg cgatgaaacg tttcaataaa ggggtccatg     600
aggacacaca caaggttcac cttctctgcc tgctagcaaa tggcttctat cgaaataaca     660
tctgcagcca gccagatctg catgctattg gcctgtccat catcccagcc cgctttacca     720
gagtgctgcc tcgagatgtg gacacctact acctctcaaa cctggtgaag tggttcattg     780
gaacatttac agttaatgca gaactttcag ccagtgaaca agataacctg cagactacat     840
tggaaaggag atttgctatt tactctgctc gagatgatga ggaattggtc catatattct     900
tactgattct ccgggctctg cagctcttga cccggctggt attgtctcta cagccaattc     960
ctctgaagtc agcaacagca aagggaaaga aaccttccaa ggaaagattg actgcggatc    1020
caggaggctc ctcagaaact tccagccaag ttctagaaaa ccacaccaaa ccaaagacca    1080
gcaaaggaac caaacaagag gaaacctttg ctaagggcac ctgcaggcca agtgccaaag    1140
ggaagaggaa caagggaggc agaaagaaac ggagcaagcc ctcctccagc gaggaagatg    1200
agggcccagg agacaagcag gagaaggcaa cccagcgacg tccgcatggc cgggagcggc    1260
gggtggcctc cagggtgtct tataaagagg agagtgggag tgatgaggct ggcagcggct    1320
ctgattttga gctctccagt ggagaagcct ctgatccctc tgatgaggat tccgaacctg    1380
gccctccaaa gcagaggaaa gccccgctc tcagaggac aaaggctggg tccaagagtg    1440
cctccaggac ccatcgtggg agccatcgta aggacccaag cttgccagcg gcatcctcaa    1500
```

```
gctcttcaag cagtaaaaga ggcaagaaaa tgtgcagcga tggtgagaag gcagaaaaaa    1560
gaagcatagc tggtatagac cagtggctag aggtgttctg tgagcaggag gaaaagtggg    1620
tatgtgtaga ctgtgtgcac ggtgtggtgg gccagcctct gacctgttac aagtacgcca    1680
ccaagcccat gacctatgtg gtgggcattg acagtgacgg ctgggtccga gatgtcacac    1740
agaggtacga cccagtctgg atgacagtga cccgcaagtg ccgggttgat gctgagtggt    1800
gggccgagac cttgagacca taccagagcc catttatgga cagggagaag aaagaagact    1860
tggagtttca ggcaaaacac atggaccagc ctttgcccac tgccattggc ttatataaga    1920
accaccctct gtatgccctg aagcggcatc tcctgaaata tgaggccatc tatcccgaga    1980
cagctgccat ccttgggtat tgtcgtggag aagcggtcta ctccagggat tgtgtgcaca    2040
ctctgcattc cagggacacg tggctgaaga aagcaagagt ggtgaggctt ggagaagtac    2100
cctacaagat ggtgaaaggc ttttctaacc gtgctcggaa agcccgactt gctgagcccc    2160
agctgcggga agaaaatgac ctgggcctgt tggctactg gcagacagag gagtatcagc    2220
ccccagtggc cgtggacggg aaggtgcccc ggaacgagtt tgggaatgtg tacctcttcc    2280
tgcccagcat gatgcctatt ggctgtgtcc agctgaacct gcccaatcta caccgcgtgg    2340
cccgcaagct ggacatcgac tgtgtccagg ccatcactgg ctttgatttc catggcggct    2400
actcccatcc cgtgactgat ggatacatcg tctgcgagga attcaaagac gtgctcctga    2460
ctgcctggga aaatgagcag gcagtcattg aaaggaagga gaaggagaaa aaggagaagc    2520
gggctctagg gaactggaag ttgctggcca aaggtctgct catcagggag aggctgaagc    2580
gtcgctacgg gcccaagagt gaggcagcag ctccccacac agatgcagga ggtggactct    2640
cttctgatga agaggagggg accagctctc aagcagaagc ggccaggata ctggctgcct    2700
cctggcctca aaaccgagaa gatgaagaaa agcagaagct gaagggtggg cccaagaaga    2760
ccaaaaggga aaagaaagca gcagcttccc acctgttccc atttgagcag ctgtgagctg    2820
agcgcccact agagggcac ccaccagttg ctgctgcccc actacaggcc ccacacctgc    2880
cctgggcatg cccagcccct ggtggtgggg gcttctctgc tgagaaggca aactgaggca    2940
gcatgcacgg aggcggggtc aggggagacg aggccaagct gaggaggtgc tgcaggtccc    3000
gtctggctcc agcccttgtc agattcaccc agggtgaagc cttcaaagct ttttgctacc    3060
aaagcccact cacccttttga gctacagaac actttgctag gagatactct tctgcctcct    3120
agacctgttc tttccatctt tagaaacatc agttttttgta tggaagccac cgggagattt    3180
ctggatggtg gtgcatccgt gaatgcgctg atcgtttctt ccagttagag tcttcatctg    3240
tccgacaagt tcactcgcct cggttgcgga cctaggacca tttctctgca ggccacttac    3300
cttcccctga gtcaggctta ctaatgctgc cctcactgcc tctttgcagt aggggagaga    3360
gcagagaagt acaggtcatc tgctgggatc tagttttcca agtaacattt tgtggtgaca    3420
gaagcctaaa aaaagctaaa atcaggaaag aaaaggaaaa atacgaattg aaaattaagg    3480
aaatgttagt aaaatagatg agtgttaaac tagattgtat tcattactag ataaaatgta    3540
taaagctctc tgtactaagg agaaatgact tttataacat tttgagaaaa taataaagca    3600
tttatctaaa aaaaaaa                                                   3618
```

<210> SEQ ID NO 28
<211> LENGTH: 903
<212> TYPE: PRT
<213> ORGANISM: Homo sapiens

<400> SEQUENCE: 28

```
Met Ala Arg Lys Arg Ala Ala Gly Gly Glu Pro Arg Gly Arg Glu Leu
1               5                   10                  15

Arg Ser Gln Lys Ser Lys Ala Lys Ser Lys Ala Arg Arg Glu Glu Glu
            20                  25                  30

Glu Glu Asp Ala Phe Glu Asp Glu Lys Pro Pro Lys Lys Ser Leu Leu
        35                  40                  45

Ser Lys Val Ser Gln Gly Lys Arg Lys Arg Gly Cys Ser His Pro Gly
50                  55                  60

Gly Ser Ala Asp Gly Pro Ala Lys Lys Val Ala Lys Val Thr Val
65                  70                  75                  80

Lys Ser Glu Asn Leu Lys Val Ile Lys Asp Glu Ala Leu Ser Asp Gly
                85                  90                  95

Asp Asp Leu Arg Asp Phe Pro Ser Asp Leu Lys Lys Ala His His Leu
            100                 105                 110

Lys Arg Gly Ala Thr Met Asn Glu Asp Ser Asn Glu Glu Glu Glu Glu
        115                 120                 125

Ser Glu Asn Asp Trp Glu Glu Ala Lys Thr Arg Glu Arg Ser Glu Lys
130                 135                 140

Ile Lys Leu Glu Phe Glu Thr Tyr Leu Arg Arg Ala Met Lys Arg Phe
145                 150                 155                 160

Asn Lys Gly Val His Glu Asp Thr His Lys Val His Leu Leu Cys Leu
                165                 170                 175

Leu Ala Asn Gly Phe Tyr Arg Asn Asn Ile Cys Ser Gln Pro Asp Leu
            180                 185                 190

His Ala Ile Gly Leu Ser Ile Ile Pro Ala Arg Phe Thr Arg Val Leu
        195                 200                 205

Pro Arg Asp Val Asp Thr Tyr Tyr Leu Ser Asn Leu Val Lys Trp Phe
210                 215                 220

Ile Gly Thr Phe Thr Val Asn Ala Glu Leu Ser Ala Ser Glu Gln Asp
225                 230                 235                 240

Asn Leu Gln Thr Thr Leu Glu Arg Arg Phe Ala Ile Tyr Ser Ala Arg
                245                 250                 255

Asp Asp Glu Glu Leu Val His Ile Phe Leu Leu Ile Leu Arg Ala Leu
            260                 265                 270

Gln Leu Leu Thr Arg Leu Val Leu Ser Leu Gln Pro Ile Pro Leu Lys
        275                 280                 285

Ser Ala Thr Ala Lys Gly Lys Lys Pro Ser Lys Glu Arg Leu Thr Ala
290                 295                 300

Asp Pro Gly Gly Ser Ser Glu Thr Ser Ser Gln Val Leu Glu Asn His
305                 310                 315                 320

Thr Lys Pro Lys Thr Ser Lys Gly Thr Lys Gln Glu Thr Phe Ala
                325                 330                 335

Lys Gly Thr Cys Arg Pro Ser Ala Lys Gly Lys Arg Asn Lys Gly Gly
            340                 345                 350

Arg Lys Lys Arg Ser Lys Pro Ser Ser Ser Glu Glu Asp Glu Gly Pro
        355                 360                 365

Gly Asp Lys Gln Glu Lys Ala Thr Gln Arg Arg Pro His Gly Arg Glu
370                 375                 380

Arg Arg Val Ala Ser Arg Val Ser Tyr Lys Glu Glu Ser Gly Ser Asp
385                 390                 395                 400

Glu Ala Gly Ser Gly Ser Asp Phe Glu Leu Ser Ser Gly Glu Ala Ser
                405                 410                 415
```

Asp Pro Ser Asp Glu Asp Ser Glu Pro Gly Pro Pro Lys Gln Arg Lys
            420                 425                 430

Ala Pro Ala Pro Gln Arg Thr Lys Ala Gly Ser Lys Ser Ala Ser Arg
            435                 440                 445

Thr His Arg Gly Ser His Arg Lys Asp Pro Ser Leu Pro Ala Ala Ser
        450                 455                 460

Ser Ser Ser Ser Ser Ser Lys Arg Gly Lys Lys Met Cys Ser Asp Gly
465                 470                 475                 480

Glu Lys Ala Glu Lys Arg Ser Ile Ala Gly Ile Asp Gln Trp Leu Glu
                485                 490                 495

Val Phe Cys Glu Gln Glu Glu Lys Trp Val Cys Val Asp Cys Val His
            500                 505                 510

Gly Val Val Gly Gln Pro Leu Thr Cys Tyr Lys Tyr Ala Thr Lys Pro
        515                 520                 525

Met Thr Tyr Val Val Gly Ile Asp Ser Asp Gly Trp Val Arg Asp Val
    530                 535                 540

Thr Gln Arg Tyr Asp Pro Val Trp Met Thr Val Thr Arg Lys Cys Arg
545                 550                 555                 560

Val Asp Ala Glu Trp Trp Ala Glu Thr Leu Arg Pro Tyr Gln Ser Pro
                565                 570                 575

Phe Met Asp Arg Glu Lys Lys Glu Asp Leu Glu Phe Gln Ala Lys His
            580                 585                 590

Met Asp Gln Pro Leu Pro Thr Ala Ile Gly Leu Tyr Lys Asn His Pro
        595                 600                 605

Leu Tyr Ala Leu Lys Arg His Leu Leu Lys Tyr Glu Ala Ile Tyr Pro
    610                 615                 620

Glu Thr Ala Ala Ile Leu Gly Tyr Cys Arg Gly Glu Ala Val Tyr Ser
625                 630                 635                 640

Arg Asp Cys Val His Thr Leu His Ser Arg Asp Thr Trp Leu Lys Lys
                645                 650                 655

Ala Arg Val Val Arg Leu Gly Glu Val Pro Tyr Lys Met Val Lys Gly
            660                 665                 670

Phe Ser Asn Arg Ala Arg Lys Ala Arg Leu Ala Glu Pro Gln Leu Arg
        675                 680                 685

Glu Glu Asn Asp Leu Gly Leu Phe Gly Tyr Trp Gln Thr Glu Glu Tyr
    690                 695                 700

Gln Pro Pro Val Ala Val Asp Gly Lys Val Pro Arg Asn Glu Phe Gly
705                 710                 715                 720

Asn Val Tyr Leu Phe Leu Pro Ser Met Met Pro Ile Gly Cys Val Gln
                725                 730                 735

Leu Asn Leu Pro Asn Leu His Arg Val Ala Arg Lys Leu Asp Ile Asp
            740                 745                 750

Cys Val Gln Ala Ile Thr Gly Phe Asp Phe His Gly Tyr Ser His
        755                 760                 765

Pro Val Thr Asp Gly Tyr Ile Val Cys Glu Glu Phe Lys Asp Val Leu
    770                 775                 780

Leu Thr Ala Trp Glu Asn Glu Gln Ala Val Ile Glu Arg Lys Glu Lys
785                 790                 795                 800

Glu Lys Lys Glu Lys Arg Ala Leu Gly Asn Trp Lys Leu Leu Ala Lys
                805                 810                 815

Gly Leu Leu Ile Arg Glu Arg Leu Lys Arg Arg Tyr Gly Pro Lys Ser
            820                 825                 830

```
Glu Ala Ala Ala Pro His Thr Asp Ala Gly Gly Leu Ser Ser Asp
            835                 840                 845

Glu Glu Glu Gly Thr Ser Ser Gln Ala Glu Ala Ala Arg Ile Leu Ala
850                 855                 860

Ala Ser Trp Pro Gln Asn Arg Glu Asp Glu Lys Gln Lys Leu Lys
865                 870                 875                 880

Gly Gly Pro Lys Lys Thr Lys Arg Glu Lys Lys Ala Ala Ala Ser His
            885                 890                 895

Leu Phe Pro Phe Glu Gln Leu
            900

<210> SEQ ID NO 29
<211> LENGTH: 3605
<212> TYPE: DNA
<213> ORGANISM: Homo sapiens

<400> SEQUENCE: 29
cgaaggggcg tggccaagcg caccgcctcg gggcggggcc ggcgttctag cgcatcgcgg      60
ccgggtgcgt cactcgcgaa gtggaatttg cccagacaag caacatggct cggaaacgcg     120
cggccggcgg ggagccgcgg ggacgcgaac tgcgcagcca gaaatccaag gccaagagca     180
aggcccggcg tgaggaggag gaggaggatg cctttgaaga tgagaaaccc caaagaaga      240 gccttctctc caaagtttca caaggaaaga ggaaaagagg ctgcagtcat cctgggggtt     300
cagcagatgg tccagcaaaa agaaagtgg ccaaggtgac tgttaaatct gaaaacctca     360
aggttataaa ggatgaagcc ctcagcgatg gggatgacct cagggacttt ccaagtgacc     420
tcaagaaggc acaccatctg aagagagggg ctaccatgaa tgaagacagc aatgaagaag     480
aggaagaaag tgaaaatgat tgggaagagg ttgaagtgaa aagataaaac tggagtttga     540
gacatatctt cggagggcga tgaaacgttt caataaaggg gtccatgagg acacacacaa     600
ggttcacctt ctctgcctgc tagcaaatgg cttctatcga ataacatct gcagccagcc      660 agatctgcat gctattggcc tgtccatcat cccagcccgc tttaccagag tgctgcctcg     720
agatgtggac acctactacc tctcaaacct ggtgaagtgg ttcattggaa catttacagt     780
taatgcagaa cttttcagcca gtgaacaaga taacctgcag actacattgg aaaggagatt     840
tgctatttac tctgctcgag atgatgagga attggtccat atattcttac tgattctccg     900
ggctctgcag ctcttgaccc ggctggtatt gtctctacag ccaattcctc tgaagtcagc     960
aacagcaaag ggaaagaaac cttccaagga agattgact gcggatccag gaggctcctc    1020
agaaacttcc agccaagttc tagaaaacca caccaaacca aagaccagca aggaaccaa    1080 acaagaggaa acctttgcta agggcacctg caggccaagt gccaagggga gaggaacaa    1140 gggaggcaga aagaaacgga gcaagccctc ctccagcgag aagatgagg gcccaggaga    1200 caagcaggag aaggcaaccc agcgacgtcc gcatggccgg gagcggcggg tggcctccag    1260
ggtgtcttat aaagaggaga gtgggagtga tgaggctggc agcggctctg attttgagct    1320
ctccagtgga gaagcctctg atccctctga tgaggattcc gaacctggcc ctccaaagca    1380
gaggaaagcc cccgctcctc agaggacaaa ggctgggtcc aagagtgcct ccaggaccca    1440
tcgtgggagc catcgtaagg acccaagctt gccagcggca tcctcaagct cttcaagcag    1500
taaaagaggc aagaaaatgt gcagcgatgg tgagaaggca gaaaaaagaa gcatagctgg    1560
tatagaccag tggctagagg tgttctgtga gcaggaggaa aagtgggtat gtgtagactg    1620
tgtgcacggt gtggtgggcc agcctctgac ctgttacaag tacgccacca gcccatgac    1680
```

```
ctatgtggtg ggcattgaca gtgacggctg ggtccgagat gtcacacaga ggtacgaccc    1740
agtctggatg acagtgaccc gcaagtgccg ggttgatgct gagtggtggg ccgagacctt    1800
gagaccatac cagagcccat ttatggacag ggagaagaaa gaagacttgg agtttcaggc    1860
aaaacacatg gaccagcctt tgcccactgc cattggctta tataagaacc accctctgta    1920
tgccctgaag cggcatctcc tgaaatatga ggccatctat cccgagacag ctgccatcct    1980
tgggtattgt cgtggagaag cggtctactc cagggattgt gtgcacactc tgcattccag    2040
ggacacgtgg ctgaagaaag caagagtggt gaggcttgga gaagtaccct acaagatggt    2100
gaaaggcttt tctaaccgtg ctcggaaagc ccgacttgct gagccccagc tgcgggaaga    2160
aaatgacctg ggcctgtttg gctactggca gacagaggag tatcagcccc cagtggccgt    2220
ggacgggaag gtgccccgga acgagtttgg gaatgtgtac ctcttcctgc ccagcatgat    2280
gcctattggc tgtgtccagc tgaacctgcc caatctacac cgcgtggccc gcaagctgga    2340
catcgactgt gtccaggcca tcactggctt tgatttccat ggcggctact cccatcccgt    2400
gactgatgga tacatcgtct gcgaggaatt caaagacgtg ctcctgactg cctgggaaaa    2460
tgagcaggca gtcattgaaa ggaaggagaa ggagaaaaag gagaagcggg ctctagggaa    2520
ctggaagttg ctggccaaag gtctgctcat cagggagagg ctgaagcgtc gctacgggcc    2580
caagagtgag gcagcagctc cccacacaga tgcaggaggt ggactctctt ctgatgaaga    2640
ggaggggacc agctctcaag cagaagcggc caggatactg gctgcctcct ggcctcaaaa    2700
ccgagaagat gaagaaaagc agaagctgaa gggtgggccc aagaagacca aagggaaaa    2760
gaaagcagca gcttcccacc tgttcccatt tgagcagctg tgagctgagc gcccactaga    2820
ggggcaccca ccagttgctg ctgccccact acaggcccca cacctgccct gggcatgccc    2880
agcccctggt ggtgggggct ctctgctgga aaggcaaac tgaggcagca tgcacggagg    2940
cggggtcagg ggagacgagg ccaagctgag gaggtgctgc aggtcccgtc tggctccagc    3000
ccttgtcaga ttcacccagg gtgaagcctt caaagctttt tgctaccaaa gcccactcac    3060
cctttgagct acagaacact ttgctaggag atactcttct gcctcctaga cctgttcttt    3120
ccatctttag aaacatcagt ttttgtatgg aagccaccgg gagatttctg gatggtggtg    3180
catccgtgaa tgcgctgatc gtttcttcca gttagagtct tcatctgtcc gacaagttca    3240
ctcgcctcgg ttgcggacct aggaccattt ctctgcaggc cacttacctt cccctgagtc    3300
aggcttacta atgctgccct cactgcctct ttgcagtagg ggagagagca gagaagtaca    3360
ggtcatctgc tgggatctag ttttccaagt aacattttgt ggtgacagaa gcctaaaaaa    3420
agctaaaatc aggaaagaaa aggaaaaata cgaattgaaa attaaggaaa tgttagtaaa    3480
atagatgagt gttaaactag attgtattca ttactagata aaatgtataa agctctctgt    3540
actaaggaga aatgacttt ataacatttt gagaaaataa taaagcattt atctaaaaaa    3600
aaaaa                                                                3605
```

<210> SEQ ID NO 30
<211> LENGTH: 8412
<212> TYPE: DNA
<213> ORGANISM: Homo sapiens

<400> SEQUENCE: 30

```
agccgcgtca acggcccttc gcagcgggcg cgctgtcaga cctcagtctg gcggctgcat      60
tgctgggcgc gccgctctcg tctgatccct gctgggacg gttgcccggg caggatcctt     120
tacgatccct tctcggtttc tccgtcgtca cagggaataa atctcgctcg aaactcactg     180
```

```
gaccgctcct agaaaggcga aaagatattc aggagccctt ccatttcct tccagtaggc      240 accgaaccca gcatttcgg caaccgctgc tggcagtttt gccaggtgtt tgttaccttg       300
aaaaatggct actggacagg atcgagtggt tgctctcgtg acatggact gttttttgt       360 tcaagtggag cagcggcaaa atcctcattt gaggaataaa ccttgtgcag ttgtacagta      420
caaatcatgg aagggtggtg gaataattgc agtgagttat gaagctcgtg catttggagt      480
cactagaagt atgtgggcag atgatgctaa gaagttatgt ccagatcttc tactggcaca      540
agttcgtgag tcccgtggga aagctaacct caccaagtac cgggaagcca gtgttgaagt      600
gatggagata atgtctcgtt ttgctgtgat tgaacgtgcc agcattgatg aggcttacgt       660
agatctgacc agtgctgtac aagagagact acaaaagcta caaggtcagc ctatctcggc      720
agacttgttg ccaagcactt acattgaagg gttgccccaa ggccctacaa cggcagaaga      780
gactgttcag aaagagggga tgcgaaaaca aggcttattt caatggctcg attctcttca      840
gattgataac ctcacctctc cagacctgca gctcaccgtg ggagcagtga ttgtggagga      900
aatgagagca gccatagaga gggagactgg ttttcagtgt tcagctggaa tttcacacaa      960
taaggtcctg gcaaaactgg cctgtggact aaacaagccc aaccgccaaa ccctggtttc     1020
acatgggtca gtcccacagc tcttcagcca aatgcccatt cgcaaaatcc gtagtcttgg     1080
aggaaagcta ggggcctctg tcattgagat cctagggata gaatacatgg gtgaactgac     1140
ccagttcact gaatcccagc tccagagtca ttttggggag aagaatgggt cttggctata     1200
tgccatgtgc cgagggattg aacatgatcc agttaaaccc aggcaactac ccaaaaccat     1260
tggctgtagt aagaacttcc caggaaaaac agctcttgct actcgggaac aggtacaatg     1320
gtggctgttg caattagccc aggaactaga ggagagactg actaaagacc gaaatgataa     1380
tgacagggta gccacccagc tggttgtgag cattcgtgta caaggagaca aacgcctcag     1440
cagcctgcgc cgctgctgtg cccttacccg ctatgatgct cacaagatga gccatgatgc     1500
atttactgtc atcaagaact gtaatacttc tggaatccag acagaatggt tcctcctct      1560 cacaatgctt ttcctctgtg ctacaaaatt ttctgcctct gccccttcat cttctacaga     1620
catcaccagc ttcttgagca gtgacccaag ttctctgcca aaggtgccag ttaccagctc     1680
agaagctaag acccagggaa gtggcccagc ggtgacagcc actaagaaag caaccacgtc     1740
tctggaatca ttcttccaaa aagctgcaga aaggcagaaa gttaagaag cttgctttc       1800 atctcttact gctcccactc aggctcccat gagcaattca ccatccaagc cctcattacc     1860 tttcaaacc agtcaaagta caggaactga gcccttcttt aagcagaaaa gtctgcttct     1920
aaagcagaaa cagcttaata attcttcagt ttcttcccc caacaaaacc catggtccaa     1980
ctgtaaagca ttaccaaact ctttaccaac agagtatcca gggtgtgtcc ctgttgtga     2040 aggggtgtcg aagctagaag aatcctctaa agcaactcct gcagagatgg atttggccca     2100
caacagccaa agcatgcacg cctcttcagc ttccaaatct gtgctggagg tgactcagaa     2160
agcaacccca atccaagtc ttctagctgc tgaggaccaa gtgccctgtg agaagtgtgg     2220
ctcctgggta ccggtatggg atatgccaga acacatggac tatcattttg cattggagtt     2280
gcagaaatcc ttttgcagc cccactcttc aaaccccag gttgtttctg ccgtatctca      2340
tcaaggcaaa agaaatccca agagcccttt ggcctgcact aataaacgcc ccaggcctga    2400
gggcatgcaa acattggaat cattttaa gccattaaca cattagtgct gccctcaggc      2460
ttgcctgtag gatttaatat ttttatctt tacagatctt tatctttaat attttatctt     2520
```

```
tacagatttc cctgagaaag ggaattatga aattttaat acaaaaaata atccatttag    2580
gtgctgagtt acggtcccat ctcttcacag gcatggattc taatcccact gctgacagag    2640
atgtaaaaat tcatcctacc agagttttta atctttagca tttagggagg cagtgtcata    2700
aagtaaaaag tgtgtgggcc ttggagtcta agagacgtgg ttgcaaactt agctctggtt    2760
attgcaatga gggccttgaa caagtcattt tcttcacatt ctcatctgta aaatggagat    2820
aataccttac agattattgc agattaataa caatgtattc aaattatgta actcggccgg    2880
gtacaatggc tcacgcctgt aatcctaaca ctttgggagg ccgaggcaga cagatcacct    2940
gaggtcagga gtttgagacc agcctggcca acatggcaaa accatctcta ctaaaaatag    3000
aaaaattagc caggcacgtt ccaggcacct gtgatcccag ctacttagag gctgaggcag    3060
aagaattgct taaccttgg aggcggaggt tgcattgagc tgagatcatg ctagtgcgct    3120
ccagcctggg caacagagcg agacttcatc tcagaaaata aaaataggg gccaggcaca    3180
gtggctcata cctgtaatgc cagcactttg ggaggccaag gcgggcagat cacgaggtca    3240
ggagtttcag accaatatgg tgaaacccca tctctactaa aattacaaaa aaaattatcc    3300
aggcgtggtg gtgcacgcct gtaatcccag ctactcagga ggctaaggca ggagaatcac    3360
ttgaacccag gaggcagagg ttggagtgag ctgagatcgc gccaccgcac tccagcctgg    3420
gcaacagagc gagactccat ctcaaacaaa aacaagaaca aaaacaaaca taaagttggc    3480
acagaaaagg gaccaagttt aaaaaagggt tttaaatgta atgagacttg catagttaaa    3540
aaaaaaaag ggattatttt tatttttatt ttttatttt gagacggagt ctccctctgt    3600
cgtcaggcta gaatgcagtg gtgcgttctc agctcaccgc aacctccgtc tcctgggttc    3660
aagcaattct cctgcctcag cctcccaagt agctgggact acaggcacgt gctaccacac    3720
tcagctaatt tttgtatttt taatagagat gaggtttcac catgttggcc aggatggtct    3780
cgattgcttg acctcatgat ccgcctgcct cgacctccca aagttgctgg gattacagat    3840
gttagccacc gatcctggcc cccccaaaaa aaggatttta agaaaaactt ctcttggccg    3900
ggcgcagtgg ctcacgcctg caatcccagc actttgggag gccgaggcgg gcggatcaca    3960
aggtcaggag atcgagacca cggtgaaacc ccgtctctac taaaaatac aaaaaaaaat    4020
tagccgggtg cggtggcagg cgcctgtagt cccagctact cgggaggctg aggcaggaga    4080
atggtgtgaa cccgggaggc ggagcttgca gtgagccgag agcgcgccac tgcactccag    4140
cctgggtgac agagcgagac tccgtctcaa aaaaaaaaa aaagaaaaa cttctctttta    4200
ggctgggtgc ggttcctcat gcctataatc ccagcattta gggaggctga ggtgagtgga    4260
ttgcaggagc tcaggagttc gagaccagcc tgggcaaggt ggcaaaaccc cgtctctact    4320
aaaaaaaatt agctgggctt ggtggcaggc gcctgtaatc ccaggtactc gggagactga    4380
ggcaggagaa ttgcttgaac ctggaaggtg gaggttgcag tgagttgaga tcacaccaat    4440
gcactccagc cagggtgaga gtgagagact gtctcaaaaa aaaaaaaac aaaagaaaaa    4500
cttctctcta gctctgtgac gggcagttca gataatacct tcaccagatt tacctgtttt    4560
cagctgaaga atgtgagatg aagccttgaa accctaaaag tgatatggta actagggcag    4620
gtctttctgt acataaaagt gacttaataa acagtgaatt tcatacaggt aaaccctatt    4680
ataccctcag ttctaaccat tggcctatct cttgcgtttt gttctaatgt agaattagat    4740
tgctacttga ctagttcagg aactctgttt agatctgata agtcataatc aaatcttgcc    4800
aggcgtggtg gtttatgcct gttatcccag cactttggga ggccaaggca ggtggaccac    4860
gtgaagtcag gagttcaaga caagcatggc caacatggcg aaaccctgta tctactaaaa    4920
```

```
atacaaaaat tagccgggca tggtggtggg tgcgtgtaat cccagctagt tgggaggctg    4980
aggcaggaga atcacttgaa cctgggaggc agaggttgca gtgagccgag atttccactg    5040
cattccagcc tgggcgatag agtaactctg tctcaaaaaa acccactaga tcatctctag    5100
aacattgcta ctcccaagta tgatttgagg aacagcagcc tcagtatcac cagggaactt    5160
attagaaata gtctcagcct caccactatt cccacttaat tgtaatctga tattaacaag    5220
atttcccaat gtgggtcagg tgtggtggct catgcctgta atcccacact tgggaggcc     5280 aaggtgggcg gatcacttga ggctgggagt tgagaccag gctggccaac atggggaaaa     5340
cccatctcta caaaaaataa caaaaattag gtgtgtgtgg tgacgcatgc gtgtaatccc    5400
agctacttag gaggctgagg caggagaatc acttgaatct gggaggcaga ggttgtagtg    5460
agctgagatt gtgccactgc actccagtct gggcaacaga gtgacactgt ttaaaaaaaa    5520
aaaaattccc aatgtgggcc gggtgcagtg gctcatgcct gtaatcccag cactttggga    5580
ggctgaggtg ggtgtatcac gaggtcaaga gatcaaggcc atcctggcca acatggtgaa    5640
accccgtctc tactgaaaat acaactgggc gtggtggtgc acgcctgtag tcccagctac    5700
ttgggaggct gaggcagaag aattgcttga cctgggaggc ggagcttgca gtgagcccag    5760
atcgtgccac tgcactgcac cctggcgaca cagcaagact gtctcaaaaa aaaaaaaatt    5820
cccaatgtgt atcttaaagt ttgagaaatg ctgatctaaa agatactaat gaccaggtgt    5880
gtagaggaca ttttcttaag cccttaagta caaatttaag aggtaagtgc ttcagccatt    5940
agggttactg gcttgttcat ctttcccact gagtgtaaat atttagctta gggtttaaaa    6000
tttgttatgt agcttttgc acttgtccat gtttatacta ctgtattatt attattttt     6060 tttgagatgg agtctcgctg tgtagccagg ctggagtgca gtggtgcaat cttggctcac    6120
tgcaacctcc gtctctcggg ttcaagcaat tctcctgcct cagcttcccg aatagctgag    6180
actacaagcg tgcaccacca tgcccagcta atttttgtat ttttagtaga gacaggtttt    6240
caccatgttg gccaggctgg tctctatcta gacctcgtga tccatccgcc tcggcctccc    6300
aaagtgctgg gattataggc atgagccacc acgcccagcc tatagtactg tattcttatt    6360
ctccactctt gtgtgtgaaa agtcagctct tttggctttt ctgttatggg gaaacttgaa    6420
ttacacaggg aacccaactg aagaaaatga actgaagtag gtggcgctgg gtgaagtggg    6480
cccagagaat ggtgtacaca tccctcccat acatataccc aaacttctat ttttttatgt    6540
gacggagttt ctctcatcgc cccggctgga atgcaatggc acgatctcgg ctcactgcaa    6600
cctccgcctc ccgggttcaa gcgattctcc tgcatcagcc tcctgagtag ctgggattat    6660
aggcatgcac catcacgcct ggctaatttt tgtattttta gtagagatgg gtttcgcca     6720 cgttggccag gctggtcttg aactcttgat ctcaagtgat ccacccgccc tggcctccca    6780
aagtgctggg attacaggcc tgagccacca ggccagcccc aacttctact ttttatttta    6840
tttataaatt ggggggggg ttctatattt agtttgaaga ggtggggaag atttgaaaac     6900
cactagattt accaggaaat tttttcttc aaaaatattt tctgctttta tgatacttga     6960
atatctaata aaagacaata tttagccagt cacggtggct gatgcttgta atcctaacac    7020
tttgggaggc tgaggtgggt ggactactgg agccctggag ttcaaaaccg gcctaagcca    7080
catggcaaaa cagtctttac aaaaaataca aagatggtgg cttatgcctg tagtcgtacc    7140
tactcaggag gctgaggttg ggaggatcac ctgaatctgg gagtttgggg ctgcaataag    7200
ccatgattgt gccgctgcac tccagcctgg gtgacagtct gagaccctgt ctcaaaaaaa    7260
```

-continued

```
aaaaaaaaaa aaaaaaaaaa aaagactaca ttcactgtat acgtggcctt ttcccctaa    7320 ctagctatgt agcttcttaa aggcaaagat tcttcatagt gctttgcaca tgataggtgc    7380
tgatactcat tggatgaatg tatatagtga agaattttag atctgattac cacaattggg    7440
atcataaaca tgtataaact ccttgggagt ctgccttata tactttttat ccccctaaat    7500
gttccattaa tgttgcagag aggctcacta gttcctggag atgtcttatt aagtactgaa    7560
atgtgatttt ccaaaatttt ctttacaata caggcaaaag ataagtaaat tgtggacaaa    7620
gctttcatct ctatcagcag ctatagagag gaagtaaaca gcttagcccc taatacagga    7680
ggaagttgtt caactacagg cttgttagta gcaagttaaa ccagttacat tttataaaac    7740
agcctgagtg gtagggaagc tatcacttta atactctaga ggcagaatgc cacataggac    7800
tttgggtcac atatttcttt tccagggtct cctcaaaatg cagtttctat ttacagttga    7860
ctttggcccc tatttaccca taaatgtca aaatcaagta gtatgaacat ggaaacagga    7920
gcagggacta aggtttggtc aagtggccct cattgttcca agagtaattt aggctatgta    7980
aacttgaaaa atatgggacc agattacctt ttgtctctaa attctactct tctttaagta    8040
gctggcactg tatctctgcc agggcacaga agtgggctcc ttactattct gaccactagc    8100
aagtggccaa ctcttcaaat acagggtagc tacctatttc acgtgaaagg cctcagtatt    8160
ctgctcactt gaactacgga aaataggcca caatacttgg ttacaatact ggaactctga    8220
acctatgtgg aggagagaaa aacaatggtg aacgagatac cagctgggct ctttccacat    8280
tcagggctca gcagtgttgg ggtttcactt gtctctaatc ctgaagaggt atctagccct    8340
ggaaggaagc tgagcctgta gctaacgcat aagcacagtg tattcaataa aacatttta    8400 ttctgtacaa ta                                                         8412
```

<210> SEQ ID NO 31
<211> LENGTH: 713
<212> TYPE: PRT
<213> ORGANISM: Homo sapiens

<400> SEQUENCE: 31

```
Met Ala Thr Gly Gln Asp Arg Val Val Ala Leu Val Asp Met Asp Cys
1               5                   10                  15

Phe Phe Val Gln Val Glu Gln Arg Gln Asn Pro His Leu Arg Asn Lys
                20                  25                  30

Pro Cys Ala Val Val Gln Tyr Lys Ser Trp Lys Gly Gly Gly Ile Ile
            35                  40                  45

Ala Val Ser Tyr Glu Ala Arg Ala Phe Gly Val Thr Arg Ser Met Trp
        50                  55                  60

Ala Asp Asp Ala Lys Lys Leu Cys Pro Asp Leu Leu Leu Ala Gln Val
65                  70                  75                  80

Arg Glu Ser Arg Gly Lys Ala Asn Leu Thr Lys Tyr Arg Glu Ala Ser
                85                  90                  95

Val Glu Val Met Glu Ile Met Ser Arg Phe Ala Val Ile Glu Arg Ala
                100                 105                 110

Ser Ile Asp Glu Ala Tyr Val Asp Leu Thr Ser Ala Val Gln Glu Arg
            115                 120                 125

Leu Gln Lys Leu Gln Gly Gln Pro Ile Ser Ala Asp Leu Leu Pro Ser
        130                 135                 140

Thr Tyr Ile Glu Gly Leu Pro Gln Gly Pro Thr Thr Ala Glu Glu Thr
145                 150                 155                 160

Val Gln Lys Glu Gly Met Arg Lys Gln Gly Leu Phe Gln Trp Leu Asp
```

-continued

```
                165                 170                 175
Ser Leu Gln Ile Asp Asn Leu Thr Ser Pro Asp Leu Gln Leu Thr Val
            180                 185                 190
Gly Ala Val Ile Val Glu Glu Met Arg Ala Ile Glu Arg Glu Thr
            195                 200                 205
Gly Phe Gln Cys Ser Ala Gly Ile Ser His Asn Lys Val Leu Ala Lys
210                 215                 220
Leu Ala Cys Gly Leu Asn Lys Pro Asn Arg Gln Thr Leu Val Ser His
225                 230                 235                 240
Gly Ser Val Pro Gln Leu Phe Ser Gln Met Pro Ile Arg Lys Ile Arg
                245                 250                 255
Ser Leu Gly Gly Lys Leu Gly Ala Ser Val Ile Glu Ile Leu Gly Ile
                260                 265                 270
Glu Tyr Met Gly Glu Leu Thr Gln Phe Thr Glu Ser Gln Leu Gln Ser
            275                 280                 285
His Phe Gly Glu Lys Asn Gly Ser Trp Leu Tyr Ala Met Cys Arg Gly
            290                 295                 300
Ile Glu His Asp Pro Val Lys Pro Arg Gln Leu Pro Lys Thr Ile Gly
305                 310                 315                 320
Cys Ser Lys Asn Phe Pro Gly Lys Thr Ala Leu Ala Thr Arg Glu Gln
                325                 330                 335
Val Gln Trp Trp Leu Leu Gln Leu Ala Gln Glu Leu Glu Glu Arg Leu
            340                 345                 350
Thr Lys Asp Arg Asn Asp Asn Asp Arg Val Ala Thr Gln Leu Val Val
            355                 360                 365
Ser Ile Arg Val Gln Gly Asp Lys Arg Leu Ser Ser Leu Arg Arg Cys
            370                 375                 380
Cys Ala Leu Thr Arg Tyr Asp Ala His Lys Met Ser His Asp Ala Phe
385                 390                 395                 400
Thr Val Ile Lys Asn Cys Asn Thr Ser Gly Ile Gln Thr Glu Trp Ser
                405                 410                 415
Pro Pro Leu Thr Met Leu Phe Leu Cys Ala Thr Lys Phe Ser Ala Ser
            420                 425                 430
Ala Pro Ser Ser Ser Thr Asp Ile Thr Ser Phe Leu Ser Ser Asp Pro
            435                 440                 445
Ser Ser Leu Pro Lys Val Pro Val Thr Ser Ser Glu Ala Lys Thr Gln
450                 455                 460
Gly Ser Gly Pro Ala Val Thr Ala Thr Lys Lys Ala Thr Thr Ser Leu
465                 470                 475                 480
Glu Ser Phe Phe Gln Lys Ala Ala Glu Arg Gln Lys Val Lys Glu Ala
                485                 490                 495
Ser Leu Ser Ser Leu Thr Ala Pro Thr Gln Ala Pro Met Ser Asn Ser
            500                 505                 510
Pro Ser Lys Pro Ser Leu Pro Phe Gln Thr Ser Gln Ser Thr Gly Thr
            515                 520                 525
Glu Pro Phe Phe Lys Gln Lys Ser Leu Leu Leu Lys Gln Lys Gln Leu
            530                 535                 540
Asn Asn Ser Ser Val Ser Ser Pro Gln Gln Asn Pro Trp Ser Asn Cys
545                 550                 555                 560
Lys Ala Leu Pro Asn Ser Leu Pro Thr Glu Tyr Pro Gly Cys Val Pro
                565                 570                 575
Val Cys Glu Gly Val Ser Lys Leu Glu Glu Ser Ser Lys Ala Thr Pro
            580                 585                 590
```

```
Ala Glu Met Asp Leu Ala His Asn Ser Gln Ser Met His Ala Ser Ser
        595                 600                 605

Ala Ser Lys Ser Val Leu Glu Val Thr Gln Lys Ala Thr Pro Asn Pro
610                 615                 620

Ser Leu Leu Ala Ala Glu Asp Gln Val Pro Cys Glu Lys Cys Gly Ser
625                 630                 635                 640

Leu Val Pro Val Trp Asp Met Pro Glu His Met Asp Tyr His Phe Ala
            645                 650                 655

Leu Glu Leu Gln Lys Ser Phe Leu Gln Pro His Ser Ser Asn Pro Gln
            660                 665                 670

Val Val Ser Ala Val Ser His Gln Gly Lys Arg Asn Pro Lys Ser Pro
            675                 680                 685

Leu Ala Cys Thr Asn Lys Arg Pro Arg Pro Glu Gly Met Gln Thr Leu
        690                 695                 700

Glu Ser Phe Phe Lys Pro Leu Thr His
705                 710
```

<210> SEQ ID NO 32
<211> LENGTH: 1870
<212> TYPE: DNA
<213> ORGANISM: Homo sapiens

<400> SEQUENCE: 32

```
ctccgagacg ggtggggccg gagctccaag ctggtttgaa caagccctgg gcatgtttgg      60
cgggaagttg gcttagctcg gctacctgtg gccccgcagt tttgtagtcc ccgccttgtt     120
tctccccaga ggcctctcaa tcctccctcc atgatcttcg catagagcac agtacccctt     180
cacacgagg acgcgatggc tcccaagaaa cgcccagaaa cccagaagac ctccgagatt     240
gtattacgcc ccaggaacaa gaggagcagg agtcccctgg agctggagcc cgaggccaag     300
aagctctgtg cgaagggctc cggtcctagc agaagatgtg actcagactg cctctgggtg     360
gggctggctg gcccacagat cctgccacca tgccgcagca tcgtcaggac cctccaccag     420
cataagctgg gcagagcttc ctggccatct gtccagcagg ggctccagca gtccttttgt     480
cacactctgg attcttaccg gatattacaa aaggctgccc cctttgacag agggctacat     540
tccttggcgt ggcacccaac tcaccccagc accgtggctg tgggttccaa agggggagat     600
atcatgctct ggaattttgg catcaaggac aaacccacct tcatcaaagg gattggagct     660
ggagggagca tcactgggct gaagtttaac cctctcaata ccaaccagtt ttacgcctcc     720
tcaatggagg gaacaactag gctgcaagac tttaaaggca acattctacg agttttttgcc     780
agctcagaca ccatcaacat ctggttttgt agcctggatg tgtctgctag tagccgaatg     840
gtggtcacag agacaacgt ggggaacgtg atcctgctga acatggacgg caaagagctt     900
tggaatctca gaatgcacaa aaagaaagtg acgcatgtgg ccctgaaccc atgctgtgat     960
tggttcctgg ccacagcctc cgtagatcaa acagtgaaaa tttggacct cgccaggtt    1020
agagggaaag ccagcttcct ctactcgctg ccgcacaggc atcctgtcaa cgcagcttgt    1080
ttcagtcccg atggagcccg gctcctgacc acggaccaga gagcgagat ccgagtttac    1140
tctgcttccc agtgggactg ccccctgggc ctgatcccgc accctcaccg tcacttccag    1200
cacctcacac ccatcaaggc agcctggcat cctcgctaca acctcattgt tgtgggccga    1260
tacccagatc ctaatttcaa aagttgtacc ccttatgaat tgaggacgat cgacgtgttc    1320
gatggaaact cagggaagat gatgtgtcag ctctatgacc cagaatcttc tggcatcagt    1380
```

-continued

```
tcgcttaatg aattcaatcc catggggac acgctggcct ctgcaatggg ttaccacatt    1440
ctcatctgga gccaggagga agccaggaca cggaagtgag agacactaaa gaaggtgtgg  1500
gccagacaag gccttggagc ccacacatgg gatcaagtcc tgcaagcaga ggtggcgatt  1560
tgttaaaggg ccaaaagtat ccaaggttag ggttggagca ggggtgctgg gacctggggc  1620
actgtgggac tgggacactt ttatgttaat gctctggact tgcctccaga gactgctcca  1680
gagttggtga cacagctgtc ccaagggccc ctctgtatct agcctggaac caaggttatc  1740
ttggaactaa atgactttc tcctctcagt gggtggtagc agagggatca agcagttatt   1800
tgatttgtgc tcactttga tatggccaat aaaaccatac cgactgagaa aaaaaaaaa    1860
aaaaaaaaaa                                                        1870
```

<210> SEQ ID NO 33
<211> LENGTH: 427
<212> TYPE: PRT
<213> ORGANISM: Homo sapiens

<400> SEQUENCE: 33

```
Met Ala Pro Lys Lys Arg Pro Glu Thr Gln Lys Thr Ser Glu Ile Val
1               5                   10                  15

Leu Arg Pro Arg Asn Lys Arg Ser Arg Ser Pro Leu Glu Leu Glu Pro
                20                  25                  30

Glu Ala Lys Lys Leu Cys Ala Lys Gly Ser Gly Pro Ser Arg Arg Cys
            35                  40                  45

Asp Ser Asp Cys Leu Trp Val Gly Leu Ala Gly Pro Gln Ile Leu Pro
        50                  55                  60

Pro Cys Arg Ser Ile Val Arg Thr Leu His Gln His Lys Leu Gly Arg
65                  70                  75                  80

Ala Ser Trp Pro Ser Val Gln Gln Gly Leu Gln Gln Ser Phe Leu His
                85                  90                  95

Thr Leu Asp Ser Tyr Arg Ile Leu Gln Lys Ala Ala Pro Phe Asp Arg
                100                 105                 110

Arg Ala Thr Ser Leu Ala Trp His Pro Thr His Pro Ser Thr Val Ala
            115                 120                 125

Val Gly Ser Lys Gly Gly Asp Ile Met Leu Trp Asn Phe Gly Ile Lys
        130                 135                 140

Asp Lys Pro Thr Phe Ile Lys Gly Ile Gly Ala Gly Gly Ser Ile Thr
145                 150                 155                 160

Gly Leu Lys Phe Asn Pro Leu Asn Thr Asn Gln Phe Tyr Ala Ser Ser
                165                 170                 175

Met Glu Gly Thr Thr Arg Leu Gln Asp Phe Lys Gly Asn Ile Leu Arg
            180                 185                 190

Val Phe Ala Ser Ser Asp Thr Ile Asn Ile Trp Phe Cys Ser Leu Asp
        195                 200                 205

Val Ser Ala Ser Ser Arg Met Val Val Thr Gly Asp Asn Val Gly Asn
    210                 215                 220

Val Ile Leu Leu Asn Met Asp Gly Lys Glu Leu Trp Asn Leu Arg Met
225                 230                 235                 240

His Lys Lys Lys Val Thr His Val Ala Leu Asn Pro Cys Cys Asp Trp
                245                 250                 255

Phe Leu Ala Thr Ala Ser Val Asp Gln Thr Val Lys Ile Trp Asp Leu
            260                 265                 270

Arg Gln Val Arg Gly Lys Ala Ser Phe Leu Tyr Ser Leu Pro His Arg
        275                 280                 285
```

```
His Pro Val Asn Ala Ala Cys Phe Ser Pro Asp Gly Ala Arg Leu Leu
    290                 295                 300
Thr Thr Asp Gln Lys Ser Glu Ile Arg Val Tyr Ser Ala Ser Gln Trp
305                 310                 315                 320
Asp Cys Pro Leu Gly Leu Ile Pro His Pro His Arg His Phe Gln His
                325                 330                 335
Leu Thr Pro Ile Lys Ala Ala Trp His Pro Arg Tyr Asn Leu Ile Val
            340                 345                 350
Val Gly Arg Tyr Pro Asp Pro Asn Phe Lys Ser Cys Thr Pro Tyr Glu
        355                 360                 365
Leu Arg Thr Ile Asp Val Phe Asp Gly Asn Ser Gly Lys Met Met Cys
    370                 375                 380
Gln Leu Tyr Asp Pro Glu Ser Ser Gly Ile Ser Ser Leu Asn Glu Phe
385                 390                 395                 400
Asn Pro Met Gly Asp Thr Leu Ala Ser Ala Met Gly Tyr His Ile Leu
                405                 410                 415
Ile Trp Ser Gln Glu Glu Ala Arg Thr Arg Lys
            420                 425

<210> SEQ ID NO 34
<211> LENGTH: 1542
<212> TYPE: DNA
<213> ORGANISM: Homo sapiens
<400> SEQUENCE: 34
atgtctcggg agtcggatgt tgaggctcag cagtctcatg cagcagtgc ctgttcacag      60
ccccatggca gcgttaccca gtcccaaggc tcctcctcac agtcccaggg catatccagc    120
tcctctacca gcacgatgcc aaactccagc cagtcctctc actccagctc tgggacactg    180
agctccttag agacagtgtc cactcaggaa ctctattcta ttcctgagga ccaagaacct    240
gaggaccaag aacctgagga gcctaccct gccccctggg ctcgattatg ggcccttcag    300
gatggatttg ccaatcttga atgtgtgaat gacaactact ggtttgggag ggacaaaagc    360
tgtgaatatt gctttgatga accactgctg aaaagaacag ataaataccg aacatacagc    420
aagaaacact ttcggatttt cagggaagtg ggtcctaaaa actcttacat tgcatacata    480
gaagatcaca gtggcaatgg aacctttgta aatacagagc ttgtagggaa aggaaaacgc    540
cgtcctttga taacaattc tgaaattgca ctgtcactaa gcagaaataa agttttgtc     600
ttttttgatc tgactgtaga tgatcagtca gtttatccta aggcattaag agatgaatac    660
atcatgtcaa aaactcttgg aagtggtgcc tgtggagagg taaagctggc tttcgagagg    720
aaaacatgta agaaagtagc cataaagatc atcagcaaaa ggaagtttgc tattggttca    780
gcaagagagg cagacccagc tctcaatgtt gaaacagaaa tagaaatttt gaaaagcta    840
aatcatcctt gcatcatcaa gattaaaaac tttttgatg cagaagatta ttatattgtt    900
ttggaattga tggaaggggg agagctgttt gacaaagtgg tggggaataa acgcctgaaa    960
gaagctacct gcaagctcta ttttaccag atgctcttgg ctgtgcagat tactgatttt   1020
gggcactcca agattttggg agagacctct ctcatgagaa ccttatgtgg aacccccacc   1080
tacttggcgc ctgaagttct gtttctgtt gggactgctg gtataaccg tgctgtggac   1140
tgctggagtt aggagttat tctttttatc tgccttagtg ggtatccacc tttctctgag   1200
cataggacte aagtgtcact gaaggatcag atcaccagtg aaaatacaa cttcattcct   1260
gaagtctggg cagaagtctc agagaaagct ctggaccttg tcaagaagtt gttggtagtg   1320
```

-continued

```
gatccaaagg cacgttttac gacagaagaa gccttaagac acccgtggct tcaggatgaa    1380
gacatgaaga gaaagtttca agatcttctg tctgaggaaa atgaatccac agctctaccc    1440
caggttctag cccagccttc tactagtcga aagcggcccc gtgaagggga agccgagggt    1500
gccgagacca caaagcgccc agctgtgtgt gctgctgtgt tg                        1542
```

<210> SEQ ID NO 35
<211> LENGTH: 514
<212> TYPE: PRT
<213> ORGANISM: Homo sapiens

<400> SEQUENCE: 35

```
Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
                20                  25                  30

Ser Gln Ser Gln Gly Ile Ser Ser Ser Thr Ser Thr Met Pro Asn
            35                  40                  45

Ser Ser Gln Ser Ser His Ser Ser Ser Gly Thr Leu Ser Ser Leu Glu
        50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Cys Val Asn Asp Asn
            100                 105                 110

Tyr Trp Phe Gly Arg Asp Lys Ser Cys Glu Tyr Cys Phe Asp Glu Pro
        115                 120                 125

Leu Leu Lys Arg Thr Asp Lys Tyr Arg Thr Tyr Ser Lys Lys His Phe
    130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190

Leu Ser Arg Asn Lys Val Phe Val Phe Phe Asp Leu Thr Val Asp Asp
        195                 200                 205

Gln Ser Val Tyr Pro Lys Ala Leu Arg Asp Glu Tyr Ile Met Ser Lys
    210                 215                 220

Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ile Ser Lys Arg Lys Phe
                245                 250                 255

Ala Ile Gly Ser Ala Arg Glu Ala Asp Pro Ala Leu Asn Val Glu Thr
            260                 265                 270

Glu Ile Glu Ile Leu Lys Lys Leu Asn His Pro Cys Ile Ile Lys Ile
        275                 280                 285

Lys Asn Phe Phe Asp Ala Glu Asp Tyr Tyr Ile Val Leu Glu Leu Met
    290                 295                 300

Glu Gly Gly Glu Leu Phe Asp Lys Val Val Gly Asn Lys Arg Leu Lys
305                 310                 315                 320

Glu Ala Thr Cys Lys Leu Tyr Phe Tyr Gln Met Leu Leu Ala Val Gln
                325                 330                 335
```

-continued

```
Ile Thr Asp Phe Gly His Ser Lys Ile Leu Gly Glu Thr Ser Leu Met
                340                 345                 350

Arg Thr Leu Cys Gly Thr Pro Thr Tyr Leu Ala Pro Glu Val Leu Val
            355                 360                 365

Ser Val Gly Thr Ala Gly Tyr Asn Arg Ala Val Asp Cys Trp Ser Leu
    370                 375                 380

Gly Val Ile Leu Phe Ile Cys Leu Ser Gly Tyr Pro Pro Phe Ser Glu
385                 390                 395                 400

His Arg Thr Gln Val Ser Leu Lys Asp Gln Ile Thr Ser Gly Lys Tyr
                405                 410                 415

Asn Phe Ile Pro Glu Val Trp Ala Glu Val Ser Glu Lys Ala Leu Asp
            420                 425                 430

Leu Val Lys Lys Leu Leu Val Val Asp Pro Lys Ala Arg Phe Thr Thr
    435                 440                 445

Glu Glu Ala Leu Arg His Pro Trp Leu Gln Asp Glu Asp Met Lys Arg
450                 455                 460

Lys Phe Gln Asp Leu Leu Ser Glu Glu Asn Glu Ser Thr Ala Leu Pro
465                 470                 475                 480

Gln Val Leu Ala Gln Pro Ser Thr Ser Arg Lys Arg Pro Arg Glu Gly
                485                 490                 495

Glu Ala Glu Gly Ala Glu Thr Thr Lys Arg Pro Ala Val Cys Ala Ala
            500                 505                 510

Val Leu
```

```
<210> SEQ ID NO 36
<211> LENGTH: 1632
<212> TYPE: DNA
<213> ORGANISM: Homo sapiens

<400> SEQUENCE: 36
```

| | | | | | |
|---|---|---|---|---|---|
| atgtctcggg | agtcggatgt | tgaggctcag | cagtctcatg | gcagcagtgc | ctgttcacag | 60 |
| ccccatggca | gcgttaccca | gtcccaaggc | tcctcctcac | agtcccaggg | catatccagc | 120 |
| tcctctacca | gcacgatgcc | aaactccagc | cagtcctctc | actccagctc | tgggacactg | 180 |
| agctccttag | agacagtgtc | cactcaggaa | ctctattcta | ttcctgagga | ccaagaacct | 240 |
| gaggaccaag | agcctgagga | gcctacccct | gcccccctggg | ctcgattatg | ggcccttcag | 300 |
| gatggatttg | ccaatcttga | atgtgtgaat | gacaactact | ggtttgggag | ggacaaaagc | 360 |
| tgtgaatatt | gctttgatga | ccactgctg | aaaagaacag | ataaataccg | aacatacagc | 420 |
| aagaaacact | tcggatttt | cagggaagtg | ggtcctaaaa | actcttacat | tgcatacata | 480 |
| gaagatcaca | gtggcaatgg | aacctttgta | aatacagagc | ttgtagggaa | aggaaaacgc | 540 |
| cgtcctttga | ataacaattc | tgaaattgca | ctgtcactaa | gcagaaataa | agttttttgtc | 600 |
| ttttttgatc | tgactgtaga | tgatcagtca | gtttatccta | aggcattaag | agatgaatac | 660 |
| atcatgtcaa | aaactcttgg | aagtggtgcc | tgtggagagg | taaagctggc | tttcgagagg | 720 |
| aaaacatgta | agaaagtagc | cataaagatc | atcagcaaaa | ggaagtttgc | tattggttca | 780 |
| gcaagagagg | cagacccagc | tctcaatgtt | gaaacagaaa | tagaaatttt | gaaaagcta | 840 |
| aatcatcctt | gcatcatcaa | gattaaaaac | ttttttgatg | cagaagatta | ttatattgtt | 900 |
| ttggaattga | tggaagggg | agagctgttt | gacaaagtgg | tggggaataa | acgcctgaaa | 960 |
| gaagctacct | gcaagctcta | ttttaccag | atgctcttgg | ctgtgcagta | ccttcatgaa | 1020 |
| aacggtatta | tacaccgtga | cttaaagcca | gagaatgttt | tactgtcatc | tcaagaagag | 1080 |

-continued

```
gactgtctta taaagattac tgattttggg cactccaaga ttttgggaga gacctctctc    1140
atgagaacct tatgtggaac ccccacctac ttggcgcctg aagttcttgt ttctgttggg    1200
actgctgggt ataaccgtgc tgtggactgc tggagtttag gagttattct ttttatctgc    1260
cttagtgggt atccaccttt ctctgagcat aggactcaag tgtcactgaa ggatcagatc    1320
accagtggaa atacaactt cattcctgaa gtctgggcag aagtctcaga gaaagctctg     1380
gaccttgtca gaagttgtt ggtagtggat ccaaaggcac gttttacgac agaagaagcc    1440
ttaagacacc cgtggcttca ggatgaagac atgaagagaa agtttcaaga tcttctgtct    1500
gaggaaaatg aatccacagc tctaccccag gttctagccc agccttctac tagtcgaaag    1560
cggccccgtg aagggaagc cgagggtgcc gagaccacaa agcgcccagc tgtgtgtgct     1620
gctgtgttgt ga                                                       1632
```

<210> SEQ ID NO 37
<211> LENGTH: 543
<212> TYPE: PRT
<213> ORGANISM: Homo sapiens

<400> SEQUENCE: 37

```
Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Thr Ser Thr Met Pro Asn
        35                  40                  45

Ser Ser Gln Ser Ser His Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Cys Val Asn Asp Asn
            100                 105                 110

Tyr Trp Phe Gly Arg Asp Lys Ser Cys Glu Tyr Cys Phe Asp Glu Pro
        115                 120                 125

Leu Leu Lys Arg Thr Asp Lys Tyr Arg Thr Tyr Ser Lys Lys His Phe
    130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190

Leu Ser Arg Asn Lys Val Phe Val Phe Phe Asp Leu Thr Val Asp Asp
        195                 200                 205

Gln Ser Val Tyr Pro Lys Ala Leu Arg Asp Glu Tyr Ile Met Ser Lys
    210                 215                 220

Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ile Ser Lys Arg Lys Phe
                245                 250                 255

Ala Ile Gly Ser Ala Arg Glu Ala Asp Pro Ala Leu Asn Val Glu Thr
            260                 265                 270
```

```
Glu Ile Glu Ile Leu Lys Lys Leu Asn His Pro Cys Ile Ile Lys Ile
            275                 280                 285

Lys Asn Phe Phe Asp Ala Glu Asp Tyr Tyr Ile Val Leu Glu Leu Met
        290                 295                 300

Glu Gly Gly Glu Leu Phe Asp Lys Val Val Gly Asn Lys Arg Leu Lys
305                 310                 315                 320

Glu Ala Thr Cys Lys Leu Tyr Phe Tyr Gln Met Leu Leu Ala Val Gln
                325                 330                 335

Tyr Leu His Glu Asn Gly Ile Ile His Arg Asp Leu Lys Pro Glu Asn
            340                 345                 350

Val Leu Leu Ser Ser Gln Glu Asp Cys Leu Ile Lys Ile Thr Asp
        355                 360                 365

Phe Gly His Ser Lys Ile Leu Gly Glu Thr Ser Leu Met Arg Thr Leu
    370                 375                 380

Cys Gly Thr Pro Thr Tyr Leu Ala Pro Glu Val Leu Val Ser Val Gly
385                 390                 395                 400

Thr Ala Gly Tyr Asn Arg Ala Val Asp Cys Trp Ser Leu Gly Val Ile
                405                 410                 415

Leu Phe Ile Cys Leu Ser Gly Tyr Pro Pro Phe Ser Glu His Arg Thr
        420                 425                 430

Gln Val Ser Leu Lys Asp Gln Ile Thr Ser Gly Lys Tyr Asn Phe Ile
    435                 440                 445

Pro Glu Val Trp Ala Glu Val Ser Glu Lys Ala Leu Asp Leu Val Lys
450                 455                 460

Lys Leu Leu Val Val Asp Pro Lys Ala Arg Phe Thr Thr Glu Glu Ala
465                 470                 475                 480

Leu Arg His Pro Trp Leu Gln Asp Glu Asp Met Lys Arg Lys Phe Gln
                485                 490                 495

Asp Leu Leu Ser Glu Glu Asn Glu Ser Thr Ala Leu Pro Gln Val Leu
        500                 505                 510

Ala Gln Pro Ser Thr Ser Arg Lys Arg Pro Arg Glu Gly Glu Ala Glu
    515                 520                 525

Gly Ala Glu Thr Thr Lys Arg Pro Ala Val Cys Ala Ala Val Leu
530                 535                 540
```

<210> SEQ ID NO 38
<211> LENGTH: 1976
<212> TYPE: DNA
<213> ORGANISM: Homo sapiens

<400> SEQUENCE: 38

```
gcaggtttag cgccactctg ctggctgagg ctgcggagag tgtgcggctc caggtgggct      60
cacgcggtcg tgatgtctcg ggagtcggat gttgaggctc agcagtctca tggcagcagt     120
gcctgttcac agcccatgg cagcgttacc cagtcccaag ctcctcctc acagtcccag      180
ggcatatcca gctcctctac cagcacgatg ccaaactcca gccagtcctc tcactccagc     240
tctgggacac tgagctccct agagacagtg tccactcagg aactctattc tattcctgag     300
gaccaagaac ctgaggacca agaacctgag gagcctaccc ctgcccctg ggctcgatta      360
tgggccttc aggatggatt tgccaatctt gaatgtgtga atgacaacta ctggtttggg     420
agggacaaaa gctgtgaata ttgctttgat gaaccactgc tgaaaagaac agataaatac     480
cgaacataca gcaagaaaca ctttcggatt ttcagggaag tgggtcctaa aaactcttac     540
attgcataca tagaagatca cagtggcaat ggaacctttg taaatacaga gcttgtaggg     600
```

```
aaaggaaaac gccgtccttt gaataacaat tctgaaattg cactgtcact aagcagaaat    660
aaagagaaaa tacttaaaat ctactctctc agctgatttt caaaaatacg gcggggcgcg    720
gtggctcacg tctttaatcc cagcactttg ggaggccgag gctggcagat cacctgagtt    780
tttgtctttt ttgatctgac tgtagatgat cagtcagttt atcctaaggc attaagagat    840
gaatacatca tgtcaaaaac tcttggaagt ggtgcctgtg agaggtaaa gctggctttc     900 gagaggaaaa catgtaagaa agtagccata aagatcatca gcaaaaggaa gtttgctatt    960
ggttcagcaa gagaggcaga cccagctctc aatgttgaaa cagaaataga aattttgaaa   1020
aagctaaatc atccttgcat catcaagatt aaaaactttt ttgatgcaga agattattat   1080
attgttttgg aattgatgga agggggagag ctgtttgaca aagtggtggg gaataaacgc   1140
ctgaaagaag ctacctgcaa gctctatttt taccagatgc tcttggctgt gcagtacctt   1200
catgaaaacg gtattataca ccgtgactta aagccagaga atgttttact gtcatctcaa   1260
gaagaggact gtcttataaa gattactgat tttgggcact ccaagatttt gggagagacc   1320
tctctcatga gaaccttatg tggaaccccc acctacttgg cgcctgaagt tcttgtttct   1380
gttgggactg ctgggtataa ccgtgctgtg gactgctgga gtttaggagt tattcttttt   1440
atctgcctta gtgggtatcc accttctctc tgagcatagga ctcaagtgtc actgaaggat   1500
cagatcacca gtggaaaata caacttcatt cctgaagtct gggcagaagt ctcagagaaa   1560
gctctggacc ttgtcaagaa gttgttggta gtggatccaa aggcacgttt tacgacagaa   1620
gaagccttaa gacacccgtg gcttcaggat gaagacatga agagaaagtt tcaagatctt   1680
ctgtctgagg aaaatgaatc cacagctcta ccccaggttc tagcccagcc ttctactagt   1740
cgaaagcggc cccgtgaagg ggaagccgag ggtgccgaga ccacaaagcg cccagctgtg   1800
tgtgctgctg tgttgtgaac tccgtggttt gaacacgaaa gaaatgtacc ttctttcact   1860
ctgtcatctt tcttttcttt gagtctgttt ttttatagtt tgtattttaa ttatgggaat   1920
aattgctttt tcacagtcac tgatgtacaa ttaaaaacct gatggaacct ggaaaa       1976
```

<210> SEQ ID NO 39
<211> LENGTH: 322
<212> TYPE: PRT
<213> ORGANISM: Homo sapiens

<400> SEQUENCE: 39

```
Met Ser Lys Thr Leu Gly Ser Gly Ala Cys Gly Glu Val Lys Leu Ala
1               5                   10                  15

Phe Glu Arg Lys Thr Cys Lys Lys Val Ala Ile Lys Ile Ile Ser Lys
            20                  25                  30

Arg Lys Phe Ala Ile Gly Ser Ala Arg Glu Ala Asp Pro Ala Leu Asn
        35                  40                  45

Val Glu Thr Glu Ile Glu Ile Leu Lys Lys Leu Asn His Pro Cys Ile
    50                  55                  60

Ile Lys Ile Lys Asn Phe Phe Asp Ala Glu Asp Tyr Tyr Ile Val Leu
65                  70                  75                  80

Glu Leu Met Glu Gly Gly Glu Leu Phe Asp Lys Val Val Gly Asn Lys
                85                  90                  95

Arg Leu Lys Glu Ala Thr Cys Lys Leu Tyr Phe Tyr Gln Met Leu Leu
            100                 105                 110

Ala Val Gln Tyr Leu His Glu Asn Gly Ile Ile His Arg Asp Leu Lys
        115                 120                 125
```

```
Pro Glu Asn Val Leu Leu Ser Ser Gln Glu Glu Asp Cys Leu Ile Lys
    130                 135                 140
Ile Thr Asp Phe Gly His Ser Lys Ile Leu Gly Glu Thr Ser Leu Met
145                 150                 155                 160
Arg Thr Leu Cys Gly Thr Pro Thr Tyr Leu Ala Pro Glu Val Leu Val
                165                 170                 175
Ser Val Gly Thr Ala Gly Tyr Asn Arg Ala Val Asp Cys Trp Ser Leu
            180                 185                 190
Gly Val Ile Leu Phe Ile Cys Leu Ser Gly Tyr Pro Pro Phe Ser Glu
        195                 200                 205
His Arg Thr Gln Val Ser Leu Lys Asp Gln Ile Thr Ser Gly Lys Tyr
    210                 215                 220
Asn Phe Ile Pro Glu Val Trp Ala Glu Val Ser Glu Lys Ala Leu Asp
225                 230                 235                 240
Leu Val Lys Lys Leu Leu Val Val Asp Pro Lys Ala Arg Phe Thr Thr
                245                 250                 255
Glu Glu Ala Leu Arg His Pro Trp Leu Gln Asp Glu Asp Met Lys Arg
            260                 265                 270
Lys Phe Gln Asp Leu Leu Ser Glu Glu Asn Glu Ser Thr Ala Leu Pro
        275                 280                 285
Gln Val Leu Ala Gln Pro Ser Thr Ser Arg Lys Arg Pro Arg Glu Gly
    290                 295                 300
Glu Ala Glu Gly Ala Glu Thr Thr Lys Arg Pro Ala Val Cys Ala Ala
305                 310                 315                 320
Val Leu

<210> SEQ ID NO 40
<211> LENGTH: 888
<212> TYPE: DNA
<213> ORGANISM: Homo sapiens

<400> SEQUENCE: 40
tcacgtgacc cgggcgcgct gcggccgccc gcgcggaccc ggcgagaggc ggcggcggga       60
gcggcggtga tggacgggtc cggggagcag cccagaggcg gggggcccac cagctctgag      120
cagatcatga agacaggggc ccttttgctt cagggtttca tccaggatcg agcagggcga      180
atgggggggg aggcacccga gctggccctg gaccgggtgc ctcaggatgc gtccaccaag      240
aagctgagcg agtgtctcaa gcgcatcggg gacgaactgg acagtaacat ggagctgcag      300
aggatgattg ccgccgtgga cacagactcc ccccgagagg tcttttttcg agtggcagct      360
gacatgtttt ctgacggcaa cttcaactgg ggccgggttg tcgcccttt ctactttgcc       420
agcaaactgg tgctcaaggc cctgtgcacc aaggtgccgg aactgatcag accatcatg       480
ggctggacat tggacttcct ccgggagcgg ctgttgggct ggatccaaga ccagggtggt      540
tgggacggcc tcctctccta ctttgggacg cccacgtggc agaccgtgac catctttgtg      600
gcgggagtgc tcaccgcctc actcaccatc tggaagaaga tgggctgagg cccccagctg      660
ccttggactg tgttttttcct ccataaaatta tggcattttt ctgggagggg tggggattgg     720
gggacgtggg cattttttctt actttttgtaa ttattggggg gtgtgtggaa gagtggtctt      780
gagggggtaa taaacctcct tcgggacaca aaaaaaaaaa aaaaaaaaaa aaaaaaaaaa      840
aaaaaaaaaa aaaaaaaaaa aaaaaaaaaa aaaaaaaaaa aaaaaaaa                   888

<210> SEQ ID NO 41
<211> LENGTH: 192
```

<212> TYPE: PRT
<213> ORGANISM: Homo sapiens

<400> SEQUENCE: 41

```
Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
                180                 185                 190
```

<210> SEQ ID NO 42
<211> LENGTH: 891
<212> TYPE: DNA
<213> ORGANISM: Homo sapiens

<400> SEQUENCE: 42

```
tcacgtgacc cgggcgcgct gcggccgccc gcgcggaccc ggcgagaggc ggcggcggga      60
gcggcggtga tggacgggtc cggggagcag cccagaggcg gggggcccac cagctctgag     120
cagatcatga agacaggggc cttttgctt cagggtttca tccaggatcg agcagggcga     180
atgggggggg aggcacccga gctggccctg gacccggtgc ctcaggatgc gtccaccaag     240
aagctgagcg agtgtctcaa gcgcatcggg gacgaactgg acagtaacat ggagctgcag     300
aggatgattg ccgccgtgga cacagactcc ccccgagagg tcttttttccg agtggcagct     360
gacatgtttt ctgacggcaa cttcaactgg ggcgggttg tcgccctttt ctactttgcc     420
agcaaactgg tgctcaaggc cctgtgcacc aaggtgccgg aactgatcag aaccatcatg     480
ggctggacat ggacttcct ccgggagcgg ctgttgggct ggatccaaga ccagggtggt     540
tgggtgagac tcctcaagcc tcctcacccc caccaccgcg ccctcaccac cgcccctgcc     600
ccaccgtccc tgcccccgc cactcctctg ggaccctggg ccttctggag caggtcacag     660
tggtgccctc tccccatctt cagatcatca gatgtggtct ataatgcgtt ttccttacgt     720
gtctgatcaa tccccgattc atctaccctg ctgacctccc agtgacccct gacctcactg     780
tgaccttgac ttgattagtg ccttctgccc tccctggagc ctccactgcc tctggaattg     840
ctcaagttca ttgatgaccc tctgacccta gctctttcct ttttttttttt t            891
```

<210> SEQ ID NO 43
<211> LENGTH: 218
<212> TYPE: PRT
<213> ORGANISM: Homo sapiens

<400> SEQUENCE: 43

```
Met Asp Gly Ser Gly Glu Gln Pro Arg Gly Gly Pro Thr Ser Ser
 1               5                  10                  15

Glu Gln Ile Met Lys Thr Gly Ala Leu Leu Leu Gln Gly Phe Ile Gln
                 20                  25                  30

Asp Arg Ala Gly Arg Met Gly Gly Glu Ala Pro Glu Leu Ala Leu Asp
             35                  40                  45

Pro Val Pro Gln Asp Ala Ser Thr Lys Lys Leu Ser Glu Cys Leu Lys
         50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                 85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
        130                 135                 140

Arg Glu Arg Leu Leu Gly Trp Ile Gln Asp Gln Gly Gly Trp Val Arg
145                 150                 155                 160

Leu Leu Lys Pro Pro His Pro His His Arg Ala Leu Thr Thr Ala Pro
                165                 170                 175

Ala Pro Pro Ser Leu Pro Pro Ala Thr Pro Leu Gly Pro Trp Ala Phe
            180                 185                 190

Trp Ser Arg Ser Gln Trp Cys Pro Leu Pro Ile Phe Arg Ser Ser Asp
            195                 200                 205

Val Val Tyr Asn Ala Phe Ser Leu Arg Val
        210                 215
```

<210> SEQ ID NO 44
<211> LENGTH: 741
<212> TYPE: DNA
<213> ORGANISM: Homo sapiens

<400> SEQUENCE: 44

```
tcacgtgacc cgggcgcgct gcggccgccc gcgcggaccc ggcgagaggc ggcggcggga    60
gcggcggtga tggacgggtc cggggagcag cccagaggcg gggggcccac cagctctgag   120
cagatcatga agacaggggc ccttttgctt caggggatga ttgccgccgt ggacacagac   180
tcccccgag  aggtcttttt ccgagtggca gctgacatgt tttctgacgg caacttcaac   240
tggggccggg ttgtcgccct tttctacttt gccagcaaac tggtgctcaa ggccctgtgc   300
accaaggtgc cggaactgat cagaaccatc atgggctgga cattggactt cctccgggag   360
cggctgttgg gctggatcca agaccagggt ggttggacg  gcctcctctc ctactttggg   420
acgcccacgt ggcagaccgt gaccatcttt gtggcgggag tgctcaccgc ctcactcacc   480
atctggaaga gatgggctg  aggcccccag ctgccttgga ctgtgttttt cctccataaa   540
ttatggcatt tttctgggag gggtggggat tggggacgt  gggcattttt cttacttttg   600
taattattgg ggggtgtggg gaagagtggt cttgaggggg taataaacct ccttcgggac   660
```

```
acaaaaaaaa aaaaaaaaaa aaaaaaaaaa aaaaaaaaaa aaaaaaaaaa aaaaaaaaaa        720
aaaaaaaaaa aaaaaaaaaa a                                                  741

<210> SEQ ID NO 45
<211> LENGTH: 143
<212> TYPE: PRT
<213> ORGANISM: Homo sapiens

<400> SEQUENCE: 45

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Met Ile Ala
                20                  25                  30

Ala Val Asp Thr Asp Ser Pro Arg Glu Val Phe Phe Arg Val Ala Ala
                35                  40                  45

Asp Met Phe Ser Asp Gly Asn Phe Asn Trp Gly Arg Val Val Ala Leu
            50                  55                  60

Phe Tyr Phe Ala Ser Lys Leu Val Leu Lys Ala Leu Cys Thr Lys Val
65              70                  75                  80

Pro Glu Leu Ile Arg Thr Ile Met Gly Trp Thr Leu Asp Phe Leu Arg
                85                  90                  95

Glu Arg Leu Leu Gly Trp Ile Gln Asp Gln Gly Gly Trp Asp Gly Leu
                100                 105                 110

Leu Ser Tyr Phe Gly Thr Pro Thr Trp Gln Thr Val Thr Ile Phe Val
            115                 120                 125

Ala Gly Val Leu Thr Ala Ser Leu Thr Ile Trp Lys Lys Met Gly
        130                 135                 140

<210> SEQ ID NO 46
<211> LENGTH: 558
<212> TYPE: DNA
<213> ORGANISM: Homo sapiens

<400> SEQUENCE: 46
cccagaggcg gggggcccac cagctctgag cagatcatga agacaggggc ccttttgctt        60
cagggtttca tccaggatcg agcagggcga atggggggg aggcacccga gctggccctg        120
gacccggtgc ctcaggatgc gtccaccaag aagctgagcg agtgtctcaa gcgcatcggg        180
gacgaactgg acagtaacat ggagctgcag aggatgattg ccgccgtgga cacagactcc        240
ccccgagagg tctttttccg agtggcagct gacatgtttt ctgacggcaa cttcaactgg        300
ggccgggttg tcgccctttt ctactttgcc agcaaactgg tgctcaaggc cctgtgcacc        360
aaggtgccgg aactgatcag aaccatcatg ggctggacat ggacttcct ccgggagcgg        420 ctgttgggct ggatccaaga ccagggtggt tgggacggcc tcctctccta ctttgggacg        480
cccacgtggc agaccgtgac catctttgtg gcgggagtgc tcaccgcctc actcaccatc        540
tggaagaaga tgggctga                                                      558

<210> SEQ ID NO 47
<211> LENGTH: 173
<212> TYPE: PRT
<213> ORGANISM: Homo sapiens

<400> SEQUENCE: 47

Met Lys Thr Gly Ala Leu Leu Leu Gln Gly Phe Ile Gln Asp Arg Ala
1               5                   10                  15
```

Gly Arg Met Gly Gly Glu Ala Pro Glu Leu Ala Leu Asp Pro Val Pro
            20                  25                  30

Gln Asp Ala Ser Thr Lys Lys Leu Ser Glu Cys Leu Lys Arg Ile Gly
            35                  40                  45

Asp Glu Leu Asp Ser Asn Met Glu Leu Gln Arg Met Ile Ala Ala Val
50                  55                  60

Asp Thr Asp Ser Pro Arg Glu Val Phe Phe Arg Val Ala Ala Asp Met
65                  70                  75                  80

Phe Ser Asp Gly Asn Phe Asn Trp Gly Arg Val Val Ala Leu Phe Tyr
                85                  90                  95

Phe Ala Ser Lys Leu Val Leu Lys Ala Leu Cys Thr Lys Val Pro Glu
                100                 105                 110

Leu Ile Arg Thr Ile Met Gly Trp Thr Leu Asp Phe Leu Arg Glu Arg
            115                 120                 125

Leu Leu Gly Trp Ile Gln Asp Gln Gly Gly Trp Asp Gly Leu Leu Ser
        130                 135                 140

Tyr Phe Gly Thr Pro Thr Trp Gln Thr Val Thr Ile Phe Val Ala Gly
145                 150                 155                 160

Val Leu Thr Ala Ser Leu Thr Ile Trp Lys Lys Met Gly
                165                 170

<210> SEQ ID NO 48
<211> LENGTH: 3083
<212> TYPE: DNA
<213> ORGANISM: Homo sapiens

<400> SEQUENCE: 48

| | |
|---|---|
| cagaggcgcg cctggcggat ctgagtgtgt tgcccgggca gcggcgcgcg ggaccaacgc | 60 |
| aaggagcagc tgacagacga agaaaagtgc tggacaggaa gggagaattc tgacgccaac | 120 |
| atgcagcgaa gtatcatgtc attttttccac cccaagaaag agggtaaagc aaagaagcct | 180 |
| gagaaggagg catccaatag cagcagagag acggagcccc ctccaaaggc ggcactgaag | 240 |
| gagtggaatg gagtggtgtc cgagagtgac tctccggtga agaggccagg gaggaaggcg | 300 |
| gcccgggtcc tgggcagcga aggggaagag gaggatgaag cccttagccc tgctaaaggc | 360 |
| cagaagcctg ccctggactg ctcacaggtc tccccgcccc gtcctgccac atctcctgag | 420 |
| aacaatgctt ccctctctga cacctctccc atggacagtt ccccatcagg gattccgaag | 480 |
| cgtcgcacag ctcggaagca gctcccgaaa cggaccattc aggaagtcct ggaagagcag | 540 |
| agtgaggacg aggacagaga agccaagagg aagaaggagg aggaagaaga ggagaccccg | 600 |
| aaagaaagcc tcacagaggc tgaagtggca acagagaagg aaggagaaga cggggaccag | 660 |
| cccaccacgc ctcccaagcc cctaaagacc tccaaagcag agaccccgac ggaaagcgtt | 720 |
| tcagagcctg aggtggccac gaagcaggaa ctgcaggagg aggaagagca gaccaagcct | 780 |
| ccccgcagag ctcccaagac gctcagcagc ttcttcaccc ccggaagcc agcagtcaaa | 840 |
| aaagaagtga aggaagagga gccagggggct ccaggaaagg agggagctgc tgagggaccc | 900 |
| ctggatccat ctggttacaa tcctgccaag aacaactatc atcccgtgga agatgcctgc | 960 |
| tggaaaccgg gccagaaggt tccttacctg gctgtggccc ggacgtttga gaagatcgag | 1020 |
| gaggtgtctg ctcggctccg gatggtggag acgctgagca acttgctgcg ctccgtggtg | 1080 |
| gccctgtcgc ctcagacct cctccctgtc ctctacctca gcctcaacca ccttgggcca | 1140 |
| ccccagcagg gcctggagct tggcgtgggt gatggtgtcc ttctcaaggc agtggcccag | 1200 |
| gccacaggtc ggcagctgga gtccgtccgg gctgaggcag ccgagaaagg cgacgtgggg | 1260 |

```
ctggtggccg agaacagccg cagcacccag aggctcatgc tgccaccacc tccgctcact    1320
gcctccgggg tcttcagcaa gttccgcgac atcgccaggc tcactggcag tgcttccaca    1380
gccaagaaga tagacatcat caaaggcctc tttgtggcct gccgccactc agaagcccgg    1440
ttcatcgcta ggtccctgag cggacggctg cgccttgggc tggcagagca gtcggtgctg    1500
gctgccctct cccaggcagt gagcctcacg cccccgggcc aagaattccc accagccatg    1560
gtggatgctg ggaagggcaa gacagcagag gccagaaaga cgtggctgga ggagcaaggc    1620
atgatcctga agcagacgtt ctgcgaggtt cccgacctgg accgaattat ccccgtgctg    1680
ctggagcacg gcctggaacg tctcccggag cactgcaagc tgagcccagg gattcccctg    1740
aaaccaatgt ggcccatcc cacccggggc atcagcgagg tcctgaaacg ctttgaggag    1800
gcagctttca cctgcgaata caaatatgac gggcagaggg cacagatcca cgccctggaa    1860
ggcggggagg tgaagatctt cagcaggaat caggaagaca cactgggaa gtacccggac    1920 atcatcagcc gcatccccaa gattaaactc ccatcggtca catccttcat cctggacacc    1980
gaagccgtgg cttgggaccg ggaaaagaag cagatccagc cattccaagt gctcaccacc    2040
cgcaaacgca aggaggtgga tgcgtctgag atccaggtgc aggtgtgttt gtacgccttc    2100
gacctcatct acctcaatgg agagtccctg gtacgtgagc ccctttcccg cgccggcag    2160 ctgctccggg agaactttgt ggagacagag ggcgagtttg tcttcgccac ctccctggac    2220
accaaggaca tcgagcagat cgccgagttc ctggagcagt cagtgaaaga ctcctgcgag    2280
gggctgatgg tgaagaccct ggatgttgat gccacctacg agatcgccaa gagatcgcac    2340
aactggctca agctgaagaa ggactacctt gatggcgtgg gtgacaccct ggacctggtg    2400
gtgatcggcg cctacctggg ccggggaag cgggccggcc ggtacggggg cttcctgctg    2460
gcctcctacg acgaggacag tgaggagctg caggccatat gcaagcttgg aactggcttc    2520
agtgatgagg agctggagga gcatcaccag agcctcaagg cgctggtgct gcccagccca    2580
cgcccttacg tgcggataga tggcgctgtg attcccgacc actggctgga ccccagcgct    2640
gtgtgggagg tgaagtgcgc tgacctctcc ctctctccca tctaccctgc tgcgcggggc    2700
ctggtggata gtgacaaggg catctccctt cgcttccctc ggtttattcg agtccgtgaa    2760
gacaagcagc cggagcaggc caccaccagt gctcaggtgg cctgttttgta ccggaagcaa    2820 agtcagattc agaaccaaca aggcgaggac tcaggctctg accctgaaga tacctactaa    2880
gccctcgccc tcctagggcc tgggtacagg gcatgagttg gacggaccc aaggttatta    2940 ttgcctttgc ttttagcaa atctgctgtg gcaggctgtg gattttgaga gtcaggggag    3000
gggtgtgtgt gtgaggggt ggcttactcc ggagtctggg attcatcccg tcatttcttt    3060
caataaataa ttattggata gct                                            3083
```

<210> SEQ ID NO 49
<211> LENGTH: 919
<212> TYPE: PRT
<213> ORGANISM: Homo sapiens

<400> SEQUENCE: 49

Met Gln Arg Ser Ile Met Ser Phe Phe His Pro Lys Lys Glu Gly Lys
1               5                   10                  15

Ala Lys Lys Pro Glu Lys Glu Ala Ser Asn Ser Ser Arg Glu Thr Glu
            20                  25                  30

Pro Pro Pro Lys Ala Ala Leu Lys Glu Trp Asn Gly Val Val Ser Glu
        35                  40                  45

```
Ser Asp Ser Pro Val Lys Arg Pro Gly Arg Lys Ala Ala Arg Val Leu
 50                  55                  60

Gly Ser Glu Gly Glu Glu Asp Glu Ala Leu Ser Pro Ala Lys Gly
 65                  70                  75                  80

Gln Lys Pro Ala Leu Asp Cys Ser Gln Val Ser Pro Pro Arg Pro Ala
                 85                  90                  95

Thr Ser Pro Glu Asn Asn Ala Ser Leu Ser Asp Thr Ser Pro Met Asp
                100                 105                 110

Ser Ser Pro Ser Gly Ile Pro Lys Arg Arg Thr Ala Arg Lys Gln Leu
                115                 120                 125

Pro Lys Arg Thr Ile Gln Glu Val Leu Glu Glu Gln Ser Glu Asp Glu
130                 135                 140

Asp Arg Glu Ala Lys Arg Lys Glu Glu Glu Glu Glu Thr Pro
145                 150                 155                 160

Lys Glu Ser Leu Thr Glu Ala Glu Val Ala Thr Glu Lys Glu Gly Glu
                165                 170                 175

Asp Gly Asp Gln Pro Thr Thr Pro Pro Lys Pro Leu Lys Thr Ser Lys
                180                 185                 190

Ala Glu Thr Pro Thr Glu Ser Val Ser Glu Pro Glu Val Ala Thr Lys
                195                 200                 205

Gln Glu Leu Gln Glu Glu Glu Gln Thr Lys Pro Pro Arg Arg Ala
210                 215                 220

Pro Lys Thr Leu Ser Ser Phe Phe Thr Pro Arg Lys Pro Ala Val Lys
225                 230                 235                 240

Lys Glu Val Lys Glu Glu Pro Gly Ala Pro Gly Lys Glu Gly Ala
                245                 250                 255

Ala Glu Gly Pro Leu Asp Pro Ser Gly Tyr Asn Pro Ala Lys Asn Asn
                260                 265                 270

Tyr His Pro Val Glu Asp Ala Cys Trp Lys Pro Gly Gln Lys Val Pro
                275                 280                 285

Tyr Leu Ala Val Ala Arg Thr Phe Glu Lys Ile Glu Glu Val Ser Ala
                290                 295                 300

Arg Leu Arg Met Val Glu Thr Leu Ser Asn Leu Leu Arg Ser Val Val
305                 310                 315                 320

Ala Leu Ser Pro Pro Asp Leu Leu Pro Val Leu Tyr Leu Ser Leu Asn
                325                 330                 335

His Leu Gly Pro Pro Gln Gln Gly Leu Glu Leu Gly Val Gly Asp Gly
                340                 345                 350

Val Leu Leu Lys Ala Val Ala Gln Ala Thr Gly Arg Gln Leu Glu Ser
                355                 360                 365

Val Arg Ala Glu Ala Ala Glu Lys Gly Asp Val Gly Leu Val Ala Glu
                370                 375                 380

Asn Ser Arg Ser Thr Gln Arg Leu Met Leu Pro Pro Pro Pro Leu Thr
385                 390                 395                 400

Ala Ser Gly Val Phe Ser Lys Phe Arg Asp Ile Ala Arg Leu Thr Gly
                405                 410                 415

Ser Ala Ser Thr Ala Lys Lys Ile Asp Ile Lys Gly Leu Phe Val
                420                 425                 430

Ala Cys Arg His Ser Glu Ala Arg Phe Ile Ala Arg Ser Leu Ser Gly
                435                 440                 445

Arg Leu Arg Leu Gly Leu Ala Glu Gln Ser Val Leu Ala Ala Leu Ser
450                 455                 460
```

```
Gln Ala Val Ser Leu Thr Pro Pro Gly Gln Glu Phe Pro Pro Ala Met
465                 470                 475                 480

Val Asp Ala Gly Lys Gly Lys Thr Ala Glu Ala Arg Lys Thr Trp Leu
                485                 490                 495

Glu Glu Gln Gly Met Ile Leu Lys Gln Thr Phe Cys Glu Val Pro Asp
                500                 505                 510

Leu Asp Arg Ile Ile Pro Val Leu Leu Glu His Gly Leu Glu Arg Leu
                515                 520                 525

Pro Glu His Cys Lys Leu Ser Pro Gly Ile Pro Leu Lys Pro Met Leu
            530                 535                 540

Ala His Pro Thr Arg Gly Ile Ser Glu Val Leu Lys Arg Phe Glu Glu
545                 550                 555                 560

Ala Ala Phe Thr Cys Glu Tyr Lys Tyr Asp Gly Gln Arg Ala Gln Ile
                565                 570                 575

His Ala Leu Glu Gly Gly Glu Val Lys Ile Phe Ser Arg Asn Gln Glu
                580                 585                 590

Asp Asn Thr Gly Lys Tyr Pro Asp Ile Ile Ser Arg Ile Pro Lys Ile
            595                 600                 605

Lys Leu Pro Ser Val Thr Ser Phe Ile Leu Asp Thr Glu Ala Val Ala
            610                 615                 620

Trp Asp Arg Glu Lys Lys Gln Ile Gln Pro Phe Gln Val Leu Thr Thr
625                 630                 635                 640

Arg Lys Arg Lys Glu Val Asp Ala Ser Glu Ile Gln Val Gln Val Cys
                645                 650                 655

Leu Tyr Ala Phe Asp Leu Ile Tyr Leu Asn Gly Glu Ser Leu Val Arg
            660                 665                 670

Glu Pro Leu Ser Arg Arg Gln Leu Leu Arg Glu Asn Phe Val Glu
            675                 680                 685

Thr Glu Gly Glu Phe Val Phe Ala Thr Ser Leu Asp Thr Lys Asp Ile
690                 695                 700

Glu Gln Ile Ala Glu Phe Leu Glu Gln Ser Val Lys Asp Ser Cys Glu
705                 710                 715                 720

Gly Leu Met Val Lys Thr Leu Asp Val Asp Ala Thr Tyr Glu Ile Ala
                725                 730                 735

Lys Arg Ser His Asn Trp Leu Lys Leu Lys Lys Asp Tyr Leu Asp Gly
                740                 745                 750

Val Gly Asp Thr Leu Asp Leu Val Ile Gly Ala Tyr Leu Gly Arg
            755                 760                 765

Gly Lys Arg Ala Gly Arg Tyr Gly Gly Phe Leu Leu Ala Ser Tyr Asp
            770                 775                 780

Glu Asp Ser Glu Glu Leu Gln Ala Ile Cys Lys Leu Gly Thr Gly Phe
785                 790                 795                 800

Ser Asp Glu Glu Leu Glu Glu His His Gln Ser Leu Lys Ala Leu Val
                805                 810                 815

Leu Pro Ser Pro Arg Pro Tyr Val Arg Ile Asp Gly Ala Val Ile Pro
            820                 825                 830

Asp His Trp Leu Asp Pro Ser Ala Val Trp Glu Val Lys Cys Ala Asp
            835                 840                 845

Leu Ser Leu Ser Pro Ile Tyr Pro Ala Ala Arg Gly Leu Val Asp Ser
850                 855                 860

Asp Lys Gly Ile Ser Leu Arg Phe Pro Arg Phe Ile Arg Val Arg Glu
865                 870                 875                 880

Asp Lys Gln Pro Glu Gln Ala Thr Thr Ser Ala Gln Val Ala Cys Leu
```

| | 885 | | 890 | | 895 | |

Tyr Arg Lys Gln Ser Gln Ile Gln Asn Gln Gln Gly Glu Asp Ser Gly
            900                 905                 910

Ser Asp Pro Glu Asp Thr Tyr
            915

<210> SEQ ID NO 50
<211> LENGTH: 2147
<212> TYPE: DNA
<213> ORGANISM: Homo sapiens

<400> SEQUENCE: 50

```
gaaagccgct ggcggaccgc gcgcagcggc cagagaccga gccctaagga gagtgcggcg      60
cttcccgagg cgtgcagctg ggaactgcaa ctcatctggg ttgtgcgcag aaggctgggg     120
caagcgagta gagaagtgga gctaatggca atgcagatgc agcttgaagc aaatgcagat     180
acttcagtgg aagaagaaag ctttggccca aacccatttt cacggttaga gcagtgtggc     240
ataaatgcca acgatgtgaa gaaattggaa gaagctggat tccatactgt ggaggctgtt     300
gcctatgcgc caagaagga gctaataaat attaagggaa ttagtgaagc aaagctgat      360
aaaattctga cggagtctcg ctctgttgcc aggctggagt gcaatagcgt gatcttggtc     420
tactgcaccc tccgcctctc aggttcaagt gattctcctg cctcagcctc ccgagtagtt     480
gggactacag gtgaattga actggatct atcacagaaa tgtttggaga attccgaact      540
gggaagaccc agatctgtca tacgctagct gtcacctgcc agcttcccat tgaccggggt     600
ggaggtgaag gaaaggccat gtacattgac actgagggta cctttaggcc agaacggctg     660
ctggcagtgg ctgagaggta tggtctctct ggcagtgatg tcctggataa tgtagcatat     720
gctcgagcgt tcaacacaga ccaccagacc cagctccttt atcaagcatc agccatgatg     780
gtagaatcta ggtatgcact gcttattgta gacagtgcca ccgccctta cagaacagac     840
tactcgggtc gaggtgagct ttcagccagg cagatgcact tggccaggtt tctgcgattg     900
cttctgcgac tcgctgatga gtttggtgta gcagtggtaa tcactaatca ggtggtagct     960
caagtggatg gagcagcgat gtttgctgct gatcccaaaa aacctattgg aggaaatatc    1020
atcgcccatg catcaacaac cagattgtat ctgaggaaag gaagagggga accagaatc    1080
tgcaaaatct acgactctcc ctgtcttcct gaagctgaag ctatgttcgc cattaatgca    1140
gatggagtgg gagatgccaa agactgaatc attgggtttt tcctctgtta aaaaccttaa    1200
gtgctgcagc ctaatgagag tgcactgctc cctggggttc tctacaggcc tcttcctgtt    1260
gtgactgcca ggataaagct tccgggaaaa cagctattat atcagctttt ctgatggtat    1320
aaacaggaga caggtcagta gtcacaaact gatctaaaat gtttattcct tctgtagtgt    1380
attaatctct gtgtgttttc tttggttttg gaggagggt atgaagtatc tttgacatgg    1440
tgccttagga atgacttggg tttaacaagc tgtctactgg acaatcttat gtttccaaga    1500
gaactaaagc tggagagacc tgaccttct ctcacttcta aattaatggt aaaataaaat    1560
gcctcagcta tgtagcaaag ggaatgggtc tgcacagatt cttttttttct gtcagtaaaa    1620
ctctcaagca ggttttaag ttgtctgtct gaatgatctt gtgtaaggtt ttggttatgg    1680
agtcttgtgc caaacctact aggccattag cccttcacca tctacctgct tggtctttca    1740
ttgctaagac taactcaaga taatcctaga gtcttaaagc atttcaggcc agtgtggtgt    1800
cttgcgcctg tactcccagc actttgggag gccgaggcag gtggatcgct tgagcccagg    1860
agttttaagt ccagcttggc caaggtggtg aaatcccatc tctacaaaaa atgcagaact    1920
```

```
taatctggac acactgttac acgtgcctgt agtcccagct actcgatagc ctgaggtggg   1980
agaatcactt aagcctggaa ggtggaagtt gcagtgagtc gagattgcac tgctgcattc   2040
cagccagggt gacagagtga gaccatgttt caaacaagaa acatttcaga gggtaagtaa   2100
acagatttga ttgtgaggct tctaataaag tagttattag tagtgaa                 2147
```

<210> SEQ ID NO 51
<211> LENGTH: 340
<212> TYPE: PRT
<213> ORGANISM: Homo sapiens

<400> SEQUENCE: 51

```
Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Thr Glu Ser Arg Ser
65                  70                  75                  80

Val Ala Arg Leu Glu Cys Asn Ser Val Ile Leu Val Tyr Cys Thr Leu
                85                  90                  95

Arg Leu Ser Gly Ser Ser Asp Ser Pro Ala Ser Ala Ser Arg Val Val
            100                 105                 110

Gly Thr Thr Gly Gly Ile Glu Thr Gly Ser Ile Thr Glu Met Phe Gly
        115                 120                 125

Glu Phe Arg Thr Gly Lys Thr Gln Ile Cys His Thr Leu Ala Val Thr
    130                 135                 140

Cys Gln Leu Pro Ile Asp Arg Gly Gly Gly Glu Gly Lys Ala Met Tyr
145                 150                 155                 160

Ile Asp Thr Glu Gly Thr Phe Arg Pro Glu Arg Leu Leu Ala Val Ala
                165                 170                 175

Glu Arg Tyr Gly Leu Ser Gly Ser Asp Val Leu Asp Asn Val Ala Tyr
            180                 185                 190

Ala Arg Ala Phe Asn Thr Asp His Gln Thr Gln Leu Leu Tyr Gln Ala
        195                 200                 205

Ser Ala Met Met Val Glu Ser Arg Tyr Ala Leu Leu Ile Val Asp Ser
    210                 215                 220

Ala Thr Ala Leu Tyr Arg Thr Asp Tyr Ser Gly Arg Gly Glu Leu Ser
225                 230                 235                 240

Ala Arg Gln Met His Leu Ala Arg Phe Leu Arg Met Leu Leu Arg Leu
                245                 250                 255

Ala Asp Glu Phe Gly Val Ala Val Val Ile Thr Asn Gln Val Val Ala
            260                 265                 270

Gln Val Asp Gly Ala Ala Met Phe Ala Ala Asp Pro Lys Lys Pro Ile
        275                 280                 285

Gly Gly Asn Ile Ile Ala His Ala Ser Thr Thr Arg Leu Tyr Leu Arg
    290                 295                 300

Lys Gly Arg Gly Glu Thr Arg Ile Cys Lys Ile Tyr Asp Ser Pro Cys
305                 310                 315                 320

Leu Pro Glu Ala Glu Ala Met Phe Ala Ile Asn Ala Asp Gly Val Gly
                325                 330                 335
```

Asp Ala Lys Asp
        340

<210> SEQ ID NO 52
<211> LENGTH: 2229
<212> TYPE: DNA
<213> ORGANISM: Homo sapiens

<400> SEQUENCE: 52

| | | | | | |
|---|---|---|---|---|---|
| ccgcgcgcag | cggccagaga | ccgagcccta | aggagagtgc | ggcgcttccc | gaggcgtgca | 60 |
| gctgggaact | gcaactcatc | tgggttgtgc | gcagaaggct | ggggcaagcg | agtagagaag | 120 |
| tggagcgtaa | gccaggggcg | ttgggggccg | tgcgggtcgg | gcgcgtgcca | cgcccgcggg | 180 |
| gtgaagtcgg | agcgcgggc | ctgctggaga | gaggagcgct | gcggaccgag | taatggcaat | 240 |
| gcagatgcag | cttgaagcaa | atgcagatac | ttcagtggaa | gaagaaagct | ttggcccaca | 300 |
| acccatttca | cggttagagc | agtgtggcat | aaatgccaac | gatgtgaaga | aattggaaga | 360 |
| agctggattc | catactgtgg | aggctgttgc | ctatgcgcca | aagaaggagc | taataaatat | 420 |
| taagggaatt | agtgaagcca | aagctgataa | aattctggct | gaggcagcta | aattagttcc | 480 |
| aatgggtttc | accactgcaa | ctgaattcca | ccaaaggcgg | tcagagatca | tacagattac | 540 |
| tactggctcc | aaagagcttg | acaaactact | tcaaggtgga | attgagactg | atctatcac | 600 |
| agaaatgttt | ggagaattcc | gaactgggaa | gacccagatc | tgtcatacgc | tagctgtcac | 660 |
| ctgccagctt | cccattgacc | ggggtggagg | tgaaggaaag | gccatgtaca | ttgacactga | 720 |
| gggtacctt | aggccagaac | ggctgctggc | agtggctgag | aggtatggtc | tctctggcag | 780 |
| tgatgtcctg | gataatgtag | catatgctcg | agcgttcaac | acagaccacc | agacccagct | 840 |
| cctttatcaa | gcatcagcca | tgatggtaga | atctaggtat | gcactgctta | ttgtagacag | 900 |
| tgccaccgcc | ctttacagaa | cagactactc | gggtcgaggt | gagctttcag | ccaggcagat | 960 |
| gcacttggcc | aggtttctgc | ggatgcttct | gcgactcgct | gatgagtttg | tgtagcagt | 1020 |
| ggtaatcact | aatcaggtgg | tagctcaagt | ggatggagca | gcgatgtttg | ctgctgatcc | 1080 |
| caaaaaacct | attggaggaa | atatcatcgc | ccatgcatca | acaaccagat | tgtatctgag | 1140 |
| gaaaggaaga | ggggaaacca | gaatctgcaa | aatctacgac | tctccctgtc | ttcctgaagc | 1200 |
| tgaagctatg | ttcgccatta | atgcagatgg | agtgggagat | gccaaagact | gaatcattgg | 1260 |
| gttttttcctc | tgttaaaaac | cttaagtgct | gcagcctaat | gagagtgcac | tgctccctgg | 1320 |
| ggttctctac | aggcctcttc | ctgttgtgac | tgccaggata | aagcttccgg | gaaaacagct | 1380 |
| attatatcag | cttttctgat | ggtataaaca | ggagacaggt | cagtagtcac | aaactgatct | 1440 |
| aaaatgttta | ttccttctgt | agtgtattaa | tctctgtgtg | ttttctttgg | ttttggagga | 1500 |
| ggggtatgaa | gtatctttga | catggtgcct | taggaatgac | ttgggtttaa | caagctgtct | 1560 |
| actggacaat | cttatgtttc | caagagaact | aaagctggag | agacctgacc | cttctctcac | 1620 |
| ttctaaatta | atggtaaaat | aaaatgcctc | agctatgtag | caaagggaat | gggtctgcac | 1680 |
| agattctttt | tttctgtcag | taaaactctc | aagcaggttt | ttaagttgtc | tgtctgaatg | 1740 |
| atcttgtgta | agggtttggt | tatggagtct | tgtgccaaac | ctactaggcc | attagcccttt | 1800 |
| caccatctac | ctgcttggtc | tttcattgct | aagactaact | caagataatc | ctagagtctt | 1860 |
| aaagcatttc | aggccagtgt | ggtgtcttgc | gcctgtactc | ccagcacttt | gggaggccga | 1920 |
| ggcaggtgga | tcgcttgagc | caggagtttt | aagtccagct | tggccaagat | ggtgaaatcc | 1980 |
| catctctaca | aaaaatgcag | aacttaatct | ggacacactg | ttacacgtgc | ctgtagtccc | 2040 |

```
agctactcta tagcctgagg tgggagaatc acttaagcct ggaaggtgga agttgcagtg    2100
agtcgagatt gcactgctgc attccagcca gggtgacaga gtgagaccat gtttcaaaca    2160
agaaacattt cagagggcaa gtaaacagat ttgattgtga ggcttctaat aaagtagtta    2220
ttagtagtg                                                            2229
```

<210> SEQ ID NO 53
<211> LENGTH: 339
<212> TYPE: PRT
<213> ORGANISM: Homo sapiens

<400> SEQUENCE: 53

| Met | Ala | Met | Gln | Met | Gln | Leu | Glu | Ala | Asn | Ala | Asp | Thr | Ser | Val | Glu |
|---|---|---|---|---|---|---|---|---|---|---|---|---|---|---|---|
| 1 | | | | 5 | | | | | 10 | | | | | 15 | |

| Glu | Glu | Ser | Phe | Gly | Pro | Gln | Pro | Ile | Ser | Arg | Leu | Glu | Gln | Cys | Gly |
| | | | | 20 | | | | | 25 | | | | | 30 | |

| Ile | Asn | Ala | Asn | Asp | Val | Lys | Lys | Leu | Glu | Glu | Ala | Gly | Phe | His | Thr |
| | | | 35 | | | | | 40 | | | | | 45 | | |

| Val | Glu | Ala | Val | Ala | Tyr | Ala | Pro | Lys | Lys | Glu | Leu | Ile | Asn | Ile | Lys |
| | 50 | | | | | 55 | | | | | 60 | | | | |

| Gly | Ile | Ser | Glu | Ala | Lys | Ala | Asp | Lys | Ile | Leu | Ala | Glu | Ala | Ala | Lys |
| 65 | | | | | 70 | | | | | 75 | | | | | 80 |

| Leu | Val | Pro | Met | Gly | Phe | Thr | Thr | Ala | Thr | Glu | Phe | His | Gln | Arg | Arg |
| | | | | 85 | | | | | 90 | | | | | 95 | |

| Ser | Glu | Ile | Ile | Gln | Ile | Thr | Thr | Gly | Ser | Lys | Glu | Leu | Asp | Lys | Leu |
| | | | | 100 | | | | | 105 | | | | | 110 | |

| Leu | Gln | Gly | Gly | Ile | Glu | Thr | Gly | Ser | Ile | Thr | Glu | Met | Phe | Gly | Glu |
| | | | | 115 | | | | | 120 | | | | | 125 | |

| Phe | Arg | Thr | Gly | Lys | Thr | Gln | Ile | Cys | His | Thr | Leu | Ala | Val | Thr | Cys |
| | 130 | | | | | 135 | | | | | 140 | | | | |

| Gln | Leu | Pro | Ile | Asp | Arg | Gly | Gly | Glu | Gly | Lys | Ala | Met | Tyr | Ile |
| 145 | | | | | 150 | | | | | 155 | | | | | 160 |

| Asp | Thr | Glu | Gly | Thr | Phe | Arg | Pro | Glu | Arg | Leu | Leu | Ala | Val | Ala | Glu |
| | | | | 165 | | | | | 170 | | | | | 175 | |

| Arg | Tyr | Gly | Leu | Ser | Gly | Ser | Asp | Val | Leu | Asp | Asn | Val | Ala | Tyr | Ala |
| | | | 180 | | | | | 185 | | | | | 190 | | |

| Arg | Ala | Phe | Asn | Thr | Asp | His | Gln | Thr | Gln | Leu | Leu | Tyr | Gln | Ala | Ser |
| | | | 195 | | | | | 200 | | | | | 205 | | |

| Ala | Met | Met | Val | Glu | Ser | Arg | Tyr | Ala | Leu | Leu | Ile | Val | Asp | Ser | Ala |
| | 210 | | | | | 215 | | | | | 220 | | | | |

| Thr | Ala | Leu | Tyr | Arg | Thr | Asp | Tyr | Ser | Gly | Arg | Gly | Glu | Leu | Ser | Ala |
| 225 | | | | | 230 | | | | | 235 | | | | | 240 |

| Arg | Gln | Met | His | Leu | Ala | Arg | Phe | Leu | Arg | Met | Leu | Leu | Arg | Leu | Ala |
| | | | | 245 | | | | | 250 | | | | | 255 | |

| Asp | Glu | Phe | Gly | Val | Ala | Val | Val | Ile | Thr | Asn | Gln | Val | Val | Ala | Gln |
| | | | | 260 | | | | | 265 | | | | | 270 | |

| Val | Asp | Gly | Ala | Ala | Met | Phe | Ala | Ala | Asp | Pro | Lys | Lys | Pro | Ile | Gly |
| | | 275 | | | | | 280 | | | | | 285 | | | |

| Gly | Asn | Ile | Ile | Ala | His | Ala | Ser | Thr | Thr | Arg | Leu | Tyr | Leu | Arg | Lys |
| | | 290 | | | | | 295 | | | | | 300 | | | |

| Gly | Arg | Gly | Glu | Thr | Arg | Ile | Cys | Lys | Ile | Tyr | Asp | Ser | Pro | Cys | Leu |
| 305 | | | | | 310 | | | | | 315 | | | | | 320 |

| Pro | Glu | Ala | Glu | Ala | Met | Phe | Ala | Ile | Asn | Ala | Asp | Gly | Val | Gly | Asp |
| | | | | 325 | | | | | 330 | | | | | 335 | |

Ala Lys Asp

<210> SEQ ID NO 54
<211> LENGTH: 339
<212> TYPE: PRT
<213> ORGANISM: Homo sapiens

<400> SEQUENCE: 54

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

HUMAN BLOOD MOLECULAR BIODOSIMETER PANEL FOR DISTINGUISHING RADIATION EXPOSURE FROM INFLAMMATION STRESS

CROSS-REFERENCE TO RELATED APPLICATIONS

This application is a non-provisional of and claims priority to U.S. Provisional Patent Application No. 61/901,372, filed on Nov. 7, 2013, hereby incorporated by reference in its entirety.

This application is related to U.S. patent application Ser. No. 14/023,968, filed on Sep. 11, 2013, which is incorporated by reference in its entirety.

STATEMENT OF GOVERNMENTAL SUPPORT

This invention was made with government support under Contract No. DE-AC02-05CH11231 awarded by the U.S. Department of Energy, under Contract No. HHSO100201000006C awarded by the Biomedical Advanced Research and Development Authority, Office of the Assistant Secretary for Preparedness and Response, Office of the Secretary, Department of Health and Human Services, and under AFRRI work units RBB4AR and RAB4AU of The Armed Forces Radiobiology Research Institute (AFRRI). The government has certain rights in the invention.

REFERENCE TO SEQUENCE LISTING AND TABLE APPENDIX

Table 2-4 attached hereto as an appendix are hereby incorporated by reference. The sequence listing in Table 4 is hereby incorporated by reference. All GenBank Accessions recited herein are also hereby incorporated by reference.

This application also incorporates by reference the sequence listing found in computer-readable form in a *.txt file entitled, "3304US_SequenceListing_ST25.txt", created on Jun. 1, 2015.

BACKGROUND OF THE INVENTION

Field of the Invention

The invention relates to the fields of diagnostic and prognostic methods of using gene and protein biomarkers to determine a subject's radiation exposure and discriminates between persons who have been exposed to radiation only, inflammation stress only, or a combination of the two.

Related Art

Biological markers of exposure to ionizing radiation (IR) in human populations are of great interest for assessing normal tissue injury in radiation oncology and for biodosimetry in nuclear incidents and accidental radiation exposures. Current approaches to radiation biodosimetry include assessments of physical effects, such as time to emesis and blood lymphocyte kinetics, and cellular determinants such as cytogenetic biodosimetry to assess radiation-induced chromosome aberrations in circulating blood lymphocytes [1]. However, these methods are time-consuming and do not provide results fast enough to identify people who would benefit the most from medical intervention immediately after irradiation. The use of biochemical markers, such as changes in transcript or protein expression or posttranslational modifications, represents an alternative method with the potential for high-throughput, deployable methods for initial triage as well as for the estimation of exposure dose (reviewed in [1,2]).

Recent studies have identified large-scale changes in transcript expression in irradiated blood lymphocytes shortly following IR exposures and that transcript changes can persist for days after exposure [3-12]. A 2006 literature review from our laboratory identified over 260 radiation-responsive proteins and ranked them according to their potential usefulness in human biodosimetric applications [13]. Genes involved in cellular DNA damage response and repair functions, including DNA repair, cell cycle functions and apoptosis were identified as priority candidates for radiation biodosimetry.

DNA is a critical cellular target of IR and the ability of the cell to repair DNA damage determines its fate after exposure. Various forms of DNA damage are induced by IR, including DNA-protein cross-links, base and sugar alterations, DNA single-strand breaks (SSBs), bulky lesions (i.e. clusters of base and sugar damage) and double-strand breaks (DSBs) [14]. The immediate response to IR-induced DNA damage is the stimulation of the DNA repair machinery and the activation of cell cycle checkpoints, followed by downstream cellular responses such as apoptosis that removes damaged cells. The predominant repair pathway is base excision repair (BER), which is responsible for the removal of damaged bases and DNA single-strand breaks through gap-filling by DNA polymerase and ligation of DNA ends [15]. Nucleotide excision repair (NER) is the major pathway for the repair of bulky DNA damages that cause DNA helical distortion [16]. NER proteins are also involved in repair of oxidative damage through stimulation of BER, including XPC and XPG, indicating cross-talk between these two repair pathways [17-21]. Several NER genes are upregulated at the gene expression level by IR, including XPC and DDB2 [4,22]. IR exposure is known to modulate transcript and/or protein levels of several cell cycle regulators (CDKN1A (p21), GADD45a, Cyclin G1 (CCNG1), CHK2-thr68) and apoptosis genes (BAX and BBC3) in diverse cell and blood model systems (in vivo, in vitro and ex vivo) [6, 8, 10, 23-28]. However, little is known of how co-exposure to confounding factors can affect the utility of individual biomarkers for radiation biodosimetry [1, 29, 30].

The human blood ex vivo irradiation exposure model has been used to investigate the early radiation-induced biological responses for potential biodosimetry applications, and was recently demonstrated to accurately reflect the in vivo peripheral blood radiation response in humans [12].

BRIEF SUMMARY OF THE INVENTION

The present invention provides for a biomarker panel of eight DNA repair genes that provides for assessment of a subject's radiation exposure and discriminates between persons who have been exposed to radiation only, inflammation stress only, or a combination of the two.

Radiation exposure significantly modulated the transcript expression of 12 biomarkers of 40 tested (2.2E-06<p<0.03), of which 8 showed no overlap between unirradiated and irradiated samples (CDKN1A, FDXR, BBC3, PCNA, GADD45a, XPC, POLH and DDB2). This panel demonstrated excellent dose response discrimination (0.5 to 8 Gy) in an independent human blood ex vivo dataset, and 100% accuracy for discriminating patients who received total body radiation. Three biomarkers of this panel (CDKN1A, FDXR and BBC3) were also highly sensitive to LPS treatment in the absence of radiation exposure, and LPS co-treatment significantly affected their radiation responses. At the protein level, BAX and pCHK2-thr68 were elevated after radiation exposure, but the pCHK2-thr68 response was significantly decreased in the presence of LPS. Our combined panel yields an estimated 4-group accuracy of ~90% to discriminate between radiation alone, inflammation alone, or combined exposures. Our findings suggest that DNA repair gene expression may be helpful to identify biodosimeters of exposure to radiation, especially within high-complexity exposure scenarios.

The nine biomarker panel comprises: PCNA, CDKN1A, pCHK2-thr68, BBC3, FDXR, DDB2, XPC, POLH, and GADD45a. In comparison to untreated sham samples, inflammation in the absence of radiation exposure upregulates CDKN1A and downregulates FDXR and BBC3. Samples exposed to 2 Gy radiation only exhibit increased expression of all nine biomarkers (PCNA, CDKN1A, pCHK2-thr68, BBC3, FDXR, DDB2, XPC, POLH, and GADD45a), whereas subjects exposed to 2 Gy plus inflammation stress show modified induction of CDKN1A, FDXR and BBC3 and abrogation of the phosphorylation of CHK2 protein. In the radiation and inflammation combined treatment group the expression of CDKN1A increases and the expression of FDXR and BBC3 decreases, relative to the radiation alone group.

The twelve-biomarker panel comprised of: cell cycle regulator genes (CDKN1A, GADD45a, PCNA and CCNG1), apoptosis regulator genes (BAX, BBC3 and FDXR) and genes involved in specific DNA repair functions (XPC, DDB2, LIG1, POLH and RAD51).

The present invention also provides for devices and methods for measuring expression levels in a sample of the presently described gene panel biomarkers. In one embodiment, a blood test using the present biochemical markers may be administered, for example, via a handheld device similar to what diabetes patients use to check their blood sugar. Such a test could help emergency personnel quickly identify people exposed to high radiation doses who need immediate care, and people exposed to lower doses who only need long-term monitoring.

In one embodiment, a kit comprising probes for detection of expression levels of a gene panel of eight DNA repair genes, CDKN1A, FDXR, BBC3, PCNA, GADD45a, XPC, POLH and DDB2, wherein said probes provide for assessment of a subject's radiation exposure and discriminates between persons who have been exposed to radiation only, inflammation stress only, or a combination of the two. In another embodiment, the kit may further comprise a probe for detection of the phosphorylation of CHK2 protein (pCHK2-thr68). In another embodiment, the kit further comprising probes for detection of expression levels of CCNG1, BAX, LIG1, and RAD51.

A method for testing whether a patient was exposed to radiation and at what level of exposure, comprising the steps of: (a) receiving a patient sample; (b) measuring the expression levels of the 8-gene biomarkers (CDKN1A, FDXR, BBC3, PCNA, GADD45a, XPC, POLH and DDB2) in comparison to a reference level; (c) transmitting said measured expression levels of the 8-gene biomarkers.

A method for triaging a patient based on patient ionizing radiation exposure and dosage, comprising the steps of: (a) receiving measured expression levels of 8-gene biomarkers (CDKN1A, FDXR, BBC3, PCNA, GADD45a, XPC, POLH, and DDB2) in comparison to a reference level for a patient; (b) recommending a clinical response for said patient as determined by the patient radiation exposure and dosage levels, wherein the determination is based on the criteria of (i) normal levels of the 8-gene biomarkers indicate the patient was not exposed to ionizing radiation; (ii) an increase by 2-fold of the average sum of the expression levels of the 8-gene biomarkers indicates the patient was exposed to about 2 Gy ionizing radiation, thereby triaging said patient based on the criteria.

A method for triaging a patient based on patient ionizing radiation exposure and dosage and distinguishing from inflammation, comprising the steps of: (a) receiving measured expression levels of 8-gene biomarkers (CDKN1A, FDXR, BBC3, PCNA, GADD45a, XPC, POLH, and DDB2) in comparison to a reference level for a patient; (b) recommending a clinical response for said patient as determined by the patient radiation exposure and dosage levels, wherein the determination is based on the criteria of (i) normal levels of the 8-gene biomarkers indicate the patient was not exposed to ionizing radiation; (ii) an increase of CDKN1A expression levels and decreased expression levels of FDXR and BBC3 and normal expression levels of PCNA, GADD45a, XPC, POLH, and DDB2 indicates the patient has inflammation present but not exposed to ionizing radiation; (iii) an increase by 2-fold of the average sum of the expression levels of the 8-gene biomarkers indicates the patient was exposed to about 2 Gy ionizing radiation, (iv) an increase of CDKN1A, PCNA, GADD45a, XPC, POLH, and DDB2 expression levels and decreased expression levels of FDXR and BBC3 indicates that the patient was exposed to about 2 Gy ionizing radiation and inflammation is present in the patient, thereby triaging said patient based on the criteria.

BRIEF DESCRIPTION OF THE DRAWINGS

(FIG. 2A) ex vivo irradiated (0, 0.5, 2, 5, 8 Gy) human blood samples obtained from five independent donors 6 and 24 hrs after radiation exposure (GSE8917; [10]) and (FIG. 2B) human in vivo irradiated blood samples obtained from patients undergoing total body irradiation (GSE20162; [12]). FIG. 2A shows the average of the summed expression for the samples in each exposure group (+/− standard error) normalized to the average expression of the 0 Gy samples for each time-point. FIG. 2B shows the plot of the summed expression of the 8-gene panel of each blood sample in the in vivo study, normalized to the average of the healthy donor samples.

FIG. 4A. A radiation exposure of 2 Gy in the absence of LPS (left panel) or LPS treatment alone (middle panel) induced CDKN1A to approximately the same level at 24 hrs: 7.3 vs 8.2-fold, respectively (T-Test p=0.47). LPS treatment in the presence of a 2 Gy radiation exposure induced CDKN1A expression ~10.2-fold (right panel), which is a 1.4-fold increase compared to 2 Gy alone (T-test p=0.03). FIG. 4B. In the absence of LPS, radiation induced BBC3~2.7-fold (left panel). LPS treatment alone (middle panel) suppresses BBC3~2.9-fold. LPS treatment in the presence of a 2 Gy radiation exposure induced BBC3 expression ~1.7-fold (right panel), a ~1.6-fold decrease in BBC3 expression when compared to 2 Gy alone (T-test p=0.03). FIG. 4C. In the absence of LPS, radiation induced FDXR ~17-fold (left panel). LPS treatment alone (middle panel) suppressed FDXR ~1.5-fold. LPS treatment in the presence of a 2 Gy radiation exposure induced FDXR expression ~10-fold (right panel), a ~1.7-fold decrease in FDXR expression when compared to 2 Gy alone (T-test p=1.2E-04).

FIGS. 13A, 13B, 13C. Radiation-induced increased protein levels of BAX and phosphorylated CHK2-thr68 in human ex vivo quiescent PBMC. FIG. 13A shows BAX and pCHK2-thr68 responses by ELISA after 0, 2 or 6 Gy at 6 and 24 hrs in independent replicate culture flasks from the same blood sample of two donors produce minimal technical variability ($R^2$=0.95 for pCHK2-thr68; $R^2$=0.92 for BAX). FIG. 13B shows levels of BAX and pCHK2-thr68 were measured by ELISA in unstimulated PBMC after 0, 2, or 6 Gy ionizing radiation. PBMC cultures from six or five unique donors were assessed for BAX and pCHK2-thr68 protein levels at 6 hrs and 24 hrs by ELISA. Data were normalized with respect to sham for each timepoint. Repeat draws from the same donor 1 month after the first blood draw are indicated with a "0.1" after the donor identifier. FIG. 13C shows T-test results (t-statistics and p-values in parentheses) identify significant mean differences in BAX and pCHK2-thr68 ELISA data for the 0- vs. 2 Gy and 0- vs. 6 Gy groups at 6 hrs and 24 hrs after irradiation.

FIGS. 13A, 13B, 13C. Radiation-induced increased protein levels of BAX and phosphorylated CHK2-thr68 in human ex vivo quiescent PBMC. FIG. 13A. BAX and pCHK2-thr68 responses by ELISA after 0, 2 or 6 Gy at 6 and 24 hrs in independent replicate culture flasks from the same blood sample of two donors produce minimal technical variability ($R^2=0.95$ for pCHK2-thr68; $R^2=0.92$ for BAX). FIG. 13B. Levels of BAX and pCHK2-thr68 were measured by ELISA in unstimulated PBMC after 0, 2, or 6 Gy ionizing radiation. PBMC cultures from six or five unique donors were assessed for BAX and pCHK2-thr68 protein levels at 6 hrs and 24 hrs by ELISA. Data were normalized with respect to sham for each timepoint. Repeat draws from the same donor ~1 month after the first blood draw are indicated with a "0.1" after the donor identifier. FIG. 13C. T-test results (t-statistics and p-values in parentheses) identify significant mean differences in BAX and pCHK2-thr68 ELISA data for the 0-vs. 2 Gy and 0-vs. 6 Gy groups at 6 hrs and 24 hrs after irradiation.

Figure 1:
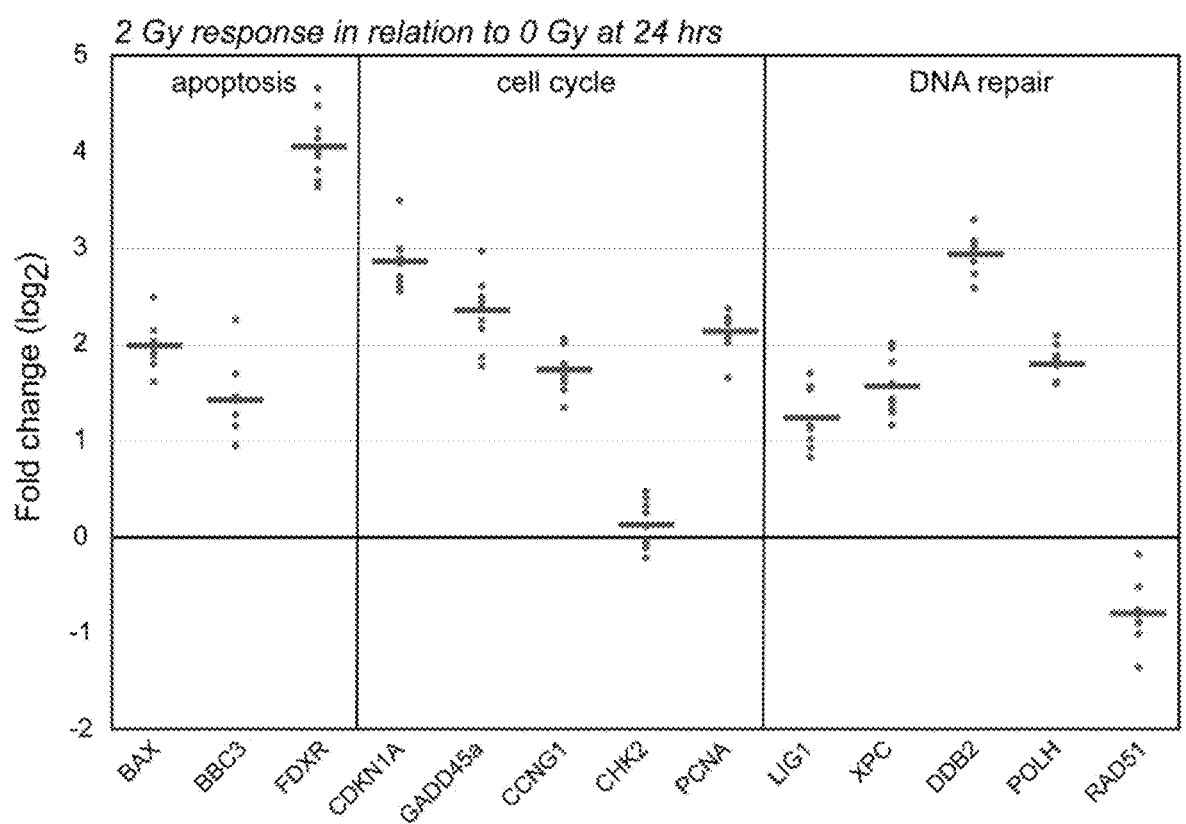
FIG. 1. Radiation-induced transcriptional responses of DNA repair genes in the human ex vivo radiation blood model. Relative transcript level responses using human blood from 5 healthy human donors measured by quantitative RT-PCR analysis 24 hrs after 2 Gy exposure with respect to sham (0 Gy) transcript levels. Expression of the sham (0 Gy) and 2 Gy transcript responses were calculated relative to the average expression of ACTB (β-Actin). The delta Ct for β-Actin between sham and 2 Gy irradiated samples was <0.3 for all but one sample, which was excluded from this analysis. The fold-change for each gene between sham and irradiated samples was calculated using the delta-delta Ct method. Similar results were obtained when normalized using GAPDH expression as endogenous control (data not shown).

Table 2. Target genes selected from DNA damage response pathways for transcript analysis.

Table 3. Average absorbance ranges of ELISA measurements.

Table 4. Transcript and protein sequences of 12 panel biomarkers.

BRIEF DESCRIPTION OF THE SEQUENCES

SEQ ID NO:1 is cyclin-dependent kinase inhibitor 1 protein [*Homo sapiens*], NP_001207706.1 GI:334085240.

SEQ ID NO:2 is *Homo sapiens* cyclin-dependent kinase inhibitor 1A (p21, Cip1) (CDKN1A), transcript variant 5, mRNA.

SEQ ID NO:3 is *Homo sapiens* ferredoxin reductase (FDXR), transcript variant 2, mRNA.

SEQ ID NO:4 is NADPH:adrenodoxin oxidoreductase, mitochondrial isoform 2 precursor protein, [*Homo sapiens*].

SEQ ID NO:5 is *Homo sapiens* ferredoxin reductase (FDXR), transcript variant 3 mRNA.

SEQ ID NO:6 is NADPH:adrenodoxin oxidoreductase, mitochondrial isoform 3 precursor protein [*Homo sapiens*].

SEQ ID NO:7 is *Homo sapiens* BCL2 binding component 3 (BBC3), transcript variant 1, mRNA.

SEQ ID NO:8 is bcl-2-binding component 3 isoform 1 protein [*Homo sapiens*].

SEQ ID NO:9 is *Homo sapiens* BCL2 binding component 3 (BBC3), transcript variant 4, mRNA.

SEQ ID NO:10 is bcl-2-binding component 3 isoform 4 protein [*Homo sapiens*].

SEQ ID NO:11 is *Homo sapiens* BCL2 binding component 3 (BBC3), transcript variant 2, mRNA.

SEQ ID NO: 12 is bcl-2-binding component 3 isoform 2 protein [*Homo sapiens*].

SEQ ID NO: 13 is *Homo sapiens* BCL2 binding component 3 (BBC3), transcript variant 3, mRNA.

SEQ ID NO: 14 is bcl-2-binding component 3 isoform 3 protein [*Homo sapiens*].

SEQ ID NO: 15 is *Homo sapiens* proliferating cell nuclear antigen (PCNA), transcript variant 1, mRNA.

SEQ ID NO:16 is proliferating cell nuclear antigen protein [*Homo sapiens*].

SEQ ID NO:17 is *Homo sapiens* full open reading frame cDNA clone RZPDo834B0222D for gene PCNA, proliferating cell nuclear antigen; complete cds, incl. stopcodon.

SEQ ID NO:18 is PCNA protein [*Homo sapiens*] from alternate accession number.

SEQ ID NO:19 is *Homo sapiens* growth arrest and DNA-damage-inducible, alpha (GADD45A), transcript variant 1, mRNA.

SEQ ID NO:20 is growth arrest and DNA damage-inducible protein GADD45 alpha isoform 1 [*Homo sapiens*].

SEQ ID NO:21 is *Homo sapiens* growth arrest and DNA-damage-inducible, alpha (GADD45A), transcript variant 2, mRNA.

SEQ ID NO:22 is growth arrest and DNA damage-inducible protein (GADD45) alpha isoform 2 [*Homo sapiens*].

SEQ ID NO:23 is *Homo sapiens* growth arrest and DNA-damage-inducible, alpha (GADD45A), transcript variant 3, mRNA.

SEQ ID NO:24 is growth arrest and DNA damage-inducible protein GADD45 alpha isoform 3 [*Homo sapiens*].

SEQ ID NO:25 is *Homo sapiens* xeroderma pigmentosum, complementation group C (XPC), transcript variant 1, mRNA.

SEQ ID NO:26 is DNA repair protein complementing XP-C cells isoform 1 protein [*Homo sapiens*].

SEQ ID NO:27 is *Homo sapiens* xeroderma pigmentosum, complementation group C (XPC), transcript variant 2, mRNA.

SEQ ID NO:28 is DNA repair protein complementing XP-C cells isoform 2 [*Homo sapiens*].

SEQ ID NO:29 is *Homo sapiens* xeroderma pigmentosum, complementation group C (XPC), transcript variant 3, non-coding RNA.

SEQ ID NO:30 is *Homo sapiens* polymerase (DNA directed), eta (POLH), mRNA.

SEQ ID NO:31 is DNA polymerase eta protein [*Homo sapiens*].

SEQ ID NO:32 is *Homo sapiens* damage-specific DNA binding protein 2, 48 kDa (DDB2), mRNA.

SEQ ID NO:33 is DNA damage-binding protein 2 [*Homo sapiens*].

SEQ ID NO:34 is *Homo sapiens* mRNA for CHK2, partial cds.

SEQ ID NO:35 is CHK2, partial protein[*Homo sapiens*]

SEQ ID NO:36 is *Homo sapiens* protein kinase CHK2 (CHK2) mRNA, complete cds.

SEQ ID NO:37 is protein kinase CHK2 [*Homo sapiens*].

SEQ ID NO:38 is *Homo sapiens* checkpoint kinase 2 (CHEK2), transcript variant 4, mRNA.

SEQ ID NO:39 is serine/threonine-protein kinase Chk2 isoform d [*Homo sapiens*].

SEQ ID NO:40 is *Homo sapiens* BCL2-associated X protein (BAX), transcript variant alpha, mRNA.

SEQ ID NO: 41 is apoptosis regulator BAX isoform alpha [*Homo sapiens*]

SEQ ID NO:42 is *Homo sapiens* BCL2-associated X protein (BAX), transcript variant beta, mRNA.

SEQ ID NO:43 is apoptosis regulator BAX isoform beta protein [*Homo sapiens*].

SEQ ID NO:44 is *Homo sapiens* BCL2-associated X protein (BAX), transcript variant delta, mRNA.

SEQ ID NO: 45 is apoptosis regulator BAX isoform delta protein [*Homo sapiens*].

SEQ ID NO:46 is *Homo sapiens* mRNA for bax isoform psi (BAX gene).

SEQ ID NO:47 is bax isoform psi protein [*Homo sapiens*].

SEQ ID NO:48 is *Homo sapiens* ligase I, DNA, ATP-dependent (LIG1), mRNA.

SEQ ID NO:49 is DNA ligase 1 [*Homo sapiens*].

SEQ ID NO:50 is *Homo sapiens* RAD51 recombinase (RAD51), transcript variant 4, mRNA.

SEQ ID NO:51 is DNA repair protein RAD51 homolog 1 isoform 2 protein [*Homo sapiens*].

SEQ ID NO:52 is *Homo sapiens* mRNA for RAD51, complete cds

SEQ ID NO:53 is RAD51 protein [*Homo sapiens*].

SEQ ID NO:54 is RAD51 protein [*Homo sapiens*] from alternate accession number.

DETAILED DESCRIPTION OF THE PREFERRED EMBODIMENT

Introduction

Our study utilized the human blood ex vivo irradiation exposure model to examine: (i) the transcriptional response of 40 well known DNA repair, cell cycle control and apoptosis genes after exposure to IR; (ii) IR-induced transcript changes associated with changes in a selected set of proteins; and (iii) transcript and protein responses in the context of inflammatory stress. Lipopolysaccharide (LPS), the principal component of the outer membrane of Gram-negative bacteria [31], elicits strong inflammatory responses and induces oxidative stress in exposed mammalian cells [32]. Our findings demonstrate that inflammation significantly confounds the radiation response of some DNA repair genes at a dose that is relevant for radiation biodosimetry. We identified a small panel of DNA repair transcripts and proteins whose expression changes can distinguish between unirradiated and 2 Gy ex vivo irradiated human blood samples, displays excellent radiation dose and time dependent responses in an independent ex vivo irradiated human dataset, shows robust non-overlapping responses in blood samples from human patients treated with total body irradiation, and with a high accuracy for classifying blood samples receiving radiation only, inflammation stress alone, or both.

These identified eight DNA-repair genes in human blood whose expression responses change more than twofold soon after blood is exposed to radiation. They also learned how these genes respond when blood is exposed to inflammation stress, which can occur because of an injury or infection. Inflammation can mimic the effects of radiation and lead to false diagnoses.

The panel of biochemical markers can discriminate between blood samples exposed to radiation, inflammation, or both. As such, these markers may be incorporated into a blood test and such a test may find uses in for example, radiation-related incidents that require an emergency response and quick triage of victims and the severity of their injury.

DESCRIPTIONS OF THE EMBODIMENTS

In various embodiments, a patient sample (e.g., blood, bodily fluid) is obtained and the expression of 8-12 specific genes associated with the DNA repair for human radiation biodosimetry is determined. In one embodiment, a panel of eight biomarkers have the ability to discriminate between radiation dose and inflammation stress. In another embodiment, a panel of nine or twelve biomarkers are provided, wherein determination of the expression levels of these genes as compared to a reference or base level permit the determination of whether a patient has been exposed to radiation. In some embodiments, the measured transcript levels can be correlated to a diagnosis of exposure level and thus provide for a recommended therapeutic response. The transcript and protein sequences of the 8, 9 or 12 biomarkers that are detected are provided in the attached Table 4.

In a survey of 40 DNA repair genes in the human peripheral blood cells ex vivo radiation model (Table 2), twelve genes showed more than two fold changes in transcript levels at 24 hours after 2 Gy exposures. These included the cell cycle regulators (CDKN1A, GADD45a, PCNA and CCNG1), apoptosis regulators (BAX, BBC3 and FDXR) and genes involved in specific DNA repair functions (XPC, DDB2, LIG1, POLH and RAD51).

Figure 2A:
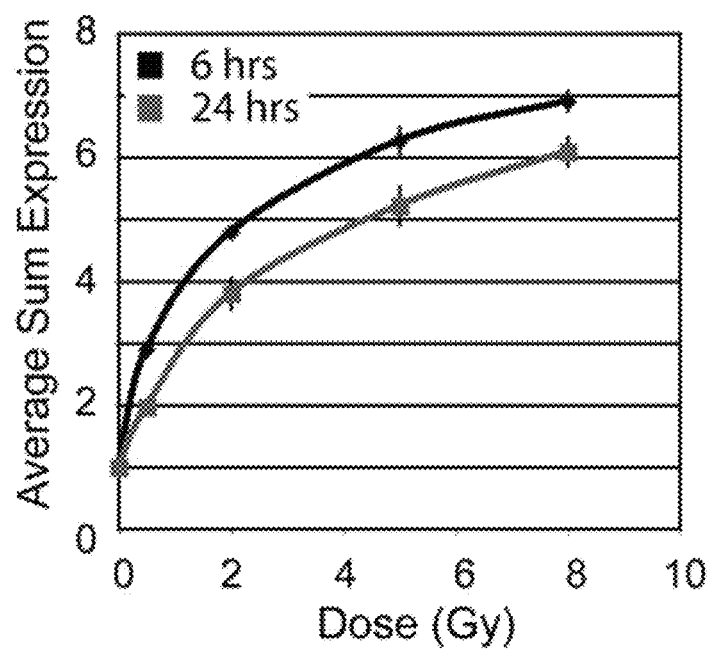
FIGS. 2A and 2B. Independent ex vivo and in vivo confirmation of the radiation response of the 8-gene panel. The robustness of our panel of 8 non-overlapping radiation biomarkers was confirmed using two published expression array data sets.

We compared the responses to radiation and inflammation stress to develop a panel of 8 genes that we validated using publicly available expression datasets for (1) an independent group of donors in a blood ex vivo model, and (2) an independent group of patients who provided blood samples before and after whole body radiation ([10,12], FIG. 2A). The eight-gene panel no overlap between unirradiated and irradiated samples and comprise the genes: CDKN1A, FDXR, BBC3, PCNA, GADD45a, XPC, POLH and DDB2. Our findings support the strength of using DNA repair related genes to detect radiation exposure in the context of inflammation stress, which may become helpful for discriminating between worried-well, those exposed to medically significant doses of ionizing radiation and those experiencing inflammation stress (Table 1). By including protein expression markers we developed a 9-gene panel that correctly discriminated irradiated from unirradiated blood samples independent of the presence or absence of inflammation stress (FIG. 7), with a ~90% 4-group classification accuracy (FIG. 8).

Figure 7:
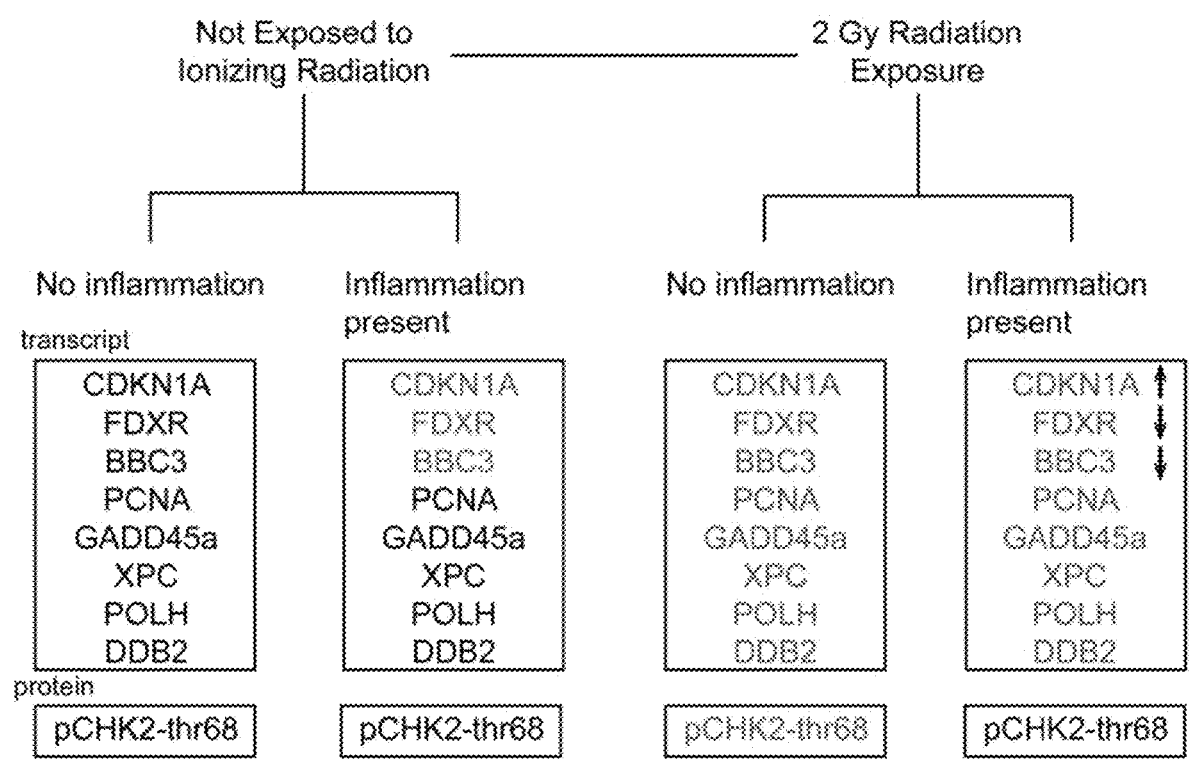
FIG. 7. Transcript and protein panel discriminates 2 Gy exposure and unirradiated samples, independent of inflammation stress. In comparison to untreated sham samples, inflammation in the absence of radiation exposure upregulates CDKN1A (red) and downregulates FDXR and BBC3 (green). Samples exposed to 2 Gy radiation only exhibit increased expression of all nine biomarkers, whereas subjects exposed to 2 Gy plus inflammation stress show modified induction of CDKN1A, FDXR and BBC3 and abrogation of the phosphorylation of CHK2 protein. The arrows in the radiation and inflammation combined treatment group indicate the direction of expression relative to the radiation alone group.
Figure 8:
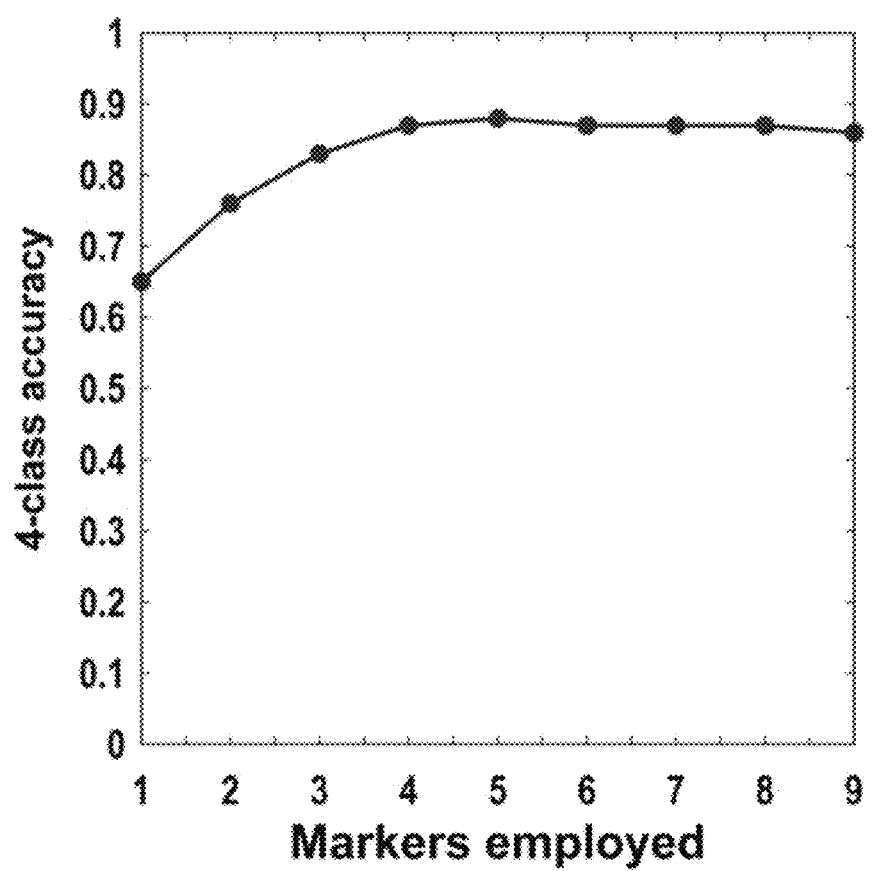
FIG. 8. Classification (4-class) accuracy of the transcript and protein panel. Classification accuracy based on ten 10-fold cross-validation as a function of the number of markers considered, based on order determined during filtering with the Gini index. The four classes used in this analysis are: radiation only (R), inflammation stress only (L), combined exposures involving both radiation and LPS (RL), and samples with no radiation exposure and no LPS treatment (N). Marker order is: PCNA, CDKN1A, pCHK2-thr68, BBC3, FDXR, DDB2, XPC, POLH, and GADD45a. Maximum classification accuracy was 0.88 for the top 5-marker set.

As described in FIG. 7, in comparison to untreated sham samples, inflammation in the absence of radiation exposure upregulates CDKN1A (red) and downregulates FDXR and BBC3 (green). Samples exposed to only 2 Gy radiation exhibit increased expression of all nine biomarkers CDKN1A, FDXR, BBC3, PCNA, GADD45a, XPC, POLH, DDB2, and pCHK2-thr68, whereas subjects exposed to 2 Gy plus inflammation stress show modified induction of CDKN1A, FDXR and BBC3 and abrogation of the phosphorylation of CHK2 protein. The arrows in the radiation and inflammation combined treatment group indicate the direction of expression relative to the radiation alone group. Thus, in one embodiment, the detection of increased expression of the 9-biomarker panel (CDKN1A, FDXR, BBC3, PCNA, GADD45a, XPC, POLH, DDB2, and pCHK2-thr68) in a subject provides for a diagnosis that the subject has received a 2 Gy radiation exposure, thereby allowing for in some embodiments, patient triage and a therapeutic regimen to be proscribed and administered.

Table 1 shows the classification sensitivity, specificity, predictive value positive (PV+), and predictive value negative (PV−) for the nine-gene panel. Results are based on ten 10-fold cross-validation runs.

TABLE 1

| Class | Sensitivity | Specificity | PV+ | PV− |
|---|---|---|---|---|
| N | 0.89 | 0.84 | 1 | 0.81 |
| R | 0.86 | 0.86 | 0.78 | 0.88 |
| L | 0.91 | 0.84 | 0.96 | 0.82 |
| RL | 0.76 | 0.89 | 0.69 | 0.91 |

The DNA repair-associated genes we surveyed are regulated by TP53 signaling [37]. The TP53 tumor suppressor protein is central to cell signaling networks following cellular stressors, including DNA damage such as that caused by ionizing radiation. TP53 modulates the main DNA repair processes in eukaryotic cells (base excision repair (BER), nucleotide excision repair (NER), non-homologous end-joining (NHEJ) and homologous recombination (HR) along with direct roles in induction of DNA damage-induced cell cycle arrest and apoptosis. TP53 is activated after DNA damage through phosphorylation to function as a transcriptional regulator inducing expression of a number of downstream target genes that directly control cellular outcomes [38]. Activators of TP53 include CHK2, a serine/threonine kinase that, upon activation directly by ATM phosphorylation (e.g., threonine-68) or indirectly by other protein kinases (e.g., DNA-PKcs), acts as both a downstream signal transducer of DNA damage and an effector for DNA repair, checkpoint control and apoptosis [39]. In our study we did not observe changes in transcript expression of CHK2 following irradiation, consistent with the role of CHK2 as an upstream mediator of TP53 rather than a downstream target, however, an increase in phosphorylated CHK2 protein was observed. Phosphorylation of TP53 at serine-20 by CHK2 prevents MDM2-mediated TP53 degradation. This enhancement of TP53 stability allows for the continuance of downstream DNA damage response pathways including apoptosis, of which BAX is an effector [40]. CHK2, a direct substrate of ATM, is an earlier DNA damage response protein than BAX. Hirao et al. [41] observed by Western blot that CHK2 levels in both sham- and 5 Gy irradiated wild-type mouse thymocytes precede BAX up until 6 h post-irradiation, which is consistent with our protein ELISA results post-irradiation.

Our radiation-response results in the ex vivo blood model are consistent with previous human studies [6, 8, 10, 23-25, 42] with the exception of RAD51, which showed a decrease in expression in our study [43]. A recent study in mice of radiation effects on gene expression showed significant increases in expression of CDKN1A, BBC 3 and GADD45a at 24 hrs after 2 Gy whole body irradiation [42]. However, in that study DDB2 was downregulated and no significant changes were observed for FDXR or XPC, which is inconsistent with our results and those of others in humans irradiated ex vivo [10]. Expression of GADD45a, LIG1 and XPC were decreased at 24 hours after 6 Gy IR in mice, whereas we observed increased expression at 24 hrs after 2 Gy in our ex vivo human blood culture model consistent with published human ex vivo and in vivo literature [7, 12, 30]. Also, our use of a 2 Gy exposure (rather than 6 Gy used in a prior mouse study [30]) is more relevant for radiation biodosimetry because individuals having a radiation exposure dosage of less than 2 Gy require no immediate treatment as opposed to those having a dosage higher than 2 Gy. The inherent differences between murine and human assays emphasize the importance of using human model systems to validate biomarkers for human radiation biodosimetry. Our study investigates the blood of unrelated people and we confirm our findings in a separate independent group of unrelated people, suggesting that interindividual variation in the transcript response is not a major factor for the genes in our panel.

Understanding the effects of confounding factors, such as inflammation stress, on radiation-responsive biomarkers is important for assessing their utility in radiation biodosimetry in practical human exposure scenarios [1, 2, 29, 30]. Of the 8 radiation-responsive genes in our study, only three (CDKN1A, FDXR and BBC3) were confounded by LPS-induced inflammation stress. CDKN1A is a canonical marker of DNA damage response and has been proposed as a biomarker of radiation exposure [7,42]. While cigarette smoking did not confound the radiation response of CDKN1A [29], our study shows that inflammatory stress induced CDKN1A transcript levels in the absence of radiation exposure. Our finding seriously undermines the promise of CDKN1 as a predictive tool for radiation exposure in individuals suffering simultaneous inflammatory stress. Studies in the murine central nervous system also identified CDKN1A as an inflammatory response gene [44] and LPS exposure upregulated CDKN1A transcripts in mice [30]. LPS-induced and the radiation-induced CDKN1A responses were indistinguishable in our human blood model, while in the mouse the upregulation of CDKN1A at 24 hours after LPS injection did not mask the ability to detect a radiation response [30]. This difference in murine vs human responses might be attributed to the differences in LPS dosage (50 ng/ml in our study vs. 0.3 mg/kg which equals 7.2 µg per mouse), LPS bioavailability and species differences in response.

We have made the new observation that LPS co-treatment confounds the transcript response of FDXR and BBC3, also compromising their utility as radiation biodosimeters. The pro-apoptotic gene, BBC3, is responsible for induction of apoptosis pathways following DNA damage. Whole Hood cultured in the presence of LPS repressed the expression of BBC3~2.5-fold, Co-treatment with LPS and radiation diminished BBC3 transcripts compared to either LPS alone or radiation alone. Consistent with our finding, LPS suppressed apoptosis in human blood monocytes [45], but some studies found opposite responses [33]. The transcription of BBC3 is regulated by a complex combination of pro-apoptotic and pro-survival mechanisms [46], suggesting that LPS may suppress BBC3 transcription in blood cultures through activation of pro-survival signals. In contrast to our findings, Tucker and colleagues observed a marginal confounding effect of LPS treatment on the radiation response of BBC3 in mice [30], again emphasizing the importance of validating biomarker panels in a human model.

The increases in protein levels of phosphorylated CHK2 after radiation-alone exposures were fully suppressed in the presence of LPS, also undermining it as a useful protein biomarker for radiation response in the context of inflammation stress. CHK2 protein is phosphorylated in response to DNA damage which activates the protein [13,36]. While we demonstrate that LPS co-treatment fully abrogates this radiation-induced CHK2 phosphorylation process, the underlying mechanisms for this confounding effect remain unclear.

Figure 12A:
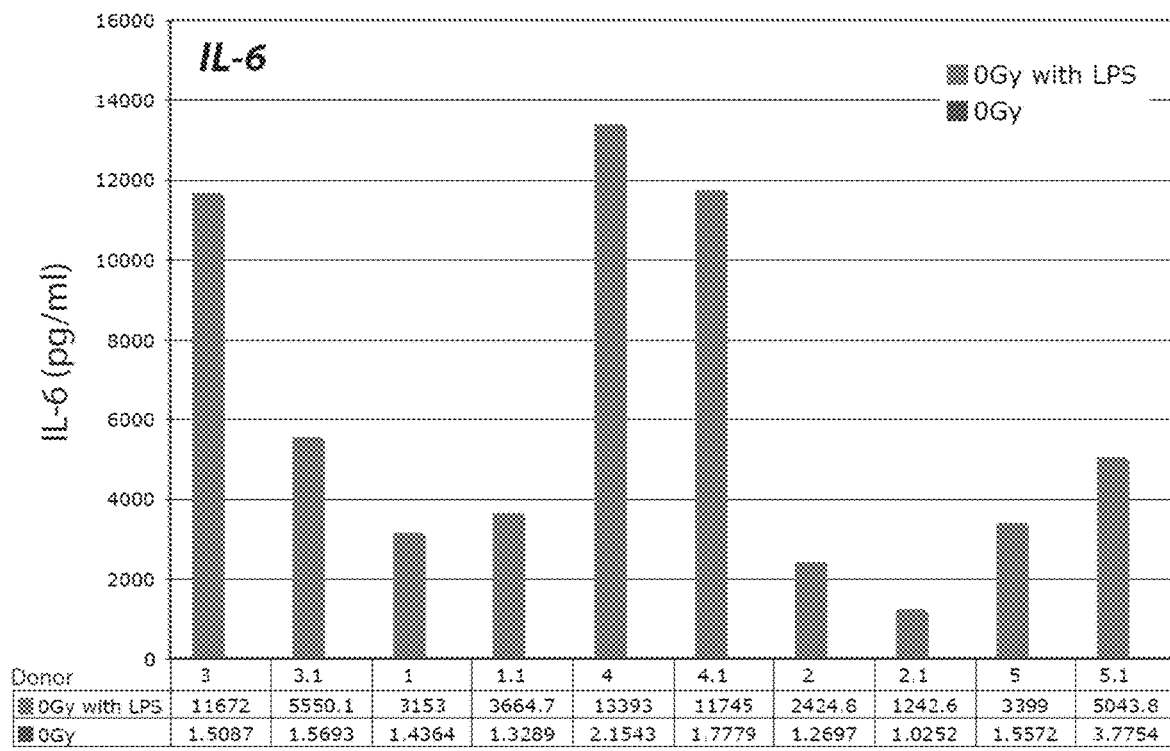
Figure 12B:
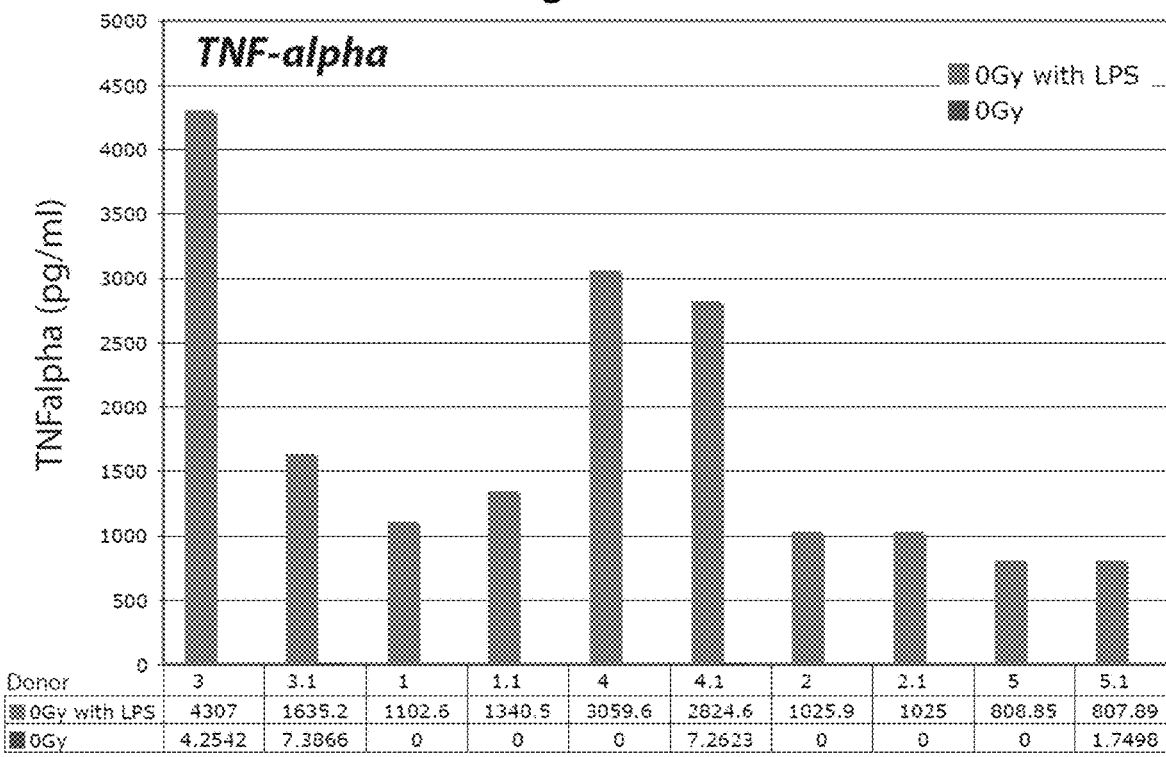
Figure 14:
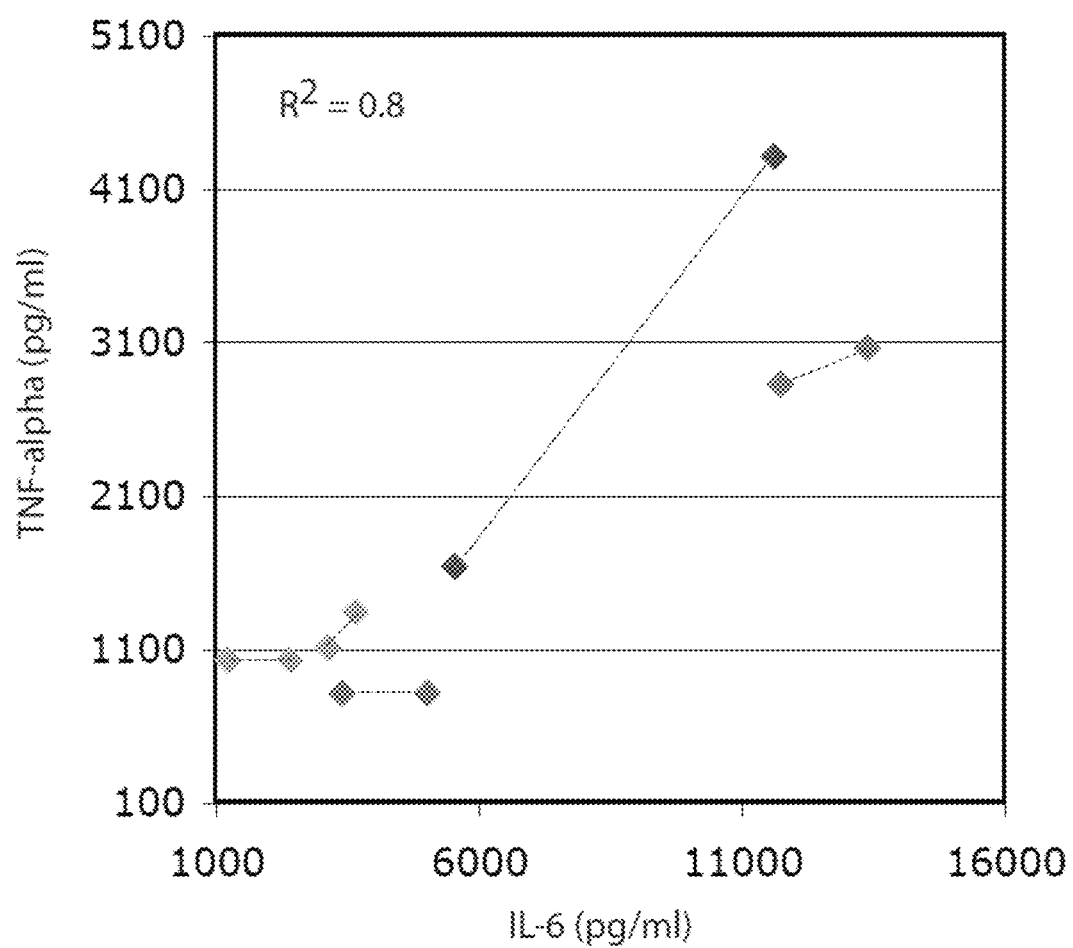
FIG. 14. Correlation between IL-6 and TNF-α responses in LPS treated whole blood cultures. Secretion of IL-6 and TNF-α were measured by ELISA for 5 donors. Each donor is represented with a different color. All donors were sampled twice at least one month apart and the responses are connected by a dotted line to illustrate the similar levels. Note that the TNF-α and IL-6 secretory response after LPS treatment is variable among donors, but highly correlated between the replicate blood draws for each donor with the exception of the donor represented in red.

The LPS-modified CDKN1A, FDXR and BBC3 transcript levels were remarkably uniform among donors, even though the secretions of IL-6 and TNF-α two genes well-known to be induced by LPS, were more variable (FIG. 12). The levels of LPS-induced IL-6 and TNF-α were highly correlated ($R^2=0.8$; FIG. 14). Among 4 of the donors, IL-6 and TNF-α levels in the first blood draw were nearly identical to those in the second blood draw, 1 month later. These findings point to the hypothesis that the induction of inflammatory response genes IL-6 and TNF-α depend on genetic background, while the inductions of CDKN1A and BBC3 are more 'switch-like'. This would predict that other confounding stimuli might also affect CDKN1A and BBC3 expression.

Our research has identified a small panel of DNA repair-related biomarkers that distinguish among human blood samples from four radiation exposure scenarios: no radiation exposure, 2 Gy radiation exposure only, inflammation stress without radiation exposure, and combined 2 Gy exposure plus inflammation stress. Independent validation for dose and time response and with in vivo total body irradiated samples further supports the utility of these biomarkers for clinical applications, accident scenarios and other situations involving potential radiation exposure. Future studies will be needed to evaluate our panel for effects of gender, age, and inter-individual variations, to examine the influence of differential radiation cytotoxicities of the white cell subtypes on expression biodosimetry [47], and to investigate the radiation specificity of our panel using other inflammation, chemical, and physical stressors that are relevant for human radiation biodosimetry applications in various hypothetical exposure scenarios.

The present methods describe the measurement and detection of transcript or expression levels of a biomarker as measured from a sample from a patient. The sample obtained may be a cell from a tissue, a biopsy, a blood sample or other bodily or bodily fluid sample. In one embodiment, the sample is blood. Such methods for obtaining such samples are well known to those skilled in the art.

Methods for detection of expression levels of a biomarker can be carried out using known methods in the art including but not limited to, fluorescent in situ hybridization (FISH), immunohistochemical analysis, fluorescence detection, comparative genomic hybridization, PCR methods including real-time and quantitative PCR, mass and imaging spectrometry and spectroscopy methods and other sequencing and analysis methods known or developed in the art. The expression level of the biomarker in question can be measured by measuring the amount or number of molecules of mRNA or transcript in a cell. The measuring can comprise directly measuring the mRNA or transcript obtained from a cell, or measuring the cDNA obtained from an mRNA preparation thereof. Such methods of extracting the mRNA or transcript from a cell, or preparing the cDNA thereof are well known to those skilled in the art. In other embodiments, the expression level of a gene can be measured by measuring or detecting the amount of protein or polypeptide expressed, such as measuring the amount of antibody that specifically binds to the protein in a dot blot or Western blot. The proteins described in the present invention can be overexpressed and purified or isolated to homogeneity and antibodies raised that specifically bind to each protein. Such methods are well known to those skilled in the art.

Comparison of the detected expression level of a gene in a patient sample is often compared to the expression levels detected in a normal tissue sample or a reference expression level. In some embodiments, the reference expression level can be the average or normalized expression level of the gene in a panel of normal cell lines or cancer cell lines. In some embodiments, the reference expression level is a baseline expression level obtained from the patient prior to the suspected event in question. For example, a patient may provide a blood sample at an earlier time before the radiation exposure occurred.

In various embodiments, the expression levels of genes or the protein level of the protein in the given biomarker panel are determined for identifying a patient that has recently experience radiation exposure, comprising: (a) measuring the amplification or expression level of each gene or protein in one of the biomarker panels in a sample from a patient; (b) determining if the amplification or expression level of said panel of genes in a patient sample has a twofold or more change in expression level as compared to a reference amplification or expression level, wherein such a twofold or more change in the expression levels indicates a recent radiation exposure; and (c) providing a radiation therapeutic regimen to the patient if such a twofold or more change in expression levels is detected.

Biomarker gene sequences and biomarker gene products that may be detected are herein identified by gene name, Entrez GeneID, GenBank Accession Version Numbers, and the publicly available content all of which are hereby incorporated by reference in their entireties for all purposes. As used herein, a "gene set forth in" a figure, table or a panel or "a gene provided in" or a "gene identified in" a figure, table or panel, and the like, are used interchangeably to refer to the gene that is listed in that figure, table or panel. For example, a gene "identified in" FIG. 7 or 11 refers to the gene that corresponds to the gene listed in Tables 2-4 and FIG. 7 or 11. As understood in the art, there are naturally occurring polymorphisms for many gene sequences. Genes that are naturally occurring allelic variations for the purposes of this invention are those genes encoded by the same genetic locus. The proteins encoded by allelic variations of a gene set forth herein typically have at least 95% amino acid sequence identity to one another, i.e., an allelic variant of a gene indicated in FIG. 7 typically encodes a protein product that has at least 95% identity, often at least 96%, at least 97%, at least 98%, or at least 99%, or greater, identity to the amino acid sequence encoded by the nucleotide sequence denoted by the Entrez GeneID (as of Nov. 7, 2013) shown in FIG. 7 for that gene. For example, an allelic variant of a gene encoding CDKN1A (gene: cyclin-dependent kinase inhibitor 1) typically has at least 95% identity, often at least 96%, at least 97%, at least 98%, or at least 99%, or greater, to the CDKN1A protein sequence encoded by the nucleic acid sequence available under the Entrez GeneID No. 1026). In some cases, a "gene identified in" a panel, such as the eight biomarker panel, may also refer to an isolated polynucleotide that can be unambiguously mapped to the same genetic locus as that of a gene assigned to a genetic locus by the Entrez Gene ID or it may also refer to an expression product that is encoded by a polynucleotide that can be unambiguously mapped to the same genetic locus as that of a gene assigned to a genetic locus by the Entrez Gene ID.

Figure 2B:
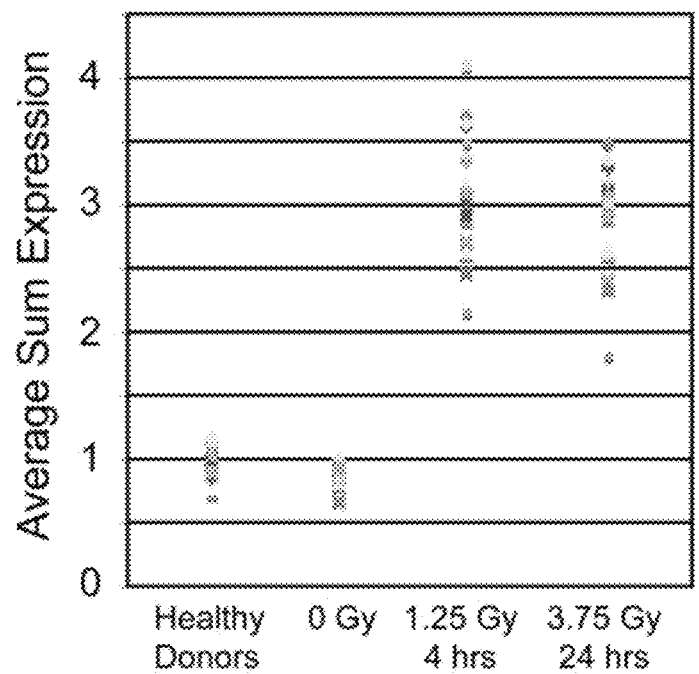

In some embodiments, a prognostic method for predicting whether a patient was exposed to radiation and at what level of exposure. As shown in FIGS. 2A and 2B, the present 8-gene biomarkers were predictive of which patient received a higher or lower dose or no dose of radiation based upon the average sum of the expression levels.

In another embodiment, a method for stratifying patients based on the radiation dose exposure, said method comprising the steps of: (a) measuring the expression level of one or more genes or protein selected from the 12-biomarker set in a blood sample from the patient; and (b) comparing the expression level of said biomarker from the patient with the expression level of the biomarker in a normal sample or a reference expression level (such as the average expression level of the gene in a cell line panel, or the like), wherein an increase in the expression level of the biomarker selected from the 12-gene set indicates whether the patients were exposed to a radiation dose of over 2 Gy or below 2 Gy.

The expression level of a gene is measured by measuring the amount or number of molecules of mRNA or transcript in a cell. The measuring can comprise directly measuring the mRNA or transcript obtained from a cell, or measuring the cDNA obtained from an mRNA preparation thereof. Such methods of extracting the mRNA or transcript from a cell, or preparing the cDNA thereof are well known to those skilled in the art. In other embodiments, the expression level of a gene can be measured by measuring or detecting the amount of protein or polypeptide expressed, such as measuring the amount of antibody that specifically binds to the protein in a dot blot or Western blot. The proteins described in the present invention can be overexpressed and purified or isolated to homogeneity and antibodies raised that specifically bind to each protein. Such methods are well known to those skilled in the art.

Methods of assaying for protein overexpression include methods that utilize immunohistochemistry (IHC) and methods that utilize fluorescence in situ hybridization (FISH). A commercially available IHC test, for example, is PathVysion® (Vysis Inc., Downers Grove, Ill.). A commercially available FISH test is DAKO HercepTest® (DAKO Corp., Carpinteria, Calif.). The expression level of a gene encoding a one of the biomarkers can be measured using an oligonucleotide derived from the nucleotide sequences of the GeneID or GenBank Accession numbers indicated or contained in the sequence listing attached.

In some embodiments of the invention, the nucleotide sequence of a suitable fragment of the gene is used, or an oligonucleotide derived thereof. The length of the oligonucleotide of any suitable length. A suitable length can be at least 10 nucleotides, 20 nucleotides, 50 nucleotides, 100 nucleotides, 200 nucleotides, or 400 nucleotides, and up to 500 nucleotides or 700 nucleotides. A suitable nucleotide is one which binds specifically to a nucleic acid encoding a target gene and not to the nucleic acid encoding another gene.

In other embodiments, detection by increased expression is carried out by quantitative PCR, expression or transcription profiling, array comparative genomic hybridization (array CGH), or other techniques known and employed in the art. Methods for such detection are described in U.S Patent Application Publication Nos. 20050118634, 20060292591, and 20080312096, hereby incorporated by reference.

Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)), which are hereby incorporated by reference.

The probes are most easily prepared by combining and labeling one or more constructs. Prior to use, constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means.

In some embodiments, amplification is detected through the hybridization of a probe of a mitotic network gene to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., Proc. Natl Acad Sci USA, 89: 5321-5325 (1992), and PCR Protocols, A Guide to Methods and Applications, Innis et al., Academic Press, Inc. N.Y., (1990)).

In another embodiment, elevated gene expression is detected using quantitative PCR. Primers can be created using the sequences of genes identified Table 4, to detect sequence amplification by signal amplification in gel electrophoresis. As is known in the art, primers or oligonucleotides are generally 15-40 by in length, and usually flank unique sequence that can be amplified by methods such as polymerase chain reaction (PCR) or reverse transcriptase PCR (RT-PCR, also known as real-time PCR). Methods for RT-PCR and its optimization are known in the art. An example is the PROMEGA PCR Protocols and Guides, found at URL:<http://www.promega.com/guides/per_guide/default.htm>, and hereby incorporated by reference. Currently at least four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA.

Two strategies are commonly employed to quantify the results obtained by real-time RT-PCR; the standard curve method and the comparative threshold method. In this method, a standard curve is first constructed from an RNA of known concentration. This curve is then used as a reference standard for extrapolating quantitative information for mRNA targets of unknown concentrations. Another quantitation approach is termed the comparative $C_t$ method. This involves comparing the $C_t$ values of the samples of interest with a control or calibrator such as a non-treated sample or RNA from normal tissue. The $C_t$ values of both the calibrator and the samples of interest are normalized to an appropriate endogenous housekeeping gene.

In one embodiment, elevated gene expression is detected using an RT-PCR assay to detect transcription levels or detected using a PCR assay to detect amplification of at least one gene from the mitotic network.

In some embodiments, elevated expression of the 12 biomarkers (e.g., pCHK2-thr68) is detected using an immunochemical assay to detect protein levels. Such immunochemical assays are known throughout the art and include Western blots and ELISAs.

In one embodiment, using known methods of antibody production, antibodies to the biomarker are made. In some embodiments, elevated gene expression is detected using an immunochemical (IHC) assay to detect gene protein levels. Anti-gene specific antibodies can be made by general methods known in the art. A preferred method of generating these antibodies is by first synthesizing peptide fragments. These peptide fragments should likely cover unique coding regions in the candidate gene. Since synthesized peptides are not always immunogenic by their own, the peptides should be conjugated to a carrier protein before use. Appropriate carrier proteins include but are not limited to Keyhole limpet hemacyanin (KLH). The conjugated phospho peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal antibodies can be purified by passing the harvested antibodies through an affinity column. Monoclonal antibodies are preferred over polyclonal antibodies and can be generated according to standard methods known in the art of creating an immortal cell line which expresses the antibody.

Nonhuman antibodies are highly immunogenic in human and that limits their therapeutic potential. In order to reduce their immunogenicity, nonhuman antibodies need to be humanized for therapeutic application. Through the years, many researchers have developed different strategies to humanize the nonhuman antibodies. One such example is using "HuMAb-Mouse" technology available from MEDAREX, Inc. and disclosed by van de Winkel, in U.S. Pat. No. 6,111,166 and hereby incorporated by reference in its entirety. "HuMAb-Mouse" is a strain of transgenic mice which harbor the entire human immunoglobin (Ig) loci and thus can be used to produce fully human monoclonal antibodies to any of the 12-genes or proteins identified herein.

In some embodiments, kits for use with any of the methods provided. Such kits typically comprise two or more components necessary for performing an assay. In various embodiments, components may be compounds, reagents, containers and/or equipment, instructions.

In one embodiment, one container within a kit may contain a set of probes for detection of increased expression of the 8-, 9- or 12-biomarkers identified in FIG. 7 and in FIG. 1. One or more additional containers may enclose elements, such as reagents or buffers, to be used in the assay. Such kits may also, or alternatively, contain a detection reagent as described above that contains a reporter group suitable for direct or indirect detection of antibody binding. In some embodiments, the probes may be present or displayed on a surface for colorimetric, fluorescent, or other identifiable detection upon hybridization or binding of the 8-, 9-, or 12-biomarkers in a sample to determine the expression levels of the biomarkers, and thereby determine the radiation dosage received by a patient.

In another embodiment, the kit may be comprised of a set of PCR primers to detect amplification and expression levels of the 8-, 9-, and/or 12-biomarker panels described herein. The kit may also contain such reagents as buffers, polymerase, Magnesium, or other elements necessary to carry out quantitative PCR.

In another embodiment, a hand-held device adapted for detection of the biomarkers of the 8-, 9-, and/or 12-gene panels described herein and their expression levels. In one embodiment, antibodies to the 8-, 9- and/or 12-gene panel biomarkers fixed on a substrate. Once hybridization occurs, second antibody hybridization provides for positive response. In another embodiment, the radiation dosage received by the patient is determined and displayed. Such a device may employ a system requiring a computer and/or software display and elements. In some embodiments, the system is connected to a network.

In various embodiments, the present methods and gene detection may be carried out with or on a system incorporating computer and/or software elements configured for performing logic operations and calculations, input/output operations, machine communications, detection of gene or protein expressions levels and analysis of the measured levels and/or the like. Such system may also be used to generate a report, determinations of the total expression levels measured, the comparison with any reference levels, and calculation of the median levels of gene and gene product expression levels. It will be appreciated by one of skill in the art that various modifications are anticipated by the present embodiments.

EXAMPLE 1

Radiation Response of Human Biomarker Panel

Human Subjects. All research involving human subjects were approved by the Lawrence Berkeley National Laboratory Institutional Review Board. Peripheral blood from healthy volunteers was obtained after written informed consent and was drawn into sodium citrate (whole blood culture model) or sodium heparin (PBMC culture model) Vacutainer tubes (Becton Dickinson and Company, Franklin Lakes, N.J.).

Whole blood ex vivo radiation model. Five donors (2 male, 3 female; age range, 20-50 years) provided two peripheral blood samples each, at least one month apart for measurement of transcript and protein responses. Blood collected in Vacutainer tubes was transferred in 18 ml aliquots into 50 ml conical tubes. Blood in tubes was exposed at room temperature to 0 or 2 Gy X-rays, (~780 mGy/min; Pantak 320 kVp X-ray machine (Precision X-ray); run at 300 kV and 10 mA). Dosimetry was performed using a RadCal AccuPro dosimeter by measuring the accumulated dose over a specific time interval. After irradiation, blood samples were diluted 1:1 with RPMI 1640 medium (Sigma-Aldrich) supplemented with 10% heat-inactivated fetal bovine serum (Invitrogen) in 50 ml centrifuge tubes, loosely capped and maintained on a 10 degree angle at 37° C. in a humidified incubator with 5% $CO_2$ for 24 hrs. LPS was added to some blood cultures immediately after irradiation (50 ng/ml LPS from *Escherichia coli* O111: B4) (Sigma Aldrich). After 24 hrs, buffy coats were extracted for protein and RNA purification. Plasma was collected, aliquoted and stored at −80° C.

RNA isolation and quantitative RT-PCR. RNA was isolated using Trizol reagent (Invitrogen) and purification was performed according to the manufacturer's instructions. In brief, cell pellets were homogenized in Trizol reagent (1.2 ml). The lysed cells were incubated for 5 min at room temperature, followed by the addition of 0.25-ml chloroform. After mixing, the samples were centrifuged at 12,000 g for 15 min at 4° C. The aqueous phase was separated and 0.625 ml ice-cold isopropanol was used to precipitate RNA. The samples were incubated at room temperature for 10 min and total RNA was collected by centrifugation at 12,000 g for 10 min at 4° C. The RNA pellet was washed with 1 ml 70% ethanol and dissolved in 40 µl RNase-free deionized water. The RNA was quantified using a NanoDrop-2000c spectrophotometer (Thermo Scientific), and quality was monitored with the Agilent 2100 Bioanalyzer (Agilent Technologies, Santa Clara, Calif.). RNA integrity numbers (RIN) ranged from between 7 to 9.5 (mean, 8.3), and 260/280 absorbance ratios ranged from 1.7 to 1.95 (mean, 1.86) [33].

For cDNA synthesis an aliquot of 4 µg of total RNA was reverse transcribed using the High-Capacity cDNA Reverse Transcription Kit (Applied Biosystems, Foster City, Calif.) according to the manufacturer's instructions. Taqman Gene Expression Assays (Applied Biosystems, Foster City, Calif., USA) were used, according to manufacturer's instructions, to detect mRNA of 40 DNA damage response genes. 13 genes were selected for further investigation (BAX, Hs00180269_m1*, BBC3, Hs00248075_m1*, FDXR, Hs01031624_m1, CDKN1A, Hs00355782_m1*, GADD45a, Hs99999173_m1, CCNG1, Hs00171112_m1*, CHK2, Hs00200485_m1*, PCNA, Hs00696862_m1, LIG1, Hs01553527_m1*, XPC, Hs01104206_m1*, DDB2, Hs03044953_m1*, POLH, Hs00982625_m1*, RAD51, Hs00153418_m1*; * indicates manufacturer's recommended assay for this gene, if more than one assay was available). See Table 3 for a full list of all 40 genes and assay numbers. The RT-PCR reactions were performed, in individual reaction format, with the ABI 7500 Fast Real Time PCR System using Taqman Fast Universal PCR Master Mix from ABI and following manufacturer's recommendations. The results were expressed as the threshold cycle (Ct), i.e. the cycle number at which the PCR product crosses the threshold of detection. The relative quantification of the target transcripts normalized to the endogenous control ACTB (β-Actin) was determined by the comparative Ct method ($\Delta Ct$) according to the manufacturer's protocol. The endogenous control gene GAPDH was run concurrently but was not used for normalization since LPS treatment induced changes in GAPDH transcript levels. Relative fold inductions were calculated by the $\Delta\Delta C_T$ method [7]. All samples were run in triplicate. A no RT qPCR control was included for all reactions to monitor for genomic DNA contamination and was negative across all reactions.

Confirmation of radiation responsiveness of our 8-biomarker transcript panel in independent expression datasets of ex vivo irradiated human blood and blood samples of human patients undergoing total body irradiation. Globally normalized whole genome microarray expression profiles of whole blood irradiated ex vivo were obtained from the NCBI GEO database (GSE8917; [10]). In that study, human peripheral blood was obtained from five donors and irradiated ex vivo (sham, 0.5, 2, 5 and 8 Gy). RNA was isolated from samples collected at 6 and 24 hrs after exposure and transcript levels were measured using Agilent-012391 Whole Human Genome Oligo Microarray G4112A [10]. We then mean normalized the expression levels of each of the eight genes in this dataset across doses, times, and donors, and then summed theses values across all 8 genes for each blood sample in each treatment group. For calculating dose response, we plotted the average and standard error for each dose group, normalized to the average value of the sham group for each of the two time points.

Globally normalized whole genome expression profiles of patients undergoing total body irradiation (TBI) were obtained from the NCBI GEO database (GSE20162; [12]). In that study, peripheral blood gene expression profiles were obtained from 18 donors undergoing TBI. Patients were exposed to a total of 3.75 Gy in one day divided in three fractions of 1.25 Gy with approximately 4 hrs between fractions. Blood was collected before irradiation, 4 hrs after the first fraction of 1.25 Gy and 20-24 hrs after the first fraction. Blood from 14 healthy donors was collected as control. RNA was extracted and transcript levels were measured using Agilent Whole Human Genome Microarray G4112A [12]. For the TBI dataset, we again mean normalized the expression levels of each of our 8 genes across all samples in the database for the patients and healthy donors. For each blood samples we calculated the sum of the normalized expression of each of the 8 genes, normalized to the average of the sum expression of the healthy donors.

Peripheral blood mononuclear cell (PBMC) ex vivo radiation model. Seven donors (6 male, 1 female; age range, 20-50 years) provided two peripheral blood samples each, at least one month apart, for protein analyses. Blood was transferred to 3 equal (~13 ml) aliquots into 50 ml conical tubes. Blood in tubes was exposed at room temperature to 0, 2 or 6 Gy X-rays at a rate of ~1.25 Gy/min (2 Gy) or ~1.30 Gy/min (6 Gy) (faxitron 160 kVp X-ray machine (Faxitron) set at 160 kV and 6.3 mA). Dosimetry was performed using a RadCal AccuPro dosimeter by measuring the accumulated dose over a specific time interval. After irradiation, blood samples were separated over Accuspin System-Histopaque-1077 (Sigma-Aldrich) according to the manufacturer's instructions. PBMC were washed in phosphate buffered saline (PBS) and resuspended in RPMI 1640 medium (Sigma-Aldrich) supplemented with 10% heat-inactivated fetal bovine serum (Invitrogen) and cultured in duplicate T25 flasks for each dose group. Cells were maintained on a rocking platform at 37° C. in a humidified incubator with 5% $CO_2$ for 6 and 24 hrs.

Figure 9:
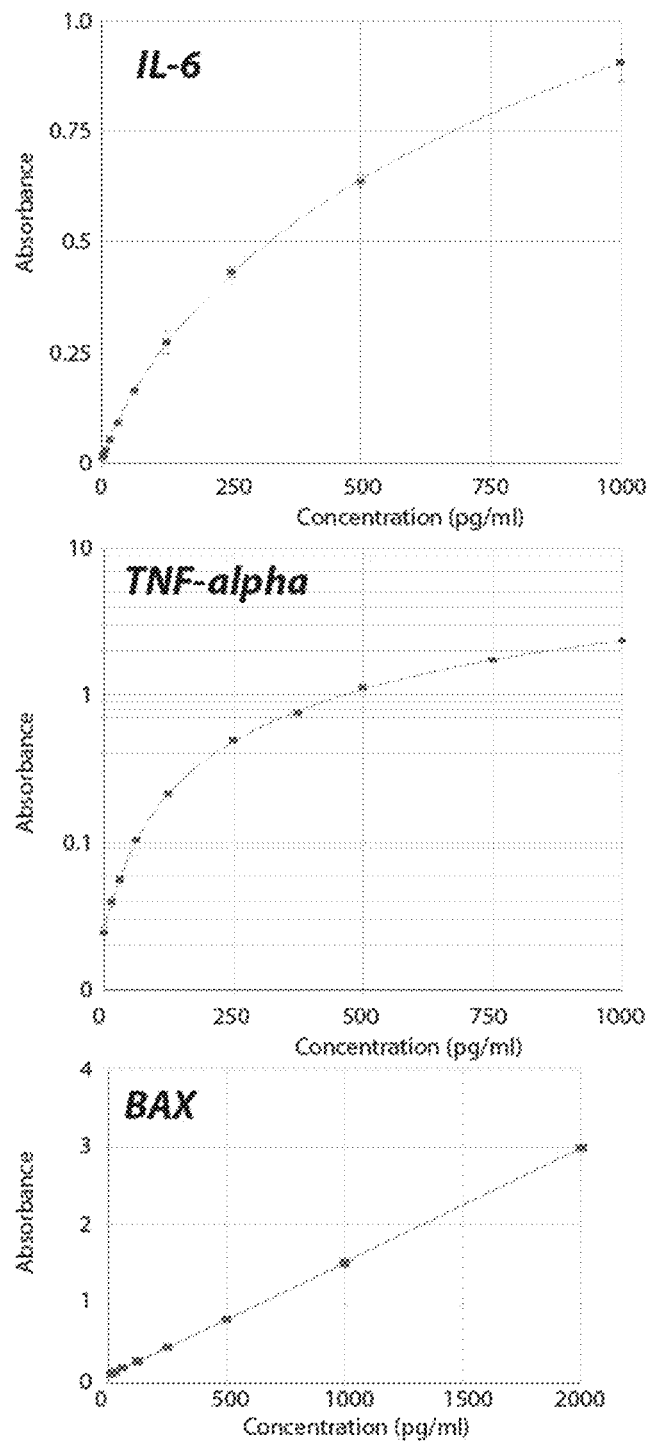
FIG. 9. Standard curves for ELISAs. BAX, IL-6 and TNF-α representative standard curves are shown. pCHK2-thr68 did not use a standard curve.

Cell lysates for protein analyses by Enzyme-Linked Immunosorbent Assays (ELISA). Buffy coats were collected from whole blood cultures and treated with a 1:3 mixture of warm (37° C.) RBC Lysis buffer (5 Prime) for two steps and then washed once with cold phosphate buffered saline. The obtained cell pellets or PBS-washed PBMC pellets, from the PBMC culture model, were then lysed with Pierce M-PER Mammalian Protein Extraction Reagent and 1×Halt protease/phosphatase inhibitors (Thermo Scientific). Extracts were collected, aliquoted and stored at −80° C. Protein concentrations were measured using Pierce BCA Protein Assay Reagent (Thermo Scientific). Amounts of protein in lysate or plasma were quantified using ELISA kits; human BAX ELISA kit (Assay Designs), human phosphorylated CHK2-thr68 ELISA kit (Cell Signalling). The biological effectiveness of LPS was confirmed by measuring secretion of IL-6 and TNF-α in plasma by ELISA following manufacturer's recommended protocol (R&D Systems). ELISAs were performed following manufacturer's instructions. BAX ELISAs were performed using 0.1-µg or 1-µg protein cell lysate per well for irradiated and non-irradiated samples respectively. pCHK2-thr68 ELISAs were performed using 25 µg of protein cell lysate for all samples. IL-6 and TNF-α ELISAs were performed using undiluted or 1:100-fold dilution of plasma for non-LPS and LPS-co-treated samples respectively. All ELISA absorbance readings were read with reference to the standard curve, except for pCHK2-thr68 that had no standard curve and used average difference data between control and test samples as readout (FIG. 9). The majority of absorbance readings were within a 0.1-0.7 range (Table 3). All samples were run in duplicate. ELISA plates were read using TECAN Infinite M200 plate reader and analyzed using the TECAN Magellan software. Raw ELISA data was $\log_e$ transformed and mean-zero standardized to obtain a standard normal distribution. We performed inferential tests of hypothesis via independent 2 sample t-tests for each dose-time experimental group for each biomarker.

Classification Analysis. We investigated the classification characteristics of our panel of transcript and protein biomarkers for assigning individual samples into their correct exposure/treatment group: no treatment (N), radiation exposure only (R), LPS treatment only (L), and samples exposed to both radiation and LPS (RL). Classification was performed using marker expression values for n=40 observations per marker, based on the replicate pair of observations per subject and 4 classes (40=2×5×4). A 4-class problem was considered for which the true class labels of observations were N, R, L, and RL. Marker order was determined via filtering by considering all possible pairs of classes, and for each pair ranking all 9 markers by their Gini index [34] for pairwise class discrimination; this involved 6 possible pairwise comparisons (6=4(3)/2). The Gini index, G, is a measure of class impurity among objects assigned to a given node in a decision tree [34]. For a given tree node, $G = 1 - \Sigma_k^K p_k^2$, where $p_k$ is the proportion of node members in class k, and K is the number of classes. Gini has range $0 \leq G \leq 1$, and is equal to zero when there is class purity in the node, and equal to unity when $K \rightarrow \infty$ and all $p_k$ tend to zero. The first gene selected was therefore the best discriminating marker for the N and R classes, followed by the best discriminating marker for the N and L class pairs. Any markers that were the best for multiple pairs of classes were selected in the order of their first appearance among ranks. After filtering to identify marker order based on discrimination, k-nearest neighbor (KNN) classification analysis was performed with K=5, so the KNN model was called 5NN. An odd value for K was chosen to prevent ties in the predicted class membership of nearest neighbors. Classification accuracy based on ten 10-fold cross-validation for predicting the correct true class label was performed using sets of the 1, 2, . . . , 9 ordered markers. Linear discriminant analysis and PCA were not performed because covariance (correlation) is undefined for one marker. Diagnostic screening was also determined for the 9-marker set to determine sensitivity, specificity, positive predictive value (PV+), and negative predictive value (PV−). Sensitivity is equal to the proportion of observations in a given class with the correct class prediction, whereas specificity is the proportion of observations not in a given class whose predicted membership is not in the given class. On the other hand, PV+ reflects the proportion of observations predicted to be in a given class that are truly in the class, while PV− is defined as the proportion of observations that are not predicted to be in a given class which are not in the given class.

Results

Figure 10A:
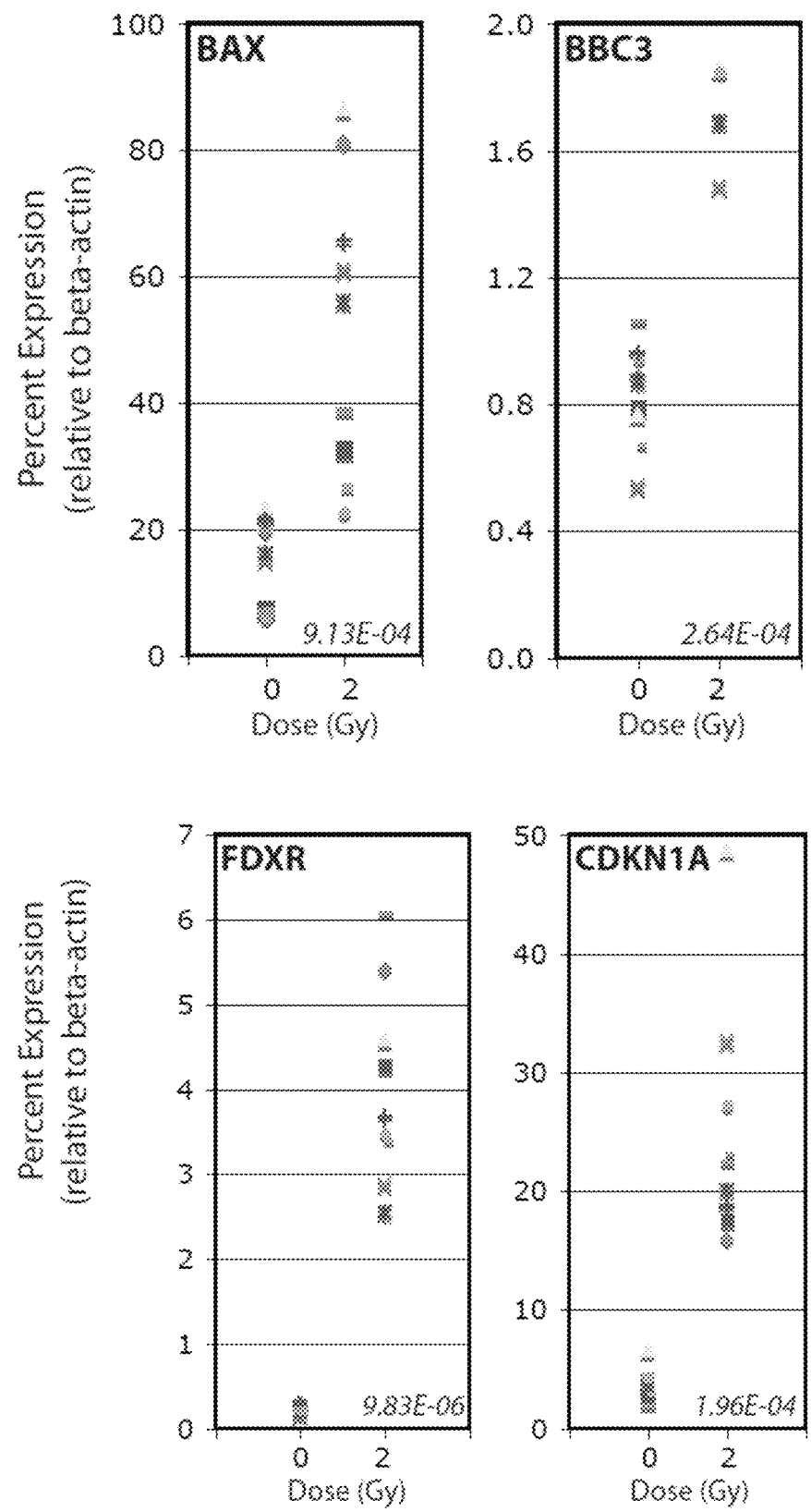
FIGS. 10A, 10B, and 10C. Transcript level radiation responses of twelve DNA repair-related biomarkers. The responses for four biomarkers BAX, BBC3, FDXR and CDKN1A are shown on FIG. 10A, the four biomarkers GADD45, CCNG1, PCNA, and LIG1 are shown on FIG. 10B, and the four biomarkers XPC, DDB2, POLH, and RAD51 are shown in FIG. 10C. Relative expression of the sham (0 Gy) and 2 Gy transcript responses were calculated relative to the mean expression of ACTB (β-Actin). Each symbol represents mean of 3 replicate relative expression levels for the designated DNA repair genes from a blood collection of a single donor. Data are plotted for 5 donors, each donating two blood samples. The delta Ct for β-Actin between sham and 2 Gy irradiated samples was <0.3 for all but one sample, which was excluded from this analysis. A two-sided T-test was performed on the distribution of expression levels between sham and irradiated samples (p-values are shown in the lower right of each box-plot).
Figure 10B:
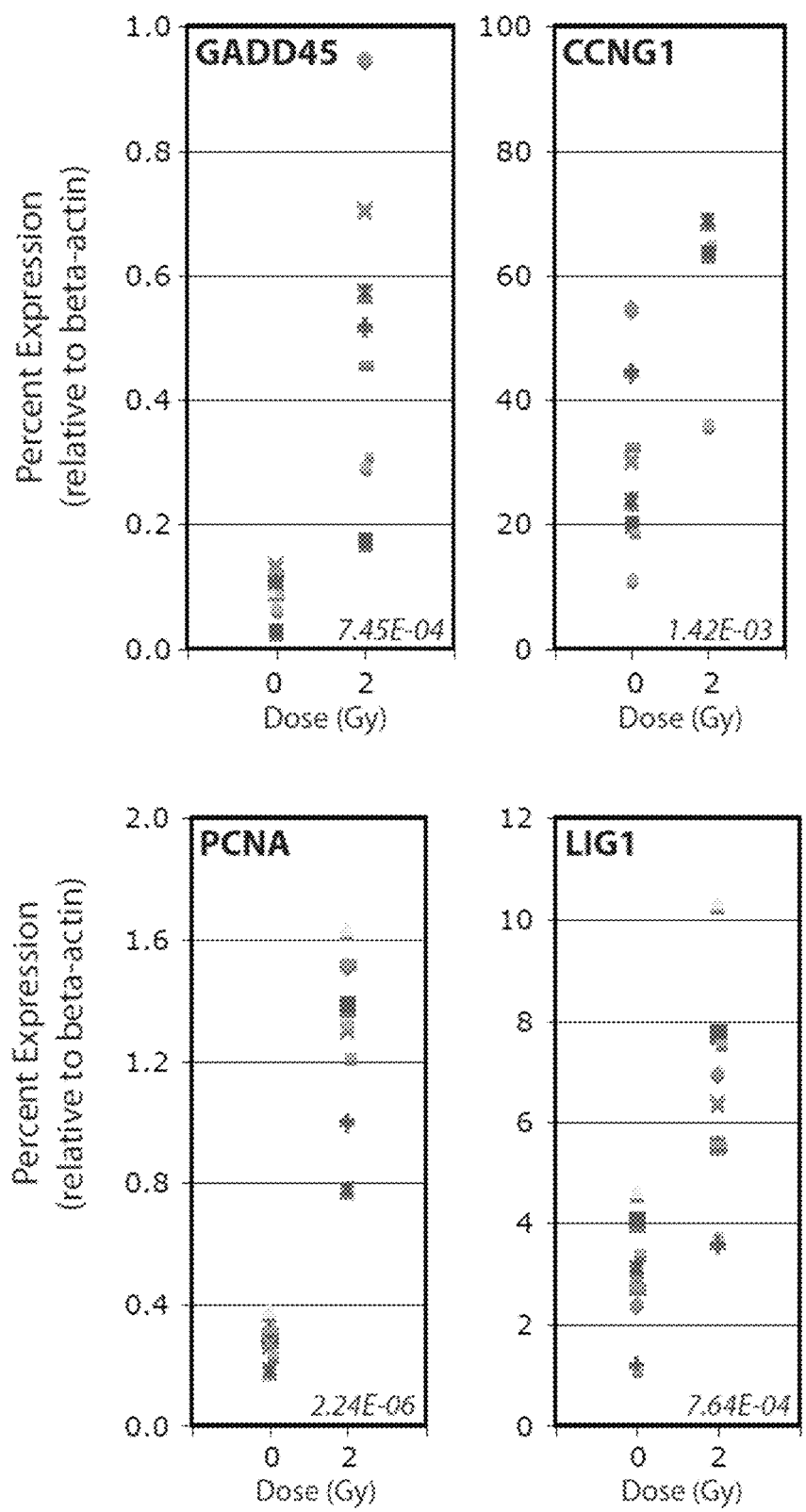
Figure 10C:
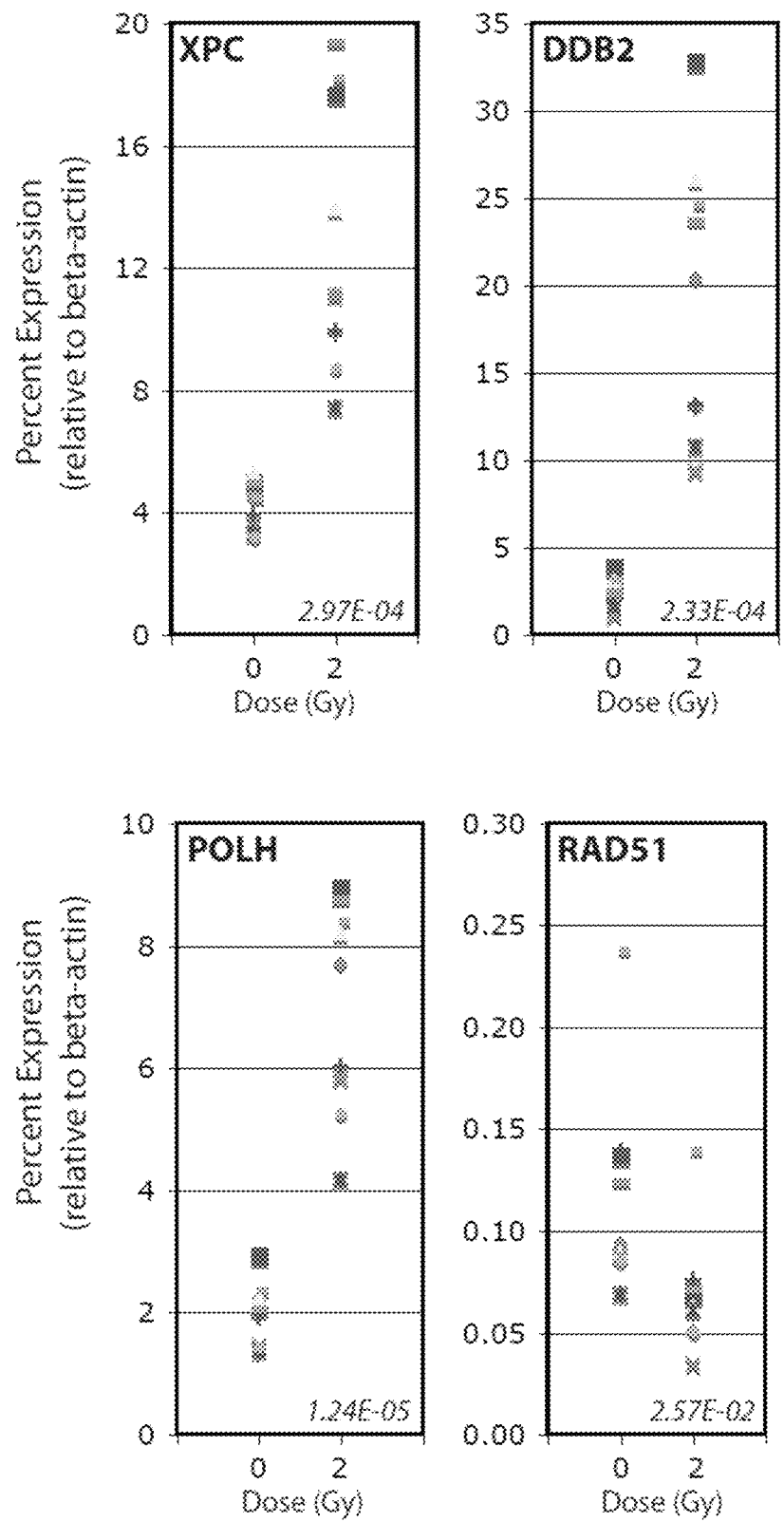

Radiation response of DNA repair genes. The radiation response of 40 genes associated with various aspects of DNA damage response (Table 2) was surveyed. Twelve genes (FIG. 1) were significantly modulated in transcript response 24 hrs after ex vivo exposure to 2 Gy X-rays, relative to sham-irradiated samples (individual t-test 2.2E-06<p<0.03; FIG. 10). Most of these genes (11 of 12) showed increased expression after exposure (FIG. 1), ranging from 2.3-fold for LIG1 to 17-fold for FDXR. RAD51, a key component of homologous recombination repair, was the only gene in this set that showed significant down regulation after exposure (2.5-fold). Expression responses for sham and irradiated samples showed little inter-individual variation and reproducible responses within donors sampled twice at approximately one month apart. These findings indicate that transcript responses of this panel of 12 DNA repair genes are robust biomarkers of radiation exposure in peripheral blood cells. Among these 12 genes, we found no overlap between sham and irradiated samples for 8 biomarkers (BBC3, FDXR, CDKN1A, GADD45a, PCNA, XPC, DDB2 and POLH; individual T-test 2.24E-06<p<7.45E-04), but found only slight overlaps for the other 4 biomarkers (BAX, CCNG1, LIG1 and RAD51; individual t-test 7.64E-04<p<2.57E-02) (FIG. 10). CHK2 is included as an example of a gene that does not respond to radiation (FIG. 1; p=0.5). Our findings predict that when blood samples prior to exposure are not available, our panel of eight DNA repair markers can distinguish between 2 Gy irradiated and unirradiated individuals with 100% accuracy 24 hrs after a 2 Gy exposure (see model in FIG. 7).

Figure 11:
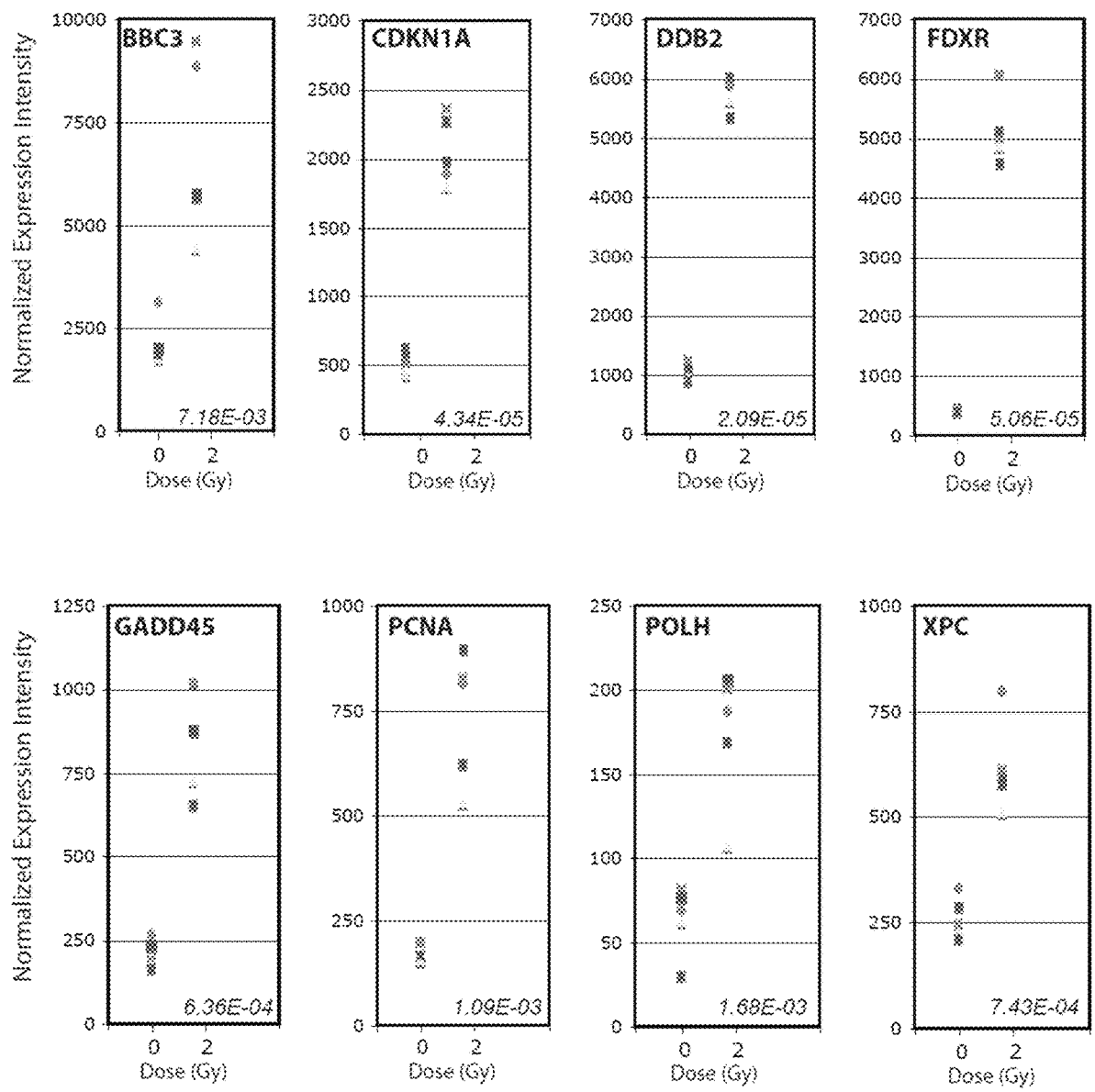
FIG. 11. Transcript level radiation responses of eight DNA repair-related biomarkers in an independent dataset. Normalized expression intensities of the sham (0 Gy) and 2 Gy transcript responses are shown. Each symbol represents expression levels for the designated DNA repair gene from a blood collection of a single donor. Data are plotted for 5 donors. A two-sided T-test was performed on the distribution of expression levels between sham and irradiated samples (p-values are shown in the lower right of each box-plot).

Validation of the dose and time response characteristics of our 8-gene transcript panel in independent human ex vivo and in vivo datasets. We tested the dose response characteristics of our 8-gene panel (BBC3, FDXR, CDKN1A, PCNA, XPC, GADD45a, DDB2 and POLH; see model in FIG. 7) using an independent public dataset containing microarray transcript expression data collected at 6 and 24 hrs after ex vivo exposures (sham, 0.5, 2, 5 and 8 Gy) in human blood from 5 independent donors. This analysis confirmed our primary finding of no overlap in transcript responses for any of the 8 genes between sham and irradiated samples at 24 hrs after 2 Gy exposures (FIG. 11). We then investigated the dose and time response characteristics of our panel using the sum expression values of the 8 genes for each donor (FIG. 2A). The average expression of our panel among the donor group was increased above sham for all dose groups tested at 6 hrs (p<5.5E-05) and 24 hrs (p<2.32E-04). The average sum expression at 6 hrs was consistently higher compared to 24 hrs for all doses tested (5.9E-04<p<0.02). Furthermore, the samples irradiated with 2 Gy were significantly different from those irradiated with 0.5 Gy (p<6.09E-03), 5 Gy (p<8.47E-03) or 8 Gy (p<1.65E-04) at 6 and 24 hrs, demonstrating the significant dose response characteristics of our panel.

We then tested whether our 8-gene panel could distinguish human patients receiving total body irradiation (TBI) from pre-irradiation patients and healthy controls. We obtained a public dataset containing microarray transcript expression data of blood collected from 14 independent healthy donors and from 18 patients who provided blood samples before TBI treatment, at 4 hrs after the first of three fractions of 1.25 Gy and at 20-24 hrs after the first fraction. We calculated the sum expression value for blood sample for each patient and control subject to investigate their variation across experimental groups. As shown in FIG. 2B, there was no overlap in expression between TBI treated blood samples and pre-TBI and control group values. The average expression of the 8-gene panel after TBI treatment was increased above the levels of healthy control group and pre-TBI blood levels for both timepoints tested, at 4 hrs after first fraction (1.25 Gy; p<1.34E-11) and 20-24 hrs after the first fraction (3.75 Gy; p<1.45E-11).

In a separate analysis of human in vivo radiation response, we compared our 8-gene panel against a 25-gene signature developed by Meadows et al [35] to distinguish healthy individuals and pre-irradiation patients from the irradiated patients. In their study, peripheral blood was obtained from TBI patients before irradiation and 6 hrs after 1.5-2.0 Gy. Peripheral blood was also obtained from a population of healthy control individuals. Interestingly, 5 of our eight biomarkers were present in their signature (XPC, PCNA, CDKN1A, DDB2 and BBC3). These comparisons against two independent groups of blood samples from irradiated human patients provide compelling in vivo corroborative support for the utility of our 8-gene panel for radiation biodosimetry in blood cells.

Figure 3:
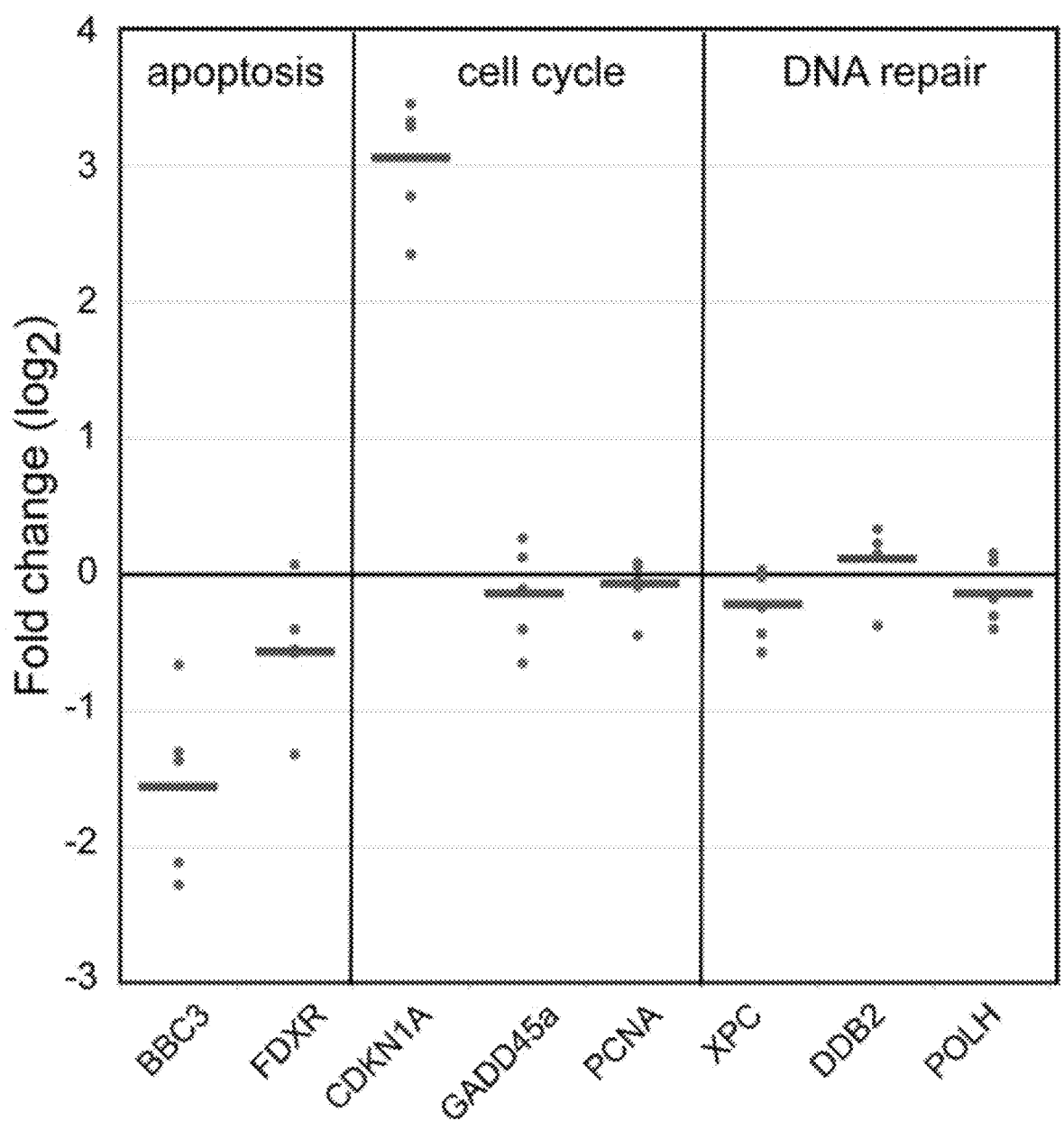
FIG. 3. Effects of LPS treatment on radiation responsive DNA repair and cell cycle genes. Transcript level responses measured by quantitative RT-PCR analysis 24 hrs after LPS treatment of whole blood of two apoptosis, three cell cycle and three DNA repair genes with respect to transcript levels in untreated blood cultures. CDKN1A was strongly upregulated (~8.2-fold) by LPS treatment alone in the absence of radiation exposure with little variation among donors. BBC3 and FDXR expression was downregulated (~3-fold and ~1.5-fold, respectively) by LPS treatment. LPS treatment did not modulate expression levels of GADD45a, PCNA, XPC, DDB2 and POLH (<1.5-fold change in expression compared to untreated samples). ACTB was used to normalize gene expression in samples in which the delta Ct of LPS treated vs untreated was less than 0.3 (donor 1.1, 3, 4.1, 5 and 5.1). GAPDH was not used to normalize since its levels varied depending on the presence of LPS (the average Ct difference between GAPDH in LPS treated and untreated samples was 0.54).

LPS modulation of transcript and protein expression in irradiated whole blood cultures. We investigated the specificity of the radiation response of our biomarkers in the ex vivo blood radiation model in the context of inflammatory stress simulated by LPS. We confirmed that LPS treatment (50 ng/ml) induced an inflammatory response in white blood cells by measuring the secretion of IL-6 and TNF-α into plasma of all donors tested, (Figure S4). LPS treatment showed no significant changes in baseline transcript expression in 5 biomarkers (fold-change <1.5; GADD45a, PCNA, XPC, DDB2, POLH) (FIG. 3). Significant changes were observed in 3 biomarkers (FIG. 3): >8-fold (±1.1) increase in CDKN1A and reduced expression in BBC3 and FDXR (2.9-fold (±0.08) and 1.5-fold (±0.1), respectively).

Figure 4A:
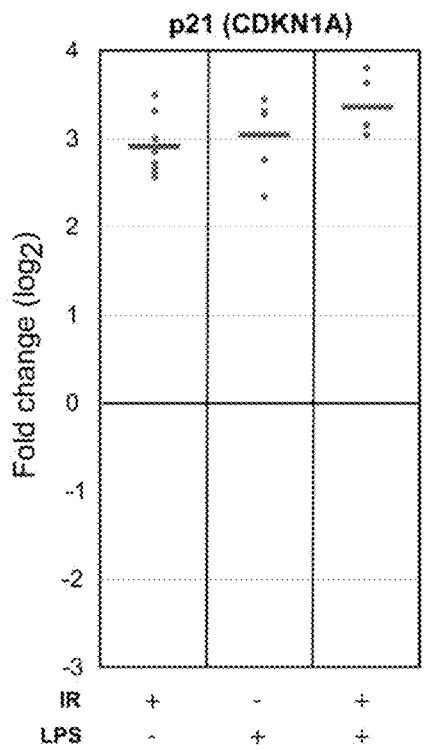
FIGS. 4A, 4B, and 4C show Radiation-induced transcript responses of CDKN1A, BBC3 and FDXR are confounded by LPS treatment. Transcript level responses measured by quantitative RT-PCR analysis 24 hrs after exposure to 2 Gy, LPS treatment, and combined LPS and 2 Gy of whole blood of CDKN1A (A), BBC3 (B), and FDXR (C) genes with respect to transcript levels in un-treated blood cultures.
Figure 4B:
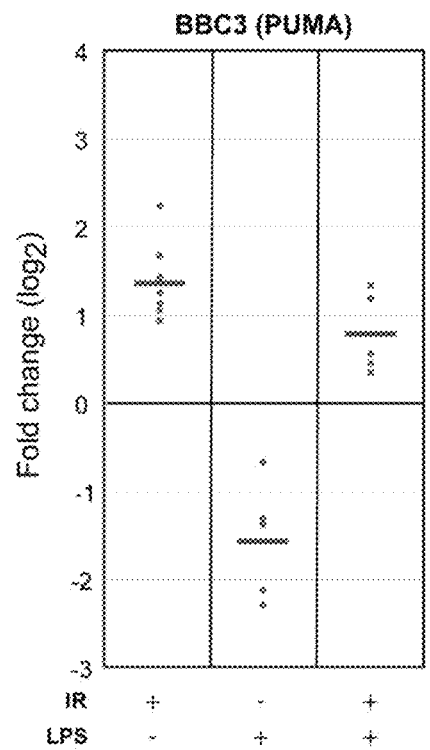
Figure 4C:
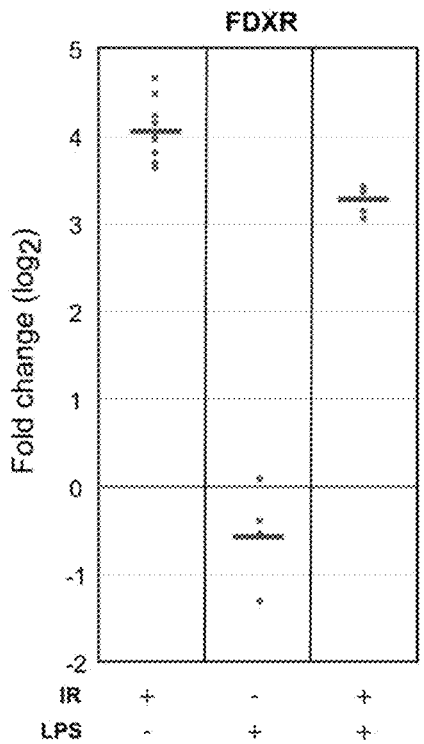
Figure 5:
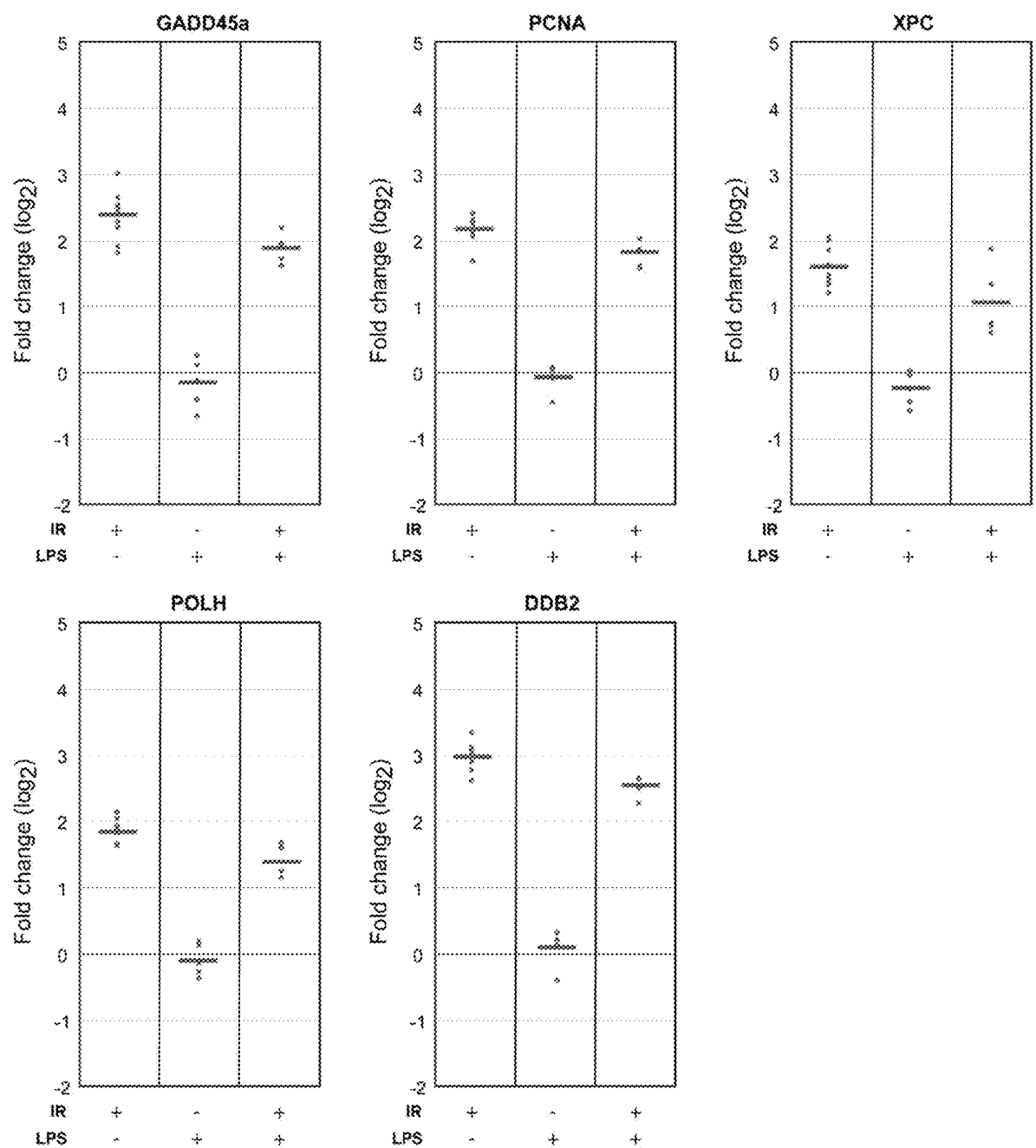
FIG. 5. Radiation-induced transcript responses of GADD45a, PCNA, XPC, POLH and DDB2 are minimally affected by LPS. Transcript level responses measured by quantitative RT-PCR analysis 24 hrs after exposure to 2 Gy, LPS treatment, and combined LPS and 2 Gy of whole blood of GADD45a, PCNA, XPC, POLH and DDB2 genes with respect to transcript levels in un-treated blood cultures. Transcript levels of none of these five genes were significantly modulated 24 hrs after 2 Gy exposure in the presence of LPS compared to 2 Gy alone (fold-change <1.4-fold or p>0.03). Interestingly, the radiation response of all five genes was slightly suppressed by LPS treatment suggesting that LPS had a small effect on the 2 Gy response of these genes.

We then investigated the effect of LPS treatment on radiation response of the 8 genes in our panel, using blood cultures exposed to 2 Gy X-rays and co-treated with LPS (50 ng/ml). The strongest effect of LPS on the radiation responses was seen for CDKN1A, BBC3 and FDXR (FIG. 4; fold-change difference >1.4-fold and p<0.03). LPS modified the radiation response of CDKN1A by an additional 1.4-fold increase over the effects of radiation on CDKN1A expression alone (p=0.03; FIG. 4A). BBC3 and FDXR expression, on the other hand, were repressed 1.6-fold (2.7-fold upregulated after radiation vs. 1.7-fold after radiation in the presence of LPS; p=0.03) and 1.7-fold (17-fold upregulated after radiation vs. 10-fold after radiation in the presence of LPS; p=1.2E-04) after radiation and subsequent culture in the presence of LPS in comparison to the effects of radiation alone (FIGS. 4B and C). The radiation responses of the remaining five biomarkers were not significantly altered by LPS treatment (FIG. 5; <1.4-fold change or p>0.03).

Figure 6:
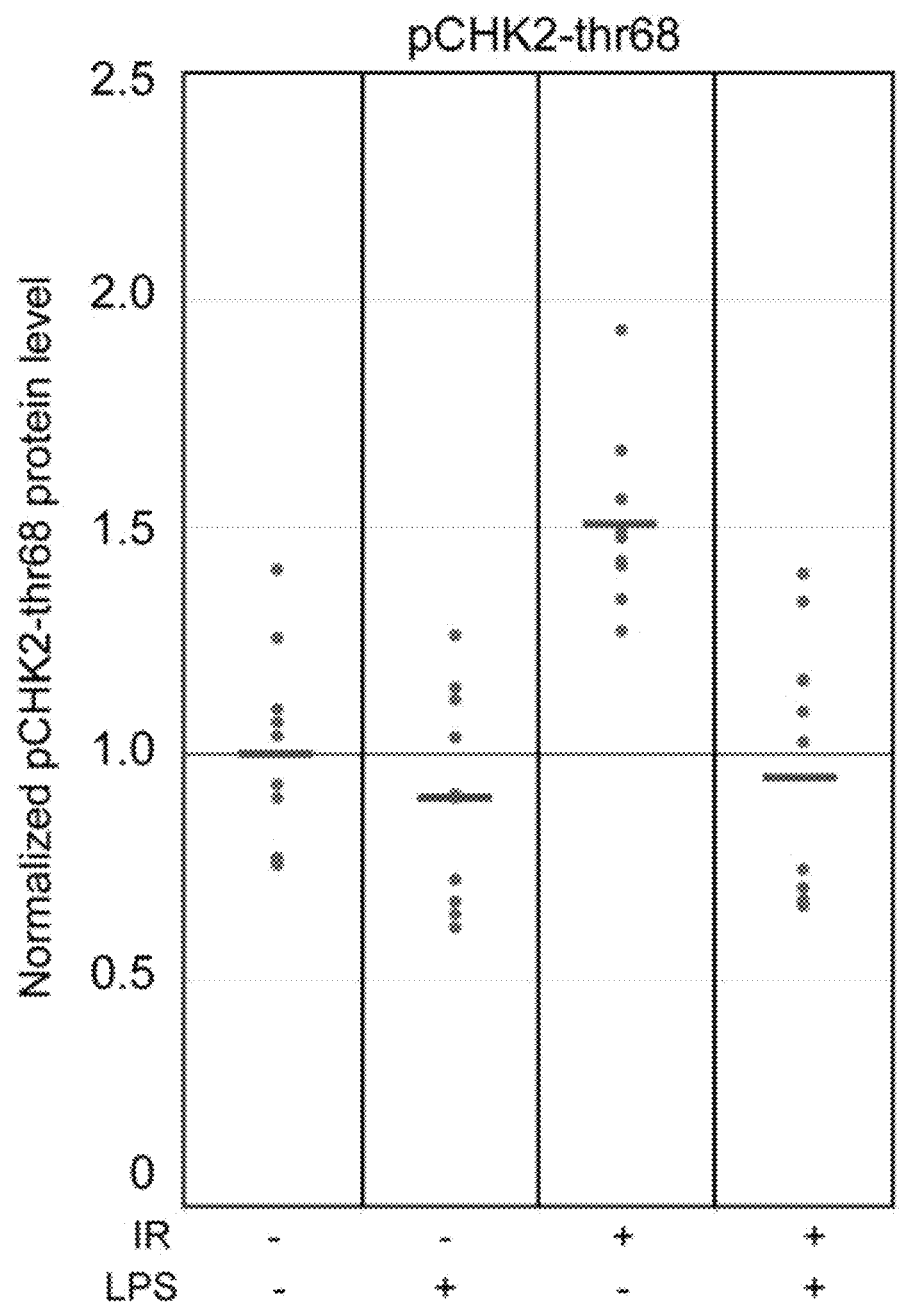
FIG. 6. LPS mediated suppression of phosphorylated CHK2-thr68 protein at 24 hrs after 2 Gy exposures. Protein levels of phosphorylated CHK2-thr68 in protein lysate from cultured whole blood in the presence or absence of LPS (50 ng/ml) were measured by ELISA. Absorbance values were normalized with respect to the average pCHK2-thr68 level in unirradiated donors. In the absence of LPS, radiation induced CHK2-thr68 levels ~1.6-fold (±0.1) relative to sham irradiated samples, whereas in the presence of LPS, CHK2-thr68 levels were indistinguishable from sham irradiated samples (p>0.4).

Our analyses of protein expression confirm that phosphorylated CHK2 protein is a radiation responsive biomarker [36], and demonstrate that the transcript levels of CHK2 were unaffected by radiation only, LPS only, and co-exposure to both agents. Phosphorylated CHK2-thr68 protein levels showed a modest ~1.6 (±0.1; p=2.9E-05) fold increase in the whole blood ex vivo culture model at 24 hours post 2 Gy irradiation compared to sham (FIG. 6). However, in the presence of LPS, this protein response was completely suppressed and indistinguishable from sham-irradiated samples without LPS co-treatment (p>0.4) (FIG. 6). This is compelling evidence that pCHK2-thr68 may not be a suitable biomarker of radiation exposure when in the context of inflammatory stress. Interestingly, we found that by including pCHK2-thr68 as a member of the panel of biomarkers improved the discrimination of radiation-exposed individuals with inflammatory stress from those exposed to radiation alone. We arrived at this conclusion by comparing the relative protein radiation responses in our PBMC model compared to our data from the whole blood culture model. We measured pCHK2-thr68 as well as BAX protein levels in PBMCs of healthy donors at 6 and 24 hours after ex vivo exposure to 2 or 6 Gy X-rays. BAX was included in this study as a surrogate indicator for the role of apoptosis in these models (FIG. 13A). As expected, the pCHK2-thr68 responses were stronger at the earlier timepoint, while the BAX responses were stronger at later time (FIG. 13B). Both BAX and pCHK2-thr68 proteins showed significant increases at 6 and 24 hrs after both 2 and 6 Gy exposures (p<0.05) (FIG. 13C). Due to the substantial variability in radiation response in the PBMC model system both among donors and between repeated blood draws of the same donor, we used the protein response data from the whole blood model in our further analyses.

Multi-group classification of blood samples by their radiation and inflammation status. We tested our combined nine-gene panel of eight transcript and one protein biomarkers in our ex vivo blood model to test its ability to discriminate among four exposure/treatment groups: radiation exposure only (R), inflammatory stress only (L), combined exposures with both radiation and LPS (RL), and samples with no radiation exposure or LPS treatment (N) (FIG. 7). Marker filtering with the Gini index (see methods) resulted in the following marker order: PCNA, CDKN1A, pCHK2-thr68, BBC3, FDXR, DDB2, XPC, POLH and GADD45a. FIG. 8 illustrates the cumulative 4-class accuracy for the sets of 1, 2, . . . , 9 markers based on their order of selection during filtering. The overall accuracy for the single best marker, PCNA, was 0.65, and the accuracy of 0.88 was attained when 5 markers were used, after which the overall accuracy leveled off. Table 1 lists the results of diagnostic screening analysis for the 9-marker set. The majority of sensitivity calculations approached 0.9 or greater. Specificity was in the 0.8-0.9 range. The positive predictive value (PV+) was unity (1.00) for the NL class, 0.96 for the L class, and below 0.8 for the R and RL classes, whereas the negative predictive value (PV−) ranged from 0.81-0.91. This analysis has identified a subpanel of 5 biomarkers that correctly assign individual blood samples to one of the four different experimental conditions with an overall classification accuracy of ~90%.

REFERENCES

1. Fenech M (2011) Current status, new frontiers and challenges in radiation biodosimetry using cytogenetic, transcriptomic and proteomic technologies. Radiation Measurements 46: 737-741.
2. Pinto M M, Santos N F, Amaral A (2010) Current status of biodosimetry based on standard cytogenetic methods. Radiat Environ Biophys 49: 567-581.
3. Falt S, Holmberg K, Lambert B, Wennborg A (2003) Long-term global gene expression patterns in irradiated human lymphocytes. Carcinogenesis 24: 1837-1845.
4. Amundson S A, Do K T, Shahab S, Bittner M, Meltzer P, et al. (2000) Identification of potential mRNA biomarkers in peripheral blood lymphocytes for human exposure to ionizing radiation. Radiat Res 154: 342-346.
5. Turtoi A, Sharan R N, Srivastava A, Schneeweiss F H (2010) Proteomic and genomic modulations induced by gamma-irradiation of human blood lymphocytes. Int J Radiat Biol 86: 888-904.
6. Kabacik S, Mackay A, Tamber N, Manning G, Finnon P, et al. (2011) Gene expression following ionising radiation: identification of biomarkers for dose estimation and prediction of individual response. Int J Radiat Biol 87: 115-129.

7. Amundson S A, Grace M B, McLeland C B, Epperly M W, Yeager A, et al. (2004) Human in vivo radiation-induced biomarkers: gene expression changes in radiotherapy patients. Cancer Res 64: 6368-6371.
8. Kang C M, Park K P, Song J E, Jeoung D I, Cho C K, et al. (2003) Possible biomarkers for ionizing radiation exposure in human peripheral blood lymphocytes. Radiat Res 159: 312-319.
9. Dressman H K, Muramoto G G, Chao N J, Meadows S, Marshall D, et al. (2007) Gene expression signatures that predict radiation exposure in mice and humans. PLoS Med 4: e106.
10. Paul S, Amundson S A (2008) Development of gene expression signatures for practical radiation biodosimetry. Int J Radiat Oncol Biol Phys 71: 1236-1244.
11. Daino K, Ichimura S, Nenoi M (2002) Early induction of CDKN1A (p21) and GADD45 mRNA by a low dose of ionizing radiation is due to their dose-dependent post-transcriptional regulation. Radiat Res 157: 478-482.
12. Paul S, Barker C A, Turner H C, McLane A, Wolden S L, et al. (2011) Prediction of in vivo radiation dose status in radiotherapy patients using ex vivo and in vivo gene expression signatures. Radiat res 175: 257-265.
13. Marchetti F, Coleman M A, Jones I M, Wyrobek A J (2006) Candidate protein biodosimeters of human exposure to ionizing radiation. Int J Radiat Biol 82: 605-639.
14. Breen A P, Murphy J A (1995) Reactions of oxyl radicals with DNA. Free Radic Biol Med 18: 1033-1077.
15. Inoue M, Shen G P, Chaudhry M A, Galick H, Blaisdell J O, et al. (2004) Expression of the oxidative base excision repair enzymes is not induced in TK6 human lymphoblastoid cells after low doses of ionizing radiation. Radiat Res 161: 409-417.
16. Batty D P, Wood R D (2000) Damage recognition in nucleotide excision repair of DNA. Gene 241: 193-204.
17. Bessho T (1999) Nucleotide excision repair 3' endonuclease XPG stimulates the activity of base excision repairenzyme thymine glycol DNA glycosylase. Nucleic Acids Res 27: 979-983.
18. Klungland A, Hoss M, Gunz D, Constantinou A, Clarkson S G, et al. (1999) Base excision repair of oxidative DNA damage activated by XPG protein. Mol Cell 3: 33-42.
19. Shimizu Y, Uchimura Y, Dohmae N, Saitoh H, Hanaoka F, et al. (2010) Stimulation of DNA Glycosylase Activities by XPC Protein Complex: Roles of Protein-Protein Interactions. J Nucleic Acids 2010.
20. Shimizu Y, Iwai S, Hanaoka F, Sugasawa K (2003) Xeroderma pigmentosum group C protein interacts physically and functionally with thymine DNA glycosylase. EMBO J 22: 164-173.
21. D'Errico M, Parlanti E, Teson M, de Jesus B M, Degan P, et al. (2006) New functions of XPC in the protection of human skin cells from oxidative damage. EMBO J 25: 4305-4315.
22. Zschenker O, Borgmann K, Streichert T, Meier I, Wrona A, et al. (2006) Lymphoblastoid cell lines differing in p53 status show clear differences in basal gene expression with minor changes after irradiation. Radiother Oncol 80: 236-249.
23. Mayer C, Popanda O, Greve B, Fritz E, Illig T, et al. (2011) A radiation-induced gene expression signature as a tool to predict acute radiotherapy-induced adverse side effects. Cancer Lett 302: 20-28.
24. Amundson S A, Do K T, Fornace A J, Jr. (1999) Induction of stress genes by low doses of gamma rays. Radiat Res 152: 225-231.
25. Brengues M, Paap B, Bittner M, Amundson S, Seligmann B, et al. (2010) Biodosimetry on small blood volume using gene expression assay. Health Phys 98: 179-185.
26. Tichy A, Zaskodova D, Rezacova M, Vavrova J, Vokurkova D, et al. (2007) Gamma-radiation-induced ATM-dependent signalling in human T-lymphocyte leukemic cells, MOLT-4. Acta biochimica Polonica 54: 281-287.
27. Wang S, Guo M, Ouyang H, Li X, Cordon-Cardo C, et al. (2000) The catalytic subunit of DNA-dependent protein kinase selectively regulates p53-dependent apoptosis but not cell-cycle arrest. Proceedings of the National Academy of Sciences of the United States of America 97: 1584-1588.
28. Zhang Y, Lim CU, Zhou J, Liber H H (2007) The effects of NBS1 knockdown by small interfering RNA on the ionizing radiation-induced apoptosis in human lymphoblastoid cells with different p53 status. Toxicology letters 171: 50-59.
29. Paul S, Amundson S A (2011) Gene expression signatures of radiation exposure in peripheral white blood cells of smokers and non-smokers. Int J Radiat Biol 87: 791-801.
30. Tucker J D, Greyer W E, Joiner M C, Konski A A, Thomas R A, et al. (2012) Gene expression-based detection of radiation exposure in mice after treatment with granulocyte colony-stimulating factor and lipopolysaccharide. Radiat res 177: 209-219.
31. Guha M, Mackman N (2001) LPS induction of gene expression in human monocytes. Cell Signal 13: 85-94.
32. Lavnikova N, Laskin D L (1995) Unique patterns of regulation of nitric oxide production in fibroblasts. J Leukoc Biol 58: 451-458.
33. Schroeder A, Mueller O, Stocker S, Salowsky R, Leiber M, et al. (2006) The RIN: an RNA integrity number for assigning integrity values to RNA measurements. BMC Mol Biol 7: 3.
34. Quinlan J R (1986) Induction of decision trees. Machine Learning 1: 81-106.
35. Meadows S K, Dressman H K, Muramoto G G, Himburg H, Salter A, et al. (2008) Gene expression signatures of radiation response are specific, durable and accurate in mice and humans. PloS one 3: e1912.
36. Ahn J Y, Schwarz J K, Piwnica-Worms H, Canman C E (2000) Threonine 68 phosphorylation by ataxia telangiectasia mutated is required for efficient activation of Chk2 in response to ionizing radiation. Cancer Res 60: 5934-5936.
37. Amundson S A, Patterson A, Do K T, Fornace A J, Jr. (2002) A nucleotide excision repair master-switch: p53 regulated coordinate induction of global genomic repair genes. Cancer biology & therapy 1: 145-149.
38. Zhang X P, Liu F, Wang W (2011) Two-phase dynamics of p53 in the DNA damage response. Proceedings of the National Academy of Sciences of the United States of America 108: 8990-8995.
39. Antoni L, Sodha N, Collins I, Garrett M D (2007) CHK2 kinase: cancer susceptibility and cancer therapy—two sides of the same coin? Nature reviews Cancer 7: 925-936.
40. Zhivotovsky B, Kroemer G (2004) Apoptosis and genomic instability. Nature reviews Molecular cell biology 5: 752-762.
41. Hirao A, Kong Y Y, Matsuoka S, Wakeham A, Ruland J, et al. (2000) DNA damage-induced activation of p53 by the checkpoint kinase Chk2. Science 287: 1824-1827.

42. Li M J, Wang W W, Chen S W, Shen Q, Min R (2011) Radiation dose effect of DNA repair-related gene expression in mouse white blood cells. Medical science monitor: international medical journal of experimental and clinical research 17: BR290-297.
43. Russell J S, Brady K, Burgan W E, Cerra M A, Oswald K A, et al. (2003) Gleevec-mediated inhibition of Rad51 expression and enhancement of tumor cell radiosensitivity. Cancer Res 63: 7377-7383.
44. Ring R H, Valo Z, Gao C, Barish M E, Singer-Sam J (2003) The Cdkn1a gene (p21Waf1/Cip1) is an inflammatory response gene in the mouse central nervous system. Neurosci Lett 350: 73-76.
45. Eslick J, Scatizzi J C, Albee L, Bickel E, Bradley K, et al. (2004) IL-4 and IL-10 inhibition of spontaneous monocyte apoptosis is associated with Flip upregulation. Inflammation 28: 139-145.
46. Han J, Flemington C, Houghton A B, Gu Z, Zambetti G P, et al. (2001) Expression of bbc3, a pro-apoptotic BH3-only gene, is regulated by diverse cell death and survival signals. Proceedings of the National Academy of Sciences of the United States of America 98: 11318-11323.
47. Riecke A, Rufa C G, Cordes M, Hartmann J, Meineke V, et al. (2012) Gene expression comparisons performed for biodosimetry purposes on in vitro peripheral blood cellular subsets and irradiated individuals. Radiat res 178: 234-243.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

TABLE 2

Target genes selected from DNA damage response pathways for transcript analysis.

| Gene Symbol | Alternative Symbol | Entrez Gene Name | Process* | AOD** |
|---|---|---|---|---|
| APEX1 | APE1 | APEX nuclease (multifunctional DNA repair enzyme) 1 | BER | Hs00172396_m1 |
| BAX | | BCL2-associated X protein | apoptosis | Hs00180269_m1 |
| BBC3 | | BCL2 binding component 3 | apoptosis | Hs00246075_m1 |
| CCNG1 | | cyclin G1 | cell cycle | Hs00171112_m1 |
| CDKN1A | p21 | cyclin-dependent kinase inhibitor 1A (p21, Clp1) | cell cycle | Hs00355782_m1 |
| CHEK2 | CHK2 | CHK2 checkpoint homolog (*S. pombe*) | cell cycle | Hs00200485_m1 |
| DDB2 | | damage-specific DNA binding protein 2, 48 kDA | NER | Hs03044953_m1 |
| ERCC1 | | excision repair cross-complementing rodent repair deficiency, complementation group 1 | NER | Hs01012158_m1 |
| ERCC2 | XPD | excision repair cross-complementing rodent repair deficiency, complementation group 2 | NER | Hs00361161_m1 |
| ERCC3 | XPB | excision repair cross-complementing rodent repair deficiency, complementation group 3 | NER | Hs01554450_m1 |
| ERCC4 | XPF | excision repair cross-complementing rodent repair deficiency, complementation group 4 | NER | Hs01063538_m1 |
| ERCC5 | XPG | excision repair cross-complementing rodent repair deficiency, complementation group 5 | NER | Hs01557031_m1 |
| ERCC6 | CSB | excision repair cross-complementing rodent repair deficiency, complementation group 6 | NER | Hs00972920_m1 |
| FDXR | | ferredoxin reductase | mitochondrial electron transport | Hs01031624_m1 |
| FEN1 | | flap structure-specific endonuclease 1 | BER | Hs00746727_s1 |
| GADD45A | | growth arrest and DNA-damage-inducible, alpha | cell cycle | Hs99999173_m1 |
| LIG1 | | ligase I, DNA, ATP-dependent | BER | Hs01553527_m1 |
| LIG3 | | ligase III, DNA, ATP-dependent | BER | Hs00242692_m1 |
| MLH1 | | mutL homolog 1, colon cancer, nonpolyposis type 2 (*E. coli*) | MMR | Hs00179866_m1 |
| MSH2 | | mutS homolog 2, colon cancer, nonpolyposis type 2 (*E. coli*) | MMR | Hs00953523_m1 |
| MSH3 | | mutS homolog 3 (*E. coli*) | MMR | Hs00989003_m1 |
| MSH6 | | mutS homolog 6 (*E. coli*) | MMR | Hs00264721_m1 |
| NTHL1 | NTH1 | nth endonuclease III-like (*E. coli*) | BER | Hs00959764_m1 |
| OGG1 | | 8-oxoguanine DNA glycosylase | BER | Hs00213454_m1 |
| PARP1 | | poly (ADP-ribose) polymerase 1 | BER | Hs00242302_m1 |
| PARP3 | | poly (ADP-ribose) polymerase family, member 3 | DSB repair | Hs00193946_m1 |
| PCNA | | proliferating cell nuclear antigen | BER | Hs00696862_m1 |
| PMS1 | | PMS1 postmeiotic segregation increased 1 (*S. cerevisiae*) | MMR | Hs00922262_m1 |
| POLB | | polymerase (DNA directed), beta | BER | Hs01099715_m1 |
| POLH | | polymerase (DNA directed), eta | BER | Hs00962625_m1 |
| POLI | | polymerase (DNA directed), iota | Other | Hs00200488_m1 |
| POLK | | polymerase (DNA directed), kappa | Other | Hs00211963_m1 |
| RAD51 | | RAD51 homolog (*S. cerevisiae*) | DSB repair | Hs00153418_m1 |
| REV1 | | REV1 homolog (*S. cerevisiae*) | Other | Hs00249411_m1 |
| RFC1 | | replication factor C (activator 1) 1, 146 kDa | NER | Hs00161340_m1 |
| RPAIN | | RPA interacting protein | NER | Hs00260434_m1 |
| XPA | | xeroderma pigmentosum, complementation group A | NER | Hs00166045_m1 |
| XPC | | xeroderma pigmentosum, complementation group C | NER | Hs01104206_m1 |

TABLE 2-continued

Target genes selected from DNA damage response pathways for transcript analysis.

| Gene Symbol | Alternative Symbol | Entrez Gene Name | Process* | AOD** |
|---|---|---|---|---|
| XRCC1 | | X-ray repair complementing defective repair in Chinese hamster cells 1 | BER | Hs00959834_m1 |
| XRCC6 | | X-ray repair complementing defective repair in Chinese hamster cells 6 | DSB repair | Hs00995262_g1 |

*BER: base excision repair;
NER: nucleotide excision repair;
MMR: mismatch repair;
DSB repair: double strand break repair
**AOD: Assay On Demand Applied Biosystems TaqMan identification

TABLE 3

Average absorbance ranges of ELISA measurements.

Average absorbance levels normalized to the reference absorbance value for BAX and pCHK2-thr68 in protein lysates of ex vivo irradiated PBMC.

| Dose | BAX | | pCHK2-thr68 | |
|---|---|---|---|---|
| | Time | | | |
| | 6 hr | 24 hr | 6 hr | 24 hr |
| 0 Gy | 0.17 (0.11-0.34) | 0.23 (0.08-0.67) | 0.17 (0.12-0.23) | 0.17 (0.12-0.26) |
| 2 Gy | 0.24 (0.12-0.59) | 0.36 (0.20-0.87) | 0.63 (0.37-0.80) | 0.32 (0.15-0.47) |
| 6 Gy | 0.28 (0.15-0.67) | 0.47 (0.15-1.31) | 0.71 (0.41-1.23) | 0.35 (0.19-0.51) |

TABLE 3-continued

Average absorbance ranges of ELISA measurements.

Average absorbance levels normalized to the reference absorbance value for pCHK2-thr68 in protein lysates of ex vivo irradiated whole blood in the presence or absence of LPS.

| Dose pCHK2-thr68 | Time | |
|---|---|---|
| | 24 hr | 24 hr |
| LPS | no | yes |
| 0 Gy | 0.19 (0.14-0.27) | 0.17 (0.12-0.24) |
| 2 Gy | 0.29 (0.24-0.37) | 0.18 (0.13-0.27) |

Average absorbance levels normalized to the reference absorbance value for pCHK2-thr68 in protein lysates of ex vivo irradiated whole blood in the presence or absence of LPS.

| | IL-6 | TNF-alpha |
|---|---|---|
| no LPS | 0.01 (0.01-0.02) | 0.03 (0.02-0.03) |
| LPS | 0.24 (0.08-1.01) | 0.16 (0.03-0.41) |

TABLE 4

GENE AND PROTEIN SEQUENCES OF PANEL BIOMARKERS

CDKN1A
GeneID: 1026
NP_001207706.1 GI: 334085240
cyclin-dependent kinase inhibitor 1 [Homo sapiens]

```
  1 msepagdvrq npcgskacrr lfgpvdseql srdcdalmag ciqearerwn fdfvtetple
 61 gdfawervrg lglpklylpt gprrgrdelg ggrrpgtspa llqgtaeedh vdlslsctlv
121 prsgeqaegs pggpgdsqgr krrqtsmtdf yhskrrlifs krkp
```

NM_001220777.1 GI: 334085239
*Homo sapiens* cyclin-dependent kinase inhibitor 1A (p21, Cip1)
(CDKN1A), transcript variant 5, mRNA
Transcript Variant: This variant (5) differs in the 5' UTR compared
to variant 1, NM_000389.4 GI: 310832422. Variants 1, 2, 4 and 5
encode the same protein

```
  1 aacatgttga gctctggcat agaagaggct ggtggctatt ttgtccttgg gctgcctgtt
 61 ttcaggcgcc atgtcagaac cggctgggga tgtccgtcag aacccatgcg gcagcaaggc
121 ctgccgccgc ctcttcggcc cagtggacag cgagcagctg agccgcgact gtgatgcgct
181 aatggcgggc tgcatccagg aggcccgtga gcgatggaac ttcgactttg tcaccgagac
241 accactggag ggtgacttcg cctgggagcg tgtgcggggc cttggcctgc ccaagctcta
301 ccttccacg gggccccggc gaggccggga tgagttggga ggaggcaggc ggcctggcac
361 ctcacctgct ctgctgcagg ggacagcaga ggaagaccat gtggacctgt cactgtcttg
421 tacccttgtg cctcgctcag gggagcaggc tgaagggtcc ccaggtggac ctggagactc
481 tcagggtcga aaacggcggc agaccagcat gacagatttc taccactcca aacgccggct
541 gatcttctcc aagaggaagc cctaatccgc ccacaggaag cctgcagtcc tggaagcgcg
601 agggcctcaa aggcccgctc tacatcttct gccttagtct cagtttgtgt gtcttaatta
661 ttatttgtgt tttaattta acacctcctc atgtacatac cctggccgcc ccctgccccc
721 cagcctctgg cattagaatt atttaaacaa aaactaggcg gttgaatgag aggttcctaa
```

TABLE 4-continued

GENE AND PROTEIN SEQUENCES OF PANEL BIOMARKERS

```
 781 gagtgctggg cattttatt  ttatgaaata ctatttaaag cctcctcatc ccgtgttctc
 841 cttttcctct ctcccggagg ttgggtgggc cggcttcatg ccagctactt cctcctcccc
 901 acttgtccgc tgggtggtac cctctggagg ggtgtggctc cttcccatcg ctgtcacagg
 961 cggttatgaa attcaccccc tttcctggac actcagacct gaattctttt tcatttgaga
1021 agtaaacaga tggcactttg aaggggcctc accgagtggg ggcatcatca aaactttgg
1081 agtcccctca cctcctctaa ggttgggcag ggtgaccctg aagtgagcac agcctagggc
1141 tgagctgggg acctggtacc ctcctggctc ttgataccc cctctgtctt gtgaaggcag
1201 ggggaaggtg gggtcctgga gcagaccacc ccgcctgccc tcatggcccc tctgacctgc
1261 actggggagc ccgtctcagt gttgagcctt ttccctcttt ggctcccctg tacctttga
1321 ggagcccag  ctacccttct tctccagctg ggctctgcaa ttcccctctg ctgctgtccc
1381 tccccttgt  ccttttcctt cagtaccctc tcagctccag ggtgctctga ggtgcctgtc
1441 ccacccccac ccccagctca atggactgga aggggaaggg acacacaaga agaagggcac
1501 cctagttcta cctcaggcag ctcaagcagc gaccgcccc  cctctagct  gtgggggtga
1561 gggtcccatg tggtggcaca ggcccccttg agtggggtta tctctgtgtt aggggtatat
1621 gatgggggag tagatctttc taggagggag acactggccc ctcaaatcgt ccagcgacct
1681 tcctcatcca ccccatccct ccccagttca ttgcactttg attagcagcg aacaaggag
1741 tcagacattt taagatggtg gcagtagagg ctatggacag ggcatgccac gtgggctcat
1801 atggggctgg gagtagttgt ctttcctggc actaacgttg agccctgga  ggcactgaag
1861 tgcttagtgt acttggagta ttggggtctg accccaaaca ccttccagct cctgtaacat
1921 actggcctgg actgttttct ctcggctccc catgtgtcct ggttcccgtt tctccaccta
1981 gactgtaaac ctctcgaggg cagggaccac accctgtact gttctgtgtc tttcacagct
2041 cctcccacaa tgctgaatat acagcaggtg ctcaataaat gattcttagt gactttactt
2101 gtaaaaaaa  aaaaaaaaa
```

FDXR
GeneID: 2232
NM_004110.3 GI: 111118982
Homo sapiens ferredoxin reductase (FDXR), transcript
variant 2, mRNA

```
   1 gcttgtgggc gggcccgggc aggagcgggc ttgccctgcg gagcagtagc taggaacaga
  61 tccacttgca ggttgctgtt cccagccatg gcttcgcgct gctggcgctg gtggggctgg
 121 tcggcgtggc ctcggacccg gctgcctccc gccgggagca ccccgagctt ctgccaccat
 181 ttctccacac aggagaagac cccccagatc tgtgtggtgg gcagtggccc agctggcttc
 241 tacacggccc aacacctgct aaagcacccc caggcccacg tggacatcta cgagaaacag
 301 cctgtgccct ttggcctggt gcgctttggt gtggcgctg  atcaccccga ggtgaagaat
 361 gtcatcaaca catttaccca gacggcccat tctggccgct gtgccttctg gggcaacgtg
 421 gaggtgggca gggacgtgac ggtgccggag ctgcgggagg cctaccacgc tgtggtgctg
 481 agctacgggg cagaggacca tcgggccctg gaaattcctg gtgaggagct gccaggtgtg
 541 tgctccgccc gggccttcgt gggctggtac aacgggcttc ctgagaacca ggagctggag
 601 ccagacctga gctgtgacac agccgtgatt ctggggcagg gaacgtggc  tctgacgtg
 661 gcccgcatcc tactgacccc acctgagcac ctggaggccc tcctttgtg  ccagagaacg
 721 gacatcacga aggcagccct gggtgtactg aggcagagtc gagtgaagac agtgtggcta
 781 gtgggccggc gtggacccgc gcaagtggcc ttcaccatta aggagcttcg ggagatgatt
 841 cagttaccgg gagcccggcc catttgggat cctgtggatt tcttgggtct ccaggacaag
 901 atcaaggagg tccccgccc  gaggaagcgg ctgacggaac tgctgcttcg aacgccaca
 961 gagaagccag ggcggcgga  agctgcccgc caggcatcgg cctcccgtgc ctggggcctc
1021 cgctttttcc gaagccccca gcaggtgctg ccctccaccag atgggcgggcg ggcagcaggt
1081 gtccgcctag cagtcactag actggagggt gtcgatgagg ccaccgtgc  agtgcccacg
1141 ggagacatgg aagacctccc ttgtgggctg gtgctcagca gcattgggta taagagccgc
1201 cctgtcgacc aagcgtgcc  ctttgactcc aagcttgggg tcatcccaa  tgtggagggc
1261 cgggttatgg atgtgccagg cctctactgc agccggctggg tgaagagagg acctacaggt
1321 gtcatagcca caaccatgac tgacagcttc ctcaccggcc agatgctgct gcaggaccta
1381 aaggctgggt tgctccctc  tggccccagg cctggctacg cagccatcca ggccctgctc
1441 agcagccgag gggtccggcc agtctctttc tcagactggg agaagctgga tgccgaggag
1501 gtggcccggg gccagggcac ggggaagccc agggagaagc tggtggatcc tcaggagatg
1561 ctgcgcctcc tgggccactg agcccagccc cagcccggc  ccccagcagg gaagggatga
1621 tgttgggag  gggaagggct gggtccgtct gagtgggact ttgcacctct gctgatcccg
1681 gccggcctg  gcttggaggc ttggctgctc ttccagcgtc tctcctccct cctggggaag
1741 gtcgcccttg cgcgcaaggt tttagctttc agcaactgag gtaaccttag ggacaggtgg
1801 aggtgtgggc cgatctaacc ccttacccat ctctctactg ctggactgtg gagggtcacc
1861 aggttgggaa catgctggaa ataaacagc  tgcaaccaag aaaaaaaaaa aaaaaaaaaa
1921 aaaaaaaaaa aaaaaa
```

NP_004101.2 GI: 111118983
NADPH: adrenodoxin oxidoreductase, mitochondrial isoform 2
precursor, [Homo sapiens]

```
   1 masrcwrwwg wsawprtrlp pagstpsfch hfstqektpq icvvgsgpag fytaqhllkh
  61 pqahvdiyek qpvpfglvrf gvapdhpevk nvintftqta hsgrcafwgn vevgrdvtvp
 121 elreayhavv lsygaedhra leipgeelpg vcsarafvgw ynglpenqel epdlscdtav
 181 ilgqgnvald varilltppe hleallllcqr tditkaalgv lrqsrvktvw lvgrrgplqv
 241 aftikelrem iqlpgarpil dpvdflglqd kikevprprk rltelllrta tekpgpaeaa
 301 rqasasrawg lrffrspqqv lpspdgrraa gvrlavtrle gvdeatravp tgdmedlpcg
 361 lvlssigyks rpvdpsvpfd sklgvipnve grvmdvpgly csgwvkrgpt gviattmtds
 421 fltgqmllqd lkagllpsgp rpgyaaiqal lssrgvrpvs fsdwekldae evargqgtgk
 481 preklvdpqe mlrllgh
```

TABLE 4-continued

GENE AND PROTEIN SEQUENCES OF PANEL BIOMARKERS

NM_001258012.1 GI: 384381461
*Homo sapiens* ferredoxin reductase (FDXR), transcript
variant 3 mRNA

```
   1 gcttgtgggc gggcccgggc aggagcgggc ttgccctgcg gagcagtagc taggaacaga
  61 tccacttgca ggttgctgtt cccagccatg gcttcgcgct gctggcgctg gtggggctgg
 121 tcggcgtggc ctcggacccg gctgcctccc gccgggagca ccccgagctt ctgccaccat
 181 ttctccacac aggagaagac cccccagatc tgtgtggtgg gcagtggccc agctggcttc
 241 tacacggccc aacacctgct aaagaggggtg gaagccttgt gttctcagcc cagggtcctg
 301 aactctcctg ctctgtctgg ggaaggggag gacctggggg cgtcccagcc tctctctctc
 361 gaccccacca gctgccaccc tgttcccccag cagcaccccc aggcccacgt ggacatctac
 421 gagaaacagc ctgtgcccctt tggcctggtg cgctttggtg tggcgcctga tcaccccgag
 481 gtgaagaatg tcatcaacac atttacccag acggcccatt ctggccgctg tgccttctgg
 541 ggcaacgtgg aggtgggcag ggacgtgacg gtgccgagc tgcgggaggc ctaccacgct
 601 gtggtgctga gctacgggc agaggaccat cgggccctgg aaattcctgg tgaggagctg
 661 ccaggtgtgt gctccgcccg ggccttcgtg ggctggtaca acgggcttcc tgagaaccag
 721 gagctggagc cagacctgag ctgtgacaca gccgtgattc tggggcaggg gaacgtggct
 781 ctggacgtgg cccgcatcct actgacccca cctgagcacc tggagagaac ggacatcacg
 841 aaggcagccc tgggtgtact gaggcagagt cgagtgaaga cagtgtggct agtgggccgg
 901 cgtggacccc tgcaagtggc cttcaccatt aaggagcttc gggagatgat tcagttaccg
 961 ggagcccggc ccattttgga tcctgtggat ttcttgggtc tccaggacaa gatcaaggag
1021 gtccccgcc cgaggaagcg gctgacggaa ctgctgcttc gaacgccac agagaagcca
1081 gggccggcgg aagctgcccg ccaggcatcg gcctcccgtg cctgggggcct ccgcttttc
1141 cgaagccccc agcaggtgct gccctcacca gatgggcggc gggcagcagg tgtccgccta
1201 gcagtcacta gactggaggg tgtcgatgag gccaccccgtg cagtgcccac gggagacatg
1261 gaagacctcc cttgtgggct ggtgctcagc agcattggt ataagagccg ccctgtcgac
1321 ccaagcgtgc cctttgactc caagcttggg gtcatcccca atgtggaggg ccgggttatg
1381 gatgtgccag gcctctactg cagcggctgg gtgaagagag gacctacagg tgtcatagcc
1441 acaaccatga ctgacagctt cctcaccggc cagatgctgc tgcaggacct gaaggctggg
1501 ttgctcccct ctggccccag gcctggctac gcagccatcc aggccctgct cagcagccga
1561 ggggtccggc cagtctcttt ctcagactgg gagaagctgg atgccgagga ggtggcccgg
1621 ggccagggca cggggaagcc cagggagaag ctggtggatc ctcaggagat gctgcgcctc
1681 ctgggccact gagcccagcc ccagcccgg ccccagcag gaagggatg agtgttggga
1741 ggggaagggc tgggtccgtc tgagtgggac tttgcacctc tgctgatccc ggccggccct
1801 ggcttggagg cttggctgct cttccagcgt ctctcctccc tcctggggaa ggtcgccctt
1861 gcgcgcaagg ttttagcttt cagcaactga ggtaacctta gggacaggtg gaggtgtggg
1921 ccgatctaac cccttaccca tctctctact gctggactgt ggagggtcac caggttggga
1981 acatgctgga aataaaacag ctgcaaccaa gaaaaaaaa aaaaaaaa
```

NP_001244941.1 GI: 384381462
NADPH: adrenodoxin oxidoreductase, mitochondrial isoform 3
precursor [*Homo sapiens*]

```
   1 masrcwrwwg wsawprtrlp pagstpsfch hfstqektpq icvvgsgpag fytaqhllkr
  61 vealcsqprv lnspalsgeg edlgasqpls ldptschpvp qqhpqahvdi yekqpvpfgl
 121 vrfgvapdhp evknvintft qtahsgrcaf wgnvevgrdv tvpelreayh avvlsygaed
 181 hraleipgee lpgvcsaraf vgwynglpen qelepdlscd tavilgqgnv aldvarillt
 241 ppehlertdi tkaalgvlrq srvktvwlvg rrgplqvaft ikelremiql pgarpildpv
 301 dflglqdkik evprprkrlt elllrtatek pgpaeaarqa sasrawglrf frspqqvlps
 361 pdgrraagvr lavtrlegvd eatravptgd medlpcglvl ssigyksrpv dpsvpfdskl
 421 gvipnvegrv mdvpglycsg wvkrgptgvi attmtdsflt gqmllqdlka gllpsgprpg
 481 yaaiqallss rgvrpvsfsd wekldaeeva rgqgtgkpre klvdpqemlr llgh
```

BBC3
GeneID: 27113
NM_001127240.2 GI: 366039929
*Homo sapiens* BCL2 binding component 3 (BBC3), transcript
variant 1, mRNA

```
   1 gaggcgattg cgattgggtg agacccagta aggatggaaa gtgtagagga gacaggaatc
  61 cacggctttg gaaaaaggaa ggacaaaact caccaaacca gagcaggggca ggaagtaaca
 121 atgagaaact gaaaaagaaa cggaatgaaa agctatgaga caggatgaaa tttggcatgg
 181 ggtctgccca gcatgtcca tgccaggtgc ccagggctgc ttccacacg tgggtcccct
 241 gccagatttg tggccccagg gagcgccatg gcccgcgcac gccaggaggg cagctccccg
 301 gagcccgtag agggcctggc ccgcgacggc cgcgcccct tcccgctcgg ccgcctggtg
 361 ccctcggcag tgtcctgcgg cctctgcgag cccggcctgg ctgccgcccc cgccgccccc
 421 accctgctgc ccgctgccta cctctgcgcc ccaccgccc cacccgccgt caccgccgcc
 481 ctggggggtt cccgctggcc tggggtcc cgcagccggc cccgaggccc gcgcccggac
 541 ggtcctcagc cctcgctctc gctggcggag cagcacctgg agtcgcccgt gcccagccgc
 601 ccgggggctc tggcgggcgg tcccacccag gcggccccgg gagtccgcgg ggaggaggaa
 661 cagtgggccc gggagatcgg ggcccagctg cggcggatgg cggacgacct caacgcacag
 721 tacgagcggc ggagacaaga ggagcagcag cggcaccgcc cctcaccctg gagggtcctg
 781 tacaatctca tcatgggact cctgccctta cccagggacc acagagcccc cgagatggag
 841 cccaattagg tgcctgcacc cgcccggtgg acgtcaggga ctcggggggc aggccctcc
 901 cacctcctga cacctggcc agcgcggggg acttttctctg caccatgtag catactggac
 961 tcccagcccct gcctgtcccg ggggcgggcc ggggcagcca ctccagcccc agcccagcct
1021 ggggtgcact gacggagatg cggactcctg ggtccctggc caagaagcca ggagagggac
1081 ggctgatgga ctcagcatcg gaaggtggcg gtgaccgagg gggtggggac tgagccgccc
```

TABLE 4-continued

GENE AND PROTEIN SEQUENCES OF PANEL BIOMARKERS

```
1141 gcctctgccg cccaccacca tctcaggaaa ggctgttgtg ctggtgcccg ttccagctgc
1201 aggggtgaca ctgggggggg ggggctctcc tctcggtgct ccttcactct gggcctggcc
1261 tcaggcccct ggtgcttccc cccctcctcc tgggaggggg cccgtgaaga gcaaatgagc
1321 caaacgtgac cactagcctc ctggagccag agagtggggc tcgtttgccg gttgctccag
1381 cccggcgccc agccatcttc cctgagccag ccggcgggtg gtgggcatgc ctgcctcacc
1441 ttcatcaggg ggtggccagg aggggcccag actgtgaatc ctgtgctctg cccgtgaccg
1501 ccccccgccc catcaatccc attgcatagg tttagagaga gcacgtgtga ccactggcat
1561 tcatttgggg ggtgggagat tttggctgaa gccgcccag ccttagtccc cagggccaag
1621 cgctgggggg aagacgggga gtcagggagg gggggaaatc tcggaagagg gaggagtctg
1681 ggagtgggga gggatggccc agcctgtaag atactgtata tgcgctgctg tagataccgg
1741 aatgaatttt ctgtacatgt ttggttaatt tttttgtac atgattttg tatgtttcct
1801 tttcaataaa atcagattgg aacagtggaa aaaaaaaa
```

NP_001120712.1 GI: 187829730
bcl-2-binding component 3 isoform 1 [Homo sapiens]

```
  1 mkfgmgsaqa cpcqvpraas ttwvpcqicg prerhgprtp ggqlpgarrg pgprrpaplp
 61 arppgalgsv lrplrarpgc rprrphpaar clplrphrpt rrhrrpggfp lawgspqpap
121 rpapgrssal alaggaapgv araqrpggsg grshpggpgs prgggtvgpg drgpaaadgg
181 rpqrtvraae trgaaaappl tlegpvqshh gtpaltqgpq sprdgaqlga ctrpvdvrds
241 ggrplpppdt lasagdflct m
```

Transcript Variant: This variant (1) includes an alternate exon in the 5' coding region, resulting in a frameshift for the remainder of the CDS, compared to variant 2. The encoded isoform (1, also known as PUMA-gamma) has the same N-terminus but is otherwise distinct and longer, compared to isoform 2.
NM_014417.4 GI: 366039932
Homo sapiens BCL2 binding component 3 (BBC3), transcript variant 4, mRNA
Transcript Variant: This variant (4) has alternate exon structure at its 5' end and it thus differs in the 5' UTR and 5' coding region, compared to variant 2. The encoded isoform (4, also known as PUMA-alpha) has a distinct N-terminus and is longer than isoform 2. Isoform 4 also includes the C-terminal BH3 domain and can localize to the mitochondria

```
   1 gcggcgcgag ccacatgcga gcgggcgcct ggcggcggcg gcggcggcac cagcgatccc
  61 agcagcggcc acgacgcgga cgcgcctgcg gcccggggag cagcagcagc cacagccaca
 121 gcagcccgcca ctgcagttag agcggcagca gcagcgacga acagcagc agccgccgcg
 181 gagagcggcg ctcggcgggc gcgccctcct gaaggaagcc gcccgcccc caccgccgcc
 241 ccctccggcg tgttcatgcc cccggggccc caggagcgc catggcccgc gcacgccagg
 301 agggcagctc cccggagccc gtagagggcc tggcccgcga cggcccgcgc ccttcccgc
 361 tcggccgcct ggtgcctcg gcagtgtcct gcggcctctg cgagcccggc ctggctgccg
 421 ccccccgccgc ccccacctg ctgcccgctg cctacctctg cgcccccacc gccccaccccg
 481 ccgtcaccgc cgcctggg ggttcccgct ggctggggg tccccgcagc cggccccgag
 541 gcccgcgccc ggacggtcct cagccctcgc tctcgctggc ggagcagcac ctggagtcgc
 601 ccgtgcccag cgccccgggg gctctgcgcg gcggtcccac ccaggcggcc ggggagtcc
 661 gcggggagga ggaacagtgg gcccgggaga tcggggccca gctgcggcgg atggcggacg
 721 acctcaacgc acagtacgag cggcggagac aagaggagca gcagcggcac cgcccctcac
 781 cctggagggt cctgtacaat ctcatcatgg gactcctgcc cttacccagg gccacagag
 841 cccccgagat ggagcccaat taggtgcctg cacccgcccg gtggacgtca gggactcggg
 901 gggcaggccc ctcccacctc ctgacaccct ggccagcgg ggggactttc tctgccaccat
 961 gtagcatact ggactcccag ccctgcctgt cccgggggcg ggccggggca gccactccag
1021 ccccagccca gcctggggtg cactgacgga gatgcggact cctgggtccc tggccaagaa
1081 gccaggagag ggacggctga tggactcagc atcggaaggt ggcggtgacc gaggggggtgg
1141 ggactgagcc gcccgcctct gccgcccacc accatctcag gaaaggctgt tgtgctggtg
1201 cccgttccag ctgcagggggt gacactgggg gggggggct ctctctcgg tgctccttca
1261 ctctgggcct ggcctcaggc cctggtgct tcccccctc ctctgggag ggggcccgtg
1321 aagagcaaat gagccaaacg tgaccactag cctcctggag ccagagagtg gggctcgttt
1381 gccggttgct ccagccccgg cgcccagccg ccagccat cttcctgag ccagccggggt
1441 atgcctgcct caccttcatc aggggtggc caggaggggc ccagactgtg aatcctgtgc
1501 tctgccgtg accgccccc gcccatcaa tcccattgca taggtttaga gagcacgt
1561 gtgaccactg gcattcattt gggggtggg agatttggc tgaagccgcc ccagccttag
1621 tccccagggc caagcgctgg ggggaagacg ggagtcagg gagggggaaatc tcggaa
1681 gaggaggag tctgggagtg gggagggatg gcccagcctg taagatactg tatatgcgct
1741 gctgtagata ccggaatgaa ttttctgtac atgtttggtt aatttttttt gtacatgatt
1801 tttgtatgtt tccttttcaa taaaatcaga ttggaacagt ggaaaaaaaa aaa
//
```

NP_055232.1 GI: 15193488
bcl-2-binding component 3 isoform 4 [Homo sapiens]

```
  1 marqegss pepvglard gprpfplgrl vpsavscglc epglaaapaa ptllpaaylc
 61 aptappavta alggsrwpgg prsrprgprp dgpqpslsla eghlespvps apgalaggpt
121 qaapgvrgee eqwareigaq lrrmaddlna qyerrrqeeq qrhrpspwrv lynlimgllp
181 lprghrapem epn
```

TABLE 4-continued

GENE AND PROTEIN SEQUENCES OF PANEL BIOMARKERS

NM_001127241.2 GI: 366039930
*Homo sapiens* BCL2 binding component 3 (BBC3), transcript variant 2,

```
   1 gaggcgattg cgattgggtg agacccagta aggatggaaa gtgtagagga gacaggaatc
  61 cacggctttg gaaaaaggaa ggacaaaact caccaaacca gagcagggca ggaagtaaca
 121 atgagaaact gaaaagaaa cggaatggaa agctatgaga caggatgaaa tttggcatgg
 181 ggtctgccca ggcatgtcca tgccaggtgc ccagggctgc ttccacgacg tgggtcccct
 241 gccagatttg tggtcctcag ccctcgctct cgctggcgga gcagcacctg gagtcgcccg
 301 tgcccagcgc cccgggggct ctggcgggcg gtcccaccca ggcggccccg ggagtccgcg
 361 gggaggagga acagtgggcc cgggagatcg gggcccagct gcggcggatg gcggacgacc
 421 tcaacgcaca gtacgagcgg cggagacaag aggagcagca gcggcaccgc ccctcacccc
 481 ggagggtcct gtacaatctc atcatgggac tcctgcccct acccaggggc cacagagccc
 541 ccgagatgga gcccaattag gtgcctgcac ccgcccgtg gacgtcaggg actcggggg
 601 caggcccctc ccacctcctg acaccctggc cagcgcgggg gactttctct gcaccatgta
 661 gcatactgga ctcccagccc tgcctgtccc ggggcgggc cggggcagcc actccagccc
 721 cagcccagcc tggggtgcac tgacggagat gcggactcct gggtccctgg ccaagaagcc
 781 aggagggga cggctgatgg actcagcatc ggaaggtggc ggtgaccgag ggggtgggga
 841 ctgagccgcc cgcctctgcc gcccaccacc atctccaggaa aggctgttgt gctggtgccc
 901 gttccagctg caggggtgac actggggggg gggggctctc ctctcggtgc tccttcactc
 961 tgggcctggc ctcaggcccc tggtgcttcc cccctcctc ctgggagggg gcccgtgaag
1021 agcaaatgag ccaaacgtga ccactagcct cctggagcca gagagtgggg ctcgtttgcc
1081 ggttgctcca gcccggcgcc cagccatctt ccctgagcca gccggcgggt ggtgggcatg
1141 cctgcctcac cttcatcagg gggtggccag gaggggccca gactgtgaat cctgtgctct
1201 gcccgtgacc gccccccgcc ccatcaatcc cattgcatag gtttagagag agcacgtgtg
1261 accactggca ttcatttggg gggtgggaga ttttggctga agccgcccca gccttagtcc
1321 ccagggccaa gcgctggggg gaagacgggg agtcagggag gggggaaat ctcggaagag
1381 ggaggagtct gggagtgggg agggatggcc cagcctgtaa gatactgtat atgcgctgct
1441 gtagataccg gaatgaattt tctgtacatg tttggttaat ttttttgta catgattttt
1501 gtatgtttcc ttttcaataa aatcagattg gaacagtgga aaaaaaaaa
```

NP_001120713.1 GI: 187829742
bcl-2-binding component 3 isoform 2 [*Homo sapiens*]

```
  1 mkfgmgsaqa cpcqvpraas ttwvpcqicg pqpslslaeq hlespvpsap galaggptqa
 61 apgvrgeeeq wareigaqlr rmaddlnaqy errrqeeqqr hrpspwrvly nlimgllplp
121 rghrapemep n
```

NM_001127242.2 GI: 366039931
*Homo sapiens* BCL2 binding component 3 (BBC3), transcript variant 3, mRNA

```
   1 gaggcgattg cgattgggtg agacccagta aggatggaaa gtgtagagga gacaggaatc
  61 cacggctttg gaaaaaggaa ggacaaaact caccaaacca gagcagggca ggaagtaaca
 121 atgagaaact gaaaaagaaa cggaatggaa agctatgaga caggatgaaa tttggcatgg
 181 ggtctgccca ggcatgtcca tgccaggtgc ccagggctgc ttccacgacg tgggtcccct
 241 gccagatttg tgagacaaga ggagcagcag cggcaccgcc cctcaccctg gagggtcctg
 301 tacaatctca tcatgggact cctgccctta cccaggggcc acagagcccc cgagatggag
 361 cccaattagg tgcctgcacc cgcccggtgg acgtcaggga ctcgggggc aggcccctcc
 421 cacctcctga caccctggcc agcgcggggg actttctctg caccatgtag catactggac
 481 tcccagccct gcctgtcccg ggggcgggcc ggggcagcca ctccagcccc agcccagccc
 541 ggggtgcact gacggagatg cggactcctg gtccctggc caagaagcca ggagagggac
 601 ggctgatgga ctcagcatcg gaaggtggcg gtgaccgagg gggtggggac tgagccgccc
 661 gcctctgccg ccaccacca tctcaggaaa ggctgttgtg ctggtgcccg ttccagctgc
 721 aggggtgaca ctgggggggg gggctctcc tctcggtgct ccttcactct gggcctggcc
 781 tcaggccct ggtgcttccc cctcctcc tgggaggggg cccgtgaaga gcaaatgagc
 841 caaacgtgac cactagcctc ctggagcag agagtgggg tcgtttgccg gttgctccag
 901 cccggcgccc agccatcttc cctgagccag ccggcgggtg gtgggcatgc ctgcctcacc
 961 ttcatcaggg ggtggccagg aggggcccag actgtgaatc ctgtgctctg cccgtgaccg
1021 ccccccgccc catcaatccc attgcatagg tttagagaga gcacgtgtga ccactggcat
1081 tcatttgggg ggtgggagat tttggctgaa gccgcccag ccttagtccc cagggccaag
1141 cgctgggggg aagacgggga gtcagggagg ggggaaatc tcggaagagg gaggagtctg
1201 ggagtgggga gggatggccc agcctgtaag atactgtata tgcgctgctg tagataccgg
1261 aatgaatttt ctgtacatgt ttggttaatt ttttttgtac atgattttg tatgtttcct
1321 tttcaataaa atcagattgg aacagtgaa aaaaaaaa
```

NP_001120714.1 GI: 187829745
bcl-2-binding component 3 isoform 3 [*Homo sapiens*].

```
  1 mkfgmgsaqa cpcqvpraas ttwvpcqice trgaaaappl tlegpvqshh gtpaltqgpq
 61 sprdgaqlga ctrpvdvrds ggrplpppdt lasagdflct m
```

TABLE 4-continued

GENE AND PROTEIN SEQUENCES OF PANEL BIOMARKERS

PCNA
GeneID: 5111
NM_002592.2 GI: 33239449
*Homo sapiens* proliferating cell nuclear antigen (PCNA),
transcript variant 1, mRNA

```
  1 ggatggccgg agctggcgcc ctggttctgg aggtaaccgg ttactgaggg cgagaagcgc   61
 61 cacccggagg ctctagcctg acaaatgctt gctgacctgg gccagagctc ttcccttacg  121
121 caagtctcag ccggtcgtcg cgacgttcgc ccgctcgctc tgaggctcct gaagccgaaa  181
181 ccagctagac tttcctcctt cccgcctgcc tgtagcggcg ttgttgccac tccgccacca  241
241 tgttcgaggc gcgcctggtc cagggctcca tcctcaagaa ggtgttggag gcactcaagg  301
301 acctcatcaa cgaggcctgc tgggatatta gctccagcgg tgtaaacctg cagagcatgg  361
361 actcgtccca cgtctctttg gtgcagctca ccctgcggtc tgagggcttc gacacctacc  421
421 gctgcgaccg caacctggcc atgggcgtga acctcaccag tatgtccaaa atactaaaat  481
481 gcgccggcaa tgaagatatc attacactaa gggccgaaga taacgcggat accttggcgc  541
541 tagtatttga agcaccaaac caggagaaag tttcagacta tgaaatgaag ttgatggatt  601
601 tagatgttga acaacttgga attccagaac aggagtacag ctgtgtagta aagatgcctt  661
661 ctggtgaatt tgcacgtata tgccgagatc tcagccatat ggagatgct gttgtaattt  721
721 cctgtgcaaa agacggagtg aaattttctg caagtggaga acttggaaat ggaaacatta  781
781 aattgtcaca gacaagtaat gtcgataaag aggaggaagc tgttaccata gagatgaatg  841
841 aaccagttca actaactttt gcactgaggt acctgaactt ctttacaaaa gccactccac  901
901 tctcttcaac ggtgacactc agtatgtctg cagatgtacc ccttgttgta gagtataaaa  961
961 ttgcggatat gggacactta aaatactact tggctcccaa gatcgaggat gaagaaggat 1021
1021 cttaggcatt cttaaaattc aagaaaataa aactaagctc tttgagaact gcttctaaga 1081
1081 tgccagcata tactgaagtc ttttctgtca ccaaatttgt acctctaagt acatatgtag 1141
1141 atattgtttt ctgtaaataa cctatttttt tctctattct ctgcaatttg tttaaagaat 1201
1201 aaagtccaaa gtcagatctg gtctagttaa cctagaagta tttttgtctc ttagaaatac 1261
1261 ttgtgatttt tataatacaa aagggtcttg actctaaatg cagttttaag aattgttttt 1321
1321 gaatttaaat aaagttactt gaatttcaaa catca
```

NP_002583.1 GI: 4505641
proliferating cell nuclear antigen [*Homo sapiens*]

```
  1 mfearlvqgs ilkkvlealk dlineacwdi sssgvnlqsm dsshvslvql tlrsegfdty   61
 61 rcdrnlamgv nltsmskilk cagnediitl raednadtla lvfeapnqek vsdyemklmd  121
121 ldveqlgipe qeyscvvkmp sgefaricrd lshigdavvi scakdgvkfs asgelgngni  181
181 klsqtsnvdk eeeavtiemn epvqltfalr ylnfftkatp lsstvtlsms advplvveyk  241
241 iadmghlkyy lapkiedeeg s
```

CR536501.1 GI: 49168489
*Homo sapiens* full open reading frame cDNA clone RZPDo834B0222D for
gene PCNA, proliferating cell nuclear antigen; complete cds, incl.
stopcodon

```
  1 atgttcgagg cgcgcctggt ccagggctcc atcctcaaga aggtgttgga ggcactcaag
 61 gacctcatca acgaggcctg ctgggatatt agctccagcg tgtaaacct gcagagcatg
121 gactcgtccc acgtctcttt ggtgcagctc accctgcggt ctgagggctt cgacacctac
181 cgctgcgacc gcaacctggc catgggcgtg aacctcacca gtatgtccaa aatactaaaa
241 tgcgccggca atgaagatat cattacacta agggccgaag ataacgcgga taccttggcg
301 ctagtatttg aagcaccaaa ccaggagaaa gtttcagact atgaaatgaa gttgatggat
361 ttagatgttg aacaacttgg aattccagaa caggagtaca gctgtgtagt aaagatgcct
421 tctggtgaat ttgcatgtat atgccgagat ctcagccata tggagatgc tgttgtaatt
481 tcctgtgcaa aagacggagt gaaattttct gcaagtggag aacttggaaa tggaaacatt
541 aaattgtcac agacaagtaa tgtcgataaa gaggaggaag ctgttaccat agagatgaat
601 gaaccagttc aactaacttt tgcactgagg tacctgaact tctttacaaa agccactcca
661 ctctcttcaa cggtgacact cagtatgtct gcagatgtac cccttgttgt agagtataaa
721 attgcggata tgggacactt aaaatactac ttggctccca agatcgagga tgaagaagga
781 tcttag
```

PCNA [*Homo sapiens*]
CAG38740.1 GI: 49168490

```
  1 mfearlvqgs ilkkvlealk dlineacwdi sssgvnlqsm dsshvslvgl tlrsegfdty
 61 rcdrnlamgv nltsmskilk cagnediitl raednadtla lvfeapnqek vsdyemklmd
121 ldveqlgipe qeyscvvkmp sgefaricrd lshigdavvi scakdgvkfs asgelgngni
181 klsqtsnvdk eeeavtiemn epvqltfalr ylnfftkatp lsstvtlsms advplvveyk
241 iadmghlkyy lapkiedeeg s
```

GADD45a
GeneID: 1647
NM_001924.3 GI: 315075321
*Homo sapiens* growth arrest and DNA-damage-inducible, alpha
(GADD45A), transcript variant 1, mRNA

```
  1 ggagagcggg gcccttttgtc ctccagtggc tggtaggcag tggctgggag gcagcggccc
 61 aattagtgtc gtgcggcccg tggcgaggcg aggtccgggg agcgagcgag caagcaaggc
121 gggaggggtg gccggagctg cggcggctgg cacaggagga ggagcccggg cgggcgaggg
181 gcggccggag agcgccaggg cctgagctgc cggagcggcc cctgtgagtg agtgcagaaa
```

TABLE 4-continued

GENE AND PROTEIN SEQUENCES OF PANEL BIOMARKERS

```
 241 gcaggcgccc gcgcgctagc cgtggcagga gcagcccgca cgccgcgctc tctccctggg
 301 cgacctgcag tttgcaatat gactttggag gaattctcgg ctggagagca gaagaccgaa
 361 aggatggata aggtggggga tgccctggag gaagtgctca gcaaagccct gagtcagcgc
 421 acgatcactg tcggggtgta cgaagcggcc aagctgctca acgtcgaccc cgataacgtg
 481 gtgttgtgcc tgctggcggc ggacgaggac gacgacagag atgtggctct gcagatccac
 541 ttcaccctga tccaggcgtt ttgctgcgag aacgacatca acatcctgcg cgtcagcaac
 601 ccggggcggc tggcggagct cctgctcttg gagaccgacg ctggccccgc ggcgagcgag
 661 ggcgccgagc agcccccgga cctgcactgc gtgctggtga cgaatccaca ttcatctcaa
 721 tggaaggatc ctgccttaag tcaacttatt tgttttgcc gggaaagtcg ctacatggat
 781 caatgggttc cagtgattaa tctccctgaa cggtgatggc atctgaatga aaataactga
 841 accaaattgc actgaagttt ttgaaatacc tttgtagtta ctcaagcagt tactccctac
 901 actgatgcaa ggattacaga aactgatgcc aaggggctga gtgagttcaa ctacatgttc
 961 tgggggcccg gagatagatg actttgcaga tggaaagagg tgaaaatgaa gaaggaagct
1021 gtgttgaaac agaaaaataa gtcaaaagga acaaaaatta caaagaacca tgcaggaagg
1081 aaaactatgt attaatttag aatggttgag ttacattaaa ataaaccaaa tatgttaaag
1141 tttaagtgtg cagccatagt ttgggtattt ttggtttata tgccctcaag taaaagaaaa
1201 gccgaaaggg ttaatcatat ttgaaaacca tattttattg tattttgatg agatattaaa
1261 ttctcaaagt tttattataa attctactaa gttattttat gacatgaaaa gttatttatg
1321 ctataaattt tttgaaacac aatacctaca ataaactggt atgaataatt gcatcatttc
1381 aaaaaaaaaa aaaaaaa
```

NP_001915.1 GI: 4503287
growth arrest and DNA damage-inducible protein GADD45 alpha isoform 1 [Homo sapiens]

```
  1 mtleefsage qktermdkvg daleevlska lsqrtitvgv yeaakllnvd pdnvvlclla
 61 adedddrdva lqihftliqa fccendinil rvsnpgrlae lllletdagp aasegaeqpp
121 dlhcvlvtnp hssqwkdpal sqlicfcres rymdqwvpvi nlper
//
```

NM_001199741.1 GI: 315075322
Homo sapiens growth arrest and DNA-damage-inducible, alpha (GADD45A), transcript variant 2, mRNA

```
  1 ggagagcggg gccctttgtc ctccagtggc tggtaggcag tggctgggag gcagcggccc
 61 aattagtgtc gtgcggcccg tggcgaggcg aggtccgggg agcgagcgag caagcaaggc
121 gggaggggtg gccggagctg cggcggctgg cacaggagga ggagcccggg cgggcgaggg
181 gcggccggag agcgccaggg cctgagctgc cggagcggcg cctgtgagtg agtgcagaaa
241 gcaggcgccc gcgcgctagc cgtggcagga gcagcccgca cgccgcgctc tctccctggg
301 cgacctgcag tttgcaatat gactttggag gaattctcgg ctggagagca gaagaccgaa
361 agcgaccccg ataacgtggt gttgtgcctg ctgcggcgg acgaggacga cgacagagat
421 gtggctctgc agatccactt caccctgatc caggcgtttt gctgcgagaa cgacatcaac
481 atcctgcgcg tcagcaaccc ggggccggctg gcggagctcc tgctcttgga gaccgacgct
541 ggccccgcgg cgagcgaggg cgccgagcag cccccggacc tgcactgcgt gctggtgacg
601 aatccacatt catctcaatg gaaggatcct gccttaagtc aacttatttg ttttgccgg
661 gaaagtcgct acatggatca atgggttcca gtgattaatc tccctgaacg gtgatggcat
721 ctgaatgaaa ataactgaac caaattgcac tgaagttttt gaaataccttt tgtagttact
781 caagcagtta ctccctacac tgatgcaagg attacagaaa ctgatgccaa ggggctgacg
841 gagttcaact acatgttctg ggggcccgga gatagatgac tttgcagatg gaaagaggtg
901 aaaatgaaga aggaagctgt gttgaaacag aaaaataagt caaaaggaac aaaaattaca
961 aagaaccatg caggaaggaa aactatgtat taatttagaa tggttgagtt acattaaaat
1021 aaaccaaata tgttaaagtt taagtgtgca gccatagttt gggtattttt tggtttatgt
1081 ccctcaagta aaagaaagc cgaaagggtt aatcatattt gaaaaccata tttttattgta
1141 ttttgatgag atattaaatt ctcaaagttt tattataaat tctactaagt tatttatga
1201 catgaaaagt tatttatgct ataaattttt tgaaacacaa tacctacaat aaactggtat
1261 gaataattgc atcatttcaa aaaaaaaaa aaaaaa
```

NP_001186670.1 GI: 315075323
growth arrest and DNA damage-inducible protein GADD45 alpha isoform 2 [Homo sapiens]

```
  1 mtleefsage qktesdpdnv vlcllaaded ddrdvalqih ftliqafcce ndinilrvsn
 61 pgrlaellll etdagpaase gaeqppdlhc vlvtnphssq wkdpalsqli cfcresrymd
121 qwvpvinlpe r
```

NM_001199742.1 GI: 315075324
Homo sapiens growth arrest and DNA-damage-inducible, alpha (GADD45A), transcript variant 3, mRNA

```
  1 ggagagcggg gccctttgtc ctccagtggc tggtaggcag tggctgggag gcagcggccc
 61 aattagtgtc gtgcggcccg tggcgaggcg aggtccgggg agcgagcgag caagcaaggc
121 gggaggggtg gccggagctg cggcggctgg cacaggagga ggagcccggg cgggcgaggg
181 gcggccggag agcgccaggg cctgagctgc cggagcggcg cctgtgagtg agtgcagaaa
241 gcaggcgccc gcgcgctagc cgtggcagga gcagcccgca cgccgcgctc tctccctggg
301 cgacctgcag tttgcaatat gactttggag gaattctcgg ctggagagca gaagaccgaa
361 aggatggata aggtggggga tgccctggag gaagtgctca gcaaagccct gagtcagcgc
421 acgatcactg tcggggtgta cgaagcggcc aagctgctca acgtaatcca cattcatctc
481 aatggaagga tcctgcctta agtcaactta tttgtttttg ccgggaaagt cgctacatgg
```

TABLE 4-continued

GENE AND PROTEIN SEQUENCES OF PANEL BIOMARKERS

```
 541 atcaatgggt tccagtgatt aatctccctg aacggtgatg gcatctgaat gaaaataact
 601 gaaccaaatt gcactgaagt ttttgaaata cctttgtagt tactcaagca gttactccct
 661 acactgatgc aaggattaca gaaactgatg ccaaggggct gagtgagttc aactacatgt
 721 tctgggggcc cggagataga tgactttgca gatggaaaga ggtgaaaatg aagaaggaag
 781 ctgtgttgaa acagaaaaat aagtcaaaag gaacaaaaat tacaaagaac catgcaggaa
 841 ggaaaactat gtattaattt agaatggttg agttacatta aaataaacca aatatgttaa
 901 agtttaagtg tgcagccata gtttgggtat ttttggttta tatgccctca agtaaaagaa
 961 aagccgaaag ggtaatcat atttgaaaac catattttat tgtattttga tgagatatta
1021 aattctcaaa gttttattat aaattctact aagttatttt atgacatgaa aagttattta
1081 tgctataaat tttttgaaac acaataccta caataaactg gtatgaataa ttgcatcatt
1141 tcaaaaaaaa aaaaaaaaaa
```

NP_001186671.1 GI: 315075325
growth arrest and DNA damage-inducible protein GADD45 alpha isoform
3 [*Homo sapiens*]

```
   1 mtleefsage qktermdkvg daleevlska lsqrtitvgv yeaakllnvi hihlngrilp
```

XPC
GeneID: 7508
NM_004628.4 GI: 224809294
*Homo sapiens* xeroderma pigmentosum, complementation group C (XPC),
transcript variant 1, mRNA

```
   1 cgaaggggcg tggccaagcg caccgcctcg gggcggggcc ggcgttctag cgcatcgcgg
  61 ccgggtgcgt cactcgcgaa gtggaatttg cccagacaag caacatggct cggaaacgcg
 121 cggccggcgg ggagccgcgg ggacgcgaac tgcgcagcca gaaatccaag gccaagagca
 181 aggcccggcg tgaggaggag gaggaggatg cctttgaaga tgagaaaccc ccaaagaaga
 241 gccttctctc caaagtttca caggaaaaga ggaaaagagg ctgcagtcat cctgggggtt
 301 cagcagatgt tccagcaaaa aagaaagtgg ccaaggtgac tgttaaatct gaaaacctca
 361 aggttataaa ggatgaagcc ctcagcgatg gggatgacct cagggacttt ccaagtgacc
 421 tcaagaaggc acaccatctg aagagagggg ctaccatgaa tgaagacagc aatgaagaag
 481 aggaagaaag tgaaaatgat tgggaagagg ttgaagaact tagtgagcct gtgctgggtg
 541 acgtgagaga aagtacagcc ttctctcgat ctcttctgcc tgtgaagcca gtggagatag
 601 agattgaaac gccagagcag gcgaagacaa gagaaagaag tgaaaagata aaactggagt
 661 ttgagacata tcttcggagg gcgatgaaac gtttcaataa aggggtccat gaggacacac
 721 acaaggttca ccttctctgc ctgctagcaa atggcttcta tcgaaataac atctgcagcc
 781 agccagatct gcatgctatt ggcctgtcca tcatcccagc ccgctttacc agagtgctgc
 841 ctcgagatgt ggacacctac tacctctcaa acctggtgaa gtggttcatt ggaacattta
 901 cagttaatgc agaactttca gccagtgaac aagtaccact ggaactacac ttggaaagga
 961 gatttgctat ttactctgct cgagatgatg aggaattggt ccatatattc ttactgattc
1021 tccgggctct gcagctcttg acccggctgg tattgtctct acagccaatt cctctgaagt
1081 cagcaacagc aaagggaaag aaaccttcca aggaaagatt gactgcggat ccaggaggct
1141 cctcagaaac ttccagccaa gttctagaaa accacaccaa accaaagacc agcaaaggaa
1201 ccaaacaaga ggaaaccttt gctaagggca cctgcaggcc aagtgccaaa gggaagagga
1261 acaagggagg cagaaagaaa cggagcaagc cctcctccag cgaggaagat gagggcccag
1321 gagacaagca ggagaaggca acccagcgac gtccgcatgg ccgggagcgg cgggtggcct
1381 ccagggtgtc ttataaagag gagagtggga gtgatgaggc tggcagcggc tctgattttg
1441 agctctccag tggagaagcc tctgatcccc tgatgaggag ttccgaacct ggccctccaa
1501 agcagaggaa agccccgct cctcagagga caaaggctgg gtccaagagt gcctccagga
1561 cccatcgtgg gagccatcgt aaggacccaa gcttgccagc ggcatcctca agctcttcaa
1621 gcagtaaaag aggcaagaaa atgtgcagcg atggtgagga ggcagaaagc agaagcatag
1681 ctggtataga ccagtggcta gaggtgttct gtgagcagga ggaaaagtgg gtatgtgtag
1741 actgtgtgca cggtgtggtg ggccagcctc tgacctgtta caagtacgcc accaagccca
1801 tgacctatgt ggtgggcatt gacagtacgg gctgggtccg agatgtcaca cagaggtacg
1861 acccagtctg gatgacagtg acccgcaagt gccgggttga tgctgagtgg tgggccgaga
1921 cctttgagacc ataccagagc ccatttatgg acagggagaa gaaagaagac ttggagtttc
1981 aggcaaaaca catggaccag cctttgccca ctgccattgg cttatataag aaccaccctc
2041 tgtatgccct gaagcggcat ctcctgaaat atgaggccat ctatcccgag acagctgcca
2101 tccttgggta ttgtcgtgga gaagcggtct actccaggga ttgtgtgcac actctgcatt
2161 ccagggacac gtggctgaag aaagcaagag tggtgaggct tggagaagta ccctacaaga
2221 tggtgaaagg ctttttctaac cgtgctcgga agcccgact tgctgagccc cagctgcggg
2281 aagaaaatga cctgggcctg tttggctact ggcagacaga ggagtatcag ccccagtgg
2341 ccgtggacgg gaaggtgccc cggaacgagt ttgggaatgt gtacctcttc ctgcccagca
2401 tgatgcctat tggctgtgtc cagctgaacc tgcccaatct acaccgcgtg gcccgcaagc
2461 tggacatcga ctgtgtccag gccatcactg gctttgattt ccatggcggc tactcccatc
2521 ccgtgactga tggatacatc gtctgcgagg aattcaaaga cgtgctcctg actgctgggg
2581 aaaatgagca ggcagtcatt gaaaggaagg agaaggagaa aaaggagaag cgggctctag
2641 ggaactggaa gttgctggcc aaaggtctgc tcatcaggga gaggtgaag cgtcgctacg
2701 ggcccaagag tgaggcagca gctccccaca cagatgcagg aggtggactc tcttctgatg
2761 aagaggaggg gaccagctct caagcagaag cggccaggat actggctgcc tcctggcctc
2821 aaaaccgaga agatgaagaa aagcagaagc tgaaggtgg gcccaagaag accaaaaggg
2881 aaaagaaagc agcagcttcc cacctgttcc catttgagga gctgtgagct gagcgcccac
2941 tagaggggca cccaccagtt gctgctgccc cactcagcca cccacacctg ccctgcgcat
3001 gcccagcccc tggtggtggg ggcttctctg ctgagaaggc aaactgaggc agcatgcacg
3061 gaggcggggt cagggagac gaggccaagc tgaggaggtg ctgcaggtcc cgtctggctc
3121 cagcccttgt cagattcacc cagggtgaag ccttcaaagc tttttgctac caaagcccac
3181 tcacccttttg agctacagaa cactttgcta ggagatactc ttctgcctcc tagacctgtt
```

TABLE 4-continued

GENE AND PROTEIN SEQUENCES OF PANEL BIOMARKERS

```
3241 ctttccatct ttagaaacat cagtttttgt atggaagcca ccgggagatt tctggatggt
3301 ggtgcatccg tgaatgcgct gatcgtttct tccagttaga gtcttcatct gtccgacaag
3361 ttcactcgcc tcggttgcgg acctaggacc atttctctgc aggccactta ccttcccctg
3421 agtcaggctt actaatgctg ccctcactgc ctctttgcag tagggagag agcagaaag
3481 tacaggtcat ctgctgggat ctagttttcc aagtaacatt ttgtggtgac agaagcctaa
3541 aaaaagctaa aatcaggaaa gaaaaggaaa aatacgaatt gaaaattaag gaaatgttag
3601 taaaatagat gagtgttaaa ctagattgta ttcattacta gataaaatgt ataaagctct
3661 ctgtactaag gagaaatgac ttttataaca ttttgagaaa ataataaagc atttatctaa
3721 aaaaaaaaa
```

NP_004619.3 GI: 224809295
DNA repair protein complementing XP-C cells isoform 1 [*Homo sapiens*]

```
   1 markraagge prgrelrsqk skakskarre eeeedafede kppkksllsk vsqgkrkrgc
  61 shpggsadgp akkkvakvtv ksenlkvikd ealsdgddlr dfpsdlkkah hlkrgatmne
 121 dsneeeeese ndweeveels epvlgdvres tafsrsllpv kpveieietp eqaktrerse
 181 kiklefetyl rramkrfnkg vhedthkvhl lcllangfyr nnicsqpdlh aiglsiipar
 241 ftrvlprdvd tyylsnlvkw figtftvnae lsaseqdnlq ttlerrfaiy sarddeelvh
 301 ifllilralq lltrlvlslq piplksatak gkkpskerlt adpggssets sqvlenhtkp
 361 ktskgtkqee tfakgtcrps akgkrnkggr kkrskpssse edegpgdkqe katqrrphgr
 421 errvasrvsy keesgsdeag sgsdfelssg easdpsdeds epgppkqrka papqrtkags
 481 ksasrthrgs hrkdpslpaa ssssssskrg kkmcsdgeka ekrsiagidq wlevfceqee
 541 kwvcvdcvhg vvgqpltcyk yatkpmtyvv gidsdgwvrd vtqrydpvwm tvtrkcrvda
 601 ewwaetlrpy qspfmdrekk edlefqakhm dqplptaigl yknhplyalk rhllkyeaiy
 661 petaailgyc rgeavysrdc vhtlhsrdtw lkkarvvrlg evpykmvkgf snrarkarla
 721 epqlreendl glfgywqtee yqppvavdgk vprnefgnvy lflpsmmpig cvqlnlpnlh
 781 rvarkldidc vqaitgfdfh ggyshpvtdg yivceefkdv lltaweneqa vierkekekk
 841 ekralgnwkl lakgllirer lkrrygpkse aaaphtdagg glssdeeegt ssqaeaaril
 901 aaswpqnred eekqklkggp kktkrekkaa ashlfpfeql
```

NM_001145769.1 GI: 224809301
*Homo sapiens* xeroderma pigmentosum, complementation group C (XPC), transcript variant 2, mRNA

```
   1 cgaaggggcg tggccaagcg caccgcctcg gggcggggcc ggcgttctag cgcatcgcgg
  61 ccgggtgcgt cactcgcgaa gtggaatttg cccagacaag caacatggct cggaaacgcg
 121 cggccgcgcg ggagccgcgg ggacgcgaac tgcgcagcca gaaatccaag gccaagagca
 181 aggcccggcg tgaggaggag gaggaggatg cctttgaaga tgagaaaccc ccaaagaaga
 241 gccttctctc caaagtttca caaggaaaga ggaaaagagg ctgcagtcat cctgggggtt
 301 cagcagatgg tccagcaaaa aagaaagtgg ccaaggtgac tgttaaatct gaaaacctca
 361 aggttataaa ggatgaagcc ctcagcgatg gggatgacct cagggacttt ccaagtgacc
 421 tcaagaaggc acaccatctg aagagagggg ctaccatgaa tgaagacagc aatgaagaag
 481 aggaagaaag tgaaaatgat tgggaagagg cgaagacaag agaaagaagt gaaaagataa
 541 aactggagtt tgagacatat cttcggaggg cgatgaaacg tttcaataaa ggggtccatg
 601 aggacacaca caaggttcac cttctctgcc tgctagcaaa tggcttctat cgaaataaca
 661 tctgcagcca gccagatctg catgctattg gcctgtccat catcccagcc cgctttacca
 721 gagtgctgcc tcgagatgtg gacacctact acctctcaaa cctggtgaag tggttcattg
 781 gaacatttac agttaatgca gaactttcag ccagtgaaca agataacctg cagactacat
 841 tggaaaggag atttgctatt tactctgctc gagatgatga ggaattggtc catatattct
 901 tactgattct ccgggctctg cagctcttga cccggctggt attgtctcta cagccaattc
 961 ctctgaagtc agcaacagca aagggaaaga aaccttccaa ggaaagattg actgcggatc
1021 caggaggctc ctcagaaact tccagccaag ttctagaaaa ccacaccaaa ccaaagacca
1081 gcaaaggaac caaacaagag gaaacctttg ctaagggcac ctgcaggcca agtgccaaag
1141 gaagaggaa caagggaggc agaaagaaac ggagcaagcc ctcctccagc gaggaagatg
1201 agggcccagg agacaagcag gagaaggcaa cccagcgacg tccgcatggc cgggagcggc
1261 gggtggcctc cagggtgtct tataaagagg agagtggagg tgatgaggct gacagcggct
1321 ctgattttga gctctccagt ggagaagcct ctgatccctc tgatgaggat tccgaacctg
1381 gccctccaaa gcagaggaaa gccccgctc tcagaggac aaaggctggg tccaagagtg
1441 cctccaggac ccatcgtggg agccatcgta aggacccaag cttgccagcg gcatcctcaa
1501 gctcttcaag cagtaaaaga ggcaagaaaa tgtgcagcga gtgagaag gcagaaaaa
1561 gaagcatagc tggtatagac cagtggctag aggtgttctg tgagcaggag gaaaagtggg
1621 tatgtgtaga ctgtgtgcac ggtgtggtgg ccagcctct gacctgttac aagtacgcca
1681 ccaagcccat gacctatgtg gtgggcattg acagtgacgg ctgggtccga gatgtcacac
1741 agaggtacga cccagtctgg atgacagtga cccgcaagtg ccgggttgat gctgagtggt
1801 gggccgagac cttgagacca taccagagcc catttatgga cagggagaag aaagaagact
1861 tggagtttca ggcaaaacac atggaccagc ctttgcccac tgccattggc ttatataaga
1921 accaccctct gtatgccctg aagcggcatc tcctgaaata tgaggccatc tatcccgaga
1981 cagctgccat ccttgggtat tgtcgtggag aagcggtcta ctccagggat tgtgtgcaca
2041 ctctgcattc cagggacacg tggctgaaga agcaagagt ggtgaggctt ggagaagtac
2101 cctacaagat ggtgaaaggc ttttctaacc gtgctcggaa agcccgactt gctgagcccc
2161 agctgcggga agaaaatgac ctgggcctgt ttggctactg gcagacagag gagtatcagc
2221 cccagtggc cgtggacggg aaggtgcccc ggaacgagtt tgggaatgtg tacctcttcc
2281 tgcccagcat gatgcctatt ggctgtgtcc agctgaacct gcccaatcta caccgcgtgg
2341 cccgcaagct ggacatcgac tgtgtccagg ccatcactgg ctttgatttc catggcggct
2401 actccatcc cgtgactgat ggatacatcg tctgcgagga attcaaagac gtgctcctga
2461 ctgcctggga aaatgagcag gcagtcattg aaaggaagga aggagaaa aaggagaagc
2521 gggctctagg gaactggaag ttgctggcca aaggtctgct catcagggag aggctgaagc
```

TABLE 4-continued

GENE AND PROTEIN SEQUENCES OF PANEL BIOMARKERS

```
2581 gtcgctacgg gcccaagagt gaggcagcag ctccccacac agatgcagga ggtggactct
2641 cttctgatga agaggagggg accagctctc aagcaggaag ggccaggata ctggctgcct
2701 cctggcctca aaaccgagaa gatgaagaaa agcagaagct gaagggtggg cccaagaaga
2761 ccaaaaggga aaagaaagca gcagcttccc acctgttccc atttgagcag ctgtgagctg
2821 agcgcccact agaggggcac ccaccagttg ctgctgcccc actacaggcc ccacacctgc
2881 cctgggcatg cccagcccct ggtggtgggg gcttctctgc tgagaaggca aactgaggca
2941 gcatgcacgg aggcggggtc aggggagacg aggccaagct gaggaggtgc tgcaggtccc
3001 gtctggctcc agcccttgtc agattcaccc agggtgaagc cttcaaagct ttttgctacc
3061 aaagcccact caccctttga gctacagaac actttgctag gagatactct tctgcctcct
3121 agacctgttc tttccatctt tagaaacatc agttttttgta tggaagccac cgggagattt
3181 ctggatggtg gtgcatccgt gaatgcgctg atcgtttctt ccagttagag tcttcatctg
3241 tccgacaagt tcactcgcct cggttgcgga cctaggacca tttctctgca ggccacttac
3301 cttcccctga gtcaggctta ctaatgctgc cctcactgcc tctttgcagt aggggagaga
3361 gcagagaagt acaggtcatc tgctgggatc tagttttcca agtaacattt tgtggtgaca
3421 gaagcctaaa aaaagctaaa atcaggaaag aaaaggaaaa atacgaattg aaaattaagg
3481 aaatgttagt aaaatagatg agtgttaaac tagattgtat tcattactag ataaaatgta
3541 taaagctctc tgtactaagg agaaatgact tttataacat tttgagaaaa taataaagca
3601 tttatctaaa aaaaaaaa
```

NP_001139241.1 GI: 224809302
DNA repair protein complementing XP-C cells isoform 2 [*Homo sapiens*]

```
  1 markraagge prgrelrsqk skakskarre eeeedafede kppkksllsk vsqgkrkrgc
 61 shpggsadgp akkkvakvtv ksenlkvikd ealsdgddlr dfpsdlkkah hlkrgatmne
121 dsneeeese ndweeaktre rsekiklefe tylrramkrf nkgvhedthk vhllcllang
181 fyrnnicsqp dlhaiglsii parftrvlpr dvdtyylsnl vkwfigtftv naelsaseqd
241 nlqttlerrf aiysarddee lvhifllilr alqlltrlvl slqpiplksa takgkkpske
301 rltadpggss etssqvlenh tkpktskgtk qeetfakgtc rpsakgkrnk ggrkkrskps
361 sseedegpgd kqekatqrrp hgrerrvasr vsykeesgsd eagsgsdfel ssgeasdpsd
421 edsepgppkq rkapapqrtk agsksasrth rgshrkdpsl paasssssss krgkkmcsdg
481 ekaekrsiag idqwlevfce qeekwvcvdc vhgvvgqplt cykyatkpmt yvvgidsdgw
541 vrdvtqrydp vwmtvtrkcr vdaewwaetl rpyqspfmdr ekkedlefqa khmdqplpta
601 iglyknhply alkrhllkye aiypetaail gycrgeavys rdcvhtlhsr dtwlkkarvv
661 rlgevpykmv kgfsnrarka rlaepqlree ndlglfgywq teeyqppvav dgkvprnefg
721 nvylflpsmm pigcvqlnlp nlhrvarkld idcvqaitgf dfhggyshpv tdgyivceef
781 kdvlltawen eqaviekek ekkekralgn wkllakglli rerlkrrygp kseaaaphtd
841 aggglssdee egtssqaeaa rilaaswpqn redeekqklk ggpkktkrek kaaashlfpf
901 eql
//
```

NR_027299.1 GI: 224809303
*Homo sapiens* xeroderma pigmentosum, complementation group C (XPC), transcript variant 3, non-coding RNA.

```
   1 cgaaggggcg tggccaagcg caccgcctcg gggcggggcc ggcgttctag cgcatcgcgg
  61 ccgggtgcgt cactcgcgaa gtggaatttg cccagacaag caacatggct cggaaacgcg
 121 cggccggccg ggagccgcgg ggacgcgaac tgcgcagcca gaaatccaag gccaagacga
 181 aggcccggcg tgaggaggag gaggaggatg cctttgaaga tgagaaaccc ccaaagaaga
 241 gccttctctc caaagtttca caaggaaaga ggaaaagagg ctgcagtcat cctgggggtt
 301 cagcagatgg tccagcaaaa aagaaagtgg ccaaggtgac tgttaaatct gaaaacctca
 361 aggttataaa ggatgaagcc ctcagcgatg gggatgacct cagggacttt ccaagtgacc
 421 tcaagaaggc acaccatctg aagagagggg ctaccatgaa tgaagacagc aatgaagaag
 481 aggaagaaag tgaaaatgat tgggaagagg ttgaagtgaa aagataaaac tggagtttga
 541 gacatatctt cggagggcga tgaaacgttt caataaaggg gtccatgagg acacacacaa
 601 ggttcacctt ctctgcctgc tagcaaatgg cttctatcga aataacatct gcagccagcc
 661 agatctgcat gctattggcc tgtccatcat cccagcccgc tttaccagag tgctgcctcg
 721 agatgtggac acctactacc tctcaaacct ggtgaagtgg ttcattggaa catttacagt
 781 taatgcagaa ctttcagcca gtgaacaaga taacctgcag actacattgg aaaggagatt
 841 tgctatttac tctgctcgag atgatgagga attggtccat atattcttac tgattctccg
 901 ggctctgcag ctcttgaccc ggctggtatt gtctctacag ccaattcctc tgaagtcagc
 961 aacagcaaag ggaaagaaac cttccaagga aagattgact gcggatccag gaggctcctc
1021 agaaacttcc agccaagttc tagaaaacca caccaaacca aagaccagca aaggaaccaa
1081 acaagaggaa acctttgcta agggcacctg caggccaagt gccaagggga agaggaacaa
1141 gggaggcaga aagaaacgga gcaagccctc ctccagcgag gaagatgagg gcccaggaga
1201 caagcaggag aaggcaaccc agcgacgtcc gcatggccgg gagcggcggg tggcctccag
1261 ggtgtcttat aaagaggaga gtgggagtga tgaggctggc agcggctctg attttgagct
1321 ctccagtgga gaagcctctg atccctctga tgaggattcc gaacctggcc ctccaaagca
1381 gaggaaagcc cccgctcctc aagggacaaa ggctgggtcc aagagtgcct ccaggaccca
1441 tcgtgggagc catcgtaagg acccaagctt gccagcggca tcctcaagct cttcaagcag
1501 taaaagaggc aagaaaatgt gcagcgatgg tgagaaggca gaaaaaagaa gcatagctgg
1561 tatagaccag tggctagagg tgttctgtga gcaggaggaa aagtgggtat gtgtagactg
1621 tgtgcacggt gtggtgggcc agcctctgac cttgtacaag tacgccacca agcccatgac
1681 ctatgtggtg ggcattgaca gtgacggctg gtccgagat gtcacacaga ggtacgaccc
1741 agtctggatg acagtgaccc gcaagtgccg ggttgatgct gagtggtggg ccgagacctt
1801 gagaccatac cagagcccat ttatggacag ggagaagaaa aagacttggg agtttcaggc
1861 aaaacacatg accagccttt gcccactgca cattggctta tataagaacc accctctgta
1921 tgccctgaag cggcatctcc tgaaatatga ggccatctat cccgagacag ctgccatcct
```

TABLE 4-continued

GENE AND PROTEIN SEQUENCES OF PANEL BIOMARKERS

```
1981 tgggtattgt cgtggagaag cggtctactc cagggattgt gtgcacactc tgcattccag
2041 ggacacgtgg ctgaagaaag caagagtggt gaggcttgga gaagtaccct acaaagatggt
2101 gaaaggcttt tctaaccgtg ctcggaaagc ccgacttgct gagccccagc tgcgggaaga
2161 aaatgacctg ggcctgtttg gctactggca gacagaggag tatcagcccc cagtggccgt
2221 ggacgggaag gtgccccgga acgagtttgg gaatgtgtac ctcttcctgc ccagcatgat
2281 gcctattggc tgtgtccagc tgaacctgcc caatctacac cgcgtggccc gcaagctgga
2341 catcgactgt gtccaggcca tcactggctt tgatttccat ggcggctact cccatcccgt
2401 gactgatgga tacatcgtct gcgaggaatt caaagacgtg ctcctgactg cctgggaaaa
2461 tgagcaggca gtcattgaaa ggaaggagaa ggagaaaaag gagaagcggg ctctagggaa
2521 ctggaagttg ctggccaaag gtctgctcat cagggagagg ctgaagcgtc gctacgggcc
2581 caagagtgag gcagcagctc cccacacaga tgcaggaggt ggactctctt ctgatgaaga
2641 ggagggggacc agctctcaag cagaagcggc caggatactg gctgcctcct ggcctcaaaa
2701 ccgagaagat gaagaaaagc agaagctgaa gggtgggccc aagaagacca aaagggaaaa
2761 gaaagcagca gcttccacc tgttcccatt tgagcagctg tgagctgagc gcccactaga
2821 ggggcaccca ccagttgctg ctgccccact acaggcccca cacctgccct gggcatgccc
2881 agccctggt ggtgggggct tctctgctga gaaggcaaac tgaggcagca tgcacggagg
2941 cgggtcagg ggagacgagg ccaagctgag gaggtgctgc aggtcccgtc tggctccagc
3001 ccttgtcaga ttcacccagg gtgaagcctt caaagctttt tgctaccaaa gcccactcac
3061 cctttgagct acagaaacct ttgctaggag atactcttct gcctcctaga cctgttcttt
3121 ccatctttag aaacatcagt ttttgtatgg aagccaccgg gagatttctg gatggtggtg
3181 catccgtgaa tgcgctgatc gtttcttcca gttagagtct tcatctgtcc gacaagttca
3241 ctcgcctcgg ttgcggacct aggaccattt ctctgcaggc cacttacctt cccctgagtc
3301 aggcttacta atgctgccct cactgcctct tgcagtagg ggagagagca gagaagtaca
3361 ggtcatctgc tgggatctag ttttccaagt aacattttgt ggtgacagaa gcctaaaaaa
3421 agctaaaatc aggaaagaaa aggaaaaata cgaattgaaa attaaggaaa tgttagtaaa
3481 atagatgagt gttaaactag attgtattca ttactagata aaatgtataa agctctctgt
3541 actaaggaga aatgacttt ataacatttt gagaaaataa taaagcattt atctaaaaaa
3601 aaaaa POLH
GeneID: 5429
NM_006502.2 GI: 170650686
Homo sapiens polymerase (DNA directed), eta (POLH), mRNA 1 agccgcgtca acggcccttc gcagcgggcg cgctgtcaga cctcagtctg gcggctgcat
  61 tgctgggcgc gccgctctcg tctgatccct gctggggacg gttgcccggg caggatccctt    121
tacgatccct tctcggtttc tccgtcgtca cagggaataa atctcgctcg aaactcactg       181
gaccgctcct agaaaggcga aaagatattc aggagcccctt ccattttcct tccagtaggc      241
accgaaccca gcattttcgg caaccgctgc tggcagtttt gccaggtgtt tgttaccttg       301
aaaaatggct actggacagg atcgatggt tgctctcgtg dacatggact gtttttttgt         361
tcaagtggag cagcggcaaa atcctcattt gaggaataaa ccttgtgcag ttgtacagta       421
caaatcatgg aaggggtggtg gaataattgc agtgagttat gaagctcgtg catttggagt      481
cactagaagt atgtgggcag atgatgctaa gaagttatgt ccagatcttc tactggcaca       541
agttcgtgag tcccgtggga aagctaacct caccaagtac gtgttgaagt                  601
gatggagata atgtctcgtt ttgctgtgat tgaacgtgcc agcattgatg aggcttacgt        661
agatctgacc agtgctgtac aagagagact acaaaagcta caaggtcagc ctatctcggc      721
agacttgttg ccaagcactt acattgaagg gttgccccaa ggcctacaa cggcagaaga       781
gactgttcag aaagaggga tgcgaaaaca aggcttatt caatggctcg attctcttca        841
gattgataac ctcacctctc cagacctgca gctcaccgtg ggagcagtga ttgtggagga      901
aatgagagca gccatagaga gggagactgg tttcagtgt tcagctggaa tttcacacaa        961
taaggtcctg gcaaaactgg cctgtggact aaacaagccc aaccgccaaa ccctggtttc     1021
acatgggtca gtcccacagc tcttcagcca aatgcccatt cgcaaaatcc gtagtcttgg     1081
aggaaagcta gggcctctg tcattgagat cctagggata gaatacatgg gtgaactgac     1141
ccagttcact gaatcccagc tccagagtca ttttggggag aagaatgggt cttggctata     1201
tgccatgtgc cgagggattg aacatgatcc agttaaaccc aggcaactac ccaaaaccat    1261
tggctgtagt aagaacttcc caggaaaaac agctcttgct actcgggaac aggtacaatg    1321
gtggctgttg caattagccc aggaactaga ggaggactg actaaagacc gaaatgataa    1381
tgacagggta gccacccagc tggttgtgag cattcgtgta caaggagaca aacgcctcag    1441
cagcctgcgc cgctgctgtg cccttacccg ctatgatgct cacaagatga gccatgatgc    1501
atttactgtc atcaagaact gtaatacttc tggaatccag acagaatggt ctcctcctct    1561
cacaatgctt ttcctctgtg ctacaaaatt ttctgcctct gcccctttcat cttctacaga    1621
catcaccagc ttcttgagca gtgacccaag ttctctgcca aaggtgccag ttaccagctc    1681
agaagctaag acccagggaa gtggcccagc ggtgacagcc actaagaaag caaccacgtc    1741
tctggaatca ttcttccaaa aagctgcaga aaggcagaaa gttaagaag cttcgctttc      1801
atctcttact gctcccactc agctcccat gagcaattca ccatccaagc cctcattacc     1861
ttttcaaacc agtcaaagta caggaactga gccctctttt aagcagaaaa gtctgcttct    1921
aaagcagaaa cagcttaata attcttcagt ttcttccccc caacaaaacc catggtccaa    1981
ctgtaaagca ttaccaaact ctttaccaac agagtatcca gggtgtgtcc ctgtttgtga    2041
aggggtgtcg aagctagaag aatcctctaa agcaactcct gcagagatgg atttggccca    2101
caacagccaa agcatgcacg cctcttcagc ttccaaatct gtgctggagg tgactcagaa     2161
agcaacccca atccaagtc ttctagctgc tgaggaccaa gtgccctgtg agaagtgtgg       2221
ctccctggta ccggtatggg atatgccaga acacatggac tatcattttg cattggagtt     2281
gcagaaatcc tttttgcagc cccactcttc aaaccccag gttgtttctg ccgtatctca     2341
tcaaggcaaa agaaatccca agagcccttt ggcctgcact aataaacgcc ccaggcctga    2401
gggcatgcaa acattggaat catttttaa gccattaaca cattagtgct gccctcaggc     2461
ttgcctgtag gattaatat tttttatctt tacagatctt tatctttaat attttatctt    2521
tacagatttc cctgagaaag ggaattatga aattttaat acaaaaaata atccatttag    2581
gtgctgagtt acggtcccat ctcttcacag gcatggattc taatcccact gctgacagag    2641
```

TABLE 4-continued

GENE AND PROTEIN SEQUENCES OF PANEL BIOMARKERS

```
atgtaaaaat tcatcctacc agagttttta atctttagca tttagggagg cagtgtcata   2701
aagtaaaaag tgtgtgggcc ttggagtcta agagacgtgg ttgcaaactt agctctggtt   2761
attgcaatga gggccttgaa caagtcattt tcttcacatt ctcatctgta aaatggagat   2821
aataccttac agattattgc agattaataa caatgtattc aaattatgta actcggccgg   2881
gtacaatggc tcacgcctgt aatcctaaca ctttgggagg ccgaggcaga cagatcacct   2941
gaggtcagga gtttgagacc agcctggcca acatggcaaa accatctcta ctaaaaatag   3001
aaaaattagc caggcacgtt ccaggcacct gtgatcccag ctacttagag gctgaggcag   3061
aagaattgct ttaaccttgg aggcggaggt tgcattgagc tgagatcatg ctagtcgcgt   3121
ccagcctggg caacagagcg agacttcatc tcagaaaata aaaaatagggg gccaggcaca   3181
gtggctcata cctgtaatgc cagcactttg ggaggccaag gcgggcagat cacgaggtca   3241
ggagtttcag accaatatgg tgaaacccca tctctactaa aattacaaaa aaaattatcc   3301
aggcgtggtg gtgcacgcct gtaatcccag ctactcagga ggctaaggca ggagaatcac   3361
ttgaacccag gaggcagagg ttggagtgag ctgagatcgc gccaccgcac tccagcctgg   3421
gcaacagagc gagactccat ctcaaacaaa acaagaaca aaaacaaaca taagttggc    3481
acagaaaagg gaccaagttt aaaaaagggt tttaaatgta atgagacttg catagtgtaaa  3541
aaaaaaaaag ggattatttt tattttttatt ttttattttt gagacggagt ctccctctgt  3601
cgtcaggcta gaatgcagtg gtgcgttctc agctcaccgc aacctccgtc tcctgggttc   3661
aagcaattct cctgcctcag cctcccaagt agctgggact acaggcacgt gctaccacac   3721
tcagctaatt tttgtatttt taatagagat gaggtttcac catgttggcc aggatggtct   3781
cgattgcttg acctcatgat ccgcctgcct cgacctccca aagttgctgg gattacagat   3841
gttagccacc gatcctggcc cccccaaaaa aaggatttta agaaaaactt ctcttggccg   3901
ggcgcagtgg ctcacgcctg caatcccagc actttgggag gccgaggcgg gcggatcaca   3961
aggtcaggag atcgagacca cggtgaaacc ccgtctctac taaaaaatac aaaaaaaaat   4021
tagccgggtg cggtggcagg cgcctgtagt cccagctact cgggaggctg aggcaggaga   4081
atggtgtgaa cccggggaggc ggagcttgca gtgagccgag agcgcgccac tgcactccag  4141
cctgggtgac agagcgagac tccgtctcaa aaaaaaaaaa aaagaaaaa cttctcttta    4201
ggctgggtgc ggttcctcat gcctataatc ccagcatttta gggaggctga ggtgagtgga  4261
ttgcaggage tcaggagttc gagaccagcc tgggcaaggt gcaaaaccc cgtctctact    4321
aaaaaaaatt agctgggctt ggtggcaggc gcctgtaatc ccaggtactc gggagactga   4381
ggcaggagaa ttgcttgaac ctggaaggtg gaggttgcag tgagttgaga tcacaccaat   4441
gcactccagc cagggtgaga gtgagagact gtctcaaaaa aaaaaaaaac aaaagaaaaa   4501
cttctctcta gctctgtgac gggcagttca gataatacct tcaccagatt tacctgtttt   4561
cagctgaaga atgtgagatg aagccttgaa accctaaaag tgatatggta actagggcag   4621
gtctttctgt acataaaagt gacttaataa acagtgaatt tcatacaggt aaaccctatt   4681
ataccctcag ttctaaccat tggcctatct cttgcgtttt gttctaatgt agaattagat   4741
tgctacttga ctagttcagg aactctgttt agatctgata agtcataatc aaatcttgcc   4801
aggcgtggtg gtttatgcct gttatcccag cactttggga ggccaaggca ggtggaccac   4861
gtgaagtcag gagttcaaga caagcatggc caacatggcg aaaccctgta tctactaaaa   4921
atacaaaaat tagccgggca tggtggtggg tgcgtgtaat cccagctagt tgggaggctg   4981
aggcaggaga atcacttgaa cctgggaggc agaggttgca gtgagccgag atttccactg   5041
cattccagcc tgggcgatag agtaactctg tctcaaaaaa acccactaga tcatctctag   5101
aacattgcta ctcccaagta tgatttgagg aacagcagcc tcagtatcac cagggaactt   5161
attagaaata gtctcagcct caccactatt cccacttaat tgtaatctga tattaacaag   5221
atttcccaat gtgggtcagg tgtggtggct catgcctgta atcccacact ttgggaggcc   5281
aaggtgggcg gatcacttga ggctgggagt ttgagaccag gctggccaac atggggaaaa   5341
cccatctcta caaaaaataa caaaattag gtgtgtgtgg tgacgcatgc gtgtaatccc   5401
agctacttag gaggctgagg caggagaatc acttgaatct gggaggcaga ggttgtagtg   5461
agctgagatt gtgccactgc actccagtct gggcaacaga gtgacactgt ttaaaaaaaa   5521
aaaaattccc aatgtgggcc gggtgcagtg gctcatgcct gtaatcccag cactttggga   5581
ggctgaggtg ggtgtatcac gaggtcaaga gatcaaggcc atcctggcca acatggtgaa   5641
accccgtctc tactgaaaat acaactgggc gtggtggtgc acgcctgtag tcccagctac   5701
tgggaggct gaggcagaag aattgcttga cctgggaggc ggaggttgca gtgagcccag   5761
atcgtgccac tgcactgcac cctggcgaca cagcaagact gtctcaaaaa aaaaaaaatt   5821
cccaatgtgt atcttaaagt ttgagaaatg ctgatctaaa agatactaat gaccaggtgt   5881
gtagaggaca ttttcttaag cccttaagta caaatttaag aggtaagtgc ttcagccatt   5941
agggttactg gcttgttcat ctttcccact gagtgtaaat atttagctta gggtttaaaa   6001
tttgttatgt agcttttttgc acttgtccat gtttatacta ctgtattatt attatttttt   6061
tttgagatgg agtctcgctg tgtagccagg ctgagtgca gtggtgcaat cttggctcac   6121
tgcaacctcc gtctctcggg ttcaagcaat tctcctgcct cagcttccg aatagctgag   6181
actacaagcg tgcaccacca tgcccagcta attttttgtat ttttagtaga gacaggtttt   6241
caccatgttg gccaggctgg tctctatcta gacctcgtga tccatccgcc tcggcctccc   6301
aaagtgctgg gattataggc atgagccacc acgcccagcc tatagtactg tattcttatt   6361
ctccactctt gtgtgtgaaa agtcagctct tttggctttt ctgttatggg gaacttgaa    6421
ttacacaggg aacccaactg aagaaaatga actgaagtag gtggcgctgg gtgaagtggg   6481
cccagagaat ggtgtacaca tccctcccat acatataccc aaacttctat ttttttatgt   6541
gacggagttt ctctcatcgc cccggctgga atgcaatggc acgatctcgg ctcactgcaa   6601
cctccgcctc ccgggttcaa gcgattctcc tgcatcagcc tcctgagtag ctgggattat   6661
aggcatgcac catcacgcct ggctaatttt tgtatttttta gtagagatgg ggtttcgcca   6721
cgttggccag gctggtcttg aactcttgat ccaagtgat ccacccgcc tggcctccca    6781
aagtgctggg attacaggcc tgagccacca ggccagcccc aacttctact tttattta    6841
tttataaattt ggggggggggg ttctatattt agtttgaaga ggtggggaag atttgaaaac   6901
cactagattt accaggaaat ttttttcttc aaaaatattt tctgcttta tgatacttga    6961
atatctaata aaagacaata ttagccagt caccgtggct gatgcttgta atcctaacac   7021
tttgggaggc tgaggtgggt ggactactga agccctggag ttcaaaaccg gcctaagcca   7081
catggcaaaa cagtctttac aaaaaatacaa aagatggtgg cttatgcctg tagtcgtacc   7141
tactcaggag gctgaggttg ggaggatcac ctgaatctgg gagtttgggg ctgcaataag   7201
ccatgattgt gccgctgcac tccagcctgg gtgcagtctc gagaccctgt ctcaaaaaaa   7261
aaaaaaaaaa aaaaaaaaaa aaagactaca ttcactgtat acgtggcctt ttccccctaa   7321
```

TABLE 4-continued

GENE AND PROTEIN SEQUENCES OF PANEL BIOMARKERS

```
ctagctatgt agcttcttaa aggcaaagat tcttcatagt gctttgcaca tgataggtgc   7381
tgatactcat tggatgaatg tatatagtga agaattttag atctgattac cacaattggg   7441
atcataaaca tgtataaact ccttgggagt ctgccttata tacttttttat ccccctaaat   7501
gttccattaa tgttgcagag aggctcacta gttcctggag atgtcttatt aagtactgaa   7561
atgtgatttt ccaaaatttt ctttacaata caggcaaaag ataagtaaat tgtggacaaa   7621
gctttcatct ctatcagcag ctatagagag gaagtaaaca gcttagcccc taatacagga   7681
ggaagttgtt caactacagg cttgttagta gcaagttaaa ccagttacat tttataaaac   7741
agcctgagtg gtagggaagc tatcactttta atactctaga ggcagaatgc cacataggac   7801
tttgggtcac atatttcttt tccagggtct cctcaaaatg cagtttctat ttacagttga   7861
ctttggcccc tatttaccca taaaatgtca aaatcaagta gtatgaacat ggaaacagga   7921
gcagggacta aggtttggtc aagtggccct cattgttcca agagtaattt aggctatgta   7981
aacttgaaaa atatgggacc agattacctt ttgtctctaa attctactct tctttaagta   8041
gctggcactg tatctctgcc agggcacaga agtgggctcc ttactattct gaccactagc   8101
aagtggccaa ctcttcaaat acagggtagc tacctatttc acgtgaaagg cctcagtatt   8161
ctgctcactt gaactacgga aaataggcca caatacttgg ttacaatact ggaactctga   8221
acctatgtgg aggagagaaa aacaatggtg aacgagatac cagctgggct ctttccacat   8281
tcagggctca gcagtgttgg ggtttcactt gtctctaatc ctgaagaggt atctagccct   8341
ggaaggaagc tgagcctgta gctaacgcat aagcacagtg tattcaataa aacattttta   8401
ttctgtacaa ta
```

NP_006493.1 GI: 5729982
DNA polymerase eta [*Homo sapiens*]

```
  1 matgqdrvva lvdmdcffvq veqrqnphlr nkpcavvqyk swkgggiiav syearafgvt    61
    rsmwaddakk lcpdlllaqv resrgkanlt kyreasvevm eimsrfavie rasideayvd   121
    ltsavqerlq klqgqpisad llpstyiegl pqgpttaeet vqkegmrkqg lfqwldslqi   181
    dnltspdlql tvgaviveem raaieretgf qcsagishnk vlaklacgln kpnrqtlvsh   241
    gsvpqlfsqm pirkirslgg klgasvieil gieymgeltq ftesqlqshf gekngswlya   301
    mcrgiehdpv kprqlpktig csknfpgkta latreqvqww llqlaqelee rltkdrndnd   361
    rvatqlvvsi rvqgdkrlss lrrccaltry dahkmshdaf tviknentsg iqtewsppt   421
    mlflcatkfs asapssstdi tsflssdpss lpkvpvtsse aktqgsgpav tatkkattsl   481
    esffqkaaer qkvkeaslss ltaptqapms nspskpslpf qtsqstgtep ffkqkslllk   541
    qkqlnnssvs spqqnpwsnc kalpnslpte ypgcvpvceg vskleesska tpaemdlahn   601
    sqsmhassas ksvlevtqka tpnpsllaae dqvpcekcgs lvpvwdmpeh mdyhfalelq   661
    ksflqphssn pqvvsavshq gkrnpkspla ctnkrprpeg mqtlesffkp lth
```

DDB2
GeneID: 1643
NM_000107.2 GI: 164419759
*Homo sapiens* damage-specific DNA binding protein 2, 48kDa (DDB2),
mRNA

```
   1 ctccgagacg ggtggggccg gagctccaag ctggtttgaa caagccctgg gcatgtttgg
  61 cgggaagttg gcttagctcg gctacctgtg gccccgcagt tttgtagtcc ccgccttgtt
 121 tctccccaga ggcctctcaa tcctccctcc atgatcttcg catagagcac agtaccccctt
 181 cacacggagg acgcgatggc tcccaagaaa cgcccagaaa cccagaagac ctccgagatt
 241 gtattacgcc ccaggaacaa gaggagcagg agtcccctgg agctggagcc cgaggcaag
 301 aagctctgtg cgaagggctc cggtcctagc agaagatgtg actcagactg cctctggggtg
 361 gggctggctg gcccacagat cctgccacca tgccgcagca tcgtcaggac cctccaccag
 421 cataagctgg gcagagcttc ctggccatct gtccagcagg ggctccagca gtccttttttg
 481 cacactctgg attcttaccg gatattacaa aaggctgccc cctttgacag gagggctaca
 541 tccttggcgt ggcacccaac tcaccccagc accgtggctg tgggttccaa agggggagat
 601 atcatgctct ggaattttgg catcaaggac aaacccacct tcatcaaagg gattggagct
 661 ggaggggagca tcactgggct gaagtttaac cctctcaata ccaaccagtt ttacgcctcc
 721 tcaatggagg gaacaactag gctgcaagac tttaaaggca acattctacg agttttttgcc
 781 agctcagaca ccatcaacat ctggttttgt agcctggatg tgtctgctag tagccgaatg
 841 gtggtcacag gagacaacgt ggggaacgtg atcctgctga acatggacgg caaagagctt
 901 tggaatctca gaatgcacaa aaagaaagtg acgcatgtgg ccctgaaccc atgctgtgat
 961 tggttcctgg ccacagcctc cgtagatcaa acagtgaaaa tttgggacct gcgccaggtt
1021 agagggaaag ccagcttcct ctactcgctg ccgcacaggc atcctgtcaa cgcagcttgt
1081 ttcagtcccg atggagcccg gctcctgacc acgaccaga agagcgagat ccgagtttac
1141 tctgctttccc agtgggactg cccccctggg ctgatcccgc accctcaccg tcacttccag
1201 cacctcacac catcaaggc agcctggcat cctcgctaca acctcattgt tgtgggccga
1261 tacccagatc ctaatttcaa aagttgtacc ccttatgaat tgaggacgat cgacgtgttc
1321 gatggaaact cagggaagat gatgtgtcag ctctatgacc cagaatccttc tggcatcagt
1381 tcgcttaatg aattcaatcc catgggggac acgctggcct ctgcaatggg ttaccacatt
1441 ctcatctgga gccaggagga agccaggaca cggaagtgag agacactaaa gaaggtgtgg
1501 gccagacaag gccttggagc ccacacatgg gatcaagtcc tgcaagcaga ggtggcgatt
1561 tgttaaaggg ccaaaagtat ccaaggttag ggttggagca ggggtgctgg gacctggggc
1621 actgtgggac tgggacactt ttatgttaat gctctgaact tgcctccaga gctgctcca
1681 gagttggtga cacagctgtc ccaagggccc ctctgtatct agcctggaac caaggttatc
1741 ttggaactaa atgactttttc tcctctcagt gggtggtagc agagggatca agcagttatt
1801 tgatttgtgc tcactttttga tatggccaat aaaaccatac cgactgagaa aaaaaaaaa
1861 aaaaaaaaaa //
```

TABLE 4-continued

GENE AND PROTEIN SEQUENCES OF PANEL BIOMARKERS

NP_000098.1 GI: 4557515
DNA damage-binding protein 2 [Homo sapiens]

```
  1 mapkkrpetq ktseivlrpr nkrsrsplel epeakklcak gsgpsrrcds dclwvglagp   61
    qilppersiv rtlhqhklgr aswpsvqqgl qqsflhtlds yrilqkaapf drratslawh  121
    pthpstvavg skggdimlwn fgikdkptfi kgigaggsit glkfnplntn qfyassmegt  181
    trlqdfkgni lrvfassdti niwfcsldvs assrmvvtgd nvgnvillnm dgkelwnlrm  241
    hkkkvthval npccdwflat asvdqtvkiw dlrqvrgkas flyslphrhp vnaacfspdg  301
    arllttdqks eirvysasqw dcplgliphp hrhfqhltpi kaawhprynl ivvgrypdpn  361
    fksctpyelr tidvfdgnsg kmmcqlydpe ssgisslnef npmgdtlasa mgyhiliwsq  421
    eeartrk
```

CHK2-thr68
GeneID: 11200
AB040105.1 GI: 11034731
Homo sapiens mRNA for CHK2, partial cds.

```
   1 atgtctcggg agtcggatgt tgaggctcag cagtctcatg gcagcagtgc ctgttcacag
  61 ccccatggca gcgttaccca gtcccaaggc tcctcctcac agtcccaggg catatccagc  121
     tcctctacca gcacgatgcc aaactccagc cagtcctctc actccagctc tgggacactg  181
     agctccttag agacagtgtc cactcaggaa ctctattcta ttcctgagga ccaagaacct  241
     gaggaccaag aacctgagga gcctacccct gcccctgggg ctcgattatg ggcccttcag  301
     gatggatttg ccaatcttga atgtgtgaat gacaactact ggtttgggag ggacaaaagc  361
     tgtgaatatt gctttgatga accactgctg aaaagaacag ataaataccg aacatacagc  421
     aagaaacact ttcggatttt cagggaagtg ggtcctaaaa actcttacat tgcatacata  481
     gaagatcaca gtggcaatgg aaccttttgta aatacagagc ttgtagggaa aggaaaacgc  541
     cgtcctttga ataacaattc tgaaattgca ctgtcactaa gcagaaataa agtttttgtc  601
     ttttttgatc tgactgtaga tgatcagtca gtttatccta aggcattaag agatgaatac  661
     atcatgtcaa aaactcttgg aagtggtgcc tgtggagagg taaagctggc tttcgagagg  721
     aaaacatgta agaaagtagc cataaagatc atcagcaaaa ggaagtttgc tattggttca  781
     gcaagagagg cagacccagc tctcaatgtt gaaacagaaa tagaaattt gaaaagcta  841
     aatcatcctt gcatcatcaa gattaaaaac ttttttgatg cagaagatta ttatattgtt  901
     ttggaattga tggaaggggg agagctgttt gacaaagtgg tggggaataa acgcctgaaa  961
     gaagctacct gcaagctcta ttttaccag atgctcttgg ctgtgcagat tactgatttt 1021
     gggcactcca agattttggg agagacctct ctcatgagaa ccttatgtgg aacccccacc 1081
     tacttggcgc ctgaagttct tgtttctgtt gggactgctg ggtataaccg tgctgtggac 1141
     tgctggagtt taggagttat tcttttttatc tgccttagtg ggtatccacc tttctctgag 1201
     cataggactc aagtgtcact gaaggatcag atcaccagtg gaaaatacaa cttcattcct 1261
     gaagtctggg cagaagtctc agagaaagct ctggaccttg tcaagaagtt gttggtagtg 1321
     gatccaaagg cacgttttac gacagaagaa gccttaagac accgtggct tcaggatgaa 1381
     gacatgaaga gaaagtttca agatcttctg tctgaggaaa atgaatccac agctctaccc 1441
     caggttctag cccagccttc tactagtcga aagcggcccc gtgaagggga agccgagggt 1501
     gccgagacca caaagcgccc agctgtgtgt gctgctgtgt tg
```

BAB17231.1 GI: 11034732
CHK2, partial [Homo sapiens]

```
  1 msresdveaq qshgssacsq phgsvtqsqg sssqsqgiss sststmpnss qsshsssgtl   61
    ssletvstqe lysipedqep edqepeeptp apwarlwalq dgfanlecvn dnywfgrdks  121
    ceycfdepll krtdkyrtys kkhfrifrev gpknsyiayi edhsgngtfv ntelvgkgkr  181
    rplnnnseia lslsrnkvfv ffdltvddqs vypkalrdey imsktlgsga cgevklafer  241
    ktckkvaiki iskrkfaigs areadpalnv eteieilkkl nhpciikikn ffdaedyyiv  301
    lelmeggelf dkvvgnkrlk eatcklyfyq mllavqitdf ghskilgets lmrtlcgtpt  361
    ylapevlvsv gtagynravd cwslgvilfi clsgyppfse hrtqvslkdq itsgkynfip  421
    evwaevseka ldlvkkllvv dpkarfttee alrhpwlqde dmkrkfqdll seenestalp  481
    qvlaqpstsr krpregeaeg aettkrpavc aavl //
```

CCNG1
AF174135.1 GI: 5726656
Homo sapiens protein kinase CHK2 (CHK2) mRNA, complete cds.

```
   1 atgtctcggg agtcggatgt tgaggctcag cagtctcatg gcagcagtgc ctgttcacag   61
  61 ccccatggca gcgttaccca gtcccaaggc tcctcctcac agtcccaggg catatccagc  121
     tcctctacca gcacgatgcc aaactccagc cagtcctctc actccagctc tgggacactg  181
     agctccttag agacagtgtc cactcaggaa ctctattcta ttcctgagga ccaagaacct  241
     gaggaccaag agcctgagga gcctacccct gcccctgggg ctcgattatg ggcccttcag  301
     gatggatttg ccaatcttga atgtgtgaat gacaactact ggtttgggag ggacaaaagc  361
     tgtgaatatt gctttgatga accactgctg aaaagaacag ataaataccg aacatacagc  421
     aagaaacact ttcggatttt cagggaagtg ggtcctaaaa actcttacat tgcatacata  481
     gaagatcaca gtggcaatgg aaccttttgta aatacagagc ttgtagggaa aggaaaacgc  541
     cgtcctttga ataacaattc tgaaattgca ctgtcactaa gcagaaataa agtttttgtc  601
     ttttttgatc tgactgtaga tgatcagtca gtttatccta aggcattaag agatgaatac  661
     atcatgtcaa aaactcttgg aagtggtgcc tgtggagagg taaagctggc tttcgagagg  721
     aaaacatgta agaaagtagc cataaagatc atcagcaaaa ggaagtttgc tattggttca  781
     gcaagagagg cagacccagc tctcaatgtt gaaacagaaa tagaaatttt gaaaagcta  841
     aatcatcctt gcatcatcaa gattaaaaac ttttttgatg cagaagatta ttatattgtt  901
     ttggaattga tggaaggggg agagctgttt gacaaagtgg tggggaataa acgcctgaaa  961
     gaagctacct gcaagctcta ttttaccag atgctcttgg ctgtgcagta ccttcatgaa 1021
```

TABLE 4-continued

GENE AND PROTEIN SEQUENCES OF PANEL BIOMARKERS

```
aacggtatta tacaccgtga cttaaagcca gagaatgttt tactgtcatc tcaagaagag   1081
gactgtctta taaagattac tgattttggg cactccaaga ttttgggaga gacctctctc   1141
atgagaacct tatgtggaac ccccacctac ttggcgcctg aagttcttgt ttctgttggg   1201
actgctgggt ataaccgtgc tgtggactgc tggagtttag gagttattct tttatctgc    1261
cttagtgggt atccacctt ctctgagcat aggactcaag tgtcactgaa ggatcagatc    1321
accagtggaa aatacaactt cattcctgaa gtctgggcag aagtctcaga gaaagctctg   1381
gaccttgtca gaaagttgtt ggtagtggat ccaaaggcac gttttacgac agaagaagcc   1441
ttaagacacc cgtggcttca ggatgaagac atgaagagaa agtttcaaga tcttctgtct   1501
gaggaaaatg aatccacagc tctacccag gttctagccc agccttctac tagtcgaaag    1561
cggccccgtg aaggggaagc cgagggtgcc gagaccacaa agcgcccagc tgtgtgtgct   1621
gctgtgttgt ga
```

AAD48504.1 GI: 5726657
protein kinase CHK2 [Homo sapiens].

```
1 msresdveaq qshgssacsq phgsvtqsqg sssqsqgiss ssttstmpnss qsshsssgtl    61
ssletvstqe lysipedqep edqepeeptp apwarlwalq dgfanlecvn dnywfgrdks    121
ceycfdepll krtdkyrtys kkhfrifrev gpknsylayi edhsgngtfv ntelvgkgkr    181
rplnnnseia lslsrnkvfv ffdltvddqs vypkalrdey imsktlgsga cgevklafer   241
ktckkvaiki iskrkfaigs areadpalnv eteleilkkl nhpciikikn ffdaedyyiv    301
lelmeggelf dkvvgnkrlk eatcklyfyq mllavqylhe ngiihrdlkp envllssqee   361
dclikitdfg hskilgetsl mrtlcgtpty lapevlvsvg tagynravdc wslgvilfic   421
lsgyppfseh rtqvslkdqi tsgkynfipe vwaevsekal dlvkkllvvd pkarfttteea  481
lrhpwlqded mkrkfqdlls eenestalpq vlaqpstsrk rpregeaega ettkrpavca   541
avl
```

NM_001257387.1 GI: 383792177
Homo sapiens checkpoint kinase 2 (CHEK2), transcript variant 4,
mRNA

```
1 gcaggtttag cgccactctg ctggctgagg ctgcggagag tgtgcggctc caggtgggct
61 cacgcggtcg tgatgtctcg ggagtcggat gttgaggctc agcagtctca tggcagcagt   121
gcctgttcac agccccatgg cagcgttacc cagtcccaag gctcctcctc acagtcccag    181
ggcatatcca gctcctctac cagcacgatg ccaaactcca gccagtcctc tcactccagc   241
tctgggacac tgagctcctt agagacagtg tccactcagg aactctattc tattcctgag   301
gaccaagaac ctgaggacca agaacctgag gagcctaccc ctgccccctg ggctcgatta   361
tgggccccttc aggatggatt tgccaatctt gaatgtgtga atgacaacta ctggtttggg   421
agggacaaaa gctgtgaata ttgctttgat gaaccactgc tgaaaagaac agataaatac   481
cgaacataca gcaagaaaca ctttcggatt tcagggaag tgggtcctaa aaactcttac    541
attgcataca tagaagatca cagtggcaat ggaacctttg taaatacaga gcttgtaggg    601
aaaggaaaac gccgtccttt gaataacaat tctgaaattg cactgtcact aagcagaaat   661
aaagagaaaa tacttaaaat ctactctctc agctgatttt caaaaatacg gcggggcgcg    721
gtggctcacg tctttaatcc cagcactttg ggaggccgag gctggcagt caccctgagtt   781
ttttgtctttt tgatctgac tgtagatgat cagtcagttt atcctaaggc attaagagat   841
gaatacatca tgtcaaaaac tcttggaagt ggtgcctgtg gagaggtaaa gctggctttc   901
gagaggaaaa catgtaagaa agtagccata agatcatca gcaaaggaa gtttgctatt     961
ggttcagcaa gagaggcaga cccagctctc aatgttgaaa cagaaataga aattttgaaa   1021
aagctaaatc atccttgcat catcaagatt aaaaacttttt ttgatgcaga agattattat   1081
attgtttttgg aattgatgga aggggggagg ctgtttgaca aagtggtggg gaataaacgc   1141
ctgaaagaag ctacctgcaa gctctatttt taccagatgc tcttggctgt gcagtacctt   1201
catgaaaacg gtattataca ccgtgactta aagccagaga atgtttact gtcatctcaa    1261
gaagaggact gtcttataaa gattactgat tttgggcact ccaagatttt gggagagacc    1321
tctctcatga gaaccttatg tggaaccccc acctacttgg cgcctgaagt tcttgttct    1381
gttgggactg ctgggtataa ccgtgctgtg gactgctgga gtttaggagt tattcttttt   1441
atctgcctta gtgggtatcc acctttctct gagcatagga ctcaagtgtc actgaaggat   1501
cagatcacca gtggaaaata caacttcatt cctgaagtct gggcagaagt ctcagagaaa   1561
gctctggacc ttgtcaagaa gttgttggta gtggatccaa aggcacgttt tacgacagaa   1621
gaagccttaa gacacccgtg gcttcaggat gaagacatga agagaaagtt tcaagatctt   1681
ctgtctgagg aaaatgaatc cacagctcta ccccaggttc tagcccagcc ttctactagt   1741
cgaaagcggc cccgtgaagg ggaagccgag ggtgccgaga ccacaaagcg cccagctgtg   1801
tgtgctgctg tgttgtgaac tccgtggttt gaacacgaaa gaaatgtacc ttctttcact   1861
ctgtcatctt tcttttcttt gagtctgttt ttttatagtt tgtatttttaa ttatgggaat   1921
aattgctttt tcacagtcac tgatgtacaa ttaaaacct gatggaacct ggaaaa
```

NP_001244316.1 GI: 383792178
serine/threonine-protein kinase Chk2 isoform d [Homo sapiens].

```
1 msktlgsgac gevklaferk tckkvaikii skrkfaigsa readpalnve teieilkkln    61
hpciikiknf fdaedyyivl elmeggelfd kvvgnkrlke atcklyfyqm llavqylhen   121
giihrdlkpe nvllssqeed clikitdfgh skilgetslm rtlcgtptyl apevlvsvgt   181
agynravdcw slgvilficl sgyppfsehr tqvslkdqit sgkynfipev waevsekald   241
lvkkllvvdp karfttteeal rhpwlqdedm krkfqdllse enestalpqv laqpstsrkr  301
pregeaegae ttkrpavcaa vl
```

TABLE 4-continued

GENE AND PROTEIN SEQUENCES OF PANEL BIOMARKERS

BAX
GeneID: 581
NM_138761.3 GI: 163659848
*Homo sapiens* BCL2-associated X protein (BAX), transcript variant
alpha, mRNA

```
  1 tcacgtgacc cgggcgcgct gcggccgccc gcgcggaccc ggcgagaggc ggcggcggga   61
 61 gcggcggtga tggacgggtc cggggagcag cccagaggcg gggggcccac cagctctgag  121
121 cagatcatga agacaggggc cttttgctt cagggtttca tccaggatcg agcagggcga  181
181 atggggggg aggcacccga gctggccctg acccgtgc ctcaggatgc gtccaccaag  241
241 aagctgagcg agtgtctcaa gcgcatcggg gacgaactgg acagtaacat ggagctgcag  301
301 aggatgattg ccgccgtgga cacagactcc ccccgagagg tcttttttccg agtggcagct  361
361 gacatgtttt ctgacggcaa cttcaactgg ggccgggttg tcgccctttt ctactttgcc  421
421 agcaaactgg tgctcaaggc cctgtgcacc aaggtgccgg aactgatcag aaccatcatg  481
481 ggctggacat tggacttcct ccgggagcgg ctgttgggct ggatccaaga ccagggtggt  541
541 tgggacggcc tcctctccta ctttgggacg cccacgtggc agaccgtgac catctttgtg  601
601 gcgggagtgc tcaccgcctc actcaccatc tggaagaaga tgggctgagg cccccagctg  661
661 ccttggactg tgttttttcct ccataaatta tggcattttt ctgggagggg tggggattgg  721
721 gggacgtggg catttttctt acttttgtaa ttattgggag gtgtgggggaa gagtggtctt  781
781 gagggggtaa taaacctcct tcgggacaca aaaaaaaaaa aaaaaaaaaa aaaaaaaaaa  841
841 aaaaaaaaaa aaaaaaaaaa aaaaaaaaaa aaaaaaaaaa aaaaaaa
```

NP_620116.1 GI: 20631958
apoptosis regulator BAX isoform alpha [*Homo sapiens*]

```
  1 mdgseqprg ggptsseqim ktgalllqgf iqdragrmgg eapelaldpv pqdastkkls   61
 61 eclkrigdel dsnmelqrmi aavdtdspre vffrvaadmf sdgnfnwgrv valfyfaskl  121
121 vlkalctkvp elirtimgwt ldflrerllg wiqdqggwdg llsyfgtptw qtvtifvagv  181
181 ltasltiwkk mg //
```

NM_004324.3 GI: 34335114
*Homo sapiens* BCL2-associated X protein (BAX), transcript variant
beta, mRNA

```
  1 tcacgtgacc cgggcgcgct gcggccgccc gcgcggaccc ggcgagaggc ggcggcggga   61
 61 gcggcggtga tggacgggtc cggggagcag cccagaggcg gggggcccac cagctctgag  121
121 cagatcatga agacaggggc cttttgctt cagggtttca tccaggatcg agcagggcga  181
181 atggggggg aggcacccga gctggccctg acccgtgc ctcaggatgc gtccaccaag  241
241 aagctgagcg agtgtctcaa gcgcatcggg gacgaactgg acagtaacat ggagctgcag  301
301 aggatgattg ccgccgtgga cacagactcc ccccgagagg tcttttttccg agtggcagct  361
361 gacatgtttt ctgacggcaa cttcaactgg ggccgggttg tcgccctttt ctactttgcc  421
421 agcaaactgg tgctcaaggc cctgtgcacc aaggtgccgg aactgatcag aaccatcatg  481
481 ggctggacat tggacttcct ccgggagcgg ctgttgggct ggatccaaga ccagggtggt  541
541 tgggtgagac tcctcaagcc tcctcacccc caccaccgcg ccctcaccac cgcccctgcc  601
601 ccaccgtccc tgccccccgc cactcctctg ggaccctggg ccttctggag caggtcacag  661
661 tggtgccctc tccccatctt cagatcatca gatgtggtct ataatgcgtt ttccttacgt  721
721 gtctgatcaa tccccgattc atctaccctg ctgacctccc agtgacccct gacctcactg  781
781 tgaccttgac ttgattagtg ccttctgccc tccctggagc ctccactgcc tctggaattg  841
841 ctcaagttca ttgatgaccc tctgacccta gctctttcct tttttttttt t
```

NP_004315.1 GI: 4757838
apoptosis regulator BAX isoform beta [*Homo sapiens*].

```
  1 mdgseqprg ggptsseqim ktgalllqgf iqdragrmgg eapelaldpv pqdastkkls   61
 61 eclkrigdel dsnmelqrmi aavdtdspre vffrvaadmf sdgnfnwgrv valfyfaskl  121
121 vlkalctkvp elirtimgwt ldflrerllg wiqdqggwvr llkpphphhr alttapapps  181
181 lppatplgpw afwsrsqwcp lpifrssdvv ynafslrv
```

NM_138763.3 GI: 163659849
*Homo sapiens* BCL2-associated X protein (BAX), transcript variant
delta, mRNA

```
  1 tcacgtgacc cgggcgcgct gcggccgccc gcgcggaccc ggcgagaggc ggcggcggga   61
 61 gcggcggtga tggacgggtc cggggagcag cccagaggcg gggggcccac cagctctgag  121
121 cagatcatga agacaggggc cttttgctt cagggatga ttgccgccgt ggacacagac  181
181 tcccccgag aggtcttttt ccgagtggca gctgacatgt ttctgacgg caacttcaac  241
241 tggggccggg ttgtcgccct tttctacttt gccagcaaac tggtgctcaa ggccctgtgc  301
301 accaaggtgc cggaactgat cagaaccatc atgggctgga cattggactt cctccgggag  361
361 cggctgttgg gctggatcca agaccagggt ggttgggacg gcctcctctc ctactttggg  421
421 acgcccacgt ggcagaccgt gaccatcttt gtggcggag tgctcaccgc ctcactcacc  481
481 atctgaaga agatgggctg aggcccccag ctgccttgtttt cctccataaa  541
541 ttatggcatt tttctgggag gggtggggat tggggacgt gggcattttt cttactttttg  601
601 taattattgg ggggtgtggg gaagagtggt cttgaggggg taataaacct ccttcgggac  661
661 acaaaaaaaa aaaaaaaaaa aaaaaaaaaa aaaaaaaaaa aaaaaaaaaa aaaaaaaaaa  721
721 aaaaaaaaaa aaaaaaaaaa a
```

TABLE 4-continued

GENE AND PROTEIN SEQUENCES OF PANEL BIOMARKERS

NP_620118.1 GI: 20631964
apoptosis regulator BAX isoform delta [Homo sapiens]

```
  1 mdgsgeqprg ggptsseqim ktgalllqgm iaavdtdspr evffrvaadm fsdgnfnwgr    61
    vvalfyfask lvlkalctkv pelirtimgw tldflrerll gwiqdqggwd gllsyfgtpt   121
    wqtvtifvag vltasltiwk kmg
```

AJ417988.1 GI: 17221408
Homo sapiens mRNA for bax isoform psi (BAX gene)

```
  1 cccagaggcg gggggcccac cagctctgag cagatcatga agacagggc ccttttgctt    61
    cagggtttca tccaggatcg agcagggcga atggggggggg aggcaccga gctggccctg   121
    gacccggtgc ctcaggatgc gtccaccaag aagctgagcg agtgtctcaa gcgcatcggg   181
    gacgaactgg acagtaacat ggagctgcag aggatgattg ccgccgtgga cacagactcc   241
    ccccgagagg tcttttttcg agtggcagct gacatgtttt ctgacggcaa cttcaactgg   301
    ggccgggttg tcgcccttt ctactttgcc agcaaactgg tgctcaaggc cctgtgcacc    361
    aaggtgccgg aactgatcag aaccatcatg ggctggacat tggacttcct ccgggagcgg   421
    ctgttgggct ggatccaaga ccagggtggt tgggacggcc tcctctccta ctttgggacg   481
    cccacgtggc agaccgtgac catctttgtg gcgggagtgc tcaccgcctc actcaccatc   541
    tggaagaaga tgggctga
```

CAD10744.1 GI: 17221409
bax isoform psi [Homo sapiens]

```
  1 mktgalllqg fiqdragrmg geapelaldp vpqdastkkl seclkrigde ldsnmelqrm    61
    iaavdtdspr evffrvaadm fsdgnfnwgr vvalfyfask lvlkalctkv pelirtimgw   121
    tldflrerll gwiqdqggwd gllsyfgtpt wqtvtifvag vltasltiwk kmg
```

LIG1
GeneID: 3978
NM_000234 XM_005258933
NM_000234.1 GI: 4557718
Homo sapiens ligase I, DNA, ATP-dependent (LIG1), mRNA

```
  1 cagaggcgcg cctggcggat ctgagtgtgt tgcccgggca gcggcgcgcg ggaccaacgc    61
    aaggagcagc tgacagacga agaaaagtgc tggacagaga gggagaattc tgacgccaac   121
    atgcagcgaa gtatcatgtc attttttccac cccaagaaag agggtaaagc aaagaagcct   181
    gagaaggagg catccaatag cagcagagag acggagcccc ctccaaaggc ggcactgaag   241
    gagtggaatg gagtggtgtc cgagagtgac tctccggtga agaggccagg gaggaaggcg   301
    gcccgggtcc tgggcagcga aggggaagag gaggatgaag cccttagcc tgctaaaggc    361
    cagaagcctg ccctggactg ctcacaggtc tccccgcccc gtcctgccac atctcctgag   421
    aacaatgctt ccctctctga cacctctccc atggacagtt cccatcagg gattccgaag    481
    cgtcgcacag ctcggaagca gctcccgaaa cggaccattc aggaagtcct ggaagagcag   541
    agtgaggacg aggacagaga agccaagagg aagaaggagg aggaagaaga cgaaccccg    601
    aaagaaagcc tcacagaggc tgaagtggca acagagaagg aaggagaaga cggggaccag   661
    cccaccacgc ctcccaagcc cctaaagacc tccaaagcag agaccccgac ggaaagcgtt   721
    tcagagcctg aggtggccac gaagcaggaa ctgcaggagg aggaagagca gaccaagcct   781
    ccccgagagg ctcccaagac gctcagcagc ttcttccac ccggaaagcc agcagtcaaa    841
    aaagaagtga aggaagagga gccaggggct ccaggaaagg agggagctgc tgagggaccc   901
    ctggatccat ctggttacaa tcctgccaag aacaactatc atcccgtgga agatgcctgc   961
    tggaaaccgg gccagaaggt tccttacctg gctgtggccc ggacgtttga gaagatcgag  1021
    gaggtgtctg ctcggctccg gatggtggag acgctgagca acttgctgcg ctccgtggtg  1081
    gccctgtcgc ctcagacct cctccctgtc ctctacctca gcctcaacca cctggccca   1141
    ccccagcagg gcctggagct tggcgtgggt gatggtgtcc ttctcaaggc agtggcccag  1201
    gccacaggtc ggcagctgga gtccgtccgg gctgaggcag ccgagaaagg cgacgtgggg  1261
    ctggtggccg agaacagccg cagcacccag aggctcatgc tgccaccacc tccgctcact  1321
    gcctccgggg tcttcagcaa gttccgcgac atcgccagc tcactggcag tgcttccaca  1381
    gccaagaaga tagacatcat caaaggcctc tttgtggcct gccgccactc agaagcccgg  1441
    ttcatcgcta ggtccctgag cggacggctg cgccttgggc tggcagagca gtcggtgctg  1501
    gctgccctct cccaggcagt gagcctcacg cccccgggcc aagaattccc accagccatg  1561
    gtggatgctg ggaagggcaa gacagcagag gccagaaaga cgtggctgga gggagcaaggc  1621
    atgatcctga agcagacgtt ctgcgaggtt cccgacctgg accgaattat ccccgtgctg  1681
    ctggagcacg gcctggaacg tctcccggag cactgcaagc tgagcccagg gattcccctg  1741
    aaaccaatgt tggcccatcc caccccggggc atcagcgagg tcctgaaacg ctttgaggag  1801
    gcagctttca cctgcgaata caaatatgac gggcagaggg cacagatcca cgccctggaa  1861
    ggcgggggagg tgaagatctt cagcaggaat caggaagaca acactgggaa gtacccggac  1921
    atcatcagcc gcatccccaa gattaaactc ccatcggtca catccttcat cctggacacc  1981
    gaagccgtgc cttgggaccg gaaaagaag cagatccagc cattccaagt gctcaccacc   2041
    cgcaaacgca aggaggtgga tgcgtctgag atccaggtgc aggtgtgttt gtacgccttc   2101
    gacctcatct acctcaatgg agagtccctg gtacgtgagc cccttccccg cgccgccgcag  2161
    ctgctccggg agaactttgt ggagacagag gcgagtttg tcttcgccac ctccctggac  2221
    accaaggaca tcgagcagat cgccgagttc ctggagcagt cagtgaaaga ctcctgcgag  2281
    gggctgatgg tgaagaccct ggatgttgat gccacctacg agatcgccaa gagatcgacc  2341
    aactggctca agctgaagaa ggactacctt gatggcgtgg gtgacaccct ggacctggtg  2401
    gtgatcggcg cctacctggg ccggggggaag cgggccggcc ggtacggggg cttcctgctg  2461
    gcctcctacg acgaggacag tgaggagctg caggccatat gcaagcttgg aactggcttc  2521
    agtgatgagg agctggagga gcatcaccag agcctcaagg cgctggtgct gcccagccca  2581
    cgcccttacg tgcggataga tggcgctgtg attccccgacc actggctgga ccccagcgct  2641
```

TABLE 4-continued

GENE AND PROTEIN SEQUENCES OF PANEL BIOMARKERS

```
gtgtgggagg tgaagtgcgc tgacctctcc ctctctccca tctaccctgc tgcgcgggc   2701
ctggtggata gtgacaaggg catctccctt cgcttccctc ggtttattcg agtccgtgaa   2761
gacaagcagc cggagcaggc caccaccagt gctcaggtgg cctgtttgta ccggaagcaa   2821
agtcagattc agaaccaaca aggcgaggac tcaggctctg accctgaaga tacctactaa   2881
gccctcgccc tcctagggcc tgggtacagg gcatgagttg gacggacccc agggttatta   2941
ttgcctttgc ttttttagcaa atctgctgtg gcaggctgtg gattttgaga gtcaggggag   3001
gggtgtgtgt gtgagggggt ggcttactcc ggagtctggg attcatcccg tcatttcttt   3061
caataaataa ttattggata gct
```

NP_000225 XP_005258990
NP_000225.1 GI: 4557719
DNA ligase 1 [*Homo sapiens*]

```
1 mqrsimsffh pkkegkakkp ekeasnssre tepppkaalk ewngvvsesd spvkrpgrka    61
  arvlgsegee edealspakg qkpaldcsqv spprpatspe nnaslsdtsp mdsspsgipk   121
  rrtarkqlpk rtiqevleeq sededreakr kkeeeeeetp keslteaeva tekegedgdq   181
  pttppkplkt skaetptesv sepevatkqe lqeeeeqtkp prrapktlss fftprkpavk   241
  kevkeeepga pgkegaaegp ldpsgynpak nnyhpvedac wkpgqkvpyl avartfekie   301
  evsarlrmve tlsnllrsvv alsppdllpv lylslnhlgp pqqglelgvg dgvllkavaq   361
  atgrqlesvr aeaaekgdvg lvaensrstq rlmlppppl asgvfskfrd iarltgsast    421
  akkidiikgl fvacrhsear fiarslsgrl rlglaeqsvl aalsqavslt ppgqefppam   481
  vdagkgktae arktwleeqg milkqtfcev pdldriipvl lehglerlpe hcklspgipl   541
  kpmlahptrg isevlkrfee aaftceykyd gqraqihale ggevkifsrn qedntgkypd   601
  iisripkikl psvtsfildt eavawdrekk qiqpfqvltt rkrkevdase iqvqvclyaf   661
  dliylngesl vreplsrrrq llrenfvete gefvfatsld tkdieqiaef leqsvkdsce   721
  glmvktldvd atyeiakrsh nwlklkkdyl dgvgdtldlv vigaylgrgk ragryggfll   781
  asydedseel qaicklgtgf sdeeleehhq slkalvlpsp rpyvridgav ipdhwldpsa   841
  vwevkcadls lspiypaarg lvdsdkgisl rfprfirvre dkqpeqatts aqvaclyrkq   901
  sqiqnqqged sgsdpedty
```

RAD51
GeneID: 5888
NM_001164269.1 GI: 256017142
*Homo sapiens* RAD51 recombinase (RAD51), transcript variant 4, mRNA.

```
  1 gaaagccgct ggcggaccgc gcgcagcggc cagagaccga gccctaagga gagtgcggcg
 61 cttcccgagg cgtgcagctg ggaactgcaa ctcatctggg ttgtgcgcag aaggctgggg   121
    caagcgagta gagaagtgga gctaatggca atgcagatgc agcttgaagc aaatgcagat   181
    acttcagtgg aagaagaaag ctttggccca aacccatt cacggttaga gcagtgtggc     241
    ataaatgcca acgatgtgaa gaaattgaa gaagctggat tccatactgt ggaggctgtt   301
    gcctatgcgc caaagaagga gctaataaat attaaggaga ttagtgaagc aaagctgat   361
    aaaattctga cggagtctcg ctctgttgcc aggctggagt gcaatagcgt gatcttggtc   421
    tactgcaccc tccgcctctc aggttcaagt gattctcctg cctcagcctc ccgagtagtt   481
    gggactacag gtggaattga gactggatcc atcacagaaa tgtttggaga attccgaact   541
    gggaagaccc agatctgtca tacgctagct gtcacctgcc agcttccat tgaccggggt    601
    ggaggtgaag gaaaggccat gtacattgac actgagggta cctttaggcc agaacggctg   661
    ctggcagtgg ctgagaggta tggtctctct ggcagtgatg tcctggataa tgtagcatat   721
    gctcgagcgt tcaacacaga ccaccagacc cagctccttt atcaagcatc agccatgatg   781
    gtagaatcta ggtatgcact gcttattgta gacagtgcca ccgccctta cagaacagac   841
    tactcgggtc gaggtgagct ttcagccagg cagatgcact tggccaggtt tctgcggatg   901
    cttctgcgac tcgctgatga gtttggtgta gcagtggtaa tcactaatca ggtggtagct   961
    caagtggatg gagcagcgat gtttgctgct gatcccaaaa aacctattgg aggaaatatc   1021
    atcgcccatg catcaacaac cagattgtat ctgaggaaag gaagagggga aaccagaatc   1081
    tgcaaaatct acgactctcc ctgtcttcct gaagctgaag ctatgttcgc cattaatgca   1141
    gatggagtgg gagatgccaa agactgaatc attgggtttt tcctctgtta aaaaccttaa   1201
    gtgctgcagc ctaatgagag tgcactgctc cctggggttc tctacaggcc tcttcctgtt   1261
    gtgactgcca ggataaagct tccggggaaa cagctattat atcagctttt ctgatggtaa   1321
    aaacaggaga caggtcagta gtcacaaact gatctaaaat gtttattcct tctgtagtgt   1381
    attaatctct gtgtgttttc tttggttttg gaggaggggt atgaagtatc tttgacatgg   1441
    tgccttagga atgacttggg tttaacaagc tgtctactgg acaatcttat gtttccaaga   1501
    gaactaaagc tggagagacc tgaccctct ctcacttcta aattaatggt aaaataaat     1561
    gcctcagcta tgtagcaaag ggaatgggtc tgcacagatt cttttttct gtcagtaaaa   1621
    ctctcaagca ggtttttaag ttgtctgtct gaatgatctt gtgtaaggtt ttggttatgg   1681
    agtcttgtgc caaacctact aggccattag cccttcacca tctacctgct tggtctttca   1741
    ttgctaagac taactcaaga taatcctaga gtcttaaagc atttcaggcc agtgtggtgt   1801
    cttgcgcctg tactcccagc actttggag gccgaggcag gtggatcgct tgagcccagg   1861
    agtttttaagt ccagcttggc caaggtggtg aaatcccatc tctacaaaaa atgcagaact   1921
    taatctggac acactgttac acgtgcctgt agtcccagct actcgatagc tgaggtgggg   1981
    agaatcactt aagcctggaa ggtggaagtt gcagtgagtc gagattgcac tgctgcattc   2041
    cagccagggt gacagagtga gaccatgtct caaacaagaa acatttcaga gggtaagtaa   2101
    acagatttga ttgtgaggct tctaataaag tagttattag tagtgaa
```

NP_001157741.1 GI: 256017143
DNA repair protein RAD51 homolog 1 isoform 2 [*Homo sapiens*]

```
1 mamqmqlean adtsveeesf gpqpisrleq cginandvkk leeagfhtve avayapkkel    61
  inikgiseak adkiltesrs varlecnsvi lvyctlrlsg ssdspasasr vvgttggiet   121
  gsitemfgef rtgktqicht lavtcqlpid rgggegkamy idtegtfrpe rllavaeryg   181
```

TABLE 4-continued

GENE AND PROTEIN SEQUENCES OF PANEL BIOMARKERS

```
lsgsdvldnv ayarafntdh qtqllyqasa mmvesryall ivdsatalyr tdysgrgels    241
arqmhlarfl rmllrladef gvavvitnqv vaqvdgaamf aadpkkpigg niiahasttr    301
lylrkgrget rickiydspc lpeaeamfai nadgvgdakd
```

D14134.1 GI: 285976
*Homo sapiens* mRNA for RAD51, complete cds

```
1   ccgcgcgcag cggccagaga ccgagcccta aggagagtgc ggcgcttccc gaggcgtgca    61
    gctgggaact gcaactcatc tgggttgtgc gcagaaggct ggggcaagcg agtagagaag   121
    tggagcgtaa gccaggggcg ttgggggccg tgcgggtcgg gcgcgtgcca cgcccgcggg   181
    gtgaagtcgg agcgcggggc ctgctggaga gaggagcgct gcggaccgag taatggcaat   241
    gcagatgcag cttgaagcaa atgcagatac ttcagtggaa gagaaagct ttggcccaca    301
    acccatttca cggttagagc agtgtggcat aaatgccaac gatgtgaaga aattggaaga   361
    agctggattc catactgtgg aggctgttgc ctatgcgcca agaaggagc taataaatat    421
    taagggaatt agtgaagcca aagctgataa aattctggct gaggcagcta aattagttcc   481
    aatgggtttc accactgcaa ctgaattcca ccaaggcgg tcagagatca tacagattac    541
    tactggctcc aaagagcttg acaaactact tcaaggtgga attgagactg gatctatcac   601
    agaaatgttt ggagaattcc gaactgggaa gacccagatc tgtcatacgc tagctgtcac   661
    ctgccagctt cccattgacc ggggtggagg tgaaggaaag gccatgtaca ttgacactga   721
    gggtacctt aggccagaac ggctgctggc agtggctgag aggtatggtc tctctggcag    781
    tgatgtcctg gataatgtag catatgctcg agcgttcaac acagaccacc agacccagct   841
    cctttatcaa gcatcagcca tgatggtaga atctaggtat gcactgctta ttgtagacag   901
    tgccaccgcc ctttacagaa cagactactc gggtcgaggt gagctttcag ccaggcagat   961
    gcacttggcc aggtttctgc ggatgcttct gcgactcgct gatgagtttg gtgtagcagt  1021
    ggtaatcact aatcaggtgg tagctcaagt ggatggagca gcgatgtttg ctgctgatcc  1081
    caaaaaacct attggaggaa atatcatcgc ccatgcatca acaacccagat tgtatctgag  1141
    gaaaggaaga ggggaaacca gaatctgcaa aatctacgac tctccctgtc ttcctgaagc  1201
    tgaagctatg ttcgccatta atgcagatgg agtgggagat gccaaagact gaatcattgg  1261
    gttttcctc tgttaaaaac cttaagtgct gcagcctaat gagagtgcac tgctccctgg   1321
    ggttctctac aggcctcttc ctgttgtgac tgccaggata aagcttccgg gaaaacagct   1381
    attatatcag cttttctgat ggtataaaca ggagacaggt cagtagtcac aaactgatct   1441
    aaaatgttta ttccttctgt agtgtattaa tctctgtgtg tttctttgg ttttggagga    1501
    ggggtatgaa gtatctttga catggtgcct taggaatgac ttgggtttaa caagctgtct   1561
    actggacaat cttatgtttc caagagaact aaagctggag agacctgacc cttctctcac   1621
    ttctaaatta atggtaaaat aaaatgcctc agctatgtag caaagggaat gggtctgcac   1681
    agattctttt tttctgtcag taaaactctc aagcaggttt ttaagttgtc tgtctgaatg   1741
    atcttgtgta agggtttggt tatggagtct tgtgccaaac ctactaggcc attagcccctt  1801
    caccatctac ctgcttggtc tttcattgct aagactaact caagataatc ctagagtctt   1861
    aaagcatttc aggccagtgt ggtgtcttgc gcctgtactc ccagcacttt gggaggccga   1921
    ggcaggtgga tcgcttgagc caggagtttt aagtccaagct tggccaagat ggtgaaatcc  1981
    catctctaca aaaaatgcag aacttaatct ggacacactg ttacacgtgc ctgtagtccc   2041
    agctactcta tagcctgagg tgggagaatc acttaagcct ggaaggtgga agttgcagtg   2101
    agtcgagatt gcactgctgc attccagcca gggtgacaga gtgagaccat gtttcaaaca   2161
    agaaacattt cagagggcaa gtaaacagat ttgattgtga ggcttctaat aaagtagtta   2221
    ttagtagtg
```

BAA03189.1 GI: 285977
RAD51 [*Homo sapiens*]

```
1   mamqmqlean adtsveeesf gpqpisrleq cginandvkk leeagfhtve avayapkkel    61
61  inikgiseak adkilaeaak lvpmgfttat efhqrrseii qittgskeld kllqggietg   121
    sitemfgefr tgktqichtl avtcqlpidr gggegkamyi dtegtfrper llavaerygl   181
    sgsdvldnva yarafntdhq tqllyqasam mvesryalli vdsatalyrt dysgrgelsa   241
    rqmhlarflr mllrladefg vavvitnqvv aqvdgaamfa adpkkpiggn iiahasttrl   301
    ylrkgrgetr ickiydspcl peaeamfain adgvgdakd
```

CAG38796.1 GI: 49168602
RAD51 [*Homo sapiens*]

```
1   mamqmqlean adtsveeesf gpqpisrleq cginandvkk leeagfhtve avayapkkel    61
    inikgiseak adkilaeaak lvpmgfttat efhqrrseii qittgskeld kllqggietg   121
    sitemfgefr tgktqichtl avtcqlpidr gggegkamyi dtegtfrper llavaerygl   181
    sgsdvldnva yarafntdhq tqllyqasam mvesryalli vdsatalyrt dysgrgelsa   241
    rqmhlarflr mllrladefg vavvitnqvv aqvdgaamfa adpkkpiggn iiahasttrl   301
    ylrkgrgetr ickiydspcl peaeamfain adgvgdakd
```

What is claimed is:

1. A kit comprising (a) nucleic acid probes for detection of expression levels of a gene panel consisting of eight DNA repair genes, CDKN1A, FDXR, BBC3, PCNA, GADD45a, XPC, POLH and DDB2, wherein said probes provide for assessment of a subject's radiation exposure and discriminates between persons who have been exposed to radiation only, inflammation stress only, or a combination of the two, wherein the probes are displayed on a surface, and (b) an antibody probe for detection of pCHK2-thr68.

2. A kit comprising (a) nucleic acid probes for detection of expression levels of a gene panel consisting of twelve DNA repair genes consisting of CDKN1A, FDXR, BBC3, PCNA, GADD45a, XPC, POLH, DDB2, CCNG1, BAX, LIG1, and RAD51, wherein said probes provide for assessment of a subject's radiation exposure and discriminates between persons who have been exposed to radiation only, inflammation stress only, or a combination of the two, wherein the probes are displayed on a surface, and (b) an antibody probe for detection of pCHK2-thr68.

3. A kit comprising antibody probes for detection of expression levels of a panel consisting of eight DNA repair proteins, CDKN1A, FDXR, BBC3, PCNA, GADD45a, XPC, POLH and DDB2 or twelve DNA repair proteins, CDKN1A, FDXR, BBC3, PCNA, GADD45a, XPC, POLH, DDB2, CCNG1, BAX, LIG1, and RAD51, wherein said probes provide for assessment of a subject's radiation exposure and discriminates between persons who have been exposed to radiation only, inflammation stress only, or a combination of the two; wherein the antibody probes are each fixed separately on a substrate.

4. A kit comprising antibody probes for detection of expression levels of a panel consisting of (a) eight DNA repair proteins, CDKN1A, FDXR, BBC3, PCNA, GADD45a, XPC, POLH and DDB2 or twelve DNA repair proteins, CDKN1A, FDXR, BBC3, PCNA, GADD45a, XPC, POLH, DDB2, CCNG1, BAX, LIG1, and RAD51, and (b) pCHK2-thr68; wherein said probes provide for assessment of a subject's radiation exposure and discriminates between persons who have been exposed to radiation only, inflammation stress only, or a combination of the two; wherein the antibody probes are each fixed separately on a substrate.

5. The kit of claim 3, wherein the panel consists of twelve DNA repair proteins, CDKN1A, FDXR, BBC3, PCNA, GADD45a, XPC, POLH, DDB2, CCNG1, BAX, LIG1, and RAD51.

* * * * *